US011053271B2

(12) United States Patent
Nunez et al.

(10) Patent No.: US 11,053,271 B2
(45) Date of Patent: Jul. 6, 2021

(54) METHODS AND COMPOSITIONS FOR NUCLEIC ACID INTEGRATION

(71) Applicant: The Regents of the University of California, Oakland, CA (US)

(72) Inventors: James K. Nunez, Berkeley, CA (US); Jennifer A. Doudna, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 15/535,393

(22) PCT Filed: Dec. 21, 2015

(86) PCT No.: PCT/US2015/067161
§ 371 (c)(1),
(2) Date: Jun. 12, 2017

(87) PCT Pub. No.: WO2016/106239
PCT Pub. Date: Jun. 30, 2016

(65) Prior Publication Data
US 2017/0360048 A1  Dec. 21, 2017

Related U.S. Application Data

(60) Provisional application No. 62/096,507, filed on Dec. 23, 2014.

(51) Int. Cl.
| | |
|---|---|
| *A61K 38/46* | (2006.01) |
| *C12N 9/22* | (2006.01) |
| *C12N 15/90* | (2006.01) |
| *C07H 21/04* | (2006.01) |
| *C07H 1/00* | (2006.01) |
| *C12N 9/52* | (2006.01) |
| *A01N 63/50* | (2020.01) |
| *C12N 15/66* | (2006.01) |
| *C12N 15/79* | (2006.01) |
| *C12P 19/34* | (2006.01) |
| *C12N 15/70* | (2006.01) |

(52) U.S. Cl.
CPC ............ *C07H 21/04* (2013.01); *A01N 63/50* (2020.01); *C07H 1/00* (2013.01); *C12N 9/52* (2013.01); *C12N 15/66* (2013.01); *C12N 15/90* (2013.01); *C12N 15/79* (2013.01); *C12P 19/34* (2013.01); *C12Y 304/22036* (2013.01); *C12Y 304/22055* (2013.01); *C12N 15/70* (2013.01); *C12N 2800/30* (2013.01); *C12N 2800/70* (2013.01)

(58) Field of Classification Search
None
See application file for complete search history.

(56) References Cited

U.S. PATENT DOCUMENTS 8,993,233 B2 * 3/2015 Zhang ..................... C12N 9/22
424/94.1

OTHER PUBLICATIONS

The new frontier of genome engineering with CRISPR-Cas9 Science Nov. 28, 2014 • vol. 346 Issue 6213 1077 and pp. 1258096-1/1258096-9.*
Nash et al Overproduction of *Escherichia coli* Integration Host Factor, a Protein with Nonidentical Subunits Journal of Bacteriology, Sep. 1987, p. 4124-4127.*
Nuclease—Wikipedia pp. 1-9, downloaded Jul. 26, 2018.*
Nunez et al Nature Structural & Molecular Biology Supplementary Information Cas1-Cas2 complex formation mediates spacer acquisition during CRISPR-Cas adaptive immunity pp. 1-7.*
Plagens et al., Characterization of the CRISPR/Cas I-A system of the hyperthermophilic Crenarchaeon Thermoproteus tenax published online ahead of print on Mar. 9, 2012 J. Bacteriol pp. 1-32.*
Pougach et al Transcription, processing and function of CRISPR cassettes in *Escherichia coli* Molecular Microbiology (2010) 77(6), 1367-1379.*
Sheflin et al 1985 Altered DNA conformations detected by mung bean nuclease occur Io promoter and terminator regiom of supercoiled pBR322 DNA Nucleic Acids Research pp. 6237-6154.*
John van der Oost Unravelling the structural and mechanistic basis of CRISPR-Cas systems Nature Reviews Microbiology vol. 12, pp. 479-492 (2014).*
Garneau et al The CRISPR/Cas bacterial immune system cleaves bacteriophage and plasmid DNA Nature 468, 67-71 (2010).*
NCBI Bookshelf. A service of the National Library of Medicine, National Institutes of Health. Alberts B, Johnson A, Lewis J, et al. Molecular Biology of the Cell. 4th edition. New York: Garland Science; 2002. pp. 1-15.*
Levy et al 2015 CRISPR adaptation biases explain preference for acquisition of foreign DNA Nture pp. 505-509.*
New England BioLabs Restriction Endonucleases; pp. 1-8; downloaded Apr. 3, 2020.*
Enzyme Finder | NEB New England Biolab 3' prime NEB Enzymes; p. 1-14 downloaded Oct. 23, 2020.*
Arslan, et al.; "Detection and characterization of spacer integration intermediates in type I-E CRISPR-Cas system"; Nucl. Acids Res.; vol. 42, No. 12, pp. 7884-7893 (Jun. 11, 2014).

(Continued)

*Primary Examiner* — Maria G Leavitt
(74) *Attorney, Agent, or Firm* — Bozicevic Field & Francis, LLP; Paula A. Borden; Kyle A. Gurley

(57) ABSTRACT

The disclosure provides methods and compositions for the integration (insertion) of a donor DNA molecule into a target DNA molecule. In general, the methods include contacting a target DNA molecule with a linear donor DNA molecule and a Cas 1 protein, where the target DNA molecule includes an AT-rich region (e.g., in some cases positioned 5 and within 50 nucleotides of a region that forms a DNA cruciform structure), where the contacting is not in a bacterial or archaeal cell (e.g., the contacting is in vitro outside of a cell, inside of a eukaryotic cell, etc.), and provides for integration of the donor DNA molecule into the target DNA molecule.

16 Claims, 54 Drawing Sheets

Specification includes a Sequence Listing.

(56) References Cited

OTHER PUBLICATIONS

Datsenko, et al.; "Molecular memory of prior infections activates the CRISPR/Cas adaptive bacterial immunity system"; Nat. Commun.; vol. 3, No. 945, 7 pages (Jul. 10, 2012).
Krupovic, et al.; "Casposons: a new superfamily of self-synthesizing DNA transposons at the origin of prokaryotic CRISPR-Cas immunity"; BMC Biology; vol. 12, No. 36, 12 pages (2014).
Nunez, et al.; "Cas1-Cas2 complex formation mediates spacer acquisition during CRISPR-Cas adaptive immunity"; Nat. Struct. Mol. Biol; vol. 21, No. 6, pp. 528-534 (Jun. 2014).
Nunez, et al.; "Foreign DNA capture during CRISPR-Cas adaptive immunity"; Nature; vol. 527, 13 pages (Nov. 26, 2015).
Nunez, et al.; "Integrase-mediated spacer acquisition during CRISPR-Cas adaptive immunity"; Nature; vol. 519, No. 7542, pp. 193-198 (Mar. 12, 2015).
Swarts, et al; "CRISPR Interference Directs Strand Specific Spacer Acquisition"; PLoS One; vol. 7, No. 4, 7 pages (Apr. 2012).
Yosef, et al.; "Proteins and DNA elements essential for the CRISPR adaptation process in *Escherichia coli*"; Nucleic Acids Research; vol. 40, No. 12, pp. 5569-5576 (Mar. 8, 2012).

* cited by examiner

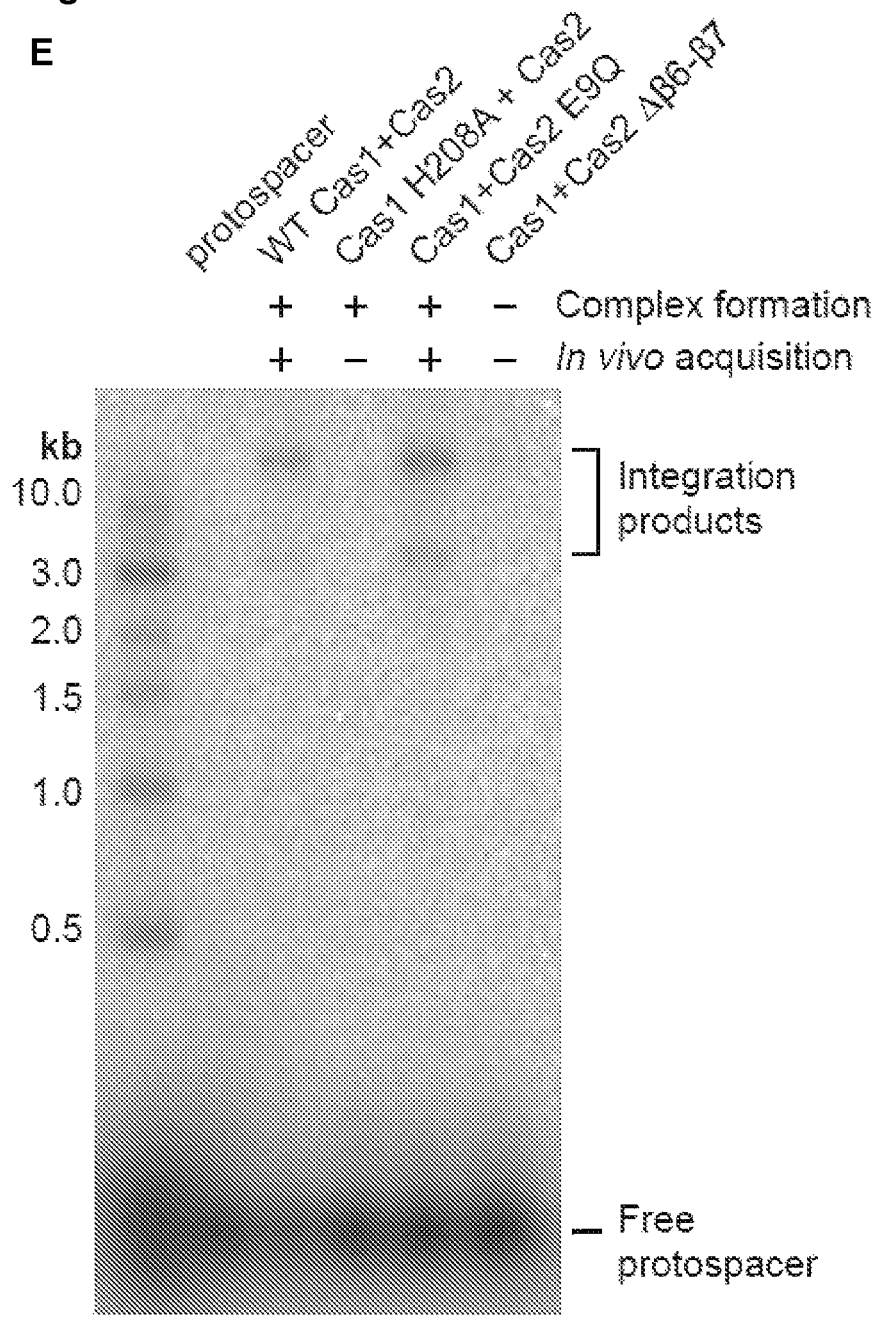

A Supercoiled pCRISPR

+ Cas1–Cas2
+ protospacers

Relaxed/Half-site

Linear/Full-site

Relaxed/Full-site

A

B

C

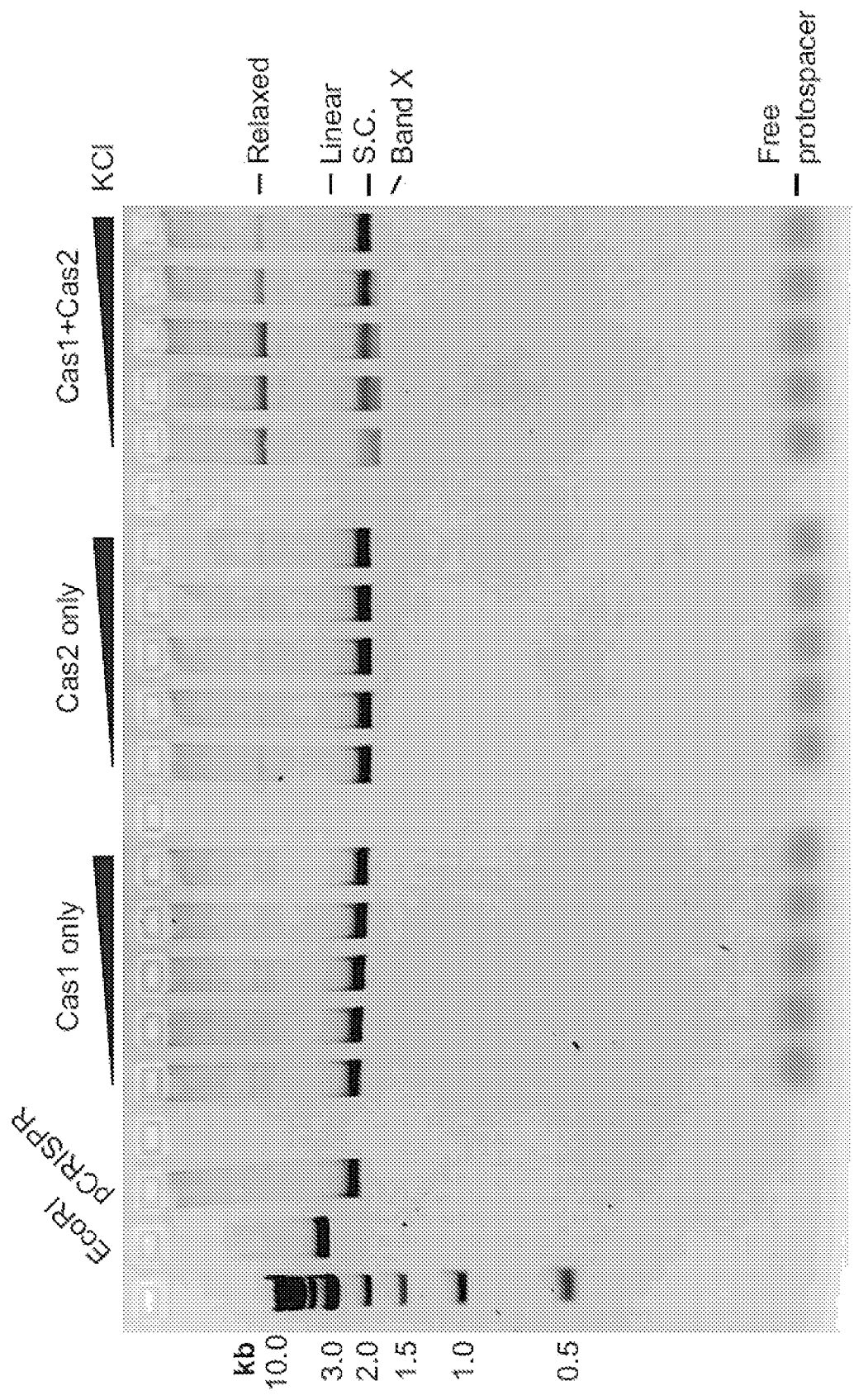

A

E

A

E    pCRISPR plus strand integration site

F    pCRISPR minus strand integration site

G    pUC19 plus strand integration site

H    pUC19 minus strand integration site

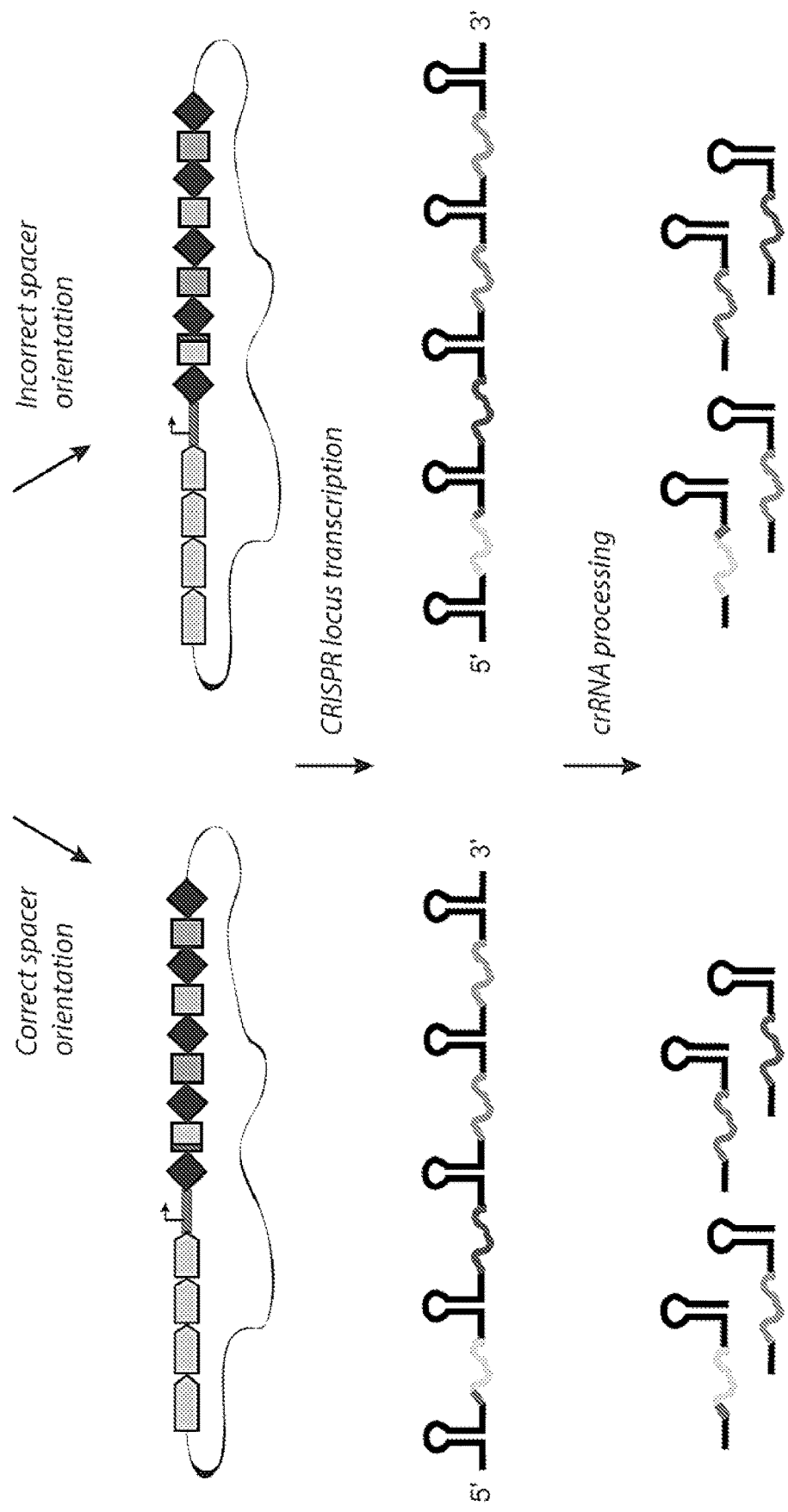
Figure 15 (Cont. 1)

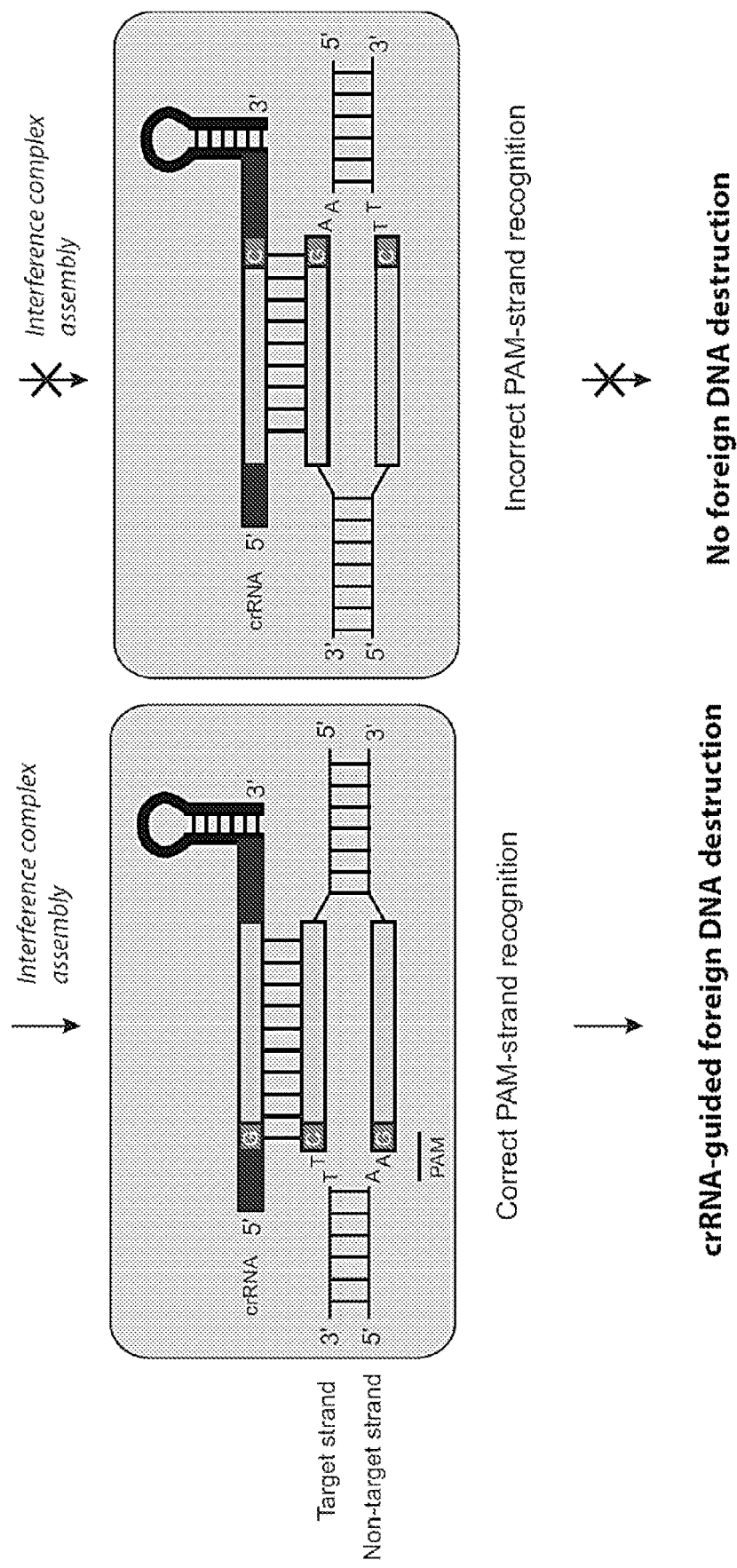
Figure 15 (Cont. 2)

Figure 16

Type I-A
*Thermoproteus tenax* (Cas1–Cas2 fusion)
>gi|503893142|ref|WP_014127136.1| CRISPR-associated protein Cas1 and
Cas2 [Thermoproteus tenax]
MDEVLLLTGGISITTRALRALLATGATVAVFSPRGEPLGIFMRPVGDATGAKRRCQYKAAEDGRGLQYAK
SWVFKKILGQRDNIKAWRRRLRGYSQYAESLAKALPGAGLHGAMETPRRRRGQDGGQAGVRGRPTHPPV
PPGAGRRSPGGAPRGQEASLRRDPQRGQSSGALHMYVIVVYDITENDVRAKVADILRAYGLARIQRSAYV
GRLPPALVKELAERLARAVRGANADIAIFKVDKRTIDTSLRIPPRPPAGHVA [SEQ ID NO: 162]

*Pyrobaculum neutrophilum* Cas1
>gi|501318854|ref|WP_012350489.1| CRISPR-associated protein Cas1
[Pyrobaculum neutrophilum]
MAAYGARIRARKGLLLVETKEGAREYPLHEVDEVLLLTGGISITTRALRALLAAGATVAVFSPRGEPLGI
FMKPIGDATGAKRRCQYKAAEDGRGLQYAKSWVFKKMLGQRDNIKAWRRRLRGYSQYAESLAKALQALRD
AASPHAVLEAEAAAAEAYWAAYREVTGFPGRDQEGRDPVNAGLNYGYGILKALVYKSLILAGLDPYVGFL
HVDKSGRPSLALDFMEQWRPRVDAVVAKMADKLESEGGLLTRRSRLELAAAVLEELHAAKRPLSAEIHRE
ARALARSICT [SEQ ID NO: 68]

*Pyrobaculum neutrophilum* Cas2
>gi|501318855|ref|WP_012350490.1| CRISPR-associated protein Cas2
[Pyrobaculum neutrophilum]
MYIIVVYDITENDVRAKVADILRAYGLARIQRSAYVGRLPPALVKELAERLARAVKGANADIAIFKVDKR
AIETALRIPPRPPAGHAALH [SEQ ID NO: 137]

Type I-B
*Haloarcula hispanica* Cas1
>gi|344209644|ref|YP_004785821.1| CRISPR-associated protein Cas1
[Haloarcula hispanica ATCC 33960]
MDRNYHVFSDGRLERSDDTLRLVPDDDGDKQYIPIENAEAFFLHGQIDFNTRLMSFLNDRTVALHIFGWE
DYYAGSVMPKRGQTSGKTVVNQVRAYEDSQHRRQLAAAIVKGSIHNMRTNVVYYNGRDHDLDSVIEDLEA
AATRVDESLPIDELMGIEATAKKAYYRSFNQILPSEFQLSQREYNPPPNEINSLISFGNSMVYANCVSAI
RATALDPTISYLHEPGERRYSLSLDIADLFKPVLADRVLFRLVNRNQISESDFETELGSCLLNEAGRKTY
TKAFEEMLERTVEHPTLNRKVSYQYLMRLEAYKLKKHLLTGEAYDSFQRWW [SEQ ID NO: 42]

*Haloarcula hispanica* Cas2
>gi|344209643|ref|YP_004785820.1| CRISPR-associated protein Cas2
[Haloarcula hispanica ATCC 33960]
MYVVMVYDLEADRTQKALKIGRRYLTHVQNSVLEGEISEGDLSNLKNEIDDLLKPGESTIIYELSSDTLL
NRTVYGDDPTEDQRFL [SEQ ID NO: 111]

Figure 16 (cont. 1)

Type I-C
*Desulfovibrio vulgaris* Cas1
>gi|387134024|ref|YP_005704014.1| CRISPR-associated protein Cas1
[Desulfovibrio vulgaris RCH1]
MKKLLNTLYVTTQGTYLAKEGECIVVRVGDEVRLRVPVHSLGGVVCFGQVSCSPFLMGFAAERGLGFSFL
TEHGRFLARVQGPVSGNVLLRREQYRRADSPEASAEVARSIVSAKVVNARGVLQRAMRDHGDKVDGVALE
AEVLHLRACLMRLQQPAGLDAVRGIEGEAAKGYFSVFDNLILTREAAFRFEGRSRRPPLDRVNCLLSFIY
TLLGHDVRSALEGVGLDSAVGFLHRDRPGRHGLALDVMEEFRAVVADRLALSLINLGKLKKSDFEIQETG
AVRMTDDARKALLVAYQKRKQDEIVHPFLNERIPLGLVFHVQAMLMARWLRGDLDGYPPFVWK [SEQ
ID NO: 36]

*Desulfovibrio vulgaris* Cas2
>gi|387134025|ref|YP_005704015.1| CRISPR-associated protein Cas2
[Desulfovibrio vulgaris RCH1]
MLVLISYDVSFEDPGGQRRLRRIAKACQDYGQRVQYSVFECVVDPAQWAKLKHRLLSEMDKEKDCLRFYY
LGANWRNKVEHVGAKPAYDPEGPLIL  [SEQ ID NO: 101]

Type I-D
*Thermofilum pendens* Cas1
>gi|500076970|ref|WP_011752983.1| CRISPR-associated protein Cas1
[Thermofilum pendens]
MRLLVLRGVDEVTVSSRSTVVIKSGNRVFERALRDVDAVLVVGSGIKISSSLPPVLALHGIPLSILAKGH
VAVLLNPVGTKYNNYRALQYTLPKNKALAIALEYLKSRVRGMASIIRNRGGRLPALPEPPDPALYEDPAR
LESDIRSWEAAASNTLWDEVFKLLDPSAARELRERYGFAGRKPGHPDPLNKAISAMYAVLYTLSTKALVA
AGLDPTYGFLHRTQYSVPLAFDYAEAFKPLAVEAALDLVNEEGLPTLSEDGDLDKDSLNKAMKRLYRYLS
AKHRETGKTPYQQIHLKAFCLAKHLEGKCSREKLAFTWDKKRYIIHE [SEQ ID NO: 82]

*Thermofilum pendens* Cas2
>gi|500076971|ref|WP_011752984.1| CRISPR-associated Cas2 family
protein [Thermofilum pendens]
MIVIVAYDISDEDRRGRLRRYLRRLGLARVNRSVYAGPGTATTAELVAERAKEIVEEGDSVFVIVVREDE
YQRAHVFDGRDYYIVSERKYEVY  [SEQ ID NO: 158]

Figure 16 (cont. 2)

Type I-E
*Escherichia coli K-12* Cas1
>gi|16130662|ref|NP_417235.1| multifunctional endonuclease Cas1,
CRISPR adaptation protein; DNA repair enzyme [Escherichia coli str. K-12 substr. MG1655]
MTWLPLNPIPLKDRVSMIFLQYGQIDVIDGAFVLIDKTGIRTHIPVGSVACIMLEPGTRVSHAAVRLAAQ
VGTLLVWVGEAGVRVYASGQPGGARSDKLLYQAKLALDEDLRLKVVRKMFELRFGEPAPARRSVEQLRGI
EGSRVRATYALLAKQYGVTWNGRRYDPKDWEKGDTINQCISAATSCLYGVTEAAILAAGYAPAIGFVHTG
KPLSFVYDIADIIKFDTVVPKAFEIARRNPGEPDREVRLACRDIFRSSKTLAKLIPLIEDVLAAGEIQPP
APPEDAQPVAIPLPVSLGDAGHRSS  [SEQ ID NO: 38]

*Escherichia coli K-12* Cas2
>gi|90111482|ref|NP_417234.2| CRISPR adaptation ssRNA endonuclease
[Escherichia coli str. K-12 substr. MG1655]
MSMLVVVTENVPPRLRGRLAIWLLEVRAGVYVGDVSAKIREMIWEQIAGLAEEGNVVMAWATNTETGFEF
QTFGLNRRTPVDLDGLRLVSFLPV  [SEQ ID NO: 104]

Type I-F
*Pseudomonas aeruginosa* M18 Cas1
>gi|386058681|ref|YP_005975203.1| CRISPR-associated protein
[Pseudomonas aeruginosa M18]
MDDISPSELKTILHSKRANLYYLQHCRVLVNGGRVEYVTDEGRHSHYWNIPIANTTSLLLGTGTSITQAA
MRELARAGVLVGFCGGGGTPLFSANEVDVEVSWLTPQSEYRPTEYLQLWVGFWFDEEKRLEAARHFQRVR
LERIRHSWLEDRVLRDAGFAVDATALAVAVEDSARALEQAPNHEHLLTEEARLSKRLFKLAAQATRYGEF
VRAKRGSGGDPANRFLDHGNYLAYGLAATATWVLGIPHGLAVLHGKTRRGGLVFDVADLIKDSLILPQAF
LSAMRGDEEQDFRQACLDNLSRAQALDFMIDTLKDVAQRSTVSA [SEQ ID NO: 65]

Figure 16 (cont. 3)

Type II-A
*Campylobacter jejuni* RM1221 Cas1
>gi|57238545|ref|YP_179676.1| CRISPR-associated Cas1 family protein
[Campylobacter jejuni RM1221]
MSYDEAFKTLLISSNAKLNLELNHLVIKQDENIAKLFLKDINIIVLESLQVSISSALFNAFARHKIILLT
CDETHSINGVFTPFLGHFQSAKIAKEQMNVSAQKKAILWQKIIKNKILNQAFILKKYNKIEQSNELINLA
KKVSLNDSKNIEAVAAALYFKTLFGTSFSRDELCFENSALNYGYAIIRACIIRAVCISGLLPWLGIKHDN
IYNSFALCDDLIEVFRASVDDCVLKLKGESEFLSKDDKRALIGNLQSKINFDGQNYPLNRAINHYVANFK
NALLYEDELKIVKFDD [SEQ ID NO: 31]

*Campylobacter jejuni* RM1221 Cas2
>gi|57238544|ref|YP_179675.1| CRISPR-associated Cas2 family protein
[Campylobacter jejuni RM1221]
MIEDKFMRVLLMFDVPTKSKKEQKLASKFRNNLIKLGYFMLQFSVYMRICKGLSSAKSSIENVKKILPPY
GNVRALIITEKQFDKMELLLGGIVFNEKVNNETNLTLFDIDSHGEFKYKNSNNEEIQLNKKQEKYHQQNL
FEF [SEQ ID NO: 93]

*Streptococcus pyogenes* MGAS1882 Cas1
>gi|383493862|ref|YP_005411538.1| CRISPR-associated protein Cas1
[Streptococcus pyogenes MGAS1882]
MAGWRTVVVNTHSKLSYKNNHLIFKDAYKTELIHLSEIDILLLETTDIVLSTMLVKRLVDENVLVIFCDD
KRLPTAMLMPFYGRHDSSLQLGKQMSWSETVKSQVWTTIIAQKILNQSCYLGACSYFEKSQSIMDLYHGL
ENFDPSNREGHAARIYFNTLFGNDFSRDLEHPTNAGLDYGYTLLLSMFAREVVVSGCMTQFGLKHANQFN
QFNFASDIMEPFRPLVDKIVYENRNQPFPKIKRELFTLFSDTFSYNGKEMYLTNIISDYTKKVVKALNNE
GKGVPEFRI [SEQ ID NO: 74]

Streptococcus pyogenes MGAS1882 Cas2
>gi|383493863|ref|YP_005411539.1| CRISPR-associated protein Cas2
[Streptococcus pyogenes MGAS1882]
MSYRYMRMILMFDMPTDTAEERKAYRKFRKFLLSEGFIMHQFSIYSKLLLNNTANNAMIGRLREHNPNKG
NITLLTVTEKQFARMIYLHGERNNCIANSDERLVFLGEAFDES [SEQ ID NO: 147]

Type II-B
*Francisella novicida* 3523 Cas1
>gi|387824702|ref|YP_005824173.1| CRISPR-associated protein Cas1
[Francisella cf. tularensis subsp. novicida 3523]
MLVGANQHAVVQARINQYRYIHENALALSTKLIIAKIKNQRATLSYFNKHHKSVNLLNAIEELKRIAQLI
KNAKTLNDVLGYEGYAANIYFSSLARDKFLSESFANREGRGSQEIANSMLNFGYAILSSYILNAVTNAGL
EPYLGFLHQKRPGKMSLVLDLMEEYRAWVVDRVVIKLREQYKNKKSIDPKLKSALISEIQATIAKKYIYN
GKKLKLEHIIQRQVYRLSGEFAGEHNYKPYIFKW [SEQ ID NO: 39]

*Francisella novicida* 3523 Cas2
>gi|383493863|ref|YP_005411539.1| CRISPR-associated protein Cas2
[Streptococcus pyogenes MGAS1882]
MSYRYMRMILMFDMPTDTAEERKAYRKFRKFLLSEGFIMHQFSIYSKLLLNNTANNAMIGRLREHNPNKG
NITLLTVTEKQFARMIYLHGERNNCIANSDERLVFLGEAFDES [SEQ ID NO: 107]

Figure 16 (cont. 4)

Type II-C
*Neisseria meningitides* 8013 Cas1
>gi|677989519|sp|C9X1G6.1|CAS1_NEIM8 RecName: Full=CRISPR-associated endonuclease Cas1
MTWRSLLIQNGGKLSLQRRQLLIQQNGESHTVPLEDIAVIIENRETLITAPLLSALAEHGATLLTCDEQ
FLPCGQWLPYAQYHRQLKILKLQLNISEPLKKQLWQHIVRQKILNQAFVADETGNDLAAKRLRTLASEVR
SGDTGNREAQAAALYFQALFGEKFTRNDNNAVNAALNYTYAVLRAAVARTLTLYGWLPALGLFHRSELNP
FNLADDFIEPLRPLADLTVIHLYEQGRLKAELTPGIKQHLIKTLHYQISIERQHFSTLAAIDKMVSSFQA
GVTDKNAKQLKLPEILPLKEYQYE   [SEQ ID NO: 61]

*Neisseria meningitides* 8013 Cas2
>gi|677990551|sp|C9X1G7.1|CAS2_NEIM8 RecName: Full=CRISPR-associated endoribonuclease Cas2
MSEAKFMRIIVFFDLPVITAAKRKAANQFRQFLLKDGYQMLQLSVYSRIVKGRDSLQKHHNRLCANLPQE
GSIRCLEITEKQYAAMKLLLGELKTQEKKVNSDQLLLF   [SEQ ID NO: 132]

Type III-A
*Staphylococcus epidermidis* RP62A Cas1
>gi|57865886|ref|YP_190006.1| CRISPR-associated Cas1 family protein [Staphylococcus epidermidis RP62A]
MKDVIYVENHYFVTAKENSIKFRNVIDKSEKFYLFEEIEAIIFDHYKSYFSHKLVIKCIENDIAIIFCDK
KHSPVTQLISSYGMVNRLKRIQSQFQLSGRTKDRIWKKIVINKIFNQTRCLENNLHNENVKLMLGFAKEV
SSGDKSNKEAHATRIYFKDLFGKQFKRGRYNDVINSGLNYGYSILRSFINKELAIHGFEMSLGIKHQSKE
NPFNLADDIIEVFRPFVDNIVYEIVFKKNIDTFDINEKKLLLNVLYERCIIDKKVVRLLDSVKIVIQSLI
RCYEENTPTYLLLPKMIEVGN [SEQ ID NO: 73]

*Staphylococcus epidermidis* RP62A Cas2
>gi|57865885|ref|YP_190005.1| CRISPR-associated Cas2 family protein [Staphylococcus epidermidis RP62A]
MYLLVSFDLPRDTKLERRIASKYRLRLIELGFSMKQFSLYERYVSNVQKKDKILEILKQEIPDTGSITLY
ILPDEVNSNQITILGKEVKLAVNKEPKLIFI [SEQ ID NO: 143]

Type III-B
*Sulfolobus islandicus* M.16.4 Cas1
>gi|238619345|ref|YP_002914170.1| CRISPR-associated protein Cas1 [Sulfolobus islandicus M.16.4]
MRTLVISEYGAYIYVKKNMLVIKKGDNKVEISPSEVDEILITASCSISTSALSLALTHGISVMFLNSRDT
PWGILLPSVITETVKTKKAQYETIVAKKDIRYGEEIISSKIYNQSVHLKYWTRLTGTRNDYKELLGKDEP
TAARIYWRNISQLLPKDIGFDGRDVDGVDQFNMALNYSYAILYNTIFKYLVIAGLDPYLGFIHKDRPGNE
SLVYDFSEMFKPYIDFLLVRALRSGFRLKVKDGLIEENSRGDLAKLIRKGMEEKVKEESDHNPKTLIQAI
RAHAVKLASSIREGKEYKGFKLVM [SEQ ID NO: 76]

*Sulfolobus islandicus* M.16.4 Cas2
>gi|238619346|ref|YP_002914171.1| CRISPR-associated protein Cas2 [Sulfolobus islandicus M.16.4]
MKLLVVYDVSDDSKRSKLANNLKKLGLERIQRSAFEGDIDSQRVKDLIRVVRLIVDTSTDIVHIIPLGVR
DWERRIVIGKEGLEEWLV [SEQ ID NO: 149]

Figure 17

Type I-A
*Thermoproteus tenax* – 7 CRISPR loci, only one Cas1–Cas2 (fusion protein)

Leader sequences

>CRISPR I
CAAAACTGCTATCATGCCACCTCAAGAGTCCGCCGAGATCAACGTCAGTCTCGTGAGAAAA
AAGCTTAAAAGCTCGTAGAAACAAAGACAACAATACCCG  [SEQ ID NO: 163]

>CRISPR II
AGAGGAATATATGAATGTAAATGGGCGTTTGAAGGCGACCGCCGGGCGGGCGGAGGATC
TGGGCAAAATTTAAATAGCCGGGGCCGCAATCGACGTGGGC  [SEQ ID NO: 164]

>CRISPR III
GGAGAATGTGTGAATGTAAAGGGCAGCGGAAAAGCGGCCGCCGGGCGGGCGGAGGATCT
GGGCAAAATTTAAATACCCGAGGCCGCAGTCAACGTGGGCG  [SEQ ID NO: 165]

>CRISPR IV
AAAGCCCTCCCCGGGGCAACACAAGGTCGCGCCGGGACTAACACAAAGACCCACAGAGG
AAAACTTAAAAATCGGCAAAAACTAAAGACCAGAAGGCCCG  [SEQ ID NO: 166]

>CRISPR V
AAAGCCCTCCCCGGGGCAACACAAGGTCGCGCCGGGACCAAGACAAAGACCCGCAGAGG
AAAACTTAAAAATCGGCAGAAACTAAAGACCAGGAGGCCCG  [SEQ ID NO: 167]

>CRISPR VI
GCAGTCCGGGGAGAGCTATCTCAAGAACACGCTGCAATCAACGCAAAACCCACCAGAGAA
AAACTTAAAAACAGCCAAAAACCAAAACCCAGAAGGCCCG  [SEQ ID NO: 168]

>CRISPR VII
AACCCCACCCCTTAGCCAACACGAGAACACGCCAGAACTAACACAAAACCCACCAGAGAA
AAACTTAAAAACAGCCAAAAGCCAAAACCCAGAAGGCCCG  [SEQ ID NO: 169]

Repeat sequences

> Repeat I
GAATCTCAGATAGAGATTTGAAGG  [SEQ ID NO: 189]

>Repeat II
AGTGGAAATCAAAAGATAGTAGAAAC  [SEQ ID NO: 190]

>Repeat III
GTGGAAATCAAAAGATAGTAGAAAG  [SEQ ID NO: 191]

>Repeat IV
GAATCTCAAAGAGAGGATTGAAAG  [SEQ ID NO: 192]

Figure 17 (cont. 1)

>Repeat V
GAATCTCAAAGAGAGGATTGAAAG [SEQ ID NO: 193]

>Repeat VI
GAATCTCAAAAAGAGGATTGAAAG [SEQ ID NO: 194]

>Repeat VII
GAATCTCAAAGAGAGGATTGAAAG [SEQ ID NO: 195]

Type I-B
*Haloarcula hispanica N601*

Leader sequence
AGGTGAATCGACAATTATCTACGAGCTGTCTTCTGATACACTGCTCAACCGGACAGTCTAC
GGCGACGATCCAACTGAGGATCAGCGGTTTCTATAGTCG [SEQ ID NO: 170]

Repeat sequence
GTTTCAGACGAACCCTCGTGGGGTTGAAGC [SEQ ID NO: 196]

Type I-C
*Desulfovibrio vulgaris RCH1*

Leader sequence
AGAAGGCCCCCTGATTCTGTAGCGCGAACCCCAAGCGACCCTGTTTTTCCCGGCAGGTTC
GCGAACATGACAATGACCTGTTTTCATTGAATTGCGTAACCTTTAATGCAGGCTGGTCACA
CATCTTGGCGGTGCTGCTGGCCCGGTTCGCGGAACCCTCGTCGCAAGGTCAATACTGCCA
ACGTGTTTGATGGCCGACA [SEQ ID NO: 171]

Repeat sequence
GTCGCCCCCCACGCGGGGGCGTGGATTGAAAC [SEQ ID NO: 197]

Type I-D
*Thermofilum pendens Hrk 5*

Leader sequence
CCGTAGGTGTCTGCGCGTAGGCTGGAGAAACGGGCGCCGAGAGGTTCGGGAACCGCTCC
TCGCATCGTCAGTCTAGGATAAGGTTGAGGCAGTTTTAGCGGAAAGATTGGGCTCTAAAAA
TTGATTGAATTGATCGTTTTTCTAAACTTTTCACGATTTTTCGAACAAGAATATTAGAGAATG
CAACCTCTTCTGTTACC [SEQ ID NO: 172]

Repeat sequence
CTCTTAGTCTTGCTGATTTTGAAC [SEQ ID NO: 198]

Figure 17 (cont. 2)

Type I-E
*Escherichia coli BL21(DE3)*
Leader sequence
ACTCTTTAACATAATGGATGTGTTGTTTGTGTGATACTATAAAGTTGGTAGATTGTGACTGG
CTTAAAAAATCATTAATTAATAATAGGTTATGTTTAGA  [SEQ ID NO: 173]

Repeat sequence
GTGTTCCCCGCGCCAGCGGGGATAAACCG  [SEQ ID NO: 199]

*Escherichia coli K-12 (MG1655)*
Leader sequence
AAGAATTAGCTGATCTTTAATAATAAGGAAATGTTACATTAAGGTTGGTGGGTTGTTTTTATG
GGAAAAAATGCTTTAAGAACAAATGTATACTTTAGA  [SEQ ID NO: 174]

Repeat sequence
GAGTTCCCCGCGCCAGCGGGGATAAACCG  [SEQ ID NO: 200]

Type I-F
*Pseudomonas aeruginosa M18* – 3 CRISPR loci

Leader sequences

>CRISPR I
TATAAATCAGCAAGTTACGAGACCTCGAAAAAGAGGGTTTCTGGCAGGAAAAACTCGGTA
TTTCCTTTTCCTTCAAATGGTTATAGGTTTTCGGGGCTA  [SEQ ID NO: 175]

>CRISPR II
TTTTAGATCAAAGGGTTAGAGATCGCTGCAAAAGAGGGTTTTCCGGGCTTTGGCGCTGG
AGCCCTTGGAGCTTGGAAGGTTGATGGTTTTGGGTCTA  [SEQ ID NO: 176]

>CRISPR III
TAGCTCCGAAAACCTATAACCATTTGAAGGAAAAAGAAATACCGAGTTTTCCCGCCAGAAA
CCCTCTTTTTTCGAGGTCTCGTAACTTGCTGATTTATA  [SEQ ID NO: 177]

Repeat sequences

>CRISPR I
GTTCACTGCCGTATAGGCAGCTAAGAAA  [SEQ ID NO: 201]

>CRISPR II
GTTCACTGCCGTATAGGCAGCTAAGAAA  [SEQ ID NO: 202]

>CRISPR III
TTTCTTAGCTGCCTACACGGCAGTGAAC  [SEQ ID NO: 203]

Figure 17 (cont. 3)

Type II-A
*Campylobacter jejuni* RM1221
Leader sequences
(Left flanking the CRISPR locus)
AGATATTTACCAGATAATGAAAATTTCGGGGTTTTTTCATGAAAAATAGCAAAAATTATGCTA
TAATCTCATAAGAAATTTAAAAAGGGACTAAAATAAA [SEQ ID NO: 178]

(Right flanking the CRISPR locus)
AGATATTTACCAGATAATGAAAATTTCGGGGTTTTTTCATGAAAAATAGCAAAAATTATGCTA
TAATCTCATAAGAAATTTAAAAAGGGACTAAAATAAA [SEQ ID NO: 179]

Repeat sequence
GTTTTAGTCCCTTTTTAAATTTCTTTATGGTAAAAT [SEQ ID NO: 204]

*Streptococcus pyogenes* MGAS1882
Leader sequences
(Left flanking the CRISPR locus)
CTCTTAATAAATGCAGTAATACAGGGGCTTTTCAAGACTGAAGTCTAGCTGAGACAAATAGT
GCGATTACGAAATTTTTAGACAAAAATAGTCTACGAG [SEQ ID NO: 180]

(Right flanking the CRISPR locus)
AACATTGCCGATGATAACTTGAGAAAGAGGGTTCATACCAGCAGTCGGATACCTTTCTATT
CTTCCTGTTAAAACGTTTTCATGTTATAATAGGCAAAAG [SEQ ID NO: 181]

Repeat sequence
GTTTTAGAGCTATGCTGTTTTGAATGGTCCCAAAAC [SEQ ID NO: 205]

Type II-B
*Francisella novicida* 3523
Leader sequences
(Left flanking the CRISPR locus)
TTGAATTGATATTTTGCTATATAACTATTTTAGCGGTTATATTATCTGATATACTTTACCCAGA
TAGAAACTTCTAAATATTATTCGTAAAATTAATTAA [SEQ ID NO: 182]

(Right flanking the CRISPR locus)
AGCCAAGACAAACCTAGAGTTTGCAAGGCTTTGAGAGAATTATTTGCTGGTGTTTTTTCGCA
AACATCCTACTTGTAAAAAAATGTAGACATTTTGCGAA [SEQ ID NO: 183]

Repeat sequence
GTTTCAGTAGCTAGATTATTTGATATACTGCTGTTAG [SEQ ID NO: 206]

Figure 17 (cont. 4)

Type II-C
*Neisseria meningitides* 8013

Leader sequence
AAAAAAGGTCAATTCAGACCAATTATTGTTATTTTAAGCCCATTTTTTCATAACAAATAAAAC
GGGAAACCCTTATGAAATAAGGATTTCCCGTCGAAGT  [SEQ ID NO: 184]

Repeat sequence
ATTGTAGCACTGCGAAATGAGAAAGGGAGCTACAAC  [SEQ ID NO: 207]

Type III-A
*Staphylococcus epidermidis* RP62A

Leader sequences
(Left flanking the CRISPR locus)
TTTCTACATAAATAACATCTTTCATTTTTCCATCCCCTAGAAATTAATCAATGCGTATTTTATT
CAAAATCTACAATTTTTTAGAGTGTTGTTAGATTTA  [SEQ ID NO: 185]

(Right flanking the CRISPR locus)
GATACTTTAACAAATGCCATCACAACTATATTTCAAGCATCATTTTTGCTGTCAAAAAATATG
ACAATCACTAGTACAAGATTATATGATATGTCACTTT  [SEQ ID NO: 186]

Repeat sequence
GTTCTCGTCCCCTTTTCTTCGGGGTGGGTATCGATCC  [SEQ ID NO: 208]

Type III-B
*Sulfolobus islandicus* M.16.4

Leader sequences
(Left flanking the CRISPR locus)
TCTTATTCGATATAAACGTACTTATATCTATTAGGACTTCGTCTTTTCCCATACGGCTTCCCT
AGATTTAGATTTCAAACAAGTCATAGAATATAGTATA  [SEQ ID NO: 187]

(Right flanking the CRISPR locus)
TGAGGGTTTATTAACTTTTATCTAATATCTTGTTCTCTCTTCGTTATTTATAAGCTTTACTCTG
TATTATCTTTTCAATTTTTCTCCTCATCCTTTCACT  [SEQ ID NO: 188]

Repeat sequence
CTTTCAATTCTATAGTAGATTATC  [SEQ ID NO: 209]

METHODS AND COMPOSITIONS FOR NUCLEIC ACID INTEGRATION

CROSS-REFERENCE

This application is a national stage application under 35 U.S.C. § 371 of PCT/US2015/067161, filed Dec. 21, 2015, which claims the benefit of U.S. Provisional Patent Application No. 62/096,507, filed Dec. 23, 2014, each of which application is incorporated herein by reference in its entirety.

INCORPORATION BY REFERENCE OF SEQUENCE LISTING PROVIDED AS A TEXT FILE

A Sequence Listing is provided herewith as a text file, "BERK-270WO SeqList_ST25.txt" created on Dec. 21, 2015 and having a size of 268 KB. The contents of the text file are incorporated by reference herein in their entirety.

INTRODUCTION

Prokaryotic adaptive immunity relies on clustered regularly interspaced short palindromic repeats (CRISPRs) together with CRISPR associated (Cas) proteins to detect and destroy foreign nucleic acids. CRISPR loci contain an A-T-rich leader sequence followed by repetitive sequence elements that flank spacer segments, each about 30 base pairs (bp) in length, that are transcribed to produce precursor CRISPR RNAs (pre-crRNAs). Spacers are frequently virus- or plasmid-derived, although "self"-derived spacers from the host chromosome are present in some CRISPR loci. After pre-crRNA processing and assembly with Cas proteins, the resulting surveillance complexes target and cleave foreign nucleic acids bearing sequences complementary to the crRNA spacer sequence. There is a need in the art for compositions and methods that utilize a Cas protein to facilitate the integration of foreign DNA into target DNA.
Publications
Nunez et al., Nat Struct Mol Biol. 2014 June; 21(6):528-34, Epub 2014 May 4; Yosef et al., Nucleic Acids Res. 2012 July; 40(12):5569-76; Krupovic et al., BMC Biol. 2014 May 19; 12:36; Swarts et al., PLoS One. 2012; 7(4):e35888, Epub 2012 Apr. 27; Datsenko et al., Nat Commun. 2012 Jul. 10; 3:945; Barrangou et al., Science. 2007 Mar. 23; 315(5819): 1709-12.

SUMMARY

The disclosure provides methods and compositions for the integration (insertion) of a donor DNA molecule into a target DNA molecule. In general, the methods include contacting a target DNA molecule with a linear donor DNA molecule and a Cas1 protein, where the target DNA molecule includes an AT-rich region (e.g., in some cases positioned 5' and within 50 nucleotides of a region that forms a DNA cruciform structure), where the contacting is not in a bacterial or archaeal cell (e.g., the contacting is in vitro outside of a cell, inside of a eukaryotic cell, etc.), and provides for integration of the donor DNA molecule into the target DNA molecule. In some cases, the contacting is performed in the presence of a Cas2 protein. In some cases, the contacting includes introducing into a target cell: (i) the Cas1 protein, or a nucleic acid having nucleotides that encode the Cas1 protein; and (ii) a linear donor DNA molecule. In some cases, the linear donor DNA molecule (e.g., introduced into a cell) has a length in a range of from 10 to 500 nucleotides (nt) (e.g., 35 to 500 nt). In some cases, the linear donor DNA molecule (e.g., introduced into a cell) has a length that is greater than 35 nucleotides (nt). In some cases, the linear donor DNA molecule includes a 3' overhang with a length of from 1 to 6 nucleotides. In some cases, the method includes introducing into the target cell a Cas2 protein, or a nucleic acid having nucleotides that encode a Cas2 protein. In some cases, the method is performed in the presence of an integration host factor (IHF) protein. Thus, in some cases, the method includes introducing into the target cell an IHF protein, or a nucleic acid comprising nucleotides that encode an IHF protein (e.g., an expression vector in which the nucleotides encoding the IHF protein are operably linked to a promoter, e.g., a promoter operable in a eukaryotic cell).

In some cases, the method includes introducing the Cas1 protein and/or the Cas2 protein, into a target cell. In some cases, a Cas1 protein and a linear donor DNA molecule are introduced into a target cell as a targeting composition including the Cas1 protein and the linear donor DNA molecule. In some cases, the targeting composition further includes a Cas2 protein. In some cases, the Cas1 protein and/or the Cas2 protein is a protein that is isolated (e.g., purified) from a cell. In some cases, the Cas1 protein and/or the Cas2 protein, has an affinity tag. In some cases, the method includes, prior to the contacting step, a step of isolating the Cas1 protein and/or the Cas2 protein from a cell. In some such cases, the Cas1 protein and/or the Cas2 protein has an affinity tag during the isolating step. In some cases, the method includes a step of removing one or more affinity tags (e.g., via cleavage) prior to the contacting step.

In some cases, the method includes a step of introducing into a target cell a nucleic acid comprising a nucleotide sequence that encodes the Cas1 protein and/or a nucleic acid comprising a nucleotide sequence that encodes a Cas2 protein. In some cases, a nucleotide sequence that encodes the Cas1 protein and a nucleotide sequence that encodes the Cas2 protein are present on the same nucleic acid molecule (e.g., on a recombinant expression vector). In some cases, the nucleotide sequence that encodes the Cas1 protein and/or the nucleotide sequence that encodes the Cas2 protein is operably linked to a promoter that is operable in the target cell.

In some embodiments, the target DNA molecule does not contain a leader sequence from a naturally existing CRISPR locus. In some cases, the target DNA molecule does not contain a repeat sequence from a naturally existing CRISPR locus. In some cases, the target DNA does not contain a leader sequence or a CRISPR repeat sequence from a naturally existing CRISPR locus. In some cases, the target DNA molecule does not contain a naturally existing CRISPR locus.

Kits are also provided for practicing the subject methods.

BRIEF DESCRIPTION OF THE DRAWINGS

FIG. 4B: top (SEQ ID NO: 230); bottom (SEQ ID NO: 231). FIG. 4E: top left (SEQ ID NO: 232); top right (SEQ ID NO: 233); bottom left (SEQ ID NO: 234); bottom right (SEQ ID NO: 235).

FIG. 10A: Strand A (SEQ ID NO: 236); Strand B (SEQ ID NO: 237); Strand C top (SEQ ID NO: 238); Strand C middle (SEQ ID NO: 239); Strand C bottom (SEQ ID NO: 240); Strand D (SEQ ID NO: 241).

FIG. 12B: top to bottom (SEQ ID NO: 242-246).

FIG. 13D: top (SEQ ID NO: 247); bottom (SEQ ID NO: 248).

FIG. 14A: top (SEQ ID NO: 249); bottom (SEQ ID NO: 250). FIG. 14C: top (SEQ ID NO: 251); bottom (SEQ ID NO: 252). FIG. 14E: top (SEQ ID NO: 253); bottom (SEQ ID NO: 254).

FIG. 16 provides Cas1 and Cas2 protein sequences from various species.

FIG. 17 provides leader sequences and repeat sequences from various species.

DEFINITIONS

Figure 1:
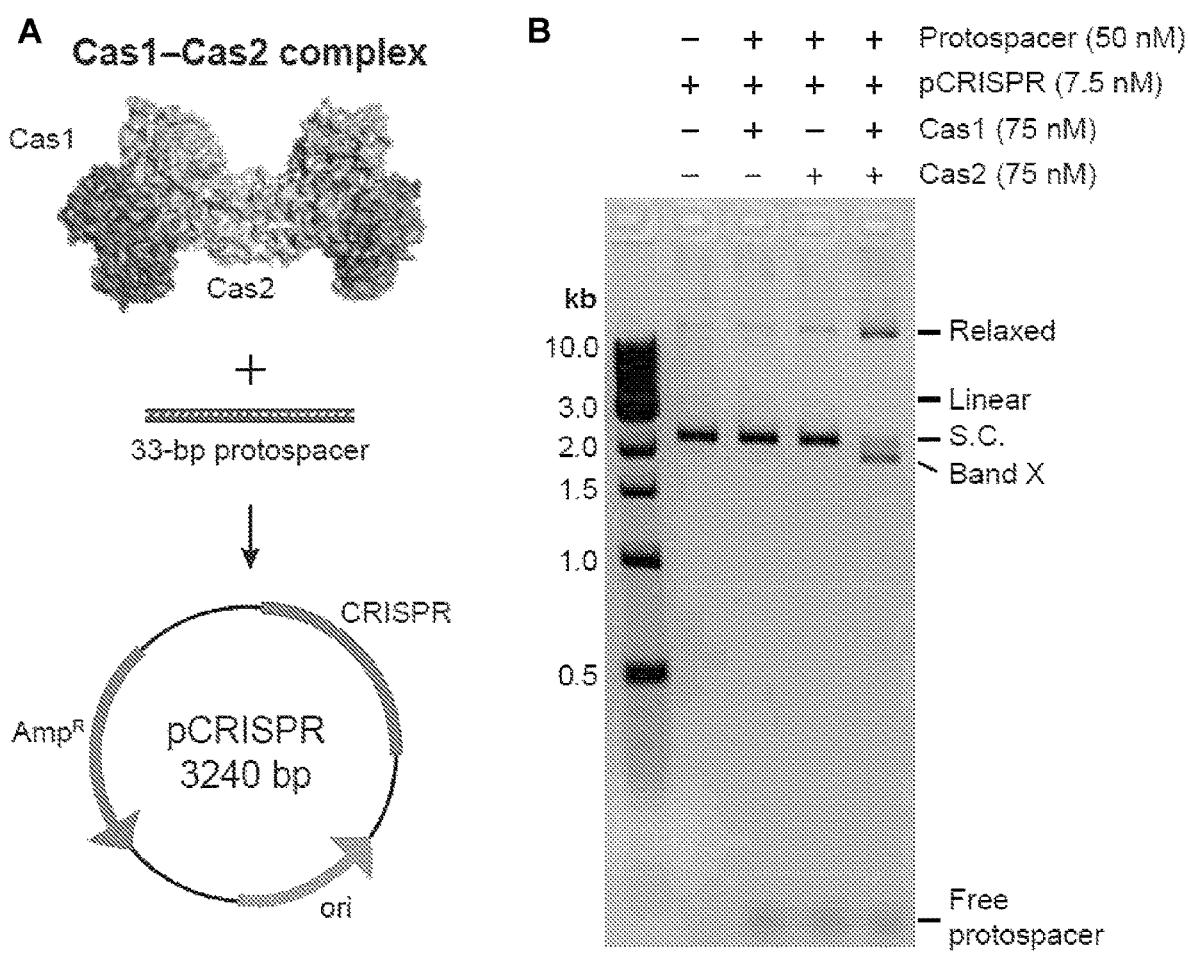
FIGS. 1A-E provide evidence related the Cas1–Cas2 complex integrating protospacers in vitro.
Figure 1:
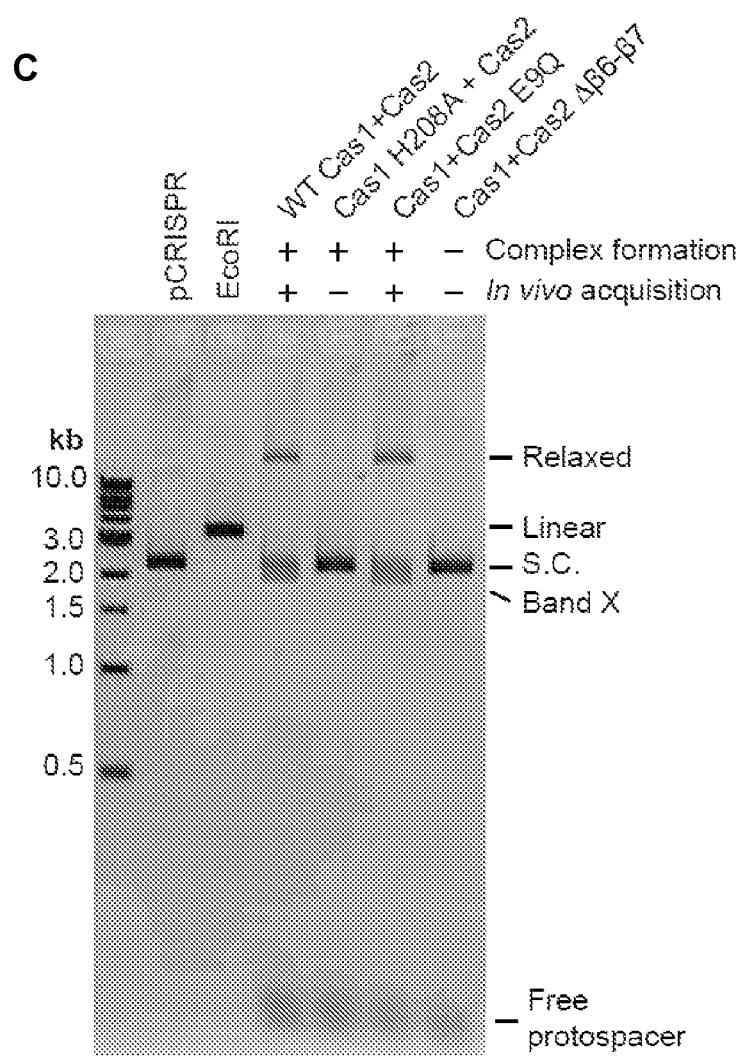
Figure 1:
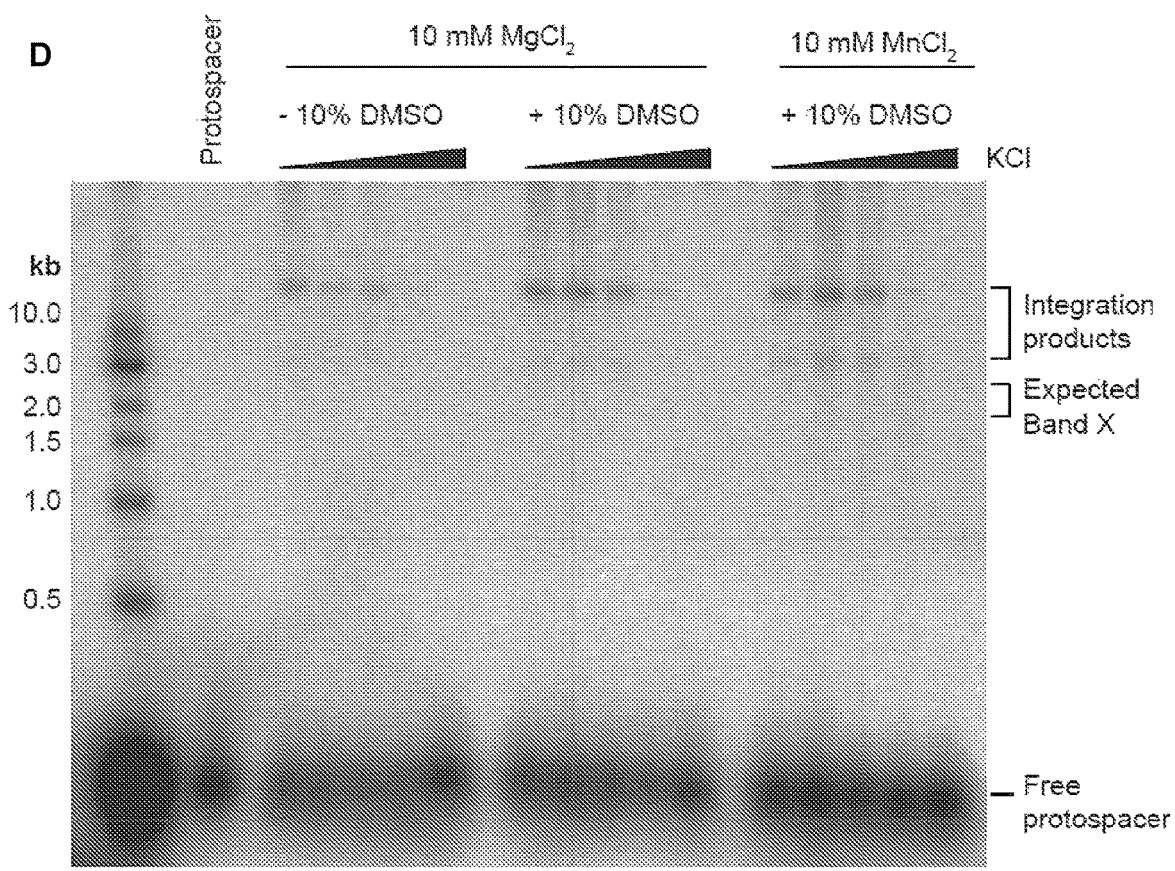

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The term "oligonucleotide" refers to a polynucleotide of between 3 and 150 nucleotides of single- or double-stranded nucleic acid (e.g., DNA, RNA, or a modified nucleic acid). However, for the purposes of this disclosure, there is no upper limit to the length of an oligonucleotide. Oligonucleotides are also known as "oligomers" or "oligos" and may be isolated from genes, transcribed (in vitro and/or in vivo), or chemically synthesized. The terms "polynucleotide" and "nucleic acid" should be understood to include, as applicable to the embodiments being described, single-stranded (such as sense or antisense) and double-stranded polynucleotides.

A "stem-loop structure" refers to a nucleic acid having a secondary structure that includes a region of nucleotides which are known or predicted to form a double strand (stem portion) that is linked on one side by a region of predominantly single-stranded nucleotides (loop portion). The terms "hairpin" and "fold-back" structures are also used herein to refer to stem-loop structures. Such structures are well known in the art and these terms are used consistently with their known meanings in the art. As is known in the art, a stem-loop structure does not require exact base-pairing. Thus, the stem may include one or more base mismatches. Alternatively, the base-pairing may be exact, i.e. not include any mismatches. In some cases, a stem-loop structure forms where there is an inverted repeat sequence. The intervening sequence of nucleotides between the initial sequence and the reverse complement of an inverted repeat can be any length including zero, and when the intervening length is zero, the composite sequence is a palindromic sequence. The length of the intervening sequence of nucleotides (i.e., the number of intervening nucleotides) determines the size of the loop portion of the stem-loop. When referring to a double stranded nucleic acid molecule (e.g., a double stranded DNA molecule), a "cruciform structure" (e.g., a DNA cruciform structure) can be formed when both strands form a stem-loop structure at the same location in the molecule. For example, an inverted repeat sequence on one strand of a double stranded DNA will lead to a stem-loop structure in both strands (and therefore a cruciform structure) because the second strand is the reverse complement of the first strand.

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine (A) pairing with thymidine (T), adenine (A) pairing with uracil (U), and guanine (G) pairing with cytosine (C) [DNA, RNA]. In addition, for hybridization between two RNA molecules (e.g., dsRNA), and for hybridization of a DNA molecule with an RNA molecule: guanine (G) can also base pair with uracil (U). For example, G/U base-pairing is partially responsible for the degeneracy (i.e., redundancy) of the genetic code in the context of tRNA anti-codon base-pairing with codons in mRNA. Thus, in the context of this disclosure, a guanine (G) is considered complementary to both a uracil (U) and to an adenine (A).

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. For hybridizations between nucleic acids with short stretches of complementarity (e.g. complementarity over 35 or less, 30 or less, 25 or less, 22 or less, 20 or less, or 18 or less nucleotides) the position of mismatches can become important (see Sambrook et al., supra, 11.7-11.8). Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more). The temperature and wash solution salt concentration may be adjusted as necessary according to factors such as length of the region of complementation and the degree of complementation.

It is understood that the sequence of a polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Examples of methods include BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein refers to a non-covalent interaction between macromolecules. While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant ($K_d$) of less than $10^{-6}$ M, less than $10^{-7}$ M, less than $10^{-8}$ M, less than $10^{-9}$ M, less than $10^{-0}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower $K_d$.

By "binding domain" it is meant a protein domain that is able to bind non-covalently to another molecule. A binding domain can bind to, for example, a DNA molecule (a DNA-binding domain), an RNA molecule (an RNA-binding domain) and/or a protein molecule (a protein-binding domain). In the case of a protein having a protein-binding domain, it can in some cases bind to itself (to form homodimers, homotrimers, etc.) and/or it can bind to one or more regions of a different protein or proteins.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various methods and computer programs (e.g., BLAST, T-COFFEE, MUSCLE, MAFFT, etc.), available over the world wide web at sites including "ncbi.nlm nili" followed by ".gov/BLAST"; "ebi.ac"followed by ".uk/Tools/msa/tcoffee/"; "ebi.ac." followed by "uk/Tools/msa/muscle/"; and "mafft.cbrc" followed by ".jp/alignment/software". See, e.g., Altschul et al. (1990), J. Mol. Bioi. 215:403-10.

A DNA sequence that "encodes" a particular RNA is a DNA nucleic acid sequence that is transcribed into RNA. A DNA polynucleotide may encode an RNA (mRNA) that is translated into protein, or a DNA polynucleotide may encode an RNA that is not translated into protein (e.g. tRNA, rRNA, microRNA (miRNA), a "non-coding" RNA (ncRNA), a guide nucleic acid, etc.).

A "protein coding sequence" or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from prokaryotic or eukaryotic mRNA, genomic DNA sequences from prokaryotic or eukaryotic DNA, and synthetic nucleic acids. A transcription termination sequence will usually be located 3' to the coding sequence.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., guide nucleic acid) or a coding sequence (e.g., Cas9 polypeptide, or Cas9 polypeptide) and/or regulate translation of an encoded polypeptide.

As used herein, a "promoter sequence" is a DNA regulatory region capable of binding RNA polymerase and initiating transcription of a downstream (3' direction) coding or non-coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention.

The term "naturally-occurring" or "unmodified" or "wild type" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is wild type (and naturally occurring).

The term "chimeric" as used herein as applied to a nucleic acid or polypeptide refers to two components that are defined by structures derived from different sources. For example, where "chimeric" is used in the context of a chimeric polypeptide, the chimeric polypeptide includes amino acid sequences that are derived from different polypeptides. A chimeric polypeptide can comprise modified and/or naturally-occurring polypeptide sequences. Similarly, "chimeric" in the context of a polynucleotide encoding a chimeric polypeptide includes nucleotide sequences derived from different coding regions.

The term "chimeric polypeptide" refers to a polypeptide which is made by the combination (i.e., "fusion") of two otherwise separated segments of amino sequence, usually through human intervention. A polypeptide that comprises a chimeric amino acid sequence is a chimeric polypeptide. Some chimeric polypeptides can be referred to as "fusion variants." "Heterologous," as used herein, means a nucleotide or polypeptide sequence that is not found in the native nucleic acid or protein, respectively. The heterologous polypeptide sequence may exhibit an activity (e.g., enzymatic activity) that will also be exhibited by the chimeric protein. A heterologous nucleic acid sequence may be linked to a naturally-occurring nucleic acid sequence (or a variant thereof) (e.g., by genetic engineering) to generate a chimeric nucleotide sequence encoding a chimeric polypeptide.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below). Alternatively, DNA sequences encoding RNA that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may be a naturally occurring amino acid sequence.

A "vector" or "expression vector" is a replicon, such as plasmid, phage, virus, or cosmid, to which another DNA segment, i.e. an "insert", may be attached so as to bring about the replication of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence if the promoter affects its transcription or expression.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

Suitable methods of genetic modification (also referred to as "transformation") include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like.

The choice of method of genetic modification is generally dependent on the type of cell being transformed and the circumstances under which the transformation is taking place (e.g., in vitro, ex vivo, or in vivo). A general discussion of these methods can be found in Ausubel, et al., Short Protocols in Molecular Biology, 3rd ed., Wiley & Sons, 1995.

A "host cell" or "target cell" as used herein, denotes an in vivo or in vitro eukaryotic cell, a prokaryotic cell (e.g., bacterial or archaeal cell), or a cell from a multicellular organism (e.g., a cell line) cultured as a unicellular entity, which eukaryotic or prokaryotic cells can be, or have been, used as recipients for a nucleic acid, and include the progeny of the original cell which has been transformed by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject bacterial host cell is a genetically modified bacterial host cell by virtue of introduction into a suitable bacterial host cell of an exogenous nucleic acid (e.g., a plasmid or recombinant expression vector) and a subject eukaryotic host cell is a genetically modified eukaryotic host cell (e.g., a mammalian germ cell), by virtue of introduction into a suitable eukaryotic host cell of an exogenous nucleic acid.

The term "stem cell" is used herein to refer to a cell (e.g., plant stem cell, vertebrate stem cell) that has the ability both to self-renew and to generate a differentiated cell type (see Morrison et al. (1997) Cell 88:287-298). In the context of cell ontogeny, the adjective "differentiated", or "differentiating" is a relative term. A "differentiated cell" is a cell that has progressed further down the developmental pathway than the cell it is being compared with. Thus, pluripotent stem cells (described below) can differentiate into lineage-restricted progenitor cells (e.g., mesodermal stem cells), which in turn can differentiate into cells that are further restricted (e.g., neuron progenitors), which can differentiate into end-stage cells (i.e., terminally differentiated cells, e.g., neurons, cardiomyocytes, etc.), which play a characteristic role in a certain tissue type, and may or may not retain the capacity to proliferate further. Stem cells may be characterized by both the presence of specific markers (e.g., proteins, RNAs, etc.) and the absence of specific markers. Stem cells may also be identified by functional assays both in vitro and in vivo, particularly assays relating to the ability of stem cells to give rise to multiple differentiated progeny.

Stem cells of interest include pluripotent stem cells (PSCs). The term "pluripotent stem cell" or "PSC" is used herein to mean a stem cell capable of producing all cell types of the organism. Therefore, a PSC can give rise to cells of all germ layers of the organism (e.g., the endoderm, mesoderm, and ectoderm of a vertebrate). Pluripotent cells are capable of forming teratomas and of contributing to ectoderm, mesoderm, or endoderm tissues in a living organism. Pluripotent stem cells of plants are capable of giving rise to all cell types of the plant (e.g., cells of the root, stem, leaves, etc.).

PSCs of animals can be derived in a number of different ways. For example, embryonic stem cells (ESCs) are derived from the inner cell mass of an embryo (Thomson et. al, Science. 1998 Nov. 6; 282(5391):1145-7) whereas induced pluripotent stem cells (iPSCs) are derived from somatic cells (Takahashi et. al, Cell. 2007 Nov. 30; 131(5): 861-72; Takahashi et. al, Nat Protoc. 2007; 2(12):3081-9; Yu et. al, Science. 2007 Dec. 21; 318(5858):1917-20. Epub 2007 Nov. 20). Because the term PSC refers to pluripotent stem cells regardless of their derivation, the term PSC encompasses the terms ESC and iPSC, as well as the term embryonic germ stem cells (EGSC), which are another example of a PSC. PSCs may be in the form of an established cell line, they may be obtained directly from primary embryonic tissue, or they may be derived from a somatic cell. PSCs can be target cells of the methods described herein.

By "embryonic stem cell" (ESC) is meant a PSC that was isolated from an embryo, typically from the inner cell mass of the blastocyst. ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells and marmoset stem cells. The stem cells may be obtained from any mammalian species, e.g. human, equine, bovine, porcine, canine, feline, rodent, e.g. mice, rats, hamster, primate, etc. (Thomson et al. (1998) Science 282:1145; Thomson et al. (1995) Proc. Natl. Acad. Sci USA 92:7844; Thomson et al. (1996) Biol. Reprod. 55:254; Shamblott et al., Proc. Natl. Acad. Sci. USA 95:13726, 1998). In culture, ESCs typically grow as flat colonies with large nucleo-cytoplasmic ratios, defined borders and prominent nucleoli. In addition, ESCs express SSEA-3, SSEA-4, TRA-1-60, TRA-1-81, and Alkaline Phosphatase, but not SSEA-1. Examples of methods of generating and characterizing ESCs may be found in, for example, U.S. Pat. Nos. 7,029,913, 5,843,780, and 6,200,806, the disclosures of which are incorporated herein by reference. Methods for proliferating hESCs in the undifferentiated form are described in WO 99/20741, WO 01/51616, and WO 03/020920.

By "embryonic germ stem cell" (EGSC) or "embryonic germ cell" or "EG cell" is meant a PSC that is derived from germ cells and/or germ cell progenitors, e.g. primordial germ cells, i.e. those that would become sperm and eggs. Embryonic germ cells (EG cells) are thought to have properties similar to embryonic stem cells as described above.

Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, the disclosures of which are incorporated herein by reference.

By "induced pluripotent stem cell" or "iPSC" it is meant a PSC that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing iPSCs may be found in, for example, U.S. Patent Publication Nos. US20090047263, US20090068742, US20090191159, US20090227032, US20090246875, and US20090304646, the disclosures of which are incorporated herein by reference. Generally, to generate iPSCs, somatic cells are provided with reprogramming factors (e.g. Oct4, SOX2, KLF4, MYC, Nanog, Lin28, etc.) known in the art to reprogram the somatic cells to become pluripotent stem cells.

By "somatic cell" it is meant any cell in an organism that, in the absence of experimental manipulation, does not ordinarily give rise to all types of cells in an organism. In other words, somatic cells are cells that have differentiated sufficiently that they will not naturally generate cells of all three germ layers of the body, i.e. ectoderm, mesoderm and endoderm. For example, somatic cells would include both neurons and neural progenitors, the latter of which may be able to naturally give rise to all or some cell types of the central nervous system but cannot give rise to cells of the mesoderm or endoderm lineages.

By "mitotic cell" it is meant a cell undergoing mitosis. Mitosis is the process by which a eukaryotic cell separates the chromosomes in its nucleus into two identical sets in two separate nuclei. It is generally followed immediately by cytokinesis, which divides the nuclei, cytoplasm, organelles and cell membrane into two cells containing roughly equal shares of these cellular components.

By "post-mitotic cell" it is meant a cell that has exited from mitosis, i.e., it is "quiescent", i.e. it is no longer undergoing divisions. This quiescent state may be temporary, i.e. reversible, or it may be permanent.

By "meiotic cell" it is meant a cell that is undergoing meiosis. Meiosis is the process by which a cell divides its nuclear material for the purpose of producing gametes or spores. Unlike mitosis, in meiosis, the chromosomes undergo a recombination step which shuffles genetic material between chromosomes. Additionally, the outcome of meiosis is four (genetically unique) haploid cells, as compared with the two (genetically identical) diploid cells produced from mitosis.

In some instances, a component (e.g., a donor DNA molecule, a protein component (e.g., a Cas1 and/or a Cas2 protein), and the like) includes a label moiety. The terms "label", "detectable label", or "label moiety" as used herein refer to any moiety that provides for signal detection and may vary widely depending on the particular nature of the assay. Label moieties of interest include both directly detectable labels (direct labels)(e.g., a fluorescent label) and indirectly detectable labels (indirect labels)(e.g., a binding pair member). A fluorescent label can be any fluorescent label (e.g., a fluorescent dye (e.g., fluorescein, Texas red, rhodamine, ALEXAFLUOR® labels, and the like), a fluorescent protein (e.g., GFP, EGFP, YFP, RFP, CFP, YFP, cherry, tomato, tangerine, and any fluorescent derivative thereof), etc.). Suitable detectable (directly or indirectly) label moieties for use in the methods include any moiety that is detectable by spectroscopic, photochemical, biochemical, immunochemical, electrical, optical, chemical, or other means. For example, suitable indirect labels include biotin (a binding pair member), which can be bound by streptavidin (which can itself be directly or indirectly labeled). Labels can also include: a radiolabel (a direct label)(e.g., $^3$H, $^{125}$I, $^{35}$S, $^{14}$C, or $^{32}$P); an enzyme (an indirect label)(e.g., peroxidase, alkaline phosphatase, galactosidase, luciferase, glucose oxidase, and the like); a fluorescent protein (a direct label)(e.g., green fluorescent protein, red fluorescent protein, yellow fluorescent protein, and any convenient derivatives thereof); a metal label (a direct label); a colorimetric label; a binding pair member; and the like. By "partner of a binding pair" or "binding pair member" is meant one of a first and a second moiety, wherein the first and the second moiety have a specific binding affinity for each other. Suitable binding pairs include, but are not limited to: antigen/antibodies (for example, digoxigenin/anti-digoxigenin, dinitrophenyl (DNP)/anti-DNP, dansyl-X-anti-dansyl, fluorescein/anti-fluorescein, lucifer yellow/anti-lucifer yellow, and rhodamine anti-rhodamine), biotin/avidin (or biotin/streptavidin) and calmodulin binding protein (CBP)/calmodulin. Any binding pair member can be suitable for use as an indirectly detectable label moiety.

Any given component, or combination of components can be unlabeled, or can be detectably labeled with a label moiety. In some cases, when two or more components are labeled, they can be labeled with label moieties that are distinguishable from one another.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The disclosure provides methods and compositions for the integration (insertion) of a donor DNA molecule into a target DNA molecule. In general, the methods include contacting a target DNA molecule with a linear donor DNA molecule and a Cas1 protein, where the target DNA molecule includes an AT-rich region (e.g., in some cases positioned 5' and within 50 nucleotides of a region that forms a DNA cruciform structure), where the contacting is not in a bacterial or archaeal cell (e.g., the contacting is in vitro outside of a cell, inside of a eukaryotic cell, etc.), and provides for integration of the donor DNA molecule into the target DNA molecule. In some cases, the contacting is performed in the presence of a Cas2 protein. "Cas1" protein refers to CRISPR associated (Cas) protein 1, and "Cas2" protein refers to CRISPR associated (Cas) protein 2.

Proteins
Cas1 Protein

A Cas1 polypeptide (used interchangeably with the term "Cas1 protein") used in the methods described herein can be any Cas1 protein (i.e., a Cas1 protein from any species). Cas1 proteins have an N-terminal β-sheet domain and a C-terminal α-helical domain [Wiedenheft, B. et al., *Structure* 17, 904-912 (2009); Babu, M. et al., *Mol. Microbiol.* 79, 484-502 (2011); Kim et al, *Biochem. Biophys. Res. Commun.* 441, 720-725 (2013)].

In some embodiments, a Cas1 protein is from an archaeal microorganism. In some embodiments, a Cas1 protein is from a Euryarchaeota microorganism. In some embodiments, a Cas1 protein is from a Crenarchaeota microorganism. In some embodiments, a Cas1 protein is from a bacterium. In some embodiments, a Cas1 polypeptide has an amino acid sequence having 60% or more amino acid sequence identity (e.g., 60% or more, 65% or more, 70% or more, 75% or more, 80% or more, 85% or more, 90% or more, 95% or more, 98% or more, 99% or more, 99.5% or more, or 100% amino acid sequence identity) to a Cas1 protein amino acid sequence as set forth in any one of SEQ ID NOs: 28-86 (e.g., see FIG. 16). In certain embodiments, Cas1 protein includes an amino acid sequence as set forth in any one of SEQ ID NOs: 28-86.

In certain embodiments, Cas1 protein may be a "functional derivative" of a naturally occurring Cas1 protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. The term "derivative" encompasses both amino acid sequence variants of polypeptide, covalent modifications, and fusions thereof. A "fusion" polypeptide is a polypeptide comprising a polypeptide or portion (e.g., one or more domains) thereof fused or bonded to heterologous polypeptide (e.g., an affinity tag).

"Cas1 protein" encompasses a full-length Cas1 polypeptide, an enzymatically active fragment of a Cas1 polypeptide, and enzymatically active derivatives of a Cas1 polypeptide or fragment thereof. Suitable derivatives of a Cas1 polypeptide or a fragment thereof include but are not limited to mutants, fusions, covalent modifications of Cas1 protein or a fragment thereof. Cas1 protein which includes Cas1 protein or a fragment thereof, as well as derivatives of Cas1 protein or a fragment thereof, may be obtainable from a cell or synthesized chemically or by a combination of these two procedures. The cell may be a cell that naturally produces Cas1 protein, or a cell that naturally produces Cas1 protein and is genetically engineered to produce the endogenous Cas1 protein at a higher expression level or to produce a Cas1 protein from an exogenously introduced nucleic acid, which nucleic acid encodes a Cas1 that is same or different from the endogenous Cas1. In some case, the cell does not naturally produce Cas1 protein and is genetically engineered to produce a Cas1 protein.

Cas2 Protein

A Cas2 polypeptide (used interchangeably with the term "Cas2 protein") used in the methods described herein can be any Cas2 protein (i.e., a Cas2 protein from any species). Cas2 proteins form symmetrical homodimers with a core ferredoxin fold Meloglazova, N. et al., *J. Biol. Chem.* 283, 20361-20371 (2008); Nam, K. H. et al., *J. Biol. Chem.* 287, 35943-35952 (2012); and Samai, P., et al., *Acta Crystallogr. Sect. F Struct. Biol. Cryst. Commun.* 66, 1552-1556 (2010)].

In some embodiments, a Cas2 protein is from an archaeal microorganism. In some embodiments, a Cas2 protein is from a Euryarchaeota microorganism. In some embodiments, a Cas2 protein is from a Crenarchaeota microorganism. In some embodiments, a Cas2 protein is from a bacterium. In some embodiments, a Cas2 polypeptide has an amino acid sequence having 60% or more amino acid sequence identity (e.g., 60% or more, 65% or more, 70% or more, 75% or more, 80% or more, 85% or more, 90% or more, 95% or more, 98% or more, 99% or more, 99.5% or more, or 100% amino acid sequence identity) to a Cas2 protein amino acid sequence as set forth in any one of SEQ ID NOs: 87-161 (e.g., see FIG. 16). In certain embodiments, Cas2 protein includes an amino acid sequence as set forth in any one of SEQ ID NOs: 87-161.

In certain embodiments, Cas2 protein may be a "functional derivative" of a naturally occurring Cas2 protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. The term "derivative" encompasses both amino acid sequence variants of polypeptide, covalent modifications, and fusions thereof. A "fusion" polypeptide is a polypeptide comprising a polypeptide or portion (e.g., one or more domains) thereof fused or bonded to heterologous polypeptide (e.g., an affinity tag).

"Cas2 protein" encompasses a full-length Cas2 polypeptide, an enzymatically active fragment of a Cas2 polypeptide, and enzymatically active derivatives of a Cas2 polypeptide or fragment thereof. Suitable derivatives of a Cas2 polypeptide or a fragment thereof include but are not limited to mutants, fusions, covalent modifications of Cas2 protein or a fragment thereof. Cas2 protein which includes Cas2 protein or a fragment thereof, as well as derivatives of Cas2 protein or a fragment thereof, may be obtainable from a cell or synthesized chemically or by a combination of these two procedures. The cell may be a cell that naturally produces Cas2 protein, or a cell that naturally produces Cas2 protein and is genetically engineered to produce the endogenous Cas2 protein at a higher expression level or to produce a Cas2 protein from an exogenously introduced nucleic acid, which nucleic acid encodes a Cas2 that is same or different from the endogenous Cas2. In some case, the cell does not naturally produce Cas2 protein and is genetically engineered to produce a Cas2 protein.

Mutants (variants) of Cas1 protein and/or Cas2 proteins may be generated by performing conservative substitutions. By conservative substitutions is intended combinations such as those from the following groups: gly, ala; val, ile, leu; asp, glu; asn, gln; ser, thr; lys, arg; and phe, tyr. Amino acids that are not present in the same group are "substantially different" amino acids. In certain cases, the conserved residues may not be substituted and the substitutions limited to the non-conserved residues.

A subject Cas1 and/or Cas2 protein can be a variant protein by virtue of being fused to a heterologous sequence. For example, a Cas1 and/or a Cas2 protein can have a label (e.g., as defined above, e.g., can have an affinity tag, can be fused to a fluorescent protein, can include a fluorescent dye label, and the like). In some cases, a subject Cas1 and/or Cas2 protein includes (i.e., is fused to) a heterologous sequence that provides for subcellular localization (e.g., a nuclear localization signal (NLS) for targeting to the nucleus; a mitochondrial localization signal for targeting to the mitochondria; a chloroplast localization signal for targeting to a chloroplast; an ER retention signal; and the like). In some cases, a subject Cas1 and/or Cas2 protein includes 2 or more, 3 or more, 4 or more, or 5 or more NLSs. In some cases, an NLS is located at or near (e.g., within 75 amino acids, 50 amino acids, or 30 amino acids) the N-terminus and/or at or near (e.g., within 75 amino acids, 50 amino acids, or 30 amino acids) the C-terminus.

A Cas1 protein and/or Cas2 protein can be provided as a protein. For example, in some cases, a target DNA molecule is contacted in vitro, outside of a cell with a Cas1 protein and/or a Cas2 protein. In some cases, a Cas1 protein and/or a Cas2 protein is introduced into a cell. In some cases, a Cas1 protein and/or a Cas2 protein is introduced into a cell in a composition that also includes a donor DNA molecule.

In some embodiments, the Cas1 protein and/or a Cas2 protein can be purified (isolated) from an organism. The organism (e.g., a bacterial cell, an archaeal cell) may be producing the Cas1 protein from an endogenous gene or from an exogenous gene. The exogenous gene may be present in the organism transiently or stably. For example, a polynucleotide encoding a Cas1 protein and/or a polynucleotide encoding a Cas2 protein can be introduced into a suitable expression vector. The expression vector can be introduced into a suitable cell, and a Cas1 and/or Cas2 protein can be isolated. Cas1 protein and/or Cas2 protein may be recovered and purified from recombinant cell cultures by any convenient method, e.g., including ammonium sulfate or ethanol precipitation, acid extraction, anion or cation exchange chromatography, phosphocellulose chromatography, hydrophobic interaction chromatography, high performance liquid chromatography, affinity chromatography, protein G affinity chromatography, for example, hydroxyapatite chromatography and lectin chromatography, etc.

Cas1 protein and/or Cas2 protein may also be recovered from: products of purified cells, whether directly isolated or cultured; products of chemical synthetic procedures; and products produced by recombinant techniques from a prokaryotic or eukaryotic host, including, for example, bacterial, yeast higher plant, insect, and mammalian cells.

In some cases, a Cas1 protein and/or a Cas2 protein includes a label (e.g., an affinity tag) that can be used to facilitate purification. In some cases, the label can be removed. For example, in some cases, a cleavage site (e.g., a tobacco etch virus (TEV) protease cleavage site) existing between the affinity tag and the rest of the protein can be used for cleavage (removal of the label) prior to use of the protein.

In some cases, a subject method includes a step of isolating (purifying) a Cas1 protein and/or a Cas2 protein prior to contacting a target DNA molecule with the protein. In some cases, contacting a target DNA molecule with a Cas1 and/or a Cas2 protein includes introducing into a cell one or nucleic acids (e.g., RNA, DNA) that include nucleotide sequences encoding a Cas1 protein and/or a Cas2 protein.

Nucleic Acids

Donor DNA Molecule

A subject donor DNA molecule is a linear DNA molecule (in some cases double stranded, in some cases single stranded). A subject donor DNA molecule is a linear molecule (e.g., not a circular molecule such as a plasmid DNA). A donor DNA molecule can have any desired sequence. In some cases, the 3' most nucleotide on at least one end of the donor DNA molecule is a C. In some cases, the 3' most nucleotide on one and only one end of the donor DNA molecule is a C. In some cases, the 3' most nucleotide on at least one end of the donor DNA molecule is a G. In some cases, the 3' most nucleotide on one and only one end of the donor DNA molecule is a G. In some cases, the 3' most nucleotide on at least one end of the donor DNA molecule is an A. In some cases, the 3' most nucleotide on one and only one end of the donor DNA molecule is an A. In some cases, the 3' most nucleotide on at least one end of the donor DNA molecule is a T. In some cases, the 3' most nucleotide on one and only one end of the donor DNA molecule is a T.

In some cases, the linear donor DNA molecule has a length in a range of from 10 to 1000 nucleotides (nt) (e.g., 15 to 500, 20 to 500, 30 to 500, 33 to 500, 35 to 500, 40 to 500, 45 to 500, 50 to 500, 15 to 250, 20 to 250, 30 to 250, 33 to 250, 35 to 250, 40 to 250, 45 to 250, 50 to 250, 15 to 150, 20 to 150, 30 to 150, 33 to 150, 35 to 150, 40 to 150, 45 to 150, 50 to 150, 15 to 100, 20 to 100, 30 to 100, 33 to 100, 35 to 100, 40 to 100, 45 to 100, 50 to 100, 15 to 50, 20 to 50, 30 to 50, 33 to 50, 35 to 50, 40 to 50, or 45 to 50 nt). In some cases, a subject method includes introducing into a cell a subject linear donor DNA molecule. In some cases, a donor DNA molecule includes a label (e.g., as defined above, e.g., a biotin label, a fluorescent dye, etc.).

In some cases, the linear donor DNA molecule includes a 3'-overhang. For example, in some cases, the linear donor DNA molecule includes a 3'-overhang having a length in a range of from 1 to 6 nucleotides (nt) (e.g., 1 to 5 nt, 1 to 4 nt, 1 to 3 nt, 1 to 2 nt, 2 to 6 nt, 2 to 5 nt, 2 to 4 nt, 2 to 3 nt, 3 to 6 nt, 3 to 5 nt, 3 to 4 nt, 4 to 6 nt, 4 to 5 nt, 5 to 6 nt, 1 nt, 2 nt, 3 nt, 4 nt, 5 nt, or 6 nt). In some cases, the linear donor DNA molecule does not have a 3'-overhang. Thus, in some cases, the linear donor DNA molecule includes a 3'-overhang having a length in a range of from 0 to 6 nucleotides (nt) (e.g., 0 to 5 nt, 0 to 4 nt, 0 to 3 nt, 0 to 2 nt, 0 to 1 nt, 1 to 6 nt, 1 to 5 nt, 1 to 4 nt, 1 to 3 nt, 1 to 2 nt, 2 to 6 nt, 2 to 5 nt, 2 to 4 nt, 2 to 3 nt, 3 to 6 nt, 3 to 5 nt, 3 to 4 nt, 4 to 6 nt, 4 to 5 nt, 5 to 6 nt, 1 nt, 2 nt, 3 nt, 4 nt, 5 nt, or 6 nt).

Target DNA Molecule

A subject donor DNA molecule is any supercoiled target DNA (e.g., a plasmid DNA, chromosomal DNA, etc.). As shown in the working examples below, a Cas1 protein (sometimes in combination with a Cas2 protein) biases insertion of a linear donor DNA molecules to a region abutting a region of the target DNA molecule having an AT-rich region (e.g., a leader sequence from a CRISPR locus) upstream of a region that forms a DNA cruciform structure (e.g., a repeat sequence from a CRISPR locus).

By "AT-rich" is meant greater than 40% AT content (e.g., 41% or more, 45% or more, 50% or more, 51% or more, 52% or more, 53% or more, 54% or more, 55% or more, 56% or more, 57% or more, 58% or more, 59% or more, or 60% or more AT content) over a stretch of at least 40 base pairs (e.g., at least 50 base pairs, at least 60 base pairs, at least 65 base pairs, at least 70 base pairs, at least 75 base pairs, at least 80 base pairs, etc.). Naturally existing leader sequences from CRISPR loci are set forth in SEQ ID NOs: 163-188. In some cases, the entire leader sequence from a naturally occurring leader sequence is not necessary. For example, in some cases, 60 bp is sufficient size for an AT-rich region. Thus, in some cases, an AT-rich region as referred to herein includes a sequence that has 60% or more sequence identity (65% or more, 70% or more, 75% or more, 80% or more, 85% or more, 90% or more, 95% or more, 98% or more, 99% or more, or 100% sequence identity) with a leader sequence from a CRISPR locus (e.g., a leader sequence set forth in any of SEQ ID NOs: 163-188) over a stretch of at least 40 base pairs (e.g., at least 50 base pairs, at least 60 base pairs, at least 65 base pairs, at least 70 base pairs, at least 75 base pairs, at least 80 base pairs, etc.), and/or that is similar to such a sequence with regard to AT content.

In some cases, a subject AT-rich region is positioned 5' (upstream of) and within 50 nucleotides (nt) (e.g., within 40 nt, 30 nt, 20 nt, 15 nt, 10 nt, 5 nt, 2 nt, or immediately adjoining) of a region that forms a DNA cruciform structure. In some cases, a subject AT-rich region is not positioned within 50 nucleotides (nt) (e.g., within 40 nt, 30 nt, 20 nt, 15 nt, 10 nt, 5 nt, 2 nt, or immediately adjoining) of a region that forms a DNA cruciform structure. In some cases, a subject AT-rich region is a naturally occurring AT-rich region positioned 5' (upstream of) and within 50 nucleotides (nt) (e.g., within 40 nt, 30 nt, 20 nt, 15 nt, 10 nt, 5 nt, 2 nt, or immediately adjoining) of a region that forms a DNA cruciform structure, and the region that forms a DNA cruciform structure is not naturally found near or in the same species as the AT-rich region. For example, in some cases a subject target DNA molecule includes a naturally occurring AT-rich region and a naturally occurring cruciform-form region, but those regions to do not naturally occur together (e.g., within 50 nucleotides of one another).

A target DNA molecule can be present in a living cell, or can be isolated from a living cell. For example, the DNA substrate can be present in a cell lysate.

In some cases, a subject target DNA molecule includes an AT-rich region positioned 5' (upstream of) and within 50 nucleotides (nt) (e.g., within 40 nt, 30 nt, 20 nt, 15 nt, 10 nt, 5 nt, 2 nt, or immediately adjoining) of a region that forms a DNA cruciform structure. The donor DNA molecule is inserted next to the DNA cruciform structure (e.g., at or near the base of the stem structure) (e.g., as described in the working examples, one strand of a double stranded donor DNA is inserted upstream of the cruciform structure on one strand (strand A) of the target DNA molecule, and the other strand of the donor DNA is inserted downstream of the cruciform structure on the other strand (strand B) of the target DNA molecule). In some cases, a subject target DNA molecule includes an AT-rich region that is not positioned 5' (upstream of) and within 50 nucleotides (nt) (e.g., within 40 nt, 30 nt, 20 nt, 15 nt, 10 nt, 5 nt, 2 nt, or immediately adjoining) of a region that forms a DNA cruciform structure (i.e., in some cases a subject target DNA molecule includes an AT-rich region that is not 5' of and within 50 nt of a region that forms a DNA cruciform structure.

As noted above, when referring to a double stranded nucleic acid molecule (e.g., a double stranded DNA molecule), a "cruciform structure" (e.g., a DNA cruciform structure) can be formed when both strands form a stem-loop structure at the same location in the molecule. For example, an inverted repeat sequence on one strand of a double stranded DNA will lead to a stem-loop structure in both strands (and therefore a cruciform structure can form) because the second strand is the reverse complement of the first strand. In some cases, the length of the upper and lower stem of the DNA cruciform structure is in a range of from 3 to 30 base pairs (bp)(e.g., 5 to 25 bp, 5 to 20 bp, 5 to 15 bp, 5 to 10 bp, 5 to 7 bp, 3 to 25 bp, 3 to 20 bp, 3 to 15 bp, 3 to 10 bp, 3 to 7 bp, or 3 to 5 bp). In some cases, the complementarity in the stem region of the stem-loop is 70% or greater (e.g., 80% or greater, 90% or greater, 95% or greater, 98% or greater, 99% or greater, 99.5% or greater, or 100%). In some cases, region that forms a DNA cruciform structure includes a sequence that has 60% or more sequence identity (65% or more, 70% or more, 75% or more, 80% or more, 85% or more, 90% or more, 95% or more, 98% or more, 99% or more, or 100% sequence identity) with a repeat sequence from a CRISPR locus (e.g., a repeat sequence set forth in any of SEQ ID NOs: 189-209), and/or that is structurally similar to such a sequence.

Using Nucleic Acids

In some cases, a subject method includes a step of introducing into a target cell (e.g., a eukaryotic cell) one or more nucleic acids (e.g., a subject donor DNA molecule, a nucleic acid that includes nucleotide sequences encoding a Cas1 protein and/or a Cas2 protein, etc.). Methods of introducing a nucleic acid into a cell are known in the art and any convenient method can be used (e.g., electroporation, lipofection, nucleofection, injection, viral vectors, etc.). In some cases, a subject DNA molecule is introduced into a cell in a composition that also includes a Cas1 protein and/or a Cas2 protein.

When one or more nucleic acids are used that include nucleotides encoding a Cas1 and/or a Cas2 protein, the sequence encoding the Cas1 and/or the Cas2 protein can be codon-optimized. A sequence encoding any suitable Cas1 and/or Cas2 protein can be codon optimized. As a non-limiting example, if the intended host cell were a mouse cell, then a mouse codon-optimized nucleotide sequence encoding a Cas1 and/or Cas2 (or variant thereof) would be suitable. While codon optimization is not required, it is acceptable and may be preferable in certain cases.

In some embodiments, one or more of the above nucleic acids a recombinant expression vector. In some embodiments, the recombinant expression vector is a viral construct, e.g., a recombinant adeno-associated virus construct (see, e.g., U.S. Pat. No. 7,078,387), a recombinant adenoviral construct, a recombinant lentiviral construct, a recombinant retroviral construct, etc.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology,* 153:516-544).

In some embodiments, a nucleotide sequence encoding a Cas1 protein and/or a Cas2 protein is operably linked to a control element, e.g., a transcriptional control element, such as a promoter. The transcriptional control element may be functional in either a eukaryotic cell, e.g., a mammalian cell; or a prokaryotic cell (e.g., bacterial or archaeal cell) (e.g, in cases where a Cas1 protein and/or a Cas2 protein will be isolated/purified prior to the contacting step). In some embodiments, a nucleotide sequence encoding a Cas1 protein and/or a Cas2 protein is operably linked to multiple control elements that allow expression of the nucleotide sequence encoding a Cas1 protein and/or a Cas2 protein in both prokaryotic and eukaryotic cells.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. In some cases, a promoter is chosen to achieve a desirable level expression (e.g., which in some cases can be as high as possible, whereas in some cases may be above or below a desirable threshold, e.g., to achieve the desired goal while reducing off-target effects). The expression vector may also contain a ribosome binding site for translation initiation and a transcription terminator. The expression vector may also include appropriate sequences for amplifying expression. The expression vector may also include nucleotide sequences encoding protein tags (e.g., 6× His tag, hemagglutinin tag, green fluorescent protein, etc.) that are fused to Cas1 and/or Cas2 protein, thus resulting in one nor more chimeric polypeptides.

In some embodiments, a nucleotide sequence encoding a Cas1 and/or a Cas2 protein is operably linked to an inducible promoter. In some embodiments, a nucleotide sequence encoding a Cas1 and/or a Cas2 protein is operably linked to a constitutive promoter.

Methods of introducing a nucleic acid into a host cell are known in the art, and any known method can be used to introduce a nucleic acid (e.g., an expression construct) into a cell. Suitable methods include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like.

Nucleic Acid Modifications

In some embodiments, a subject nucleic acid (e.g., a donor DNA molecule) comprises one or more modifications, e.g., a base modification, a backbone modification, etc, to provide the nucleic acid with a new or enhanced feature (e.g., improved stability). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Backbones and Modified Internucleoside Linkages

Examples of suitable nucleic acids containing modifications include nucleic acids containing modified backbones or non-natural internucleoside linkages. Nucleic acids (having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid comprises one or more phosphorothioate and/or heteroatom internucleoside linkages, in particular —CH$_2$—NH—O—CH$_2$—, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). MMI type internucleoside linkages are disclosed in the above referenced U.S. Pat. No. 5,489,677. Suitable amide internucleoside linkages are disclosed in t U.S. Pat. No. 5,602,240.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Mimetics

A subject nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—CH$_2$—), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (Wahlestedt et al., Proc. Natl. Acad. Sci. U.S.A., 2000, 97, 5633-5638).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Modified Sugar Moieties

A subject nucleic acid can also include one or more substituted sugar moieties. Suitable polynucleotides comprise a sugar substituent group selected from: OH; F; O-, S-, or N-alkyl; O-, S-, or N-alkenyl; O, S- or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Particularly suitable are O((CH$_2$)$_n$O)$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON((CH$_2$)$_n$CH$_3$)$_2$, where n and m are from 1 to about 10. Other suitable polynucleotides comprise a sugar substituent group selected from: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—CH$_2$ CH$_2$OCH$_3$, also known as 2'-O—(2-methoxyethyl) or 2'-MOE) (Martin et al., Hely. Chim. Acta, 1995, 78, 486-504) i.e., an alkoxyalkoxy group. A further suitable modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$.

Other suitable sugar substituent groups include methoxy (—O—CH$_3$), aminopropoxy (—O CH$_2$ CH$_2$ CH$_2$NH$_2$), allyl (—CH$_2$—CH=CH$_2$), —O-allyl (—O—CH$_2$—CH=CH$_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278) and are suitable base substitutions, e.g., when combined with 2'-O-methoxyethyl sugar modifications.

Conjugates

Another possible modification of a subject nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937.\

A conjugate may include a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus of a polypeptide (e.g., a Cas1 and/or Cas2 protein). In some embodiments, a PTD is covalently linked to the carboxyl terminus of a polypeptide (e.g., a Cas1 and/or Cas2 protein). In some embodiments, a PTD is covalently linked to the carboxyl terminus and the amino terminus of a polypeptide (e.g., a Cas1 and/or Cas2 protein). In some cases a PTD includes a nuclear localization signal (NLS) (e.g, in some cases 2 or more, 3 or more, 4 or more, or 5 or more NLSs). In some embodiments, a PTD is covalently linked to a nucleic acid (e.g., a nucleic acid encoding a Cas1 and/or Cas2 protein, a donor DNA molecule, etc.). Exemplary PTDs include but are not limited to a minimal undecapeptide protein transduction domain (corresponding to residues 47-57 of HIV-1 TAT comprising YGRKKRRQRRR; SEQ ID NO: 210); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an Drosophila Antennapedia protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQRRTSKLMKR (SEQ ID NO:211); Transportan GWTLNSAGYLLGKINLKA-LAALAKKIL (SEQ ID NO:212); KALAWEAKLAKA-LAKALAKHLAKALAKALKCEA (SEQ ID NO:213); and RQIKIWFQNRRMKWKK (SEQ ID NO:214). Exemplary PTDs include but are not limited to, YGRKKRRQRRR (SEQ ID NO:210), RKKRRQRRR (SEQ ID NO:215); an arginine homopolymer of from 3 arginine residues to 50 arginine residues; Exemplary PTD domain amino acid sequences include, but are not limited to, any of the following: YGRKKRRQRRR (SEQ ID NO:210); RKKRRQRR (SEQ ID NO:216); YARAAARQARA (SEQ ID NO:217); THRLPRRRRRR (SEQ ID NO:218); and GGR-RARRRRRR (SEQ ID NO:219). In some embodiments, the PTD is an activatable CPP (ACPP) (Aguilera et al. (2009) Integr Biol (Camb) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

In some cases, a subject method is performed in vitro outside of a cell. When performed in vitro outside of a cell, The duration of the contacting step may be 0.1 hour-48 hours, for example, from 0.1 hour to 0.2 hour, from 0.2 hour to 0.3 hour, from 0.3 hour to 0.5 hour, from 0.5 hour to 1 hour, from 0.3 hour to 46 hours, 0.5 hour-45 hours, 1 hour-40 hours, 2 hours-35 hours, 4 hours-30 hours, 6 hours-24 hours, 8 hours-20 hours, 10 hours-18 hours, or 12 hours-16 hours, such as, 0.3 hour, 0.5 hour, 1 hour, 3 hours, 10 hours, 13 hours, 16 hours, or 18 hours.

The amount of Cas1 protein and/or Cas2 protein that is employed is can be from 10 units/ml-50,000 units/ml, for example, from 20 units/ml-30,000 units/ml, 30 units/ml-10,000 units/ml, 50 units/ml-5000 units/ml, 100 units/ml-3000 units/ml, 200 units/ml-2000 units/ml, 300 units/ml-1000 units/ml, such as, 100 units/ml, 300 units/ml, 1000 units/ml, 2000 units/ml, 5000 units/ml, 10,000 units/ml, 20,000 units/ml, or 50,000 units/ml.

The temperature at which the method is carried out is can be from 4° C.-50° C., for example, about 10° C.-45° C., about 16° C.-40° C., about 20° C.-37° C., about 25° C.-35° C., about 30° C.-33° C., e.g., 10° C., 18° C., 25° C., 30° C., 37° C., or 45° C.

The contacting step may be carried out in conditions suitable for Cas1 mediated integration. In certain embodiments, the conditions suitable for Cas1 mediated integration are conditions in which a divalent metal ion such as magnesium ($Mg^{2+}$) is present. In some cases, the $Mg^{2+}$ concentration can range from 1 mM-25 mM, for example, 1.5 mM-20 mM, 2 mM-15 mM, 2 mM-10 mM, 3 mM-8 mM, or 5 mM-6 mM, such as, 2 mM, 2.5 mM, 3 mM, or 5 mM.

In certain embodiments, the conditions suitable for Cas1 mediated integration are conditions in which a divalent metal ion such as Manganese ($Mn^{2+}$) is present. In some cases, the $Mn^{2+}$ concentration can range from 1 mM-25 mM, for example, 1.5 mM-20 mM, 2 mM-15 mM, 2 mM-10 mM, 3 mM-8 mM, or 5 mM-6 mM, such as, 2 mM, 2.5 mM, 3 mM, or 5 mM.

Under the conditions suitable for Cas1 endonuclease activity, the pH typically ranges from about pH 4.5-pH 10, for example, pH 5-pH 8.5, pH 7-pH 8.5, or pH 7-pH 8, such as, pH 7, pH 7.5, pH 8, or pH 8.5.

IHF

In some embodiments, the subject methods, compositions, and/or kits include an integration host factor (IHF) protein, or a nucleic acid encoding an IHF protein. Thus, in some cases, a subject method (e.g., contacting a contacting a target DNA molecule with a donor DNA molecule and a Cas1 protein, contacting a contacting a target DNA molecule with a donor DNA molecule and a Cas1 protein and a Cas2 protein, and the like) is performed in the presence of an integration host factor (IHF) protein. In some cases, inclusion of IHF increases sequence specificity of integration into the target DNA molecule. In some cases, a subject method (e.g., contacting a contacting a target DNA molecule with a donor DNA molecule and a Cas1 protein, contacting a contacting a target DNA molecule with a donor DNA molecule and a Cas1 protein and a Cas2 protein, and the like) includes a step of introducing into a target cell an IHF protein, or a nucleic acid comprising a nucleotide sequence that encodes an IHF protein.

IHF can be made up of two separate subunits, an alpha subunit and a beta subunit. As a non-limiting, illustrative example, the IHF alpha subunit of *Escherichia coli* (str. K-12 substr. MG1655) is:

(SEQ ID NO: 255)
MALTKAEMSEYLFDKLGLSKRDAKELVELFFEEIRRALENGEQVKLSGFG

NFDLRDKNQRPGRNPKTGEDIPITARRVVTFRPGQKLKSRVENASPKDE.

As a non-limiting, illustrative example, the IHF beta subunit of *Escherichia coli* (str. K-12 substr. MG1655) is: MTKSELIERLATQQSHIPAKTVEDAVKEMLEHMAST-LAQGERIEIRGFGSFSLHYRAPRT GRNPKTGDKVELEGKYVPHFKPGKELRDRANIYG (SEQ ID NO: 256). Any alpha/beta subunit combination can be used (e.g., including corresponding subunits, where both subunits are from or are derived from the same species). In some cases, the IHF protein is from (or derived from) the same species that the Cas1 and/or Cas2 protein(s) is from or derived from.

In some cases, a suitable IHF comprises an alpha subunit comprising an amino acid sequence having at least 50%, at least 60%, at least 70%, at least 80%, at least 85%, at least 90%, at least 95%, at least 98%, at least 99%, or 100%, amino acid sequence identity to the amino acid sequence set forth in SEQ ID NO:255. In some cases, a suitable IHF comprises an beta subunit comprising an amino acid sequence having at least 50%, at least 60%, at least 70%, at least 80%, at least 85%, at least 90%, at least 95%, at least 98%, at least 99%, or 100%, amino acid sequence identity to the amino acid sequence set forth in SEQ ID NO:256.

Target Cells

The subject methods can be performed outside of a bacterial or archaeal cell (e.g., not in a bacterial or archaeal cell). For example, subject methods can be performed in vitro outside of a cell, or can be performed in a eukaryotic cell. A target cell of interest can include a cell from any non-bacterial or archaeal organism (e.g. a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens, C. agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.).

Any type of cell may be of interest (e.g. a stem cell, e.g. an embryonic stem (ES) cell, an induced pluripotent stem (iPS) cell, a germ cell; a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro. Target cells are in many embodiments unicellular organisms, or are grown in culture.

If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. are most conveniently harvested by biopsy. An appropriate solution may be used for dispersion or suspension of the harvested cells. Such solution will generally be a balanced salt solution, e.g. normal saline, phosphate-buffered saline (PBS), Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

Kits

The present disclosure provides kits for carrying out a subject method. A subject kit can include one or more of (in any combination): a Cas1 protein, a nucleic acid having nucleotides encoding a Cas1 protein, a Cas2 protein, a nucleic acid having nucleotides encoding a Cas2 protein, and a subject linear DNA molecule. A kit can further include one or more additional reagents, where such additional reagents can be selected from: a dilution buffer; a reconstitution solution; a wash buffer; a control reagent; a control expression vector or RNA polynucleotide; a reagent for in vitro production of a Cas1 and/or Cas2 protein from DNA, and the like. The components of a subject kit can be in the same or different containers (in any desired combination).

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Utility

The subject compositions, kits, and methods find use for the integration of a donor DNA molecule into any desirable supercoiled target DNA molecule. The following uses are merely illustrative examples, and are by no means meant to limit the use of the subject methods. The compositions, kits, and methods can find use in vitro outside of a cell (e.g., to modify a plasmid DNA, to modify an isolated chromosomal DNA, etc.), and can find use inside of a eukaryotic cell (e.g., in vitro and/or in in vivo and/or ex vivo). The subject compositions, kits, and methods can be used to insert and/or modify a control element (e.g., a transcriptional control element such as an enhancer, a promoter, a transcription terminator, etc.). The subject compositions, kits, and methods can be used to modify a target gene (e.g., in some cases disrupting the expression of the target gene, in some cases, modifying the transcribed RNA, etc.). The subject compositions, kits, and methods can be used to modify a coding and/or a non-coding sequence (e.g., modify a gene coding sequence, modify a sequence that codes for a non-coding RNA such as a microRNA).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Integrase-Mediated Spacer Acquisition During CRISPR-Cas Adaptive Immunity

Bacteria and archaea insert spacer sequences acquired from foreign DNAs into CRISPR loci to generate immunological memory. The *Escherichia coli* Cas1–Cas2 complex mediates spacer acquisition, but the molecular mechanism of this process is not known. The data presented below show that the purified Cas1–Cas2 complex integrates linear DNA substrates into acceptor DNA to yield products similar to those generated by retroviral integrases and DNA transposases. Cas1 is the catalytic subunit, whereas Cas2 increases DNA integration activity. Integration occurs preferentially at the ends of CRISPR repeats and at sequences adjacent to cruciform structures abutting A-T rich regions. The results demonstrate the Cas1–Cas2 complex to be the minimal machinery required to catalyze spacer DNA acquisition and explain the significance of CRISPR repeats in providing sequence and structural specificity for Cas1–Cas2-mediated adaptive immunity.

Methods

Cas1, Cas2 and DNA Preparation

Cas1 and Cas2 from *E. coli* K12 (MG1655) were separately purified as previously described[15]. The proteins were stored in 100 mM KCl, 20 mM HEPES-NaOH, 5% glycerol and 1 mM TCEP at −80° C. prior to use. Single-stranded DNAs were synthesized (Integrated DNA Technologies). Double-stranded DNA protospacers were annealed in 20 mM HEPES-NaOH, pH 7.5, 25 mM KCl, 10 mM $MgCl_2$ or $MnCl_2$, 1 mM DTT, 10% DMSO by heating at 95° C. for 3 min and slow cooling to room temperature. The sequence of the 33 bp protospacer used in this study was shown to be the most acquired in vivo in *E. coli* K12 after M13 bacteriophage infection[13]: Strand 1 (5'-GCCCAATTTAC-TACTCGTTCTGGTGTTTCTCGT-3') (SEQ ID NO: 220) and Strand 2 (5'-ACGAGAAACACCAGAACGAGTAGTAAATTGGGC-3')(SEQ ID NO: 221).

In Vitro Integration Assays.

The integration reactions were performed in 20 mM HEPES-NaOH, pH 7.5, 25 mM KCl, 10 mM $MgCl_2$ or $MnCl_2$, 1 mM DTT and 10% DMSO. All of the reactions were conducted with $MgCl_2$ unless otherwise noted. For reactions with the Cas1–Cas2 complex, separately purified Cas1 and Cas2 were pre-incubated for 20-30 min at 4° C. to allow complex formation. The protospacer DNAs were incubated with the protein(s) for 10-15 min at 4° C., followed by the addition of the target pCRISPR or pUC19 plasmid DNA. The reactions were conducted at 37° C. for 1 h and quenched with DNA loading buffer containing a final concentration of 50 mM EDTA. The products were analyzed on 1.5% agarose gels pre-stained with ethidium bromide. All of the reactions, except those shown in FIG. 1 and FIG. 6a, c-e, were conducted with 75 nM protein, 200 nM protospacers and 7.5 nM pCRISPR to clearly visualize Band X from pCRISPR. Reactions in FIG. 1 and FIG. 6a, c, e were performed with 50 nM protospacers.

Radiolabeled Protospacer Integration Assays

Pre-annealed double-stranded protospacer DNA substrates were 5'-radiolabeled using [γ-$^{32}$P]-ATP (PerkinElmer) and T4 polynucleotide kinase (New England Biolabs). Protospacers with 3'-$PO_4$ ends were 5'-radiolabeled using T4 polynucleotide kinase with 3' phosphatase minus activity (New England Biolabs). The reactions were carried out in the same buffer as above. Unless otherwise noted, 200 nM of Cas1–Cas2 was first incubated with 20 nM protospacers at 4° C. for 10-15 min, followed by the addition of 200 ng (~5 nM) of pCRISPR. The reactions were conducted at 37° C. for 1 h and quenched with 25 mM EDTA and 0.4% SDS. The DNAs were deproteinized with 30 μg of Proteinase K for 1 h at 37° C. and ethanol precipitated. The reactions were analyzed on 1.5% agarose gels. After electrophoresis, the gels were dried onto positively charged nylon transfer membrane (GE Healthcare) and imaged using Phosphor Screens (GE Healthcare). The restriction enzyme digest experiments were performed by first conducting the integration reaction, followed by addition of the respective enzymes (New England Biolabs), which were allowed to digest for an additional 1 h at 37° C.

Disintegration Assays

The four single stranded DNA substrates were annealed to form the Y DNA in a stepwise manner: 95° C. for 3 min, 65° C. for 20 min, 50° C. for 20 min, and gradual cooling to room temperature. The annealing reactions were analyzed on a 15% native polyacrylamide gel to confirm the formation of the Y DNA (FIG. 10b). The disintegration assay was performed in the integration reaction buffer with 50 nM protein and 5 nM Y DNA at 37° C. for 1 h. For native polyacrylamide gel analysis, the reaction was quenched with DNA loading buffer with 50 mM EDTA and analyzed on 15% polyacrylamide gels. For denaturing polyacrylamide gel analysis, the reactions were quenched with formamide buffer and heating at 95° C. prior to loading on 15% 8M urea-polyacrylamide gels. The sequences of the four strands are as follows:

A (5'-GGCCCCAGTGCTGCAATGAT-3'); (SEQ ID NO: 222)

B (5'-GTGAGCGTGGGTCTCGCGGTATCATTGCAGCACTGGGGCC-3'); (SEQ ID NO: 223)

C (5'-GCCCAATTTACTACTCGTTCTGGTGTTTCTCGTACCGCGAG ACCCACGCTCAC-3'); (SEQ ID NO: 224)
and

D (5'-ACGAGAAACACCAGAACGAGTAGTAAATTGGGC-3'). (SEQ ID NO: 225)

High-Throughput Sequencing

The integration reaction was performed with 75 nM Cas1–Cas2, 200 nM protospacer and 7.5 nM pCRISPR in 20 mM HEPES, pH 7.5, 25 mM KCl, 10 mM MgCl$_2$, 10% DMSO and 1 mM DTT. The DNAs were isolated by phenol-chloroform extraction and ethanol precipitation. The excess protospacers were removed using 100K MWCO Amicon Ultra-0.5 ml centrifugal filters. The resulting integration products were digested into smaller DNA fragments using dsDNA Fragmentase (New England Biolabs) for 75 min at 37° C. and quenched at 65° C. for 15 min. Fragments were end repaired using T4 DNA Polymerase (NEB), Klenow (NEB) and T4 PNK (NEB) and A-tailed with Klenow exo (3' to 5' exo minus) (NEB). Adapters were ligated onto fragments using T4 DNA ligase (NEB) and cDNA libraries were amplified by PCR using Phusion (NEB). Libraries were sequenced on an Illumina HiSeq2500 on rapid run mode. The oligonucleotides used are:

Universal adapter:
5'-AATGATACGGCGACCACCGAGATCTACACTCTTTCCCTACACGA (SEQ ID NO: 226)
CGCTCTTCCGATC*T-3' (*phosphorothioate bond);

Indexed adapter:
5'-/5Phos/GATCGGAAGAGCACACGTCTGAACTCCAGTCAC- (SEQ ID NO: 227)
index-ATCTCGTATGCCGTCTTCTGCTTG-3');

PCR primers:
5'-AATGATACGGCGACCACCGAGATCTACACTCTTTCCCTACACGA-3', (SEQ ID NO: 228)

5'-CAAGCAGAAGACGGCATACGAGAT-3'. (SEQ ID NO: 229)

Computational Analysis

For preprocessing, 3' adapters were removed from raw Illumina reads using Cutadapt ("http://" followed by "code.google." followed by "com/p/cutadapt/"), discarding reads shorter than 15 nt. Reads containing integrated protospacer were selected using Cutadapt, requiring the presence of at least 10 nt of protospacer sequence with no errors. After creating Bowtie[46] indexes from fasta files of the pUC19 empty and pCRISPR plasmid sequences, these reads were mapped to the respective plasmids using Bowtie, allowing up to 2 mismatches and requiring unique mapping. Sequence motif analysis depicted in FIG. 14 were generated using WebLogo, utilizing integration sites that are represented at least ten times in the sequencing data[47].

Results

The Cas1–Cas2 Complex Integrates Protospacer DNA in Vitro

Experiments were designed to test whether the Cas1–Cas2 complex was sufficient to catalyze the mobilization of protospacer substrate DNA in vitro. DNA recombination assays were conducted using purified Cas1–Cas2 complex, 33 bp protospacer DNA and an acceptor "target" plasmid consisting of the pUC19 backbone with an inserted CRISPR locus (pCRISPR) (FIG. 1a). Co-incubation of these reagents converted the supercoiled plasmid into three main products: relaxed and linear plasmid species, and a fast-migrating species we term Band X (FIG. 1b, c and FIG. 6a). Product formation was dependent on Cas1, Cas2 and the protospacer DNA, and was enhanced at low salt concentration and by the presence of $Mg^{2+}$ or $Mn^{2+}$ (FIG. 6b-d). Target DNA was fully converted to products in the presence of ~26-fold molar excess of protospacer DNA (FIG. 6d). Little difference was observed in product DNA migration when reactions were post-treated with EDTA, EDTA and phenol-chloroform extraction or Proteinase K in the presence of EDTA and detergent (FIG. 6e), indicating that product DNAs are unlikely to be bound to Cas1 and/or Cas2. Consistent with product DNA resulting from covalent integration of protospacer DNA into the plasmid, the relaxed and linear forms of pCRISPR became radiolabeled in reactions containing $^{32}$P-labeled protospacer DNA (FIG. 1d and FIG. 7). Although Cas1 alone catalyzed a low level of protospacer integration in the presence of $Mn^{2+}$, the reaction was enhanced significantly by the presence of Cas2 (FIG. 7b).

Figure 3:
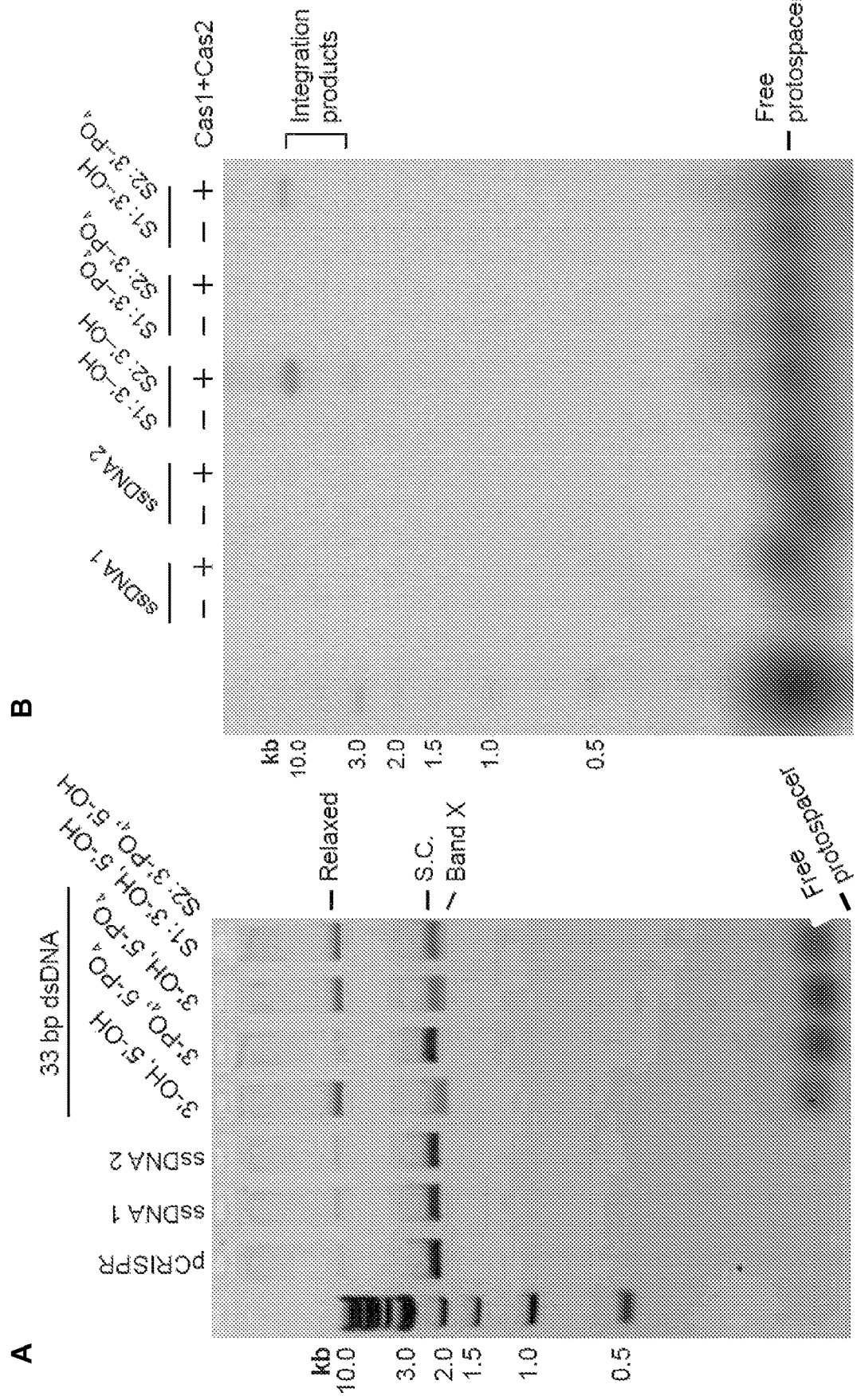
FIGS. 3A-E provide evidence related to integration requiring 3'-OH protospacer ends and supercoiled target DNA.
Figure 3:
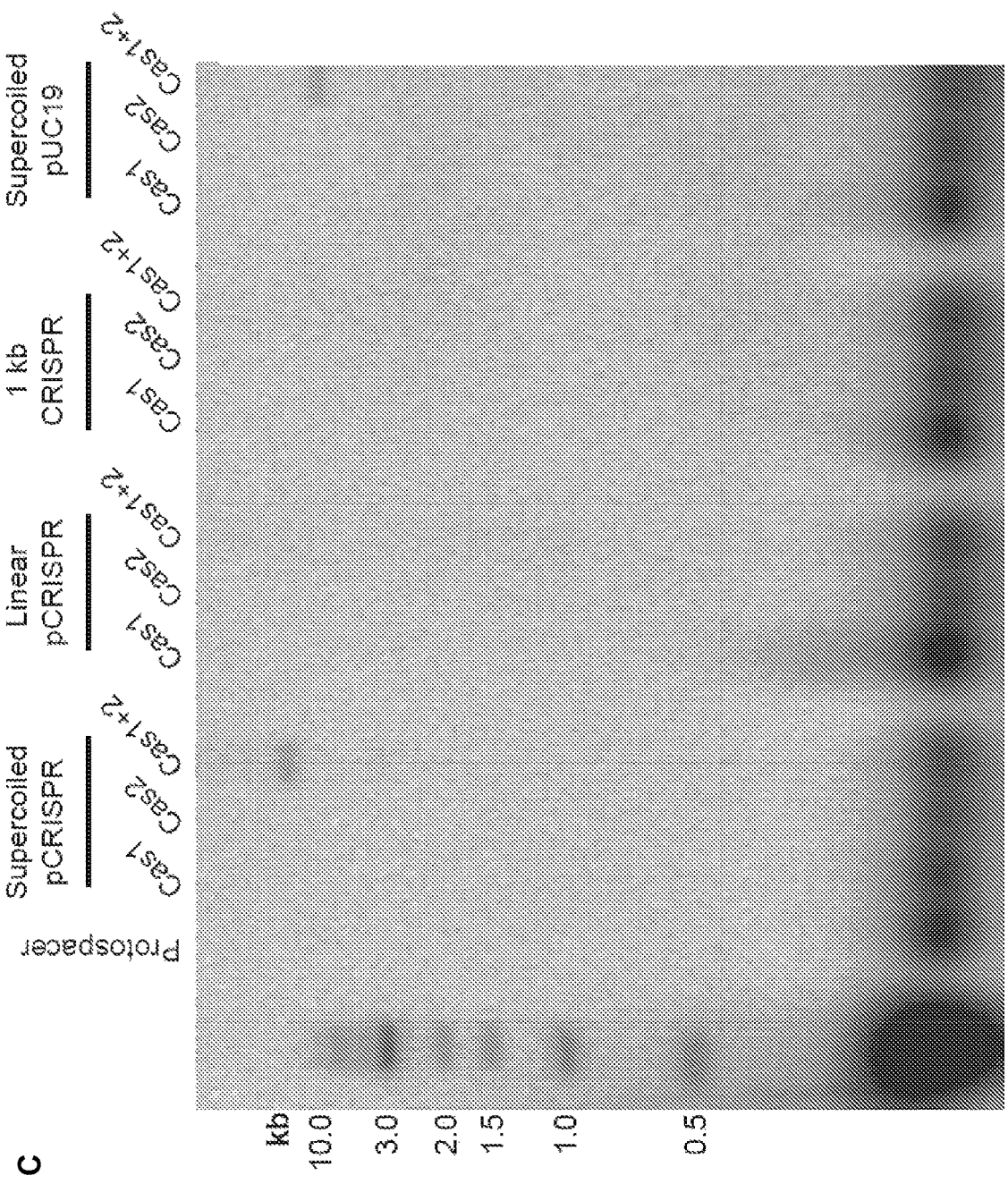
Figure 3:
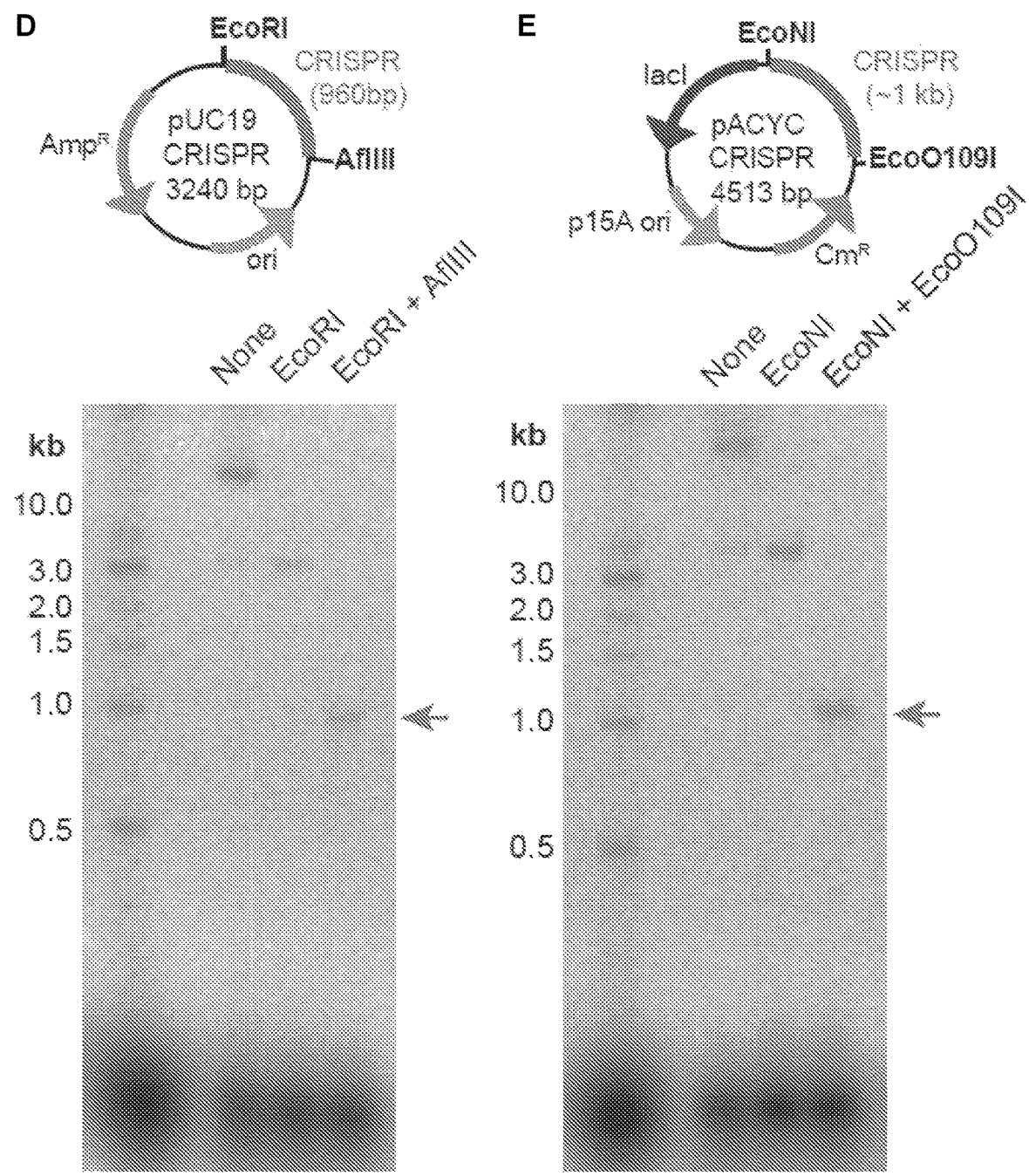

Cas1 active site mutants H208A and D221A were defective for protospacer integration in vitro, whereas the Cas2 E9Q active-site mutant supported integration (FIG. 1c, e and Extended FIG. 3). The Cas2 C-terminal β6-β7 deletion mutant, which is defective for complex formation with Cas1 and spacer acquisition in vivo, failed to support Cas1-mediated integrase activity (FIG. 1c, e). These data show that the in vitro assay recapitulates the in vivo functions of Cas1 and Cas2 during spacer acquisition and that Cas2 likely functions primarily as a scaffold, perhaps by bridging the protospacer nucleoprotein complex and target DNA.

FIG. 1. The Cas1–Cas2 complex integrates protospacers in vitro. a, Schematic of the in vitro integration assay. b, The presence of Cas1, Cas2 and a protospacer results in the conversion of the supercoiled pCRISPR into relaxed, linear and Band X products. c, Neither the Cas1 H208A active site mutant nor and the complex formation-defective Cas2 β6-β7 deletion mutant support the reaction. The Cas2 E9Q active site mutant (lane 5 from the marker) is as active as the wild-type. d, Salt- and metal-dependence of radiolabeled protospacer integration into pCRISPR. e, Same as c except using radiolabeled protospacers.

Figure 6:
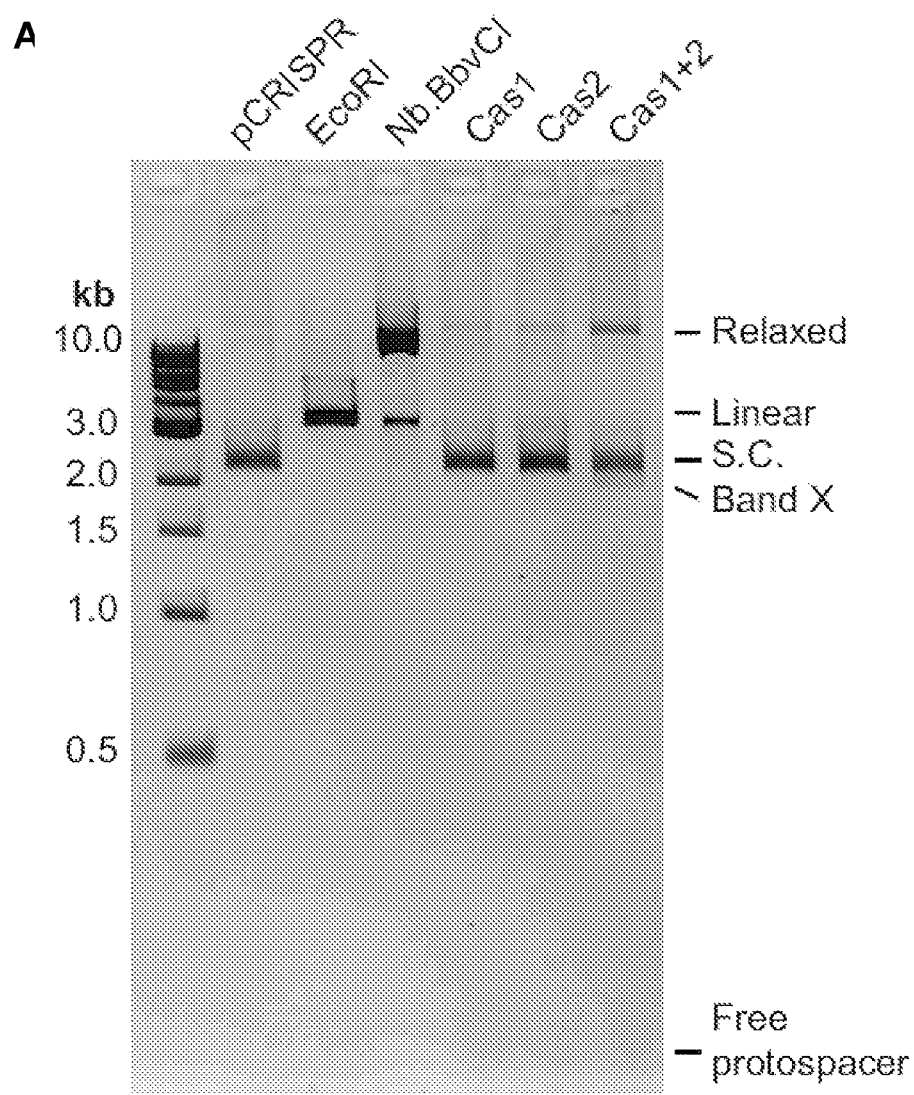
FIGS. 6A-E provide evidence related to the integration reaction being dependent on the presence of protospacers, low salt and divalent metal ions.
Figure 6:
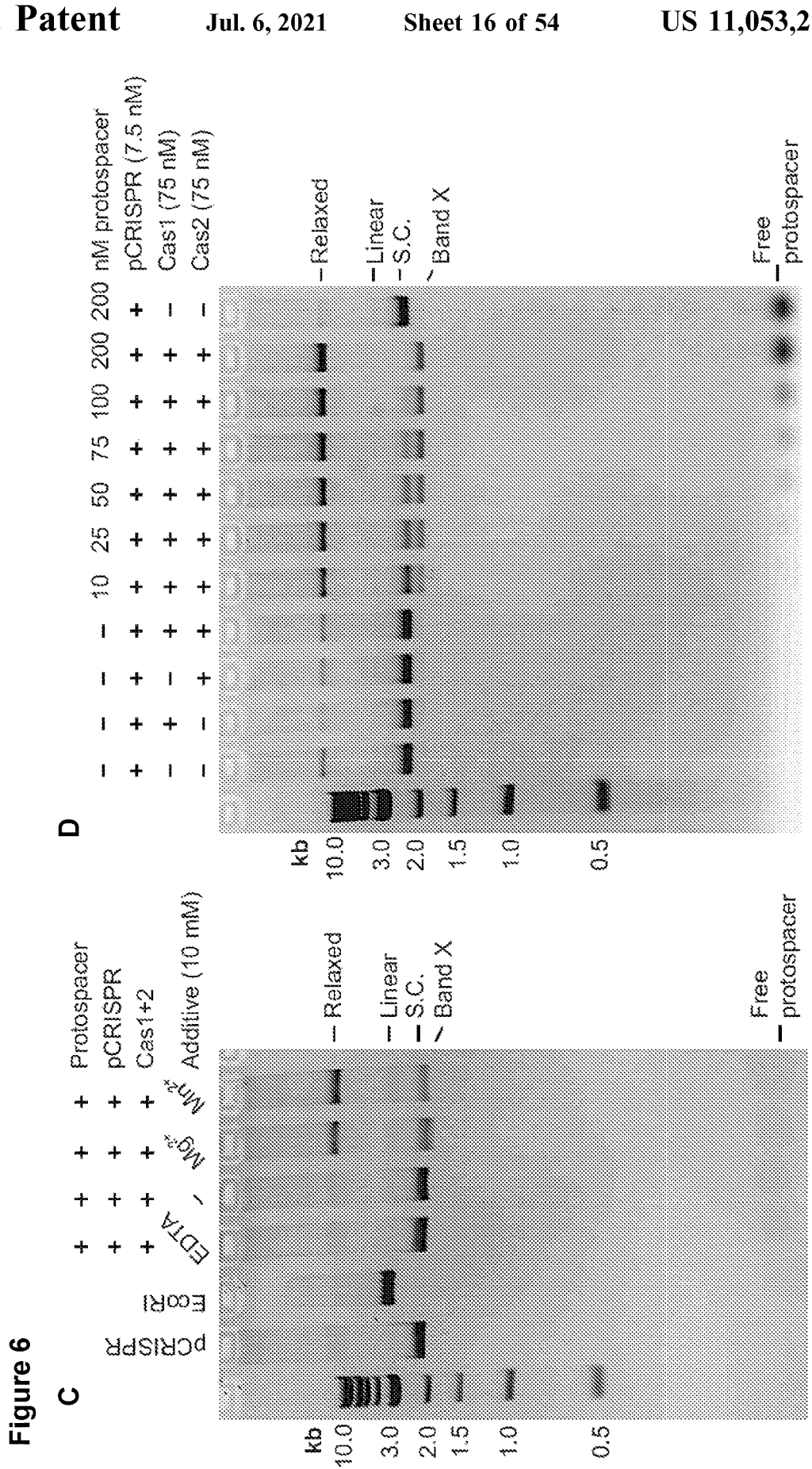
Figure 6:
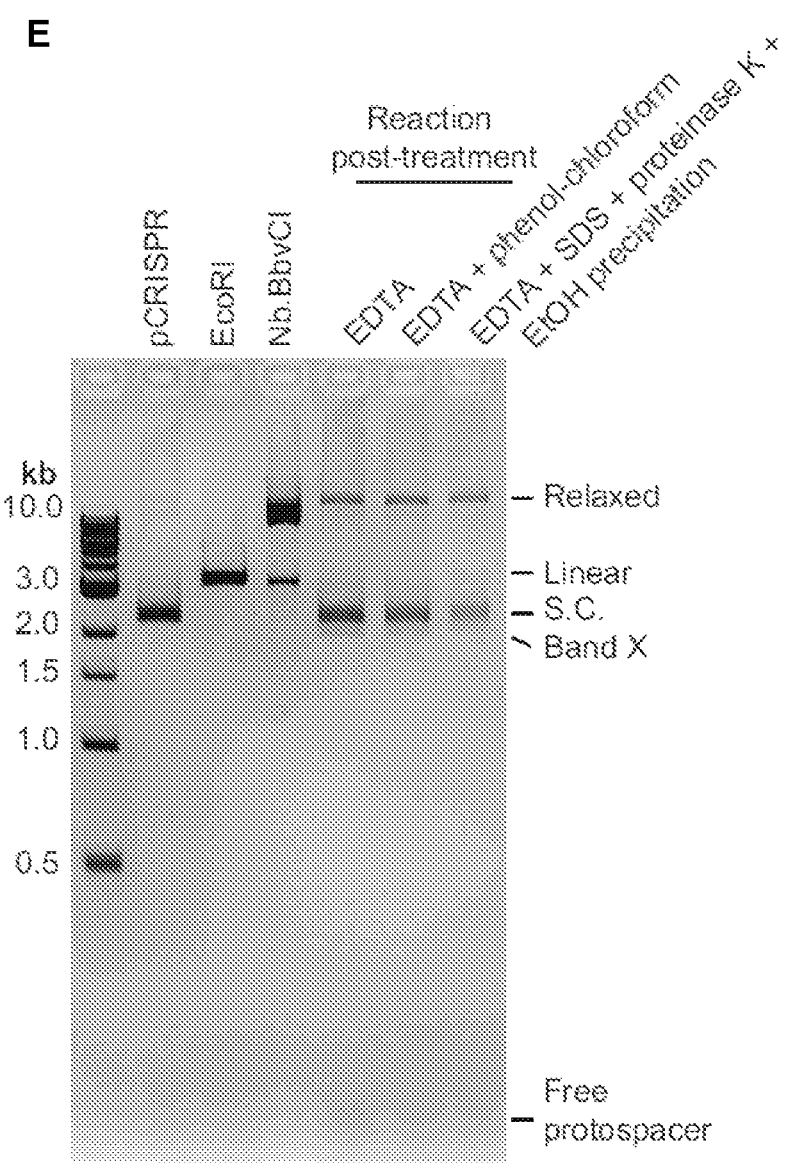
Figure 7:
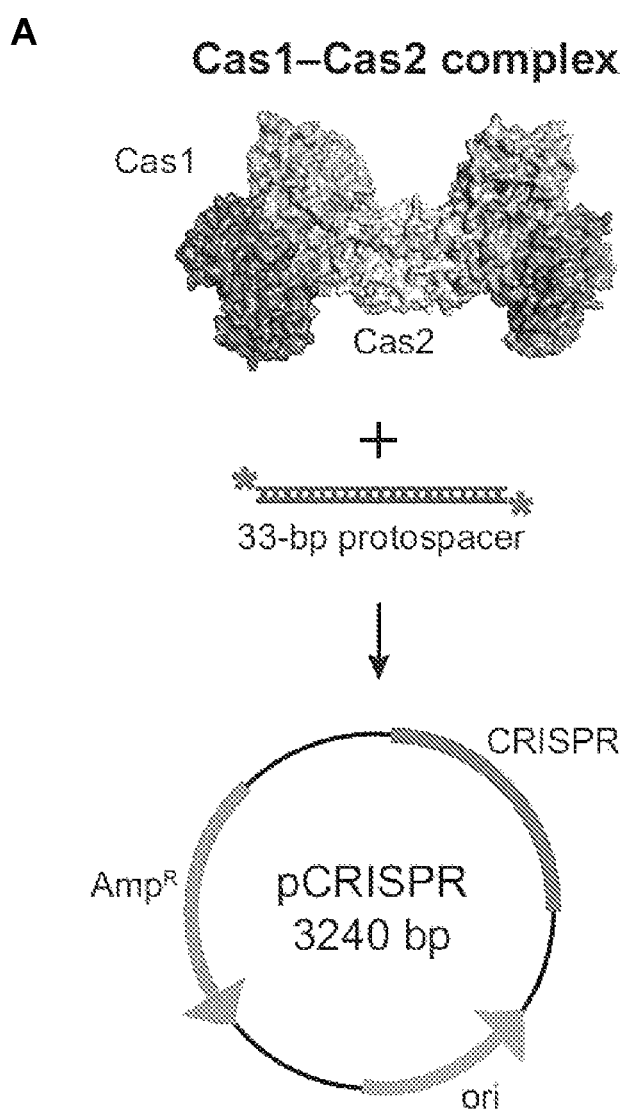
FIGS. 7A-C provide evidence related to Cas1 and Cas2 together providing for robust protospacer integration.
Figure 7:
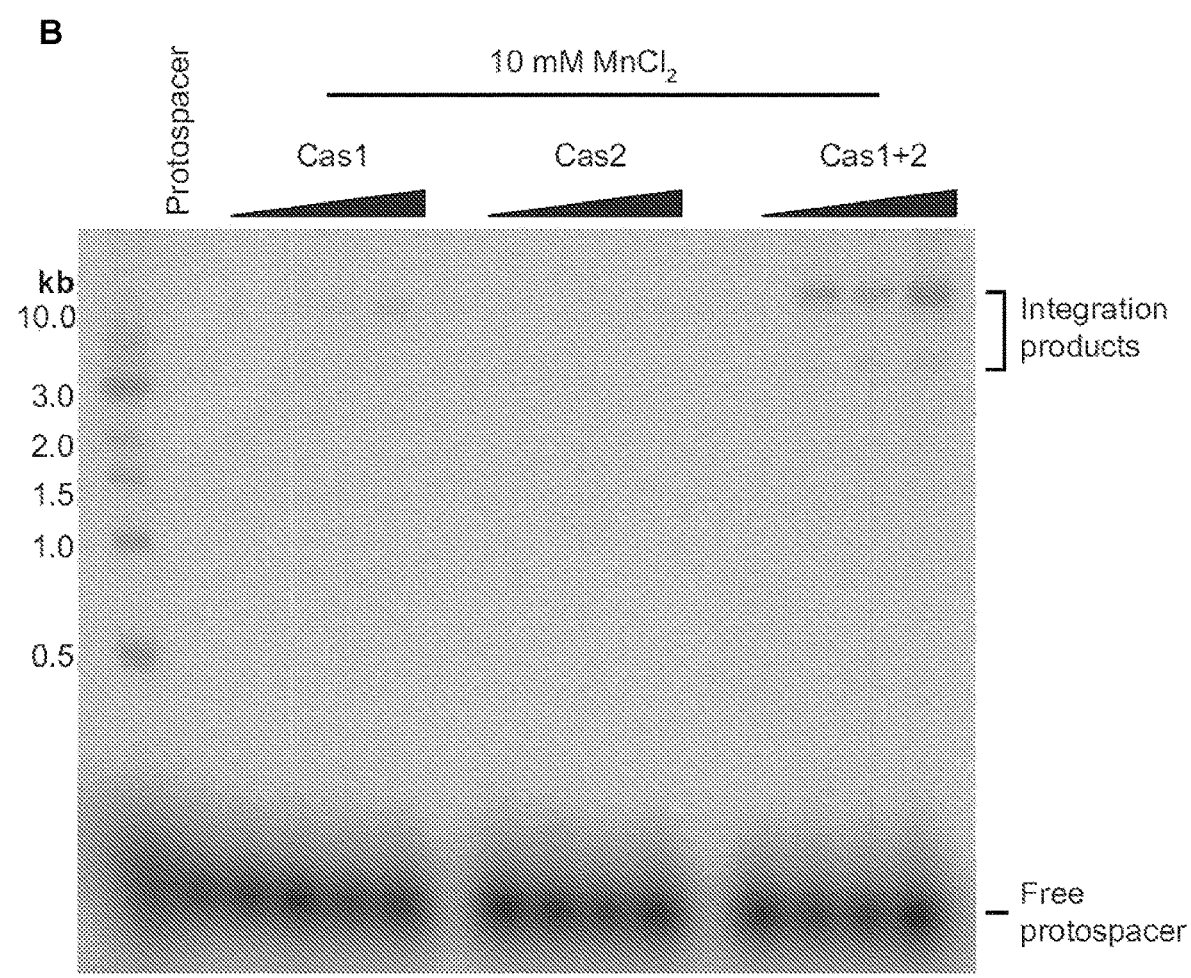
Figure 7:
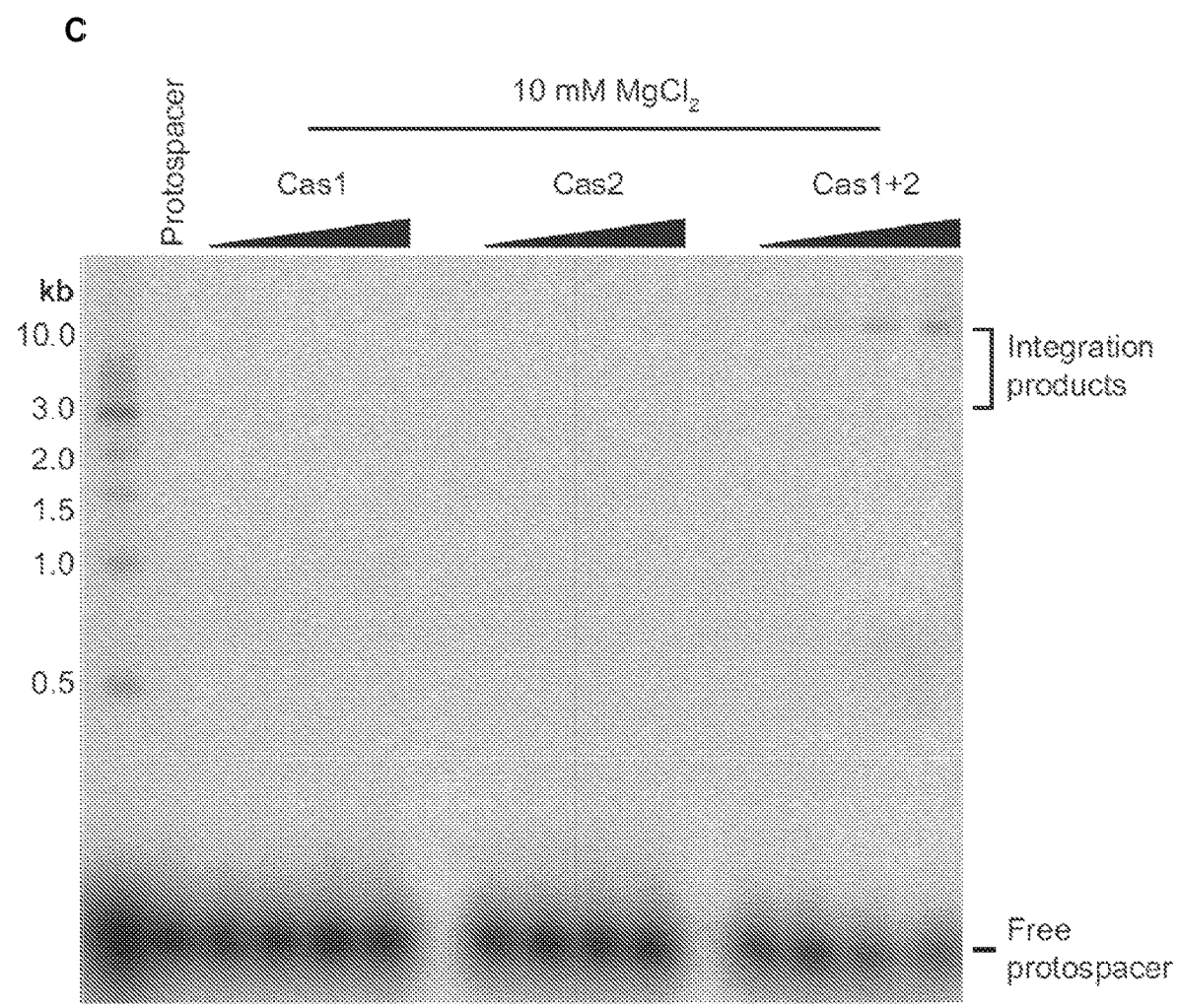

FIG. 6. The integration reaction is dependent on the presence of protospacers, low salt and divalent metal ions. a, In vitro integration assay alongside EcoRI- and Nb.BbvCI nickase-treated pCRISPR. b, Salt-dependence assay using Cas1 or Cas2 only and Cas1+Cas2. The titration corresponds to 0, 25, 50, 100 and 200 nM KCl, on top of the salt carried in from the reaction reagents. c, Integration assays in the presence of 10 mM EDTA, $Mg^{2+}$, $Mn^{2+}$ or no additive. d, Integration assays with increasing protospacer concentrations. e, A comparison of post-reaction treatments as indicated.

FIG. 7. Cas1 requires Cas2 for robust protospacer integration. a, Schematic of the integration assays using $^{32}$P-labeled protospacers. b, Integration assays in the presence of increasing protein and 10 mM $MnCl_2$. The titration corresponds to 0, 50, 100 and 200 nM protein. c, Same as b except in the presence of 10 mM $MgCl_2$.

Figure 8:
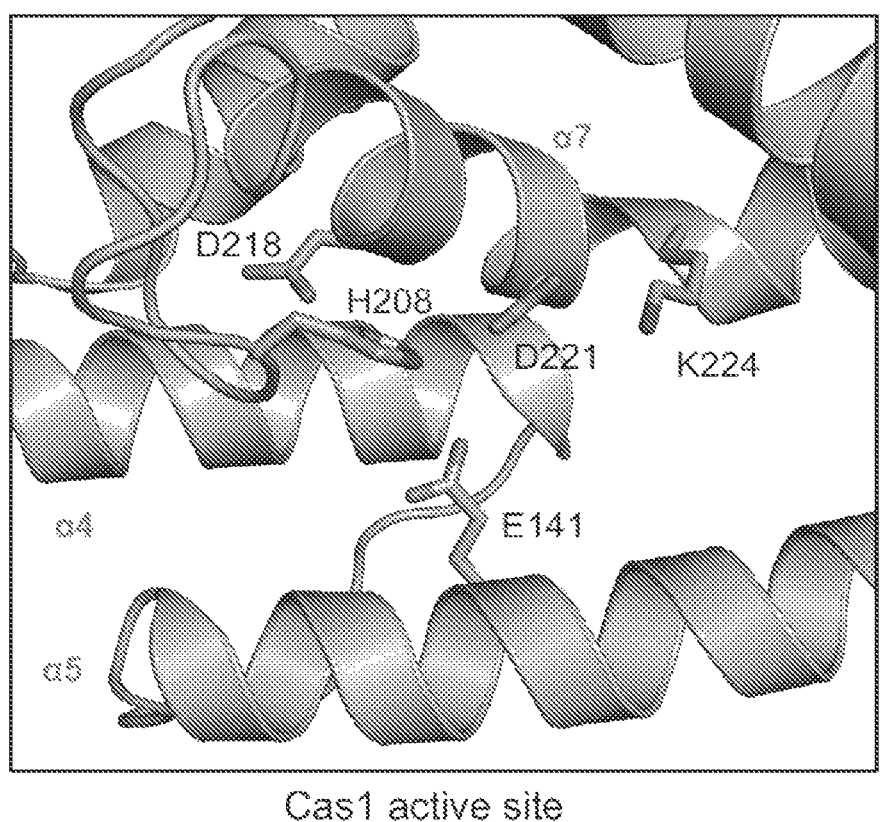
FIGS. 8A-C provide evidence related to the catalytic activity of Cas1 being required for integration.
Figure 8:
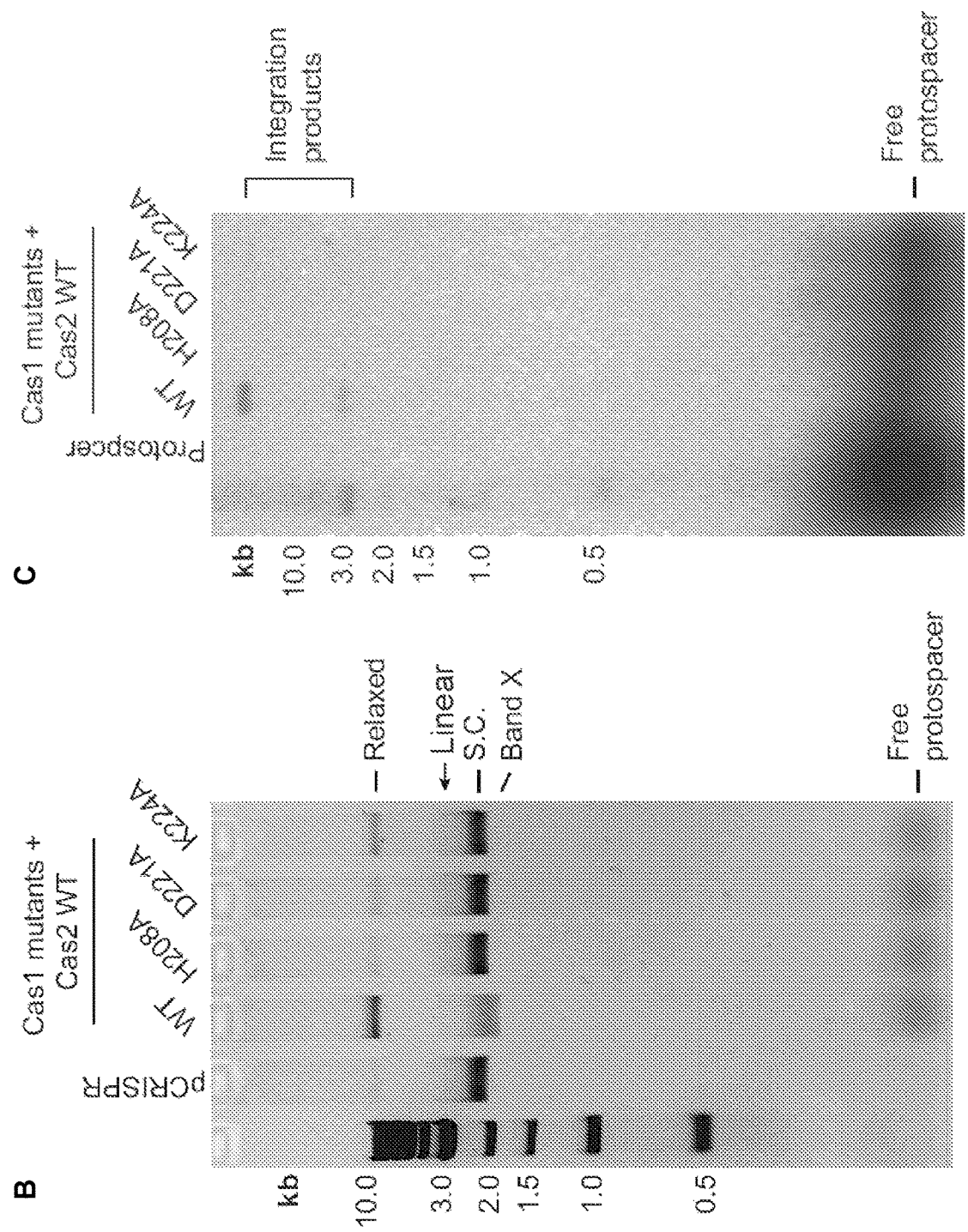

FIG. 8. The catalytic activity of Cas1 is required for integration. a, Close-up view of the Cas1 active site with the conserved residues shown in stick configurations (PDB 4P6I) b, Integration assays of purified Cas1 active site mutants complexed with wild type Cas2. c, The same as b except using radiolabeled protospacers.

Cas1–Cas2-Catalyzed Recombination Leads to Half-Site and Full-Site Integration as well as pCRISPR Topoisomers It was then tested whether the reaction products of Cas1–Cas2-mediated DNA integration resemble those formed by the strand transfer activity of retroviral integrases and cut-and-paste tranposases[23-26]. These enzymes generated two main products in vitro corresponding to half-site and full-site integration events (FIG. 2a). The integration of one strand of donor DNA into one strand of the target yields half-site products, which co-migrate with relaxed plasmid DNA during agarose gel electrophoresis. Full-site products can co-migrate with relaxed or linear plasmid DNA depending on whether one or two copies of donor DNA are utilized during integration. Similar gel mobility of the slowly migrating DNA product generated by Cas1–Cas2 and Nb.BbvCI nickase-digested pCRISPR was observed, consistent with the slow-migrating relaxed DNA species corresponding to half-site products and/or products resulting from full-site integration of one protospacer molecule (FIG. 6a). Digestion with EcoRI, which cuts pCRISPR once, converted the reaction products to linear DNAs (FIG. 2b, compare lane 4 to lane 2, and FIG. 2c). Tus, both the relaxed and Band X DNA products comprise unit-sized pCRISPR circles.

Band X did not become radiolabeled in reactions conducted with $^{32}$P-labeled protospacer DNA. A time course analysis revealed relaxed DNA product formation within the first minute, followed by accumulation of Band X between 10 and 30 min (FIG. 2d). To determine the properties of Band X, the purified product was analyzed in two different types of agarose gels—one pre-stained with ethidium bromide, similar to the gels presented thus far, and the other stained with ethidium bromide after electrophoresis (post-stained) (FIG. 9a). Although Band X migrated as a single species in the pre-stained gel, a ladder of species that migrated faster than the relaxed products was observed in the post-stained gel (FIG. 2e, f). These intermediates are reminiscent of plasmid topoisomers[27,28]. The same pre- and post-stained agarose gel analysis was performed on the entire integration reaction, generating similar results to those observed with purified Band X (FIG. 9b, c). PCR analysis of various segments of pCRISPR using gel-purified Band X as the template yielded amplification products indistinguishable from those generated using unreacted supercoiled pCRISPR or relaxed integration products, supporting the conclusion that Band X corresponds to pCRISPR topoisomers (FIG. 9d).

Band X might therefore arise from the excision of the protospacer from half-site integration products to yield fully enclosed pCRISPR in different states of supercoiling (FIG. 2g). The process of disintegration has been previously observed in in vitro reactions with retroviral integrases and transposases[29,30]. To test this hypothesis, four single-stranded DNAs were annealed to produce a synthetic Y-structured DNA intermediate that mimics the half-site integration product (FIG. 10a,b). The 5'-end of the extended protospacer arm was radiolabeled, such that the liberated 33 bp protospacer DNA could be detected following disintegration activity. Using this substrate Cas1 catalyzed disintegration activity either by itself or in the presence of Cas2 (FIG. 2h). Disintegration activity was confirmed by radiolabeling the 20-nt target DNA strand and monitoring the formation of the joined 40 bp target DNA product (FIG. 10c, d). Thus, Cas1–Cas2 integration and disintegration activities are similar to those of retroviral integrases and transposases, although the in vivo function of disintegration, if any, remains unknown.

Figure 2:
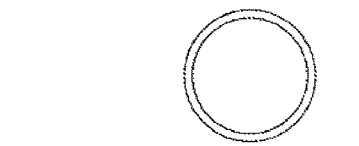
FIGS. 2A-H provide evidence related to half-site integration, full-site integration, and pCRISPR topoisomer products. Note, the gel depicted in panel E was pre-stained with ethidium bromide (EtBr) while the gel depicted in panel F was post-stained with EtBr.
Figure 2:
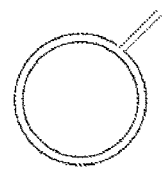
Figure 2:
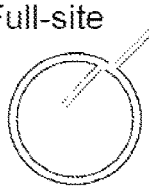
Figure 2:
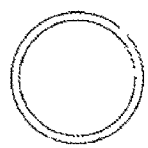
Figure 2:
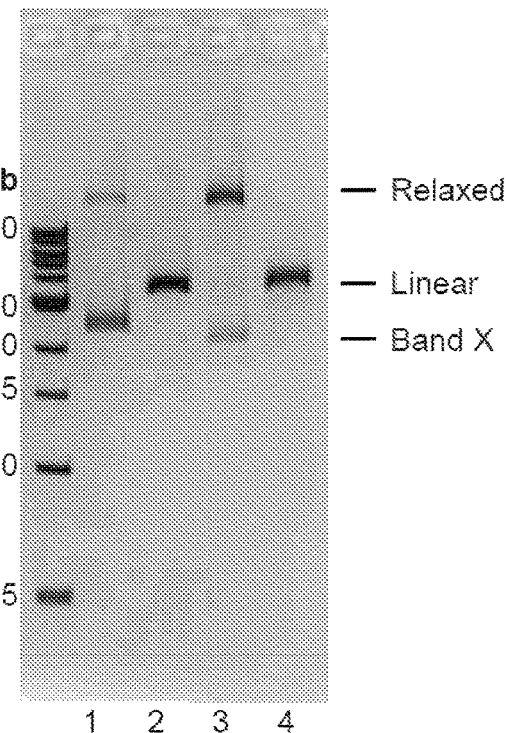
Figure 2:
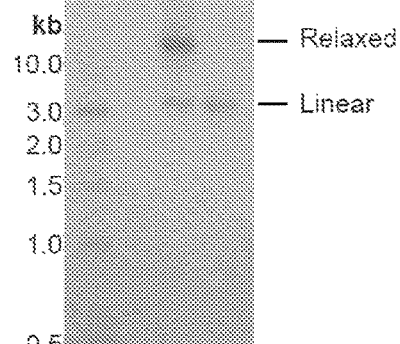
Figure 2:
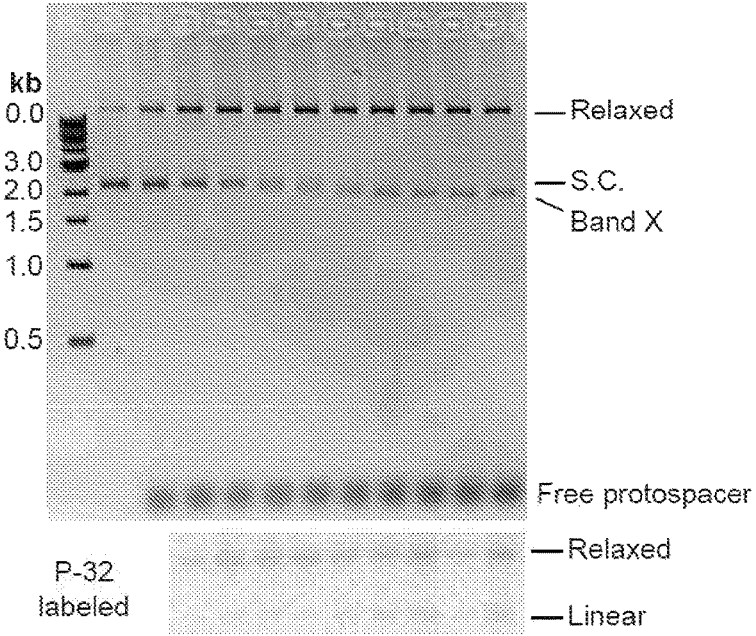
Figure 2:
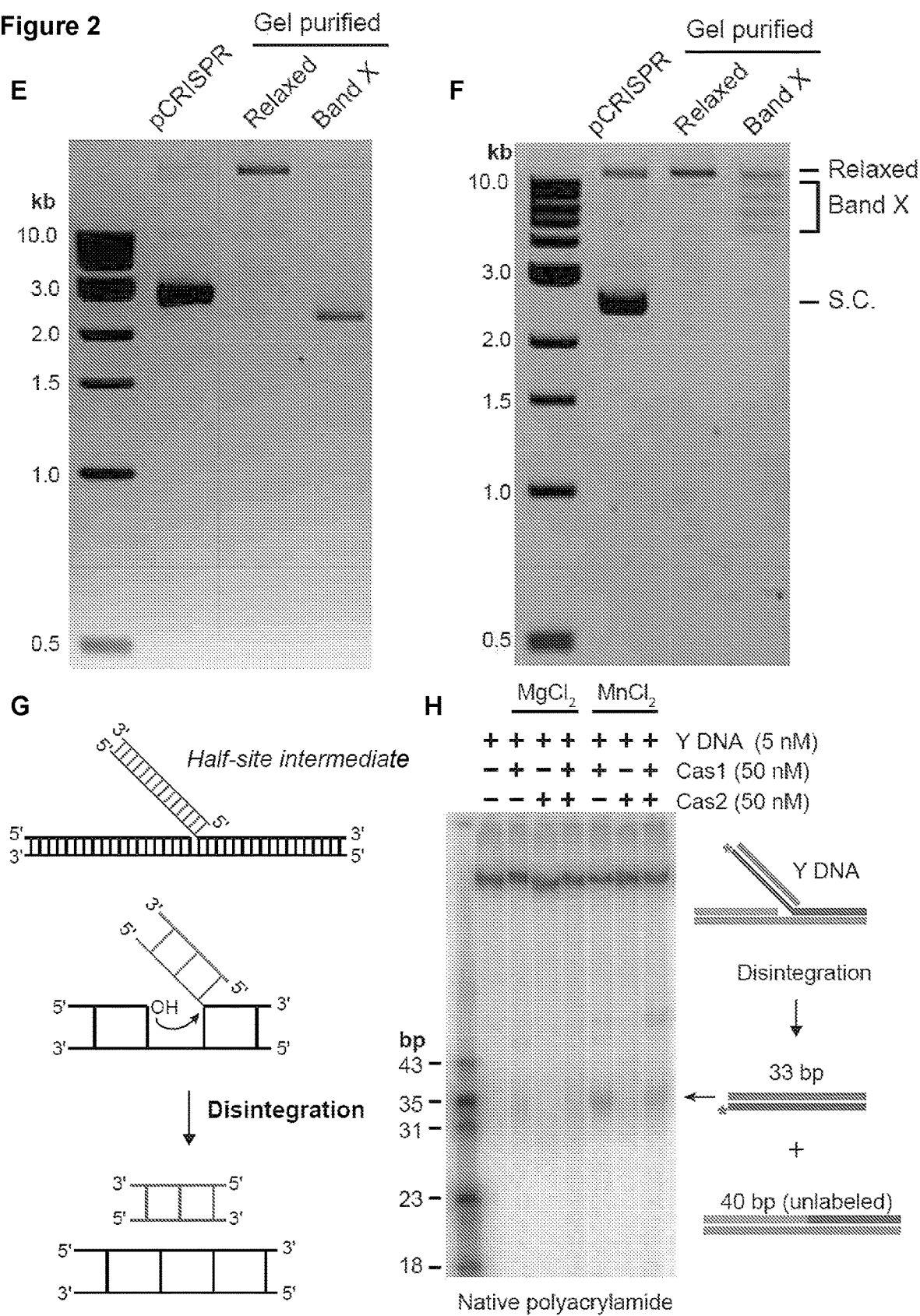

FIG. 2. Half-site, full-site integration and pCRISPR topoisomer products. a, Schematic of half-site and full-site integration products. b, Linearization of the integration products (lane 4). Lane 3 is the un-treated reaction products. c, Linearization of integration products from radiolabeled protospacer reactions. d, The time course reveals the initial formation of relaxed products, followed by Band X. The inset reveals the products detected using $^{32}$P-labeled protospacers. e,f, Analysis of gel-purified relaxed and Band X on agarose gels pre-stained with ethidium bromide (e) or post-stained after electrophoresis (f). g, Schematic of the disintegration reaction. h, Native polyacrylamide gel analysis of the disintegration reaction.

Figure 9:
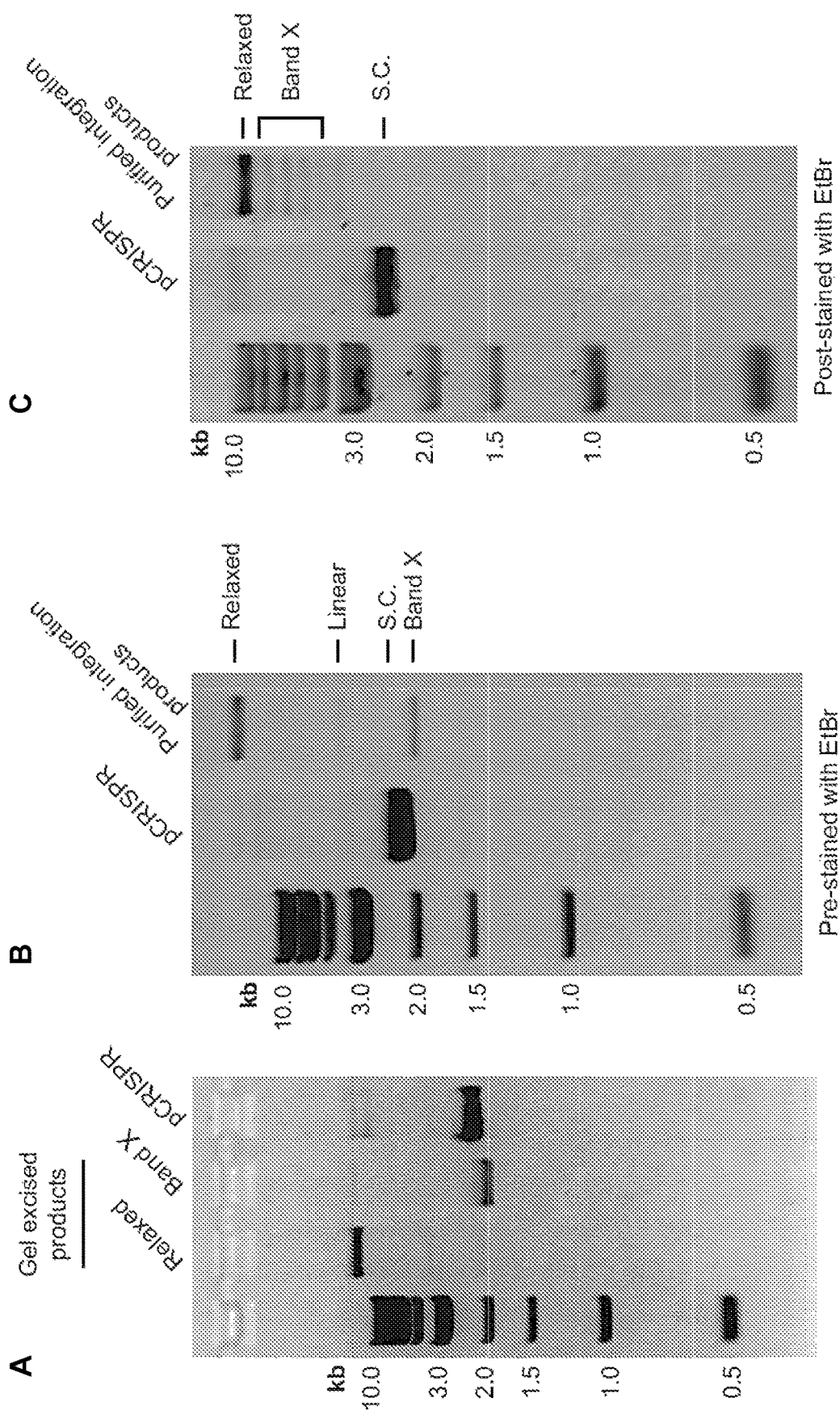
FIGS. 9A-D provide evidence related to band X corresponding to topoisomers of pCRISPR.
Figure 9:
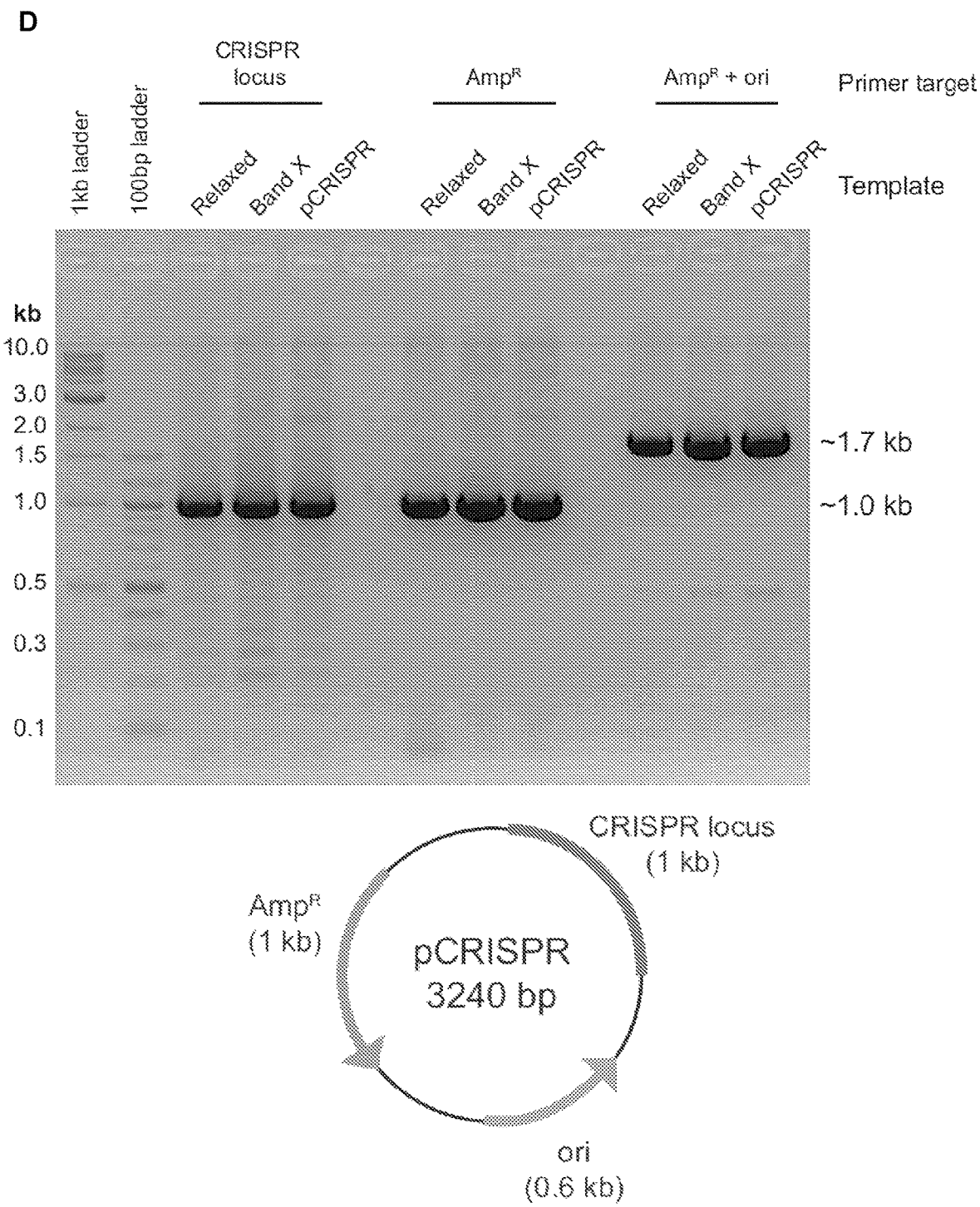

FIG. 9. Band X corresponds to topoisomers of pCRISPR. a, Agarose gel of purified relaxed and Band X integration products. b, Analysis of the total reaction products, after phenol chloroform extraction and ethanol precipitation, on a pre-stained agarose gel. c, Same as b except ethidium bromide staining was performed after electrophoresis. d, PCR amplification products of various segments of pCRISPR using the relaxed, Band X or pCRISPR template shown in a. The laddering effect of minor products using CRISPR locus primers likely reflects the propensity of CRISPR repeats to form DNA hairpins.

Figure 10:
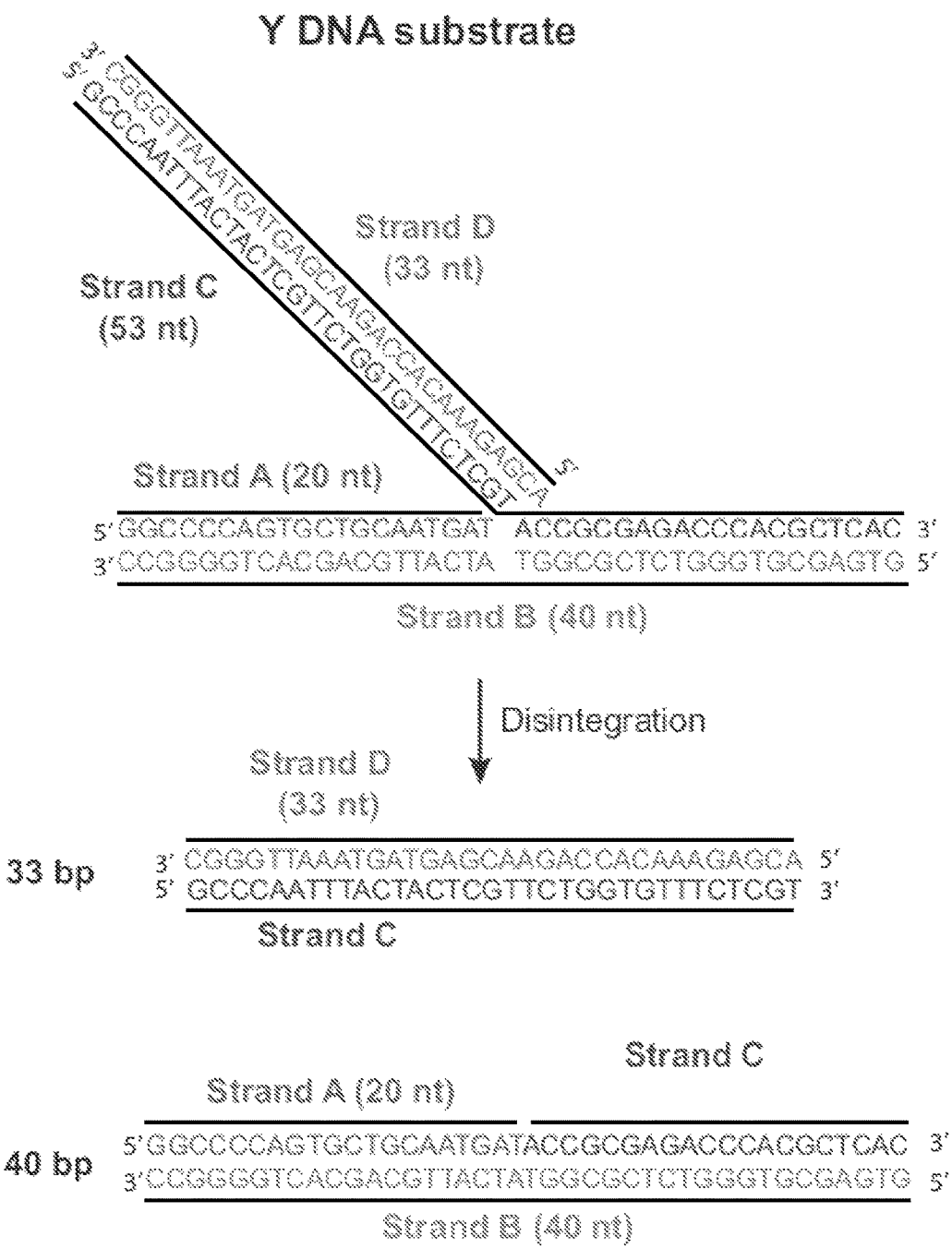
FIGS. 10A-D provide evidence related to Cas1 catalyzing the disintegration of half-site integrated protospacers.
Figure 10:
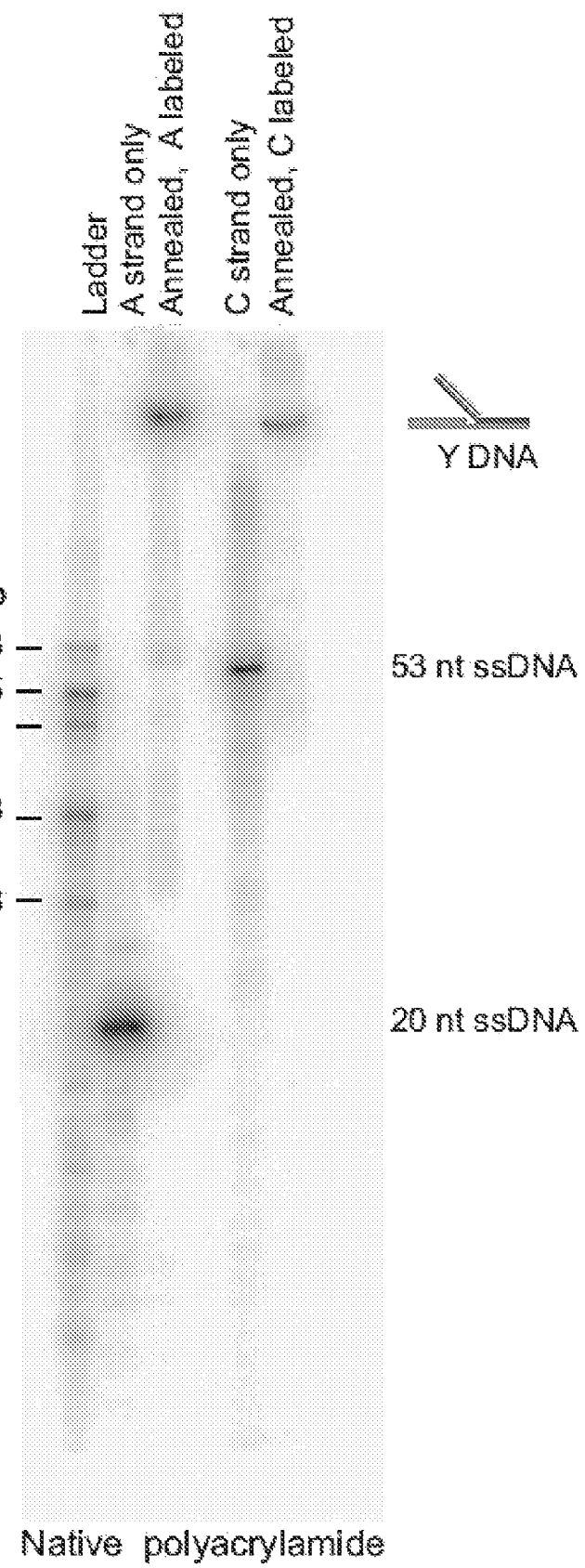
Figure 10:
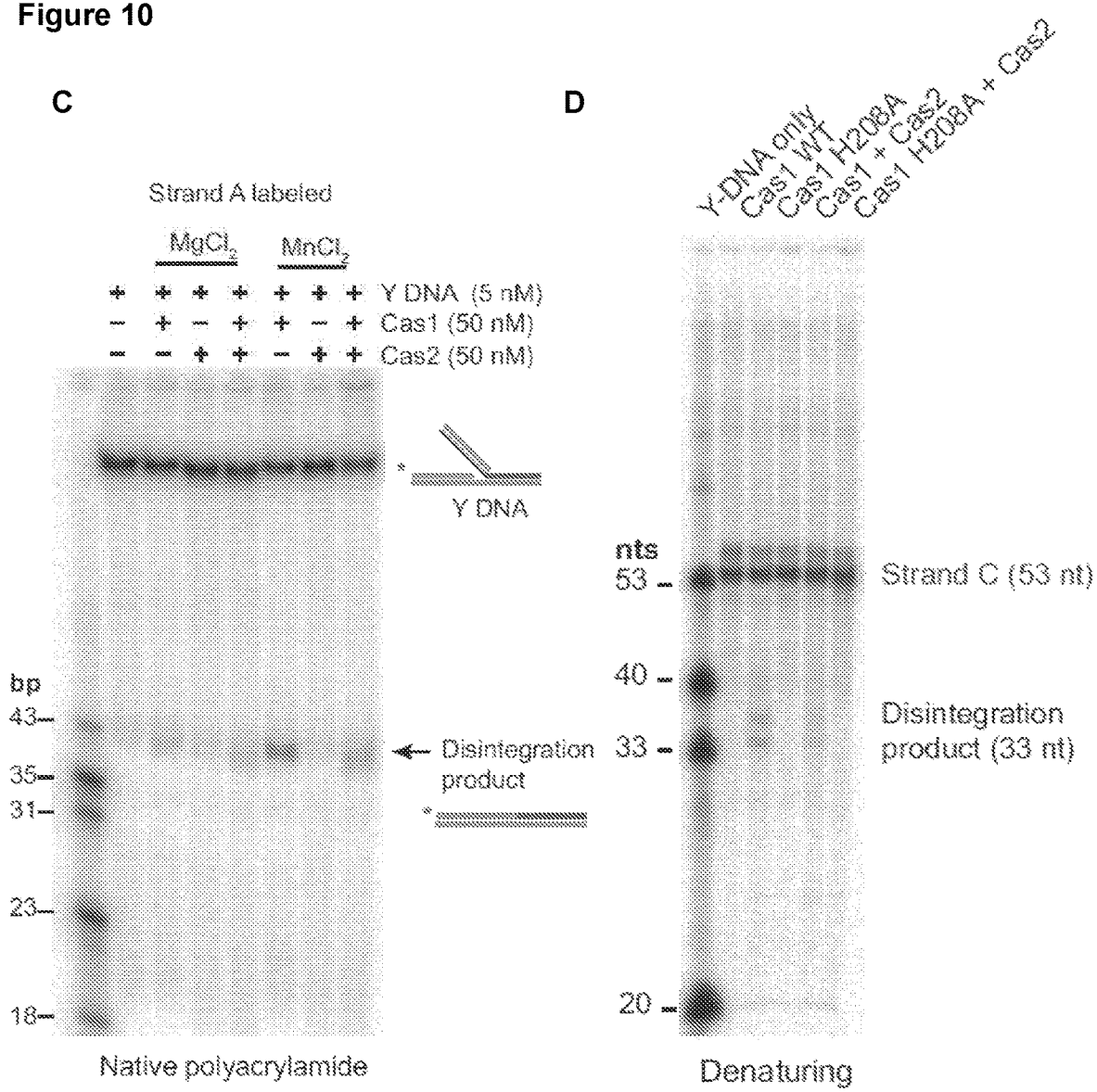

FIG. 10. Cas1 catalyzes the disintegration of half-site integrated protospacers. a, Schematic of the four strands constituting the Y DNA substrate used in the disintegration assays. b, Native polyacrylamide gel analysis of the annealing products with either Strand A or Strand C radiolabeled. c, Native polyacrylamide gel analysis of disintegration assay products using Y DNA substrates with Strand A labeled. d, Denaturing gel analysis of the disintegration assay products with Strand A labeled Integration Requires 3'-OH Protospacer Ends The DNA protospacer and target DNA requirements for integration were next investigated. Single-stranded protospacer DNA failed to support the reaction (FIG. 3a, b). The Cas1–Cas2 complex accommodated various protospacer lengths in vitro despite the strict 33 bp requirement for spacer acquisition in vivo (FIG. 11a). This suggests that the length requirement in vivo is pre-determined before integration by an unknown mechanism. The Cas1–Cas2 complex integrated DNA substrates with blunt-ends or with 3'-overhangs up to 5 nt in length (FIG. 11b). In contrast to retroviral integrases[31], substrates with 5'-overhangs were nonviable (FIG. 11b).

Retroviral integration and transposition reactions proceed via nucleophilic attack of DNA 3'-OH groups at target DNA phosphodiester bonds[31,32]. Phosphorylation of both 3'-ends of the protospacer ablated integration, whereas phosphorylation of only one 3' end strongly limited integration (FIG. 3a, b). By analogy to known integrase enzyme mechanisms, DNA integration could proceed by Cas1-catalyzed direct nucleophilic attack of the substrate 3'-OH on the target DNA, or by formation of a Cas1-DNA intermediate, as occurs in the serine and tyrosine families of recombinases[33]. Based on available crystal structures of Cas1[17-19], there are four tyrosine residues in the vicinity of the Cas1 active site that could be involved in forming such a covalent intermediate (FIG. 12a,b). Four mutants of Cas1 were constructed in which each tyrosine was individually changed to alanine. The purified Cas1 mutant proteins supported protospacer integration in vitro at levels comparable to wild type Cas1- Cas2 (FIG. 12c). Thus, the integration reaction likely proceeds via direct nucleophilic attack of protospacer 3'-OH ends onto the target DNA phosphodiester bonds, a mechanism previously hypothesized to occur in vivo[34].

FIG. 3. Integration requires 3'-OH protospacer ends and supercoiled target DNA. a,b, Integration assays using single-stranded DNAs and either —OH or —$PO_4$ at the 3' or 5' ends of (a) unlabeled or (b) radiolabeled protospacers. 51 corresponds to one strand of the protospacer and S2 corresponds to the complementary strand. c, Comparison of protospacer integration into different DNA targets. d,e, Restriction enzyme digestion of pCRISPR, either in a pUC19 (d) or pACYC backbone (e), after the integration assay detects integration into the CRISPR fragment (green arrows).

Figure 11:
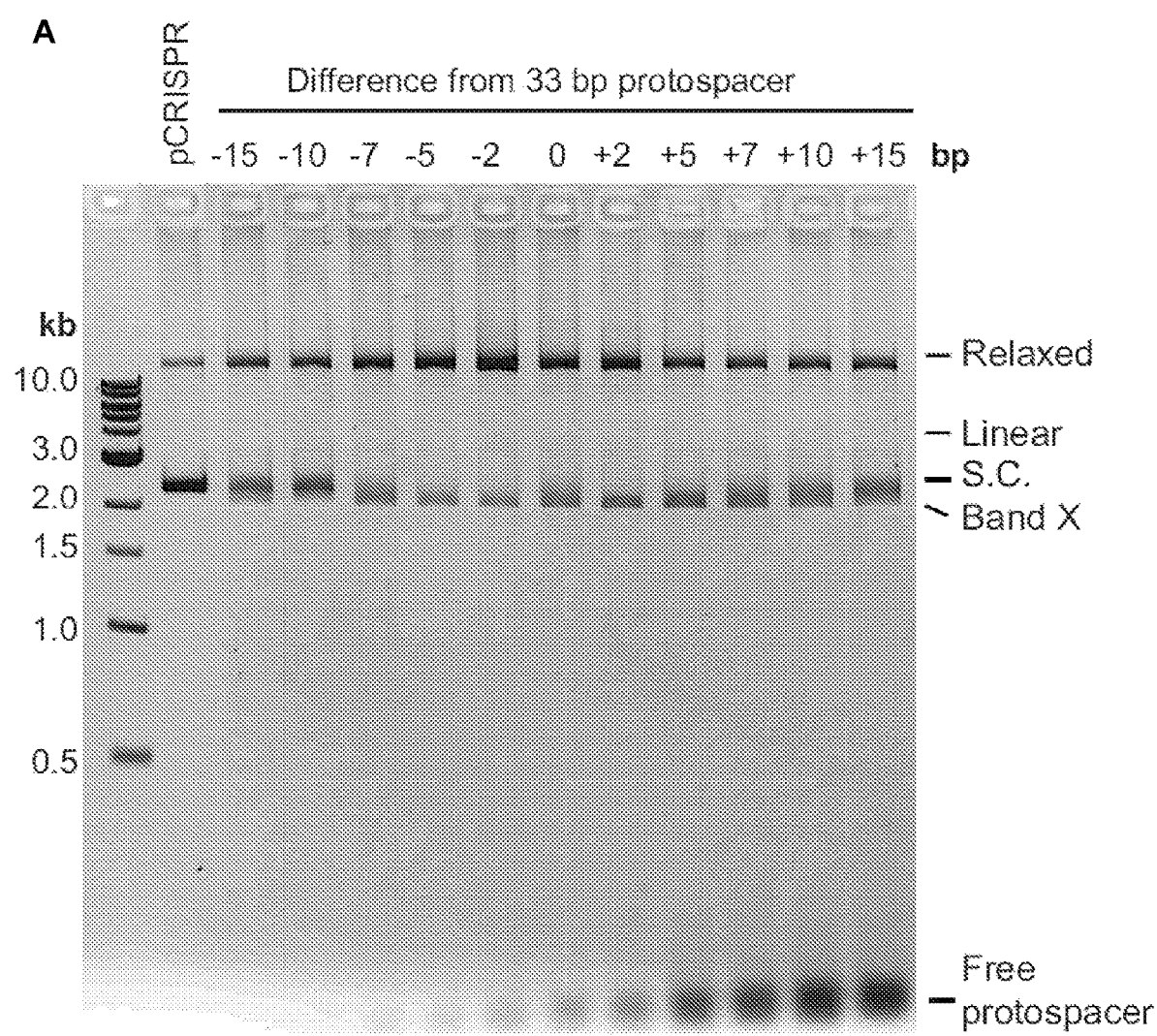
FIGS. 11A-E provide evidence related to Cas1–Cas2 being able to integrate various lengths of double-stranded DNA with blunt and 3'-overhang ends into a supercoiled target plasmid.
Figure 11:
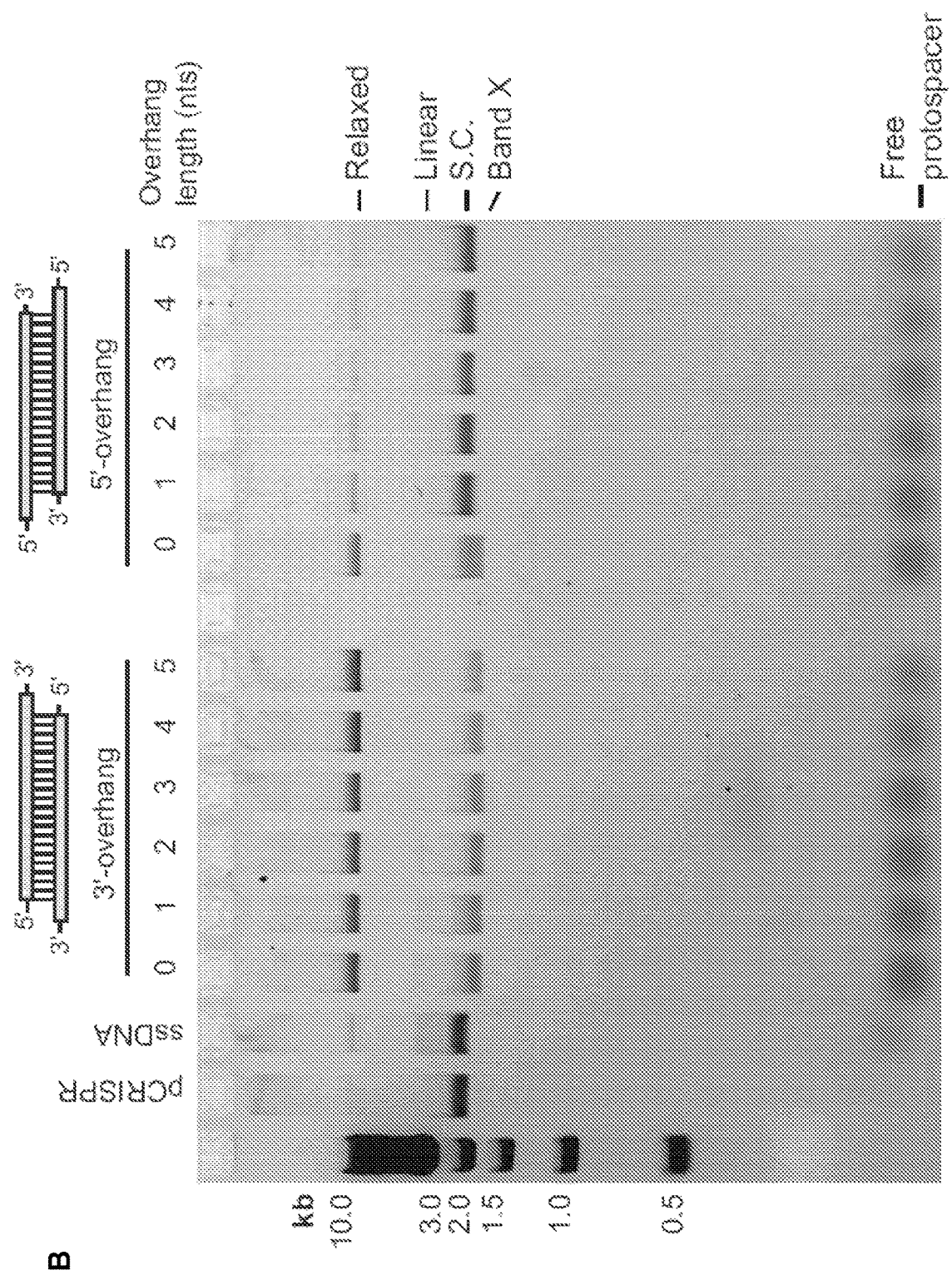
Figure 11:
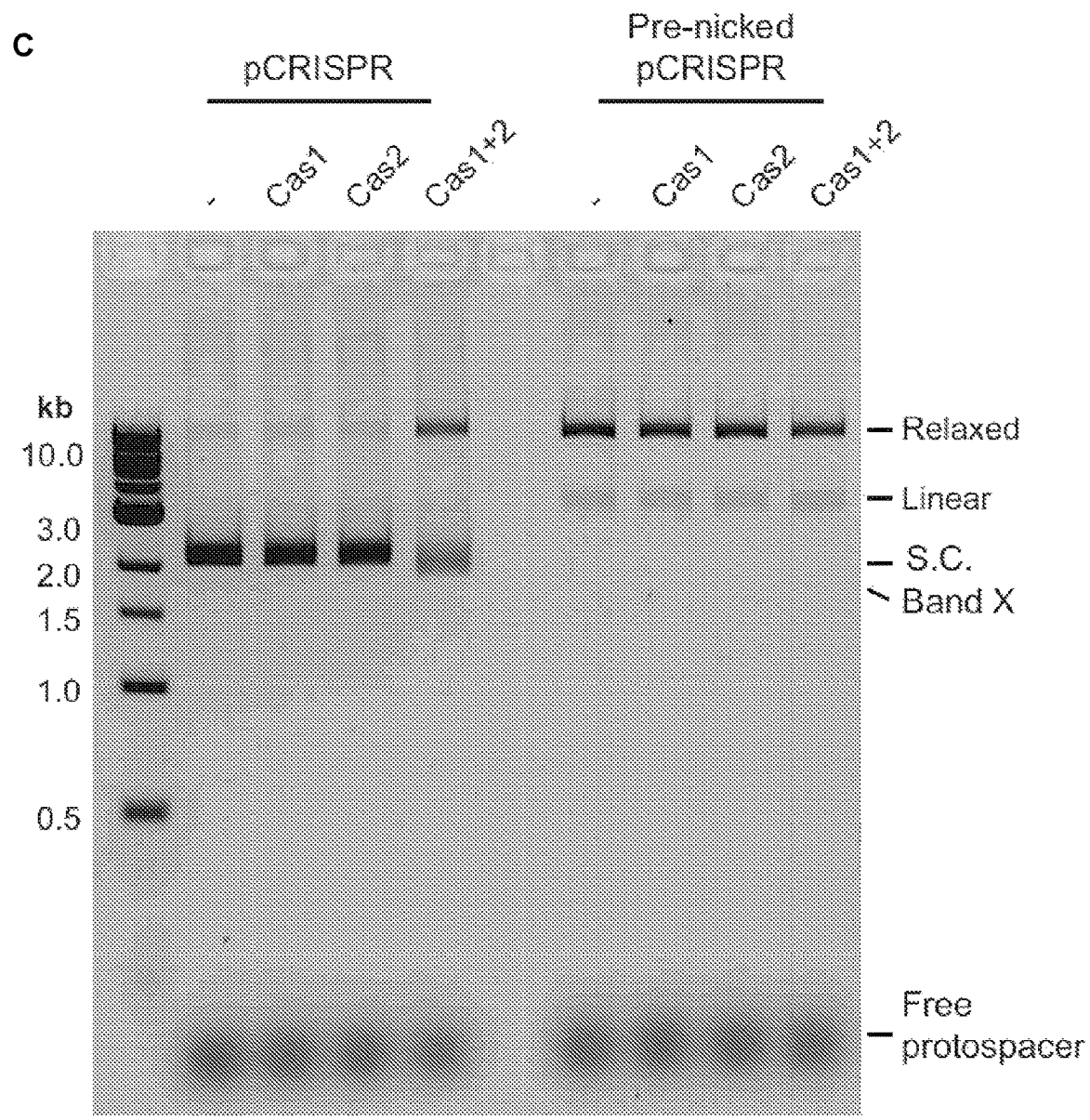
Figure 11:
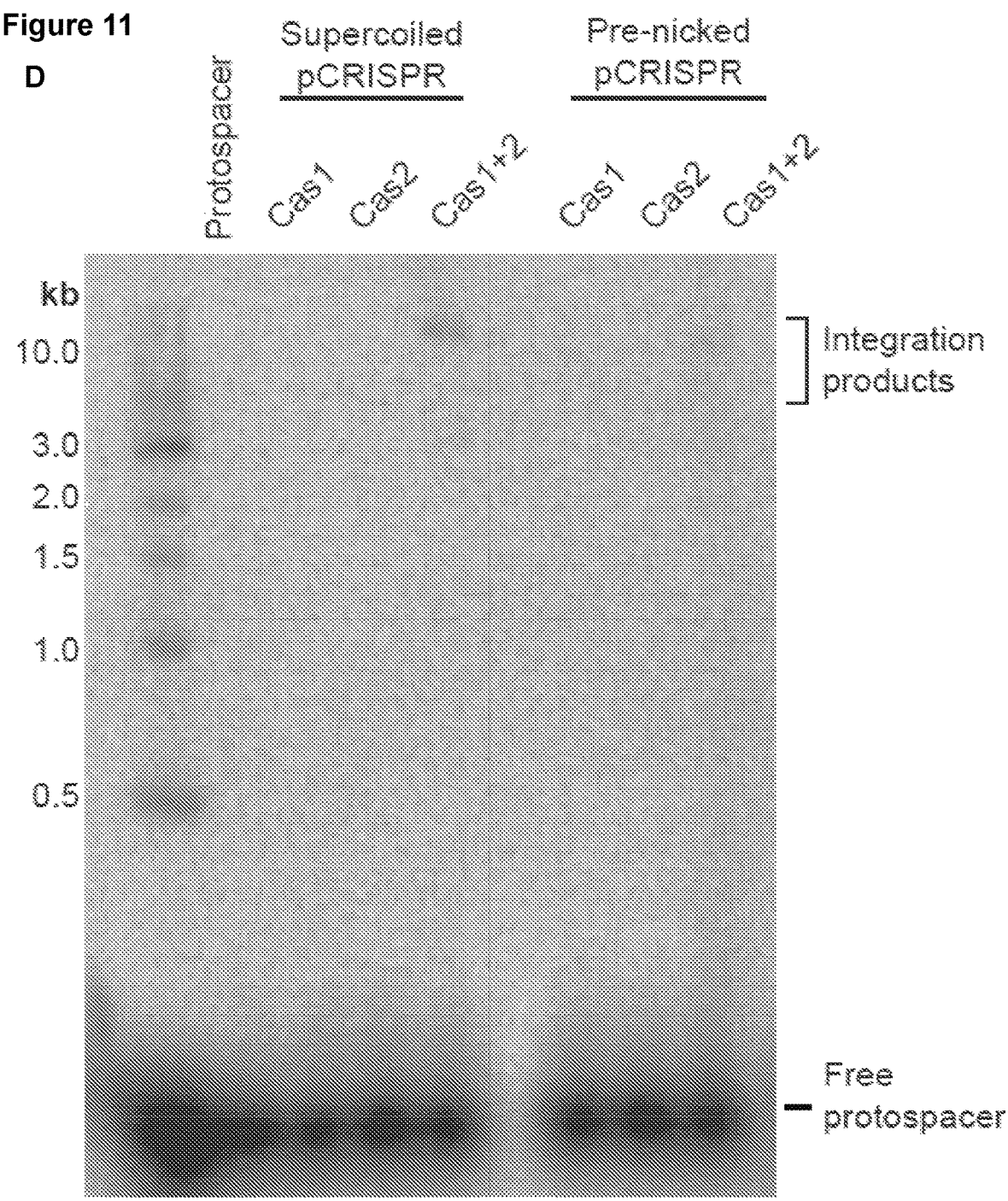
Figure 11:
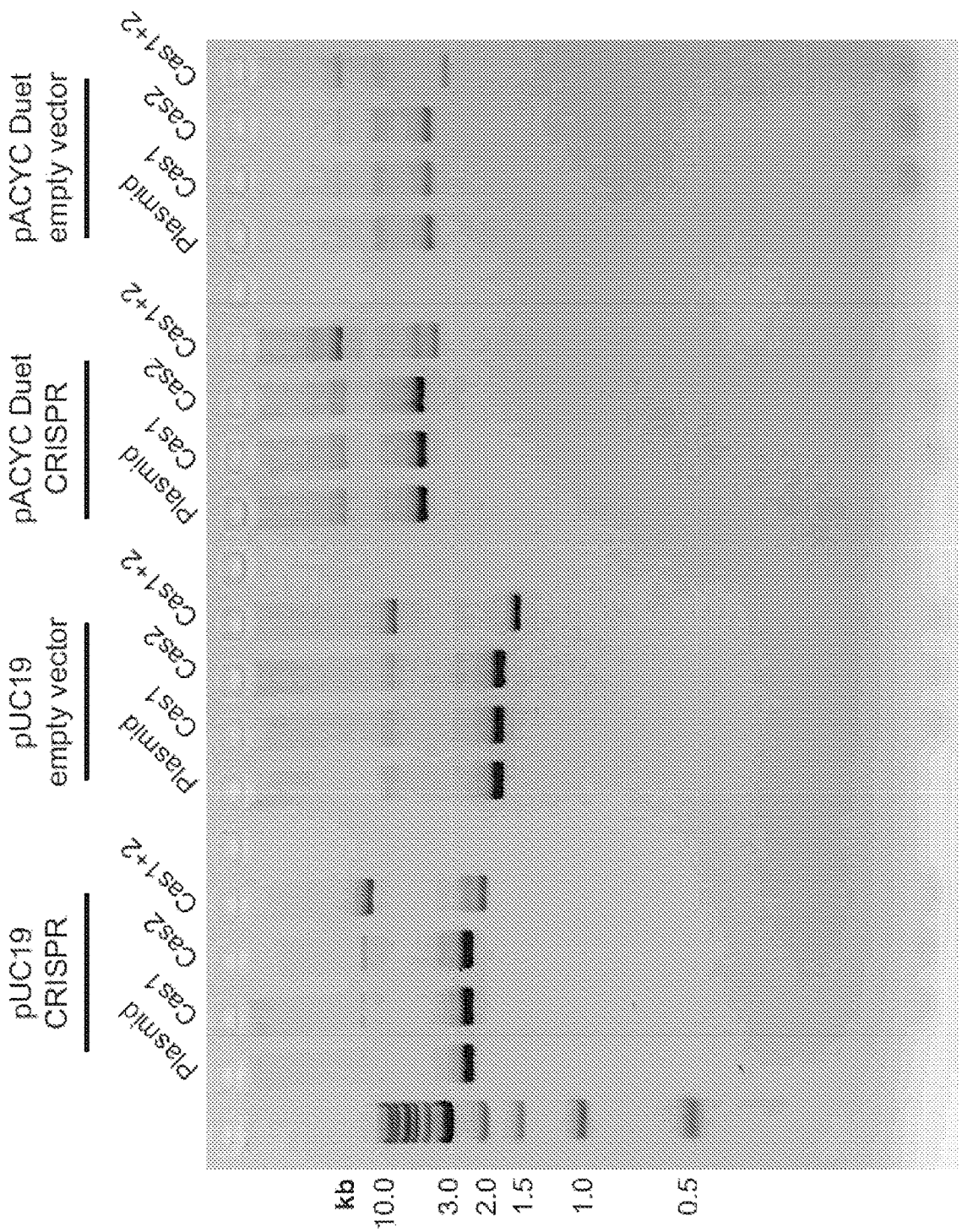

FIG. 11. Cas1-Cas2 can integrate various lengths of double-stranded DNA with blunt- or 3'-overhang ends into a supercoiled target plasmid. a, Integration assays using the indicated lengths of protospacer DNA. b, Integration assays using varying 5' or 3' overhang lengths. c,d, A comparison of integration assays using pCRISPR or Nb.BbvCI-nicked pCRISPR target. e, Integration assay using different target plasmids with or without a CRISPR locus.

Figure 12:
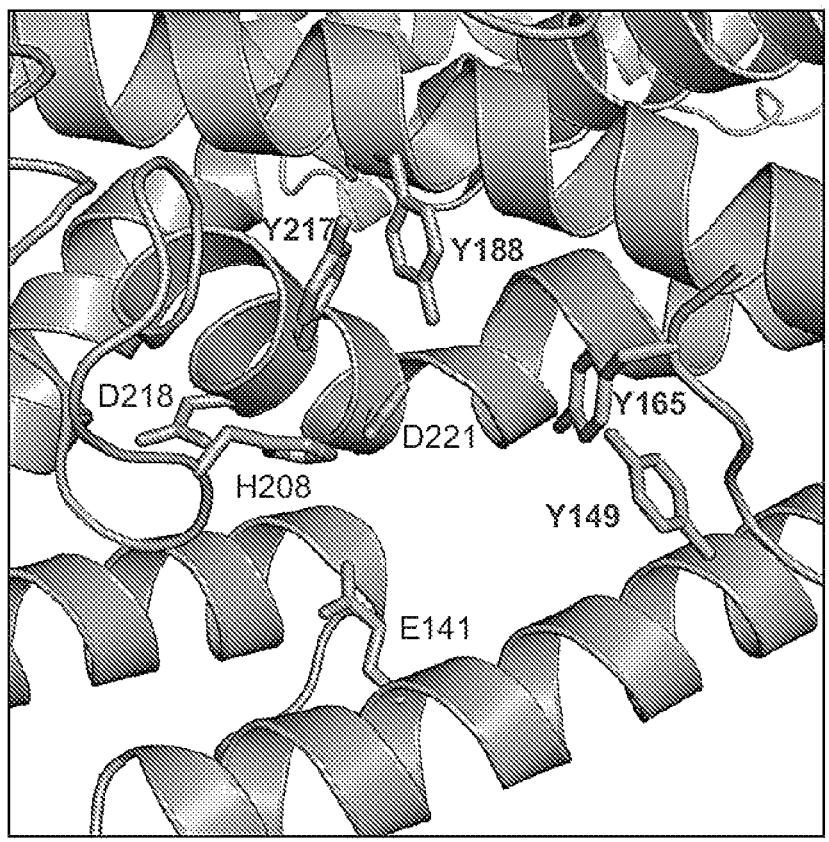
FIGS. 12A-C provide evidence related to Tyr residues in the vicinity of the Cas1 active site.
Figure 12:
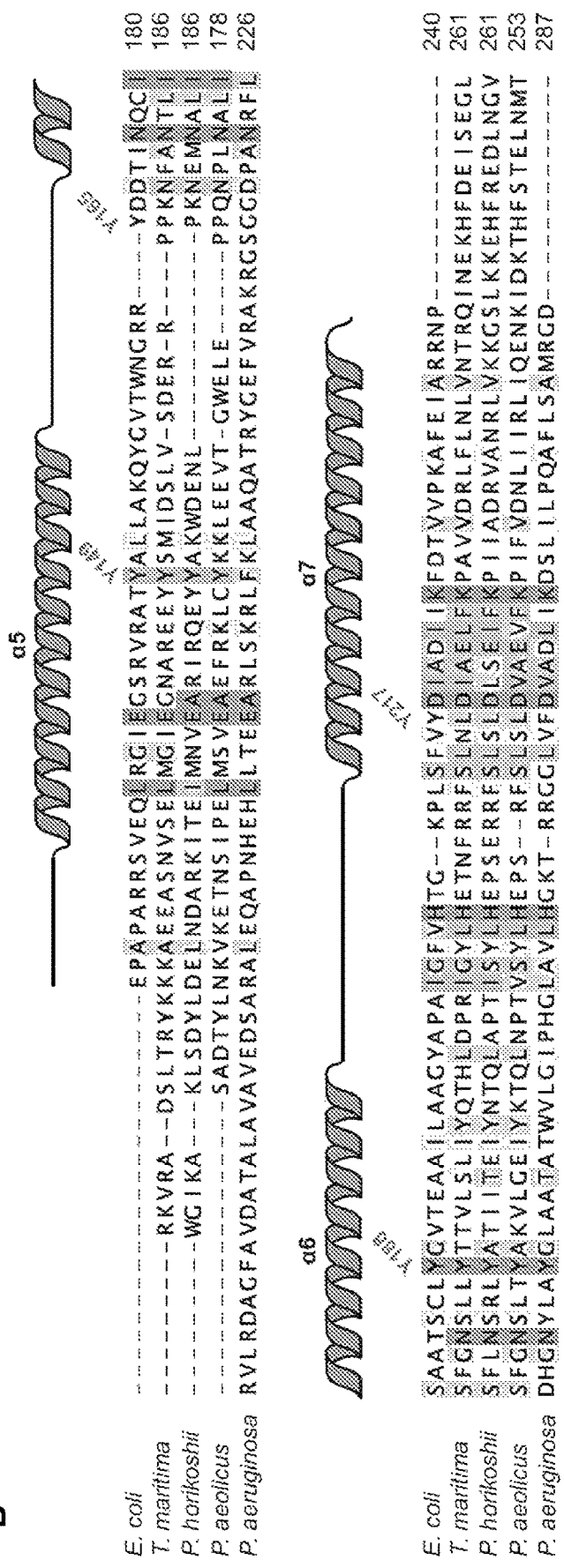
Figure 12:
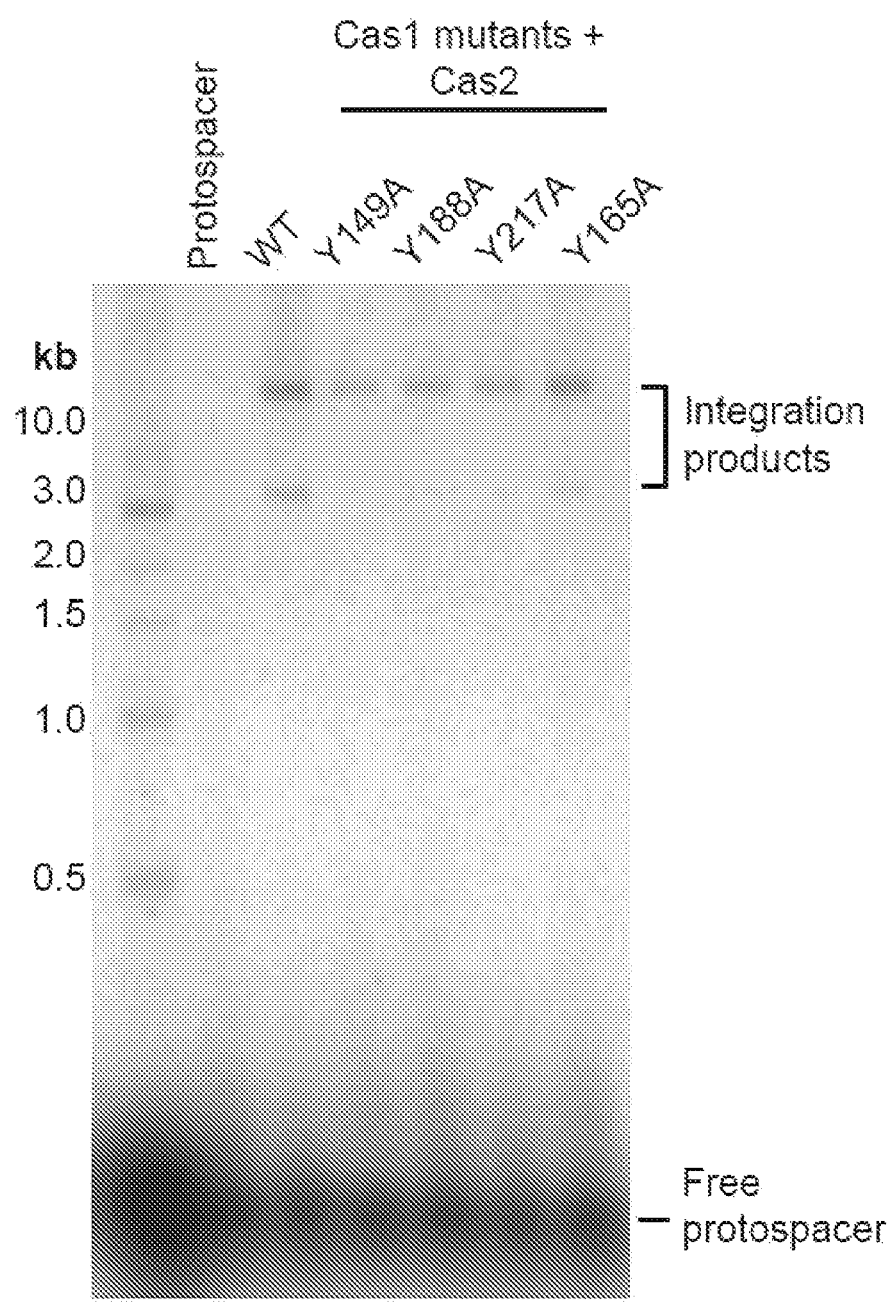

FIG. 12. Cas1 tyrosine mutants support integration activity in vitro. a, A close-up of the Cas1 active site with the tyrosine residues labeled in blue. b, Structure-based sequence alignment of Cas1 proteins, highlighting the tyrosine residues mutated to alanine in this study. c, Radiolabeled protospacer integration assay of Cas1 tyrosine mutants complexed with WT Cas2.

Protospacer Integration Requires Supercoiled Target DNA and Favors the CRISPR Locus Cas1 and Cas2 overexpression leads to site-selective spacer acquisition proximal to the leader end of the CRISPR locus, a result consistent with observations in native populations of CRISPR-containing bacteria[13-15,35]. To determine what drives such site-specific integration, various forms of the pCRISPR plasmid DNA were tested to determine target DNA requirements. Integration requires target DNA supercoiling, as neither relaxed nor linear pCRISPR, nor the isolated 1 kb CRISPR locus, supported integration (FIG. 3c and FIG. 11c,d).

As a control, supercoiled pUC19 DNA was used, the parental plasmid of pCRISPR that lacks a CRISPR locus, and integration products upon incubation with Cas1 and Cas2 in the presence of protospacer DNA were observed (FIG. 3c and FIG. 11e). This finding raised two possibilities: 1) in vitro spacer integration is non-specific with respect to target DNA sequence or 2) structures and/or sequence(s) favoring integration are present in the pUC19 plasmid. To determine if integration preferentially occurred at the CRISPR locus of pCRISPR, products of radiolabeled reactions were double-digested to separate the CRISPR locus (960 bp) from the pUC19 plasmid backbone (~2.27 kb). Suggestive of CRISPR-specific integration, the $^{32}$P-radiolabel migrated solely with the CRISPR locus fragment (FIG. 3d). The same result was observed when the experiment was conducted using a target plasmid containing the CRISPR locus and a different backbone sequence (pACYC) (FIG. 3e).

The CRISPR Repeats Provide Specificity for Integration

To determine the exact sites of protospacer integration in these reactions, high-throughput sequencing was performed of reaction products that resulted from using either pCRISPR or the parental pUC19 vector as the target of integration. Reaction products were fragmented, end-repaired, adapter ligated, PCR amplified and analyzed by Illumina sequencing (FIG. 13a). Of the 7,866 protospacer-pCRISPR junctions retrieved, ~71% mapped to the CRISPR locus (FIG. 4a and FIG. 13b). Analysis of the DNA integration sites within the CRISPR locus revealed spacer sequence insertion into the borders of each repeat, with the most preferred site at the first repeat adjacent to the leader (FIG. 4b). The minus strand of each repeat (the bottom strand in FIG. 4a,b that runs 5'-to-3' towards the leader sequence) is also highly preferred, highlighting the role of CRISPR repeats in providing sequence specificity for the Cas1-Cas2 complex (FIG. 4b). Sequence alignment of the integration sites revealed strong preference for sequences resembling the CRISPR repeat on both strands of pCRISPR, further supporting the selection of CRISPR repeat borders by the Cas1-Cas2 complex (FIG. 13d-f).

The most frequent integration site in the pUC19 control plasmid mapped to the amp resistance gene adjacent to the A-T rich promoter sequence (~8.8% of 5,524 total retrieved junctions, FIG. 4c and FIG. 13c). An inverted repeat sequence with a propensity to form a DNA cruciform[36] occurs 9 nt adjacent to this integration site (plus strand sequence: 5'-TTCAATATTATTGAA-3'; SEQ ID NO://), suggesting that potential DNA cruciform formation adjacent to A-T rich sequences is important for protospacer integration. Sequence analysis of pUC19 target sites revealed a propensity for a G nucleotide to occur at the −2 and +1 positions of the protospacer insertion site, similar to the preferred pCRISPR sites, but otherwise little sequence specificity surrounding the integration sites relative to the pCRISPR repeats (FIG. 13g, h). This observation implies that pCRISPR repeat sequence selectivity stems from the unique structural features of these sites, such as their ability to form cruciforms (FIG. 4a, b, e).

Figure 14:
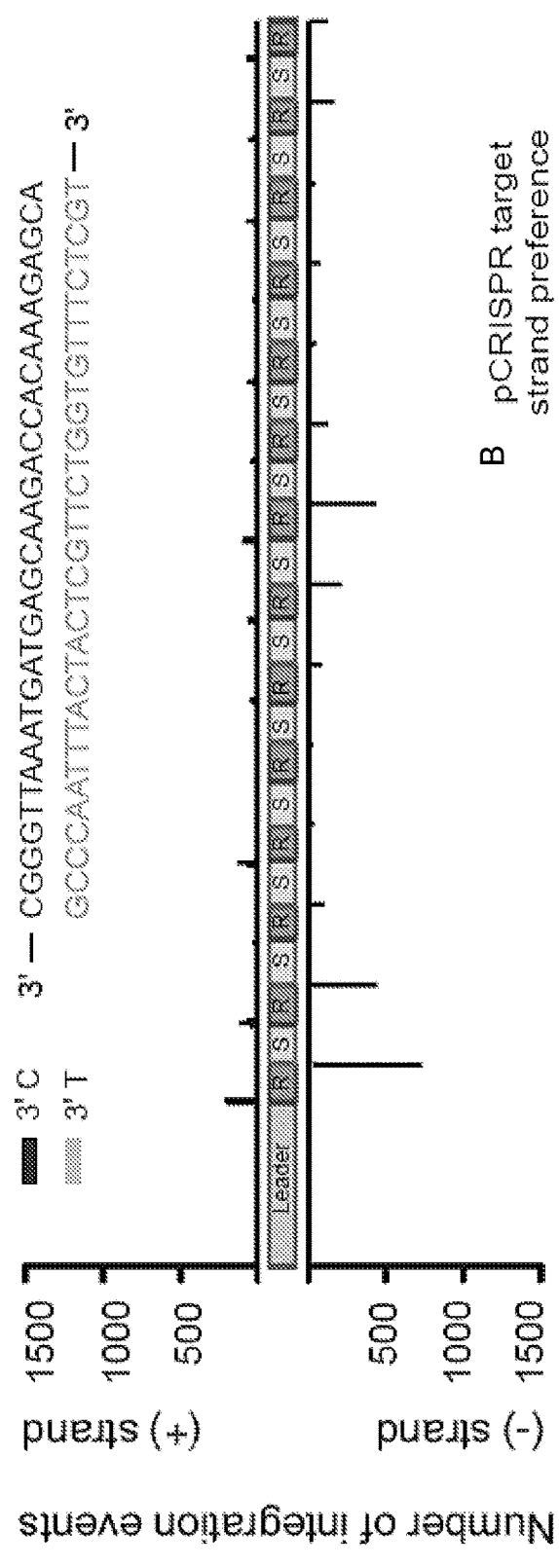
FIGS. 14A-F provide evidence related to Cas1 and Cas2 correctly orienting the protospacer during integration.
Figure 14:
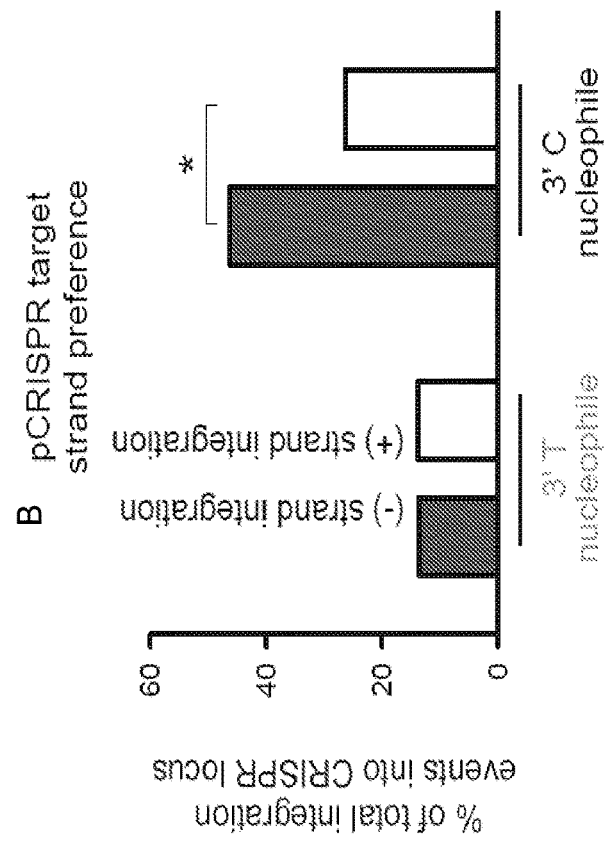
Figure 14:
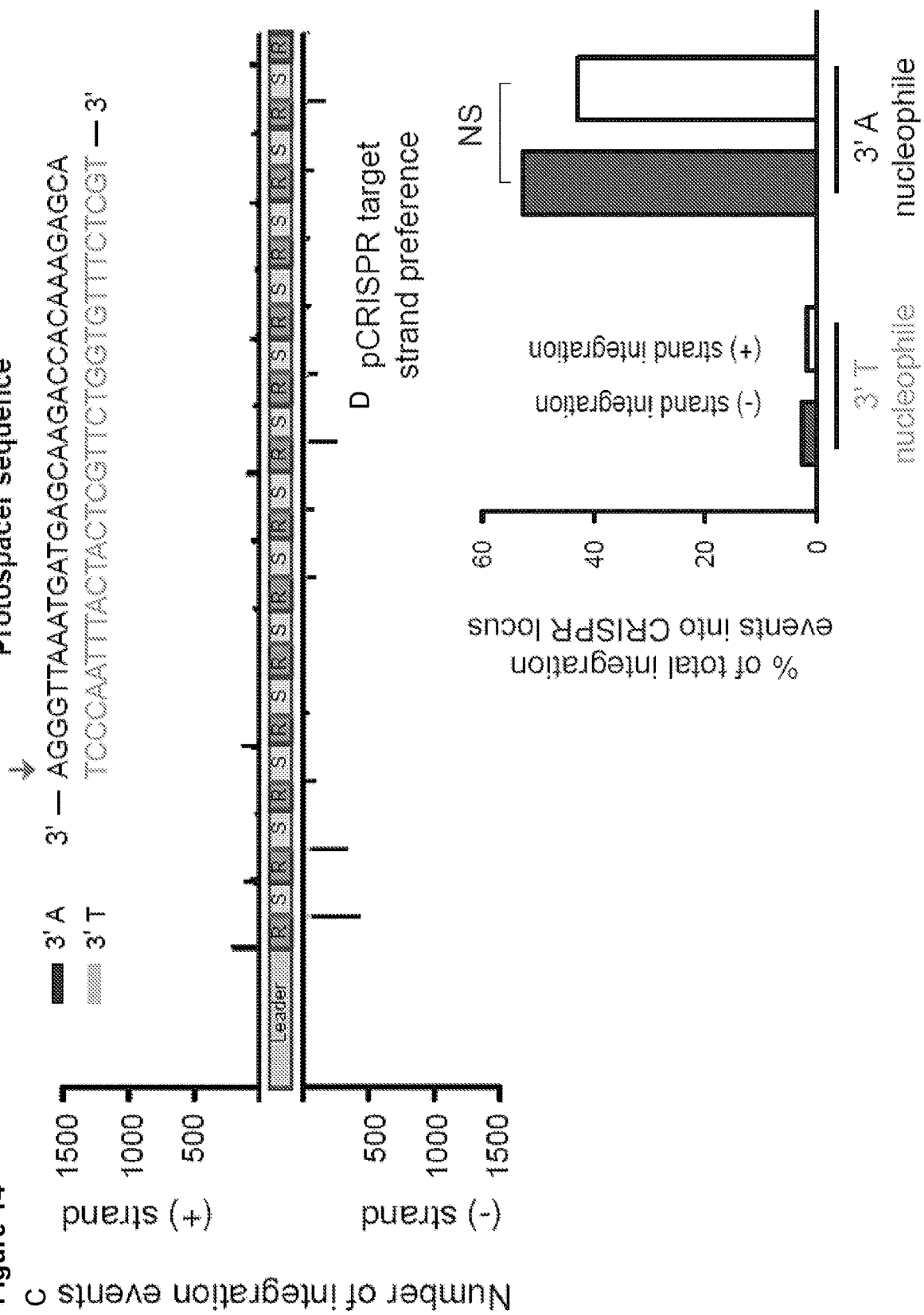
Figure 14:
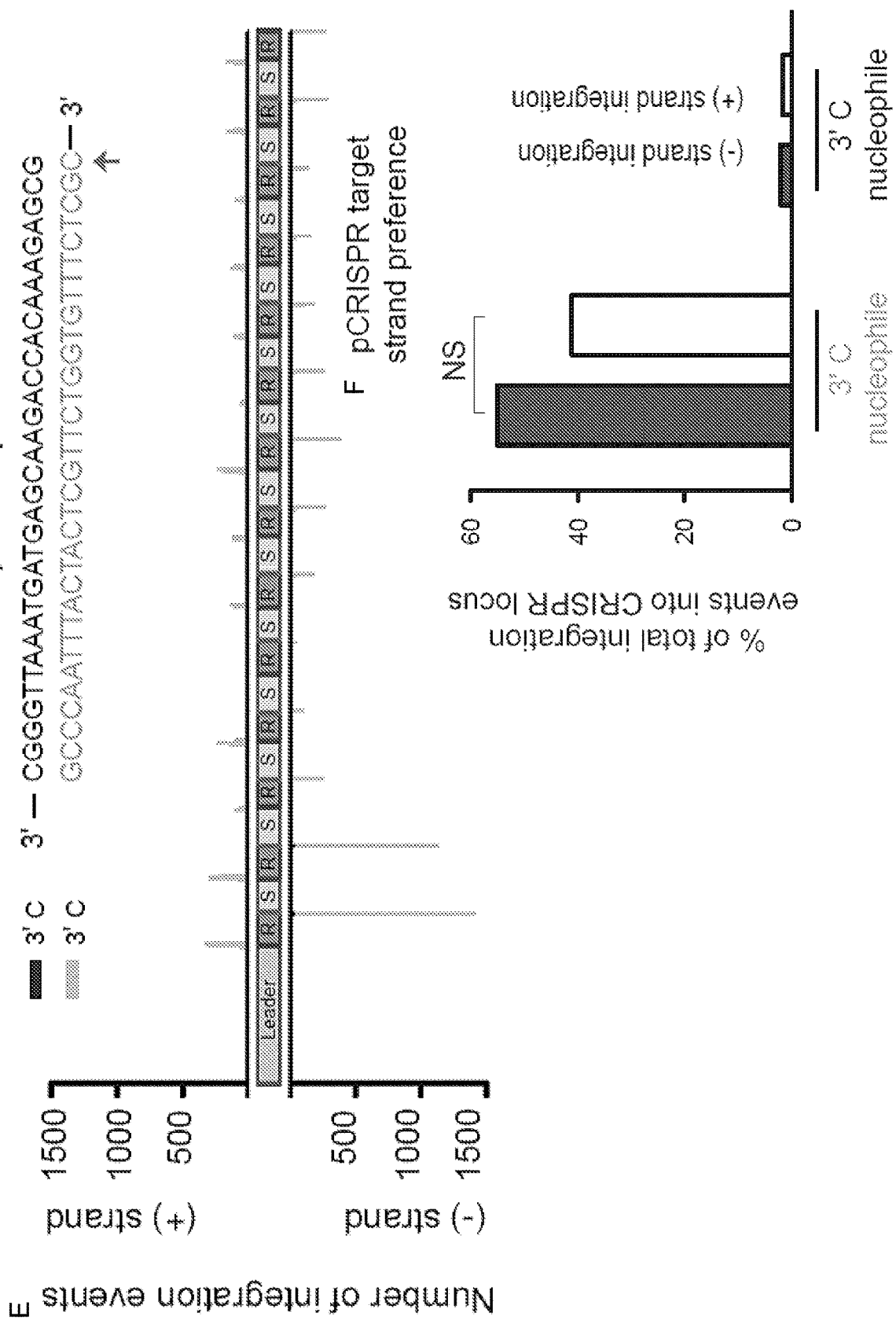

In E. coli, newly acquired spacers harbor a 5' G as the first nucleotide flanking the leader-proximal end of the repeats, which originates from the last nucleotide of the AAG PAM in the foreign DNA[13-15,37-39]. Such positional specificity is critical for crRNA-guided interference, as a mutation in this position of the corresponding crRNA disrupts PAM binding and subsequent target destruction[40-42]. The sequencing data here was used to determine if the Cas1-Cas2 complex preferentially utilized the terminal 3' C or T of protospacer DNA during integration (see FIG. 4b for protospacer sequence). About 73% of all integration events into pCRISPR utilized the C 3'-OH end, and there was a strong preference for this nucleotide to attack the minus strand of the repeat sequence (FIG. 4b, d, e). A similar nucleotide bias was observed in the pUC19 target plasmid sequence data (FIG. 4d). This preference positions the G at the 5' end of the protospacer substrate as the first nucleotide of the newly integrated spacer in the CRISPR locus (FIG. 5). When protospacer DNAs lacking a 3' C or bearing 3' C on both ends were used, the preference for integration into the minus strand of the CRISPR locus was significantly decreased (FIG. 14). This observation results in the loss of preferential orientation of the protospacer after full integration. Thus, the Cas1–Cas2 complex plays a critical role in correctly orienting the C 3'-OH end of protospacer DNA substrates for incorporation within the CRISPR locus.

Figure 4:
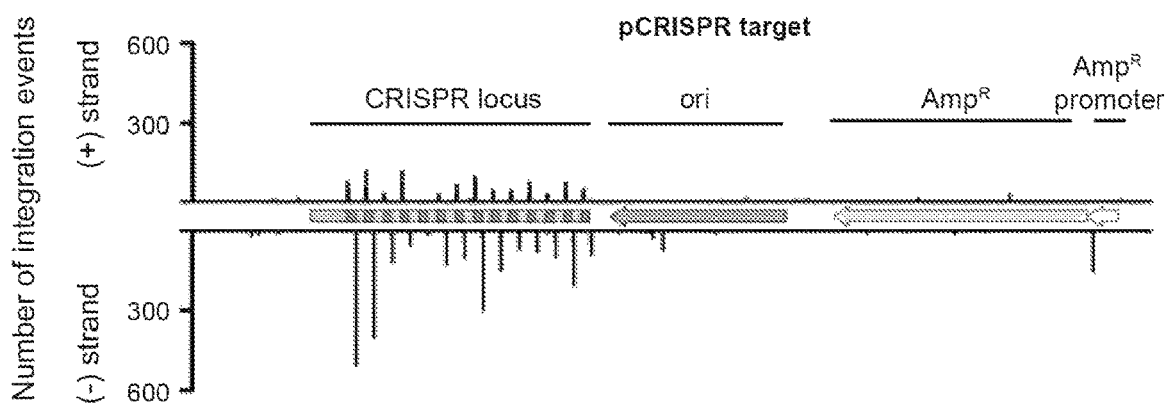
FIGS. 4A-E provide evidence related to protospacers specifically integrating into the CRISPR locus.
Figure 4:
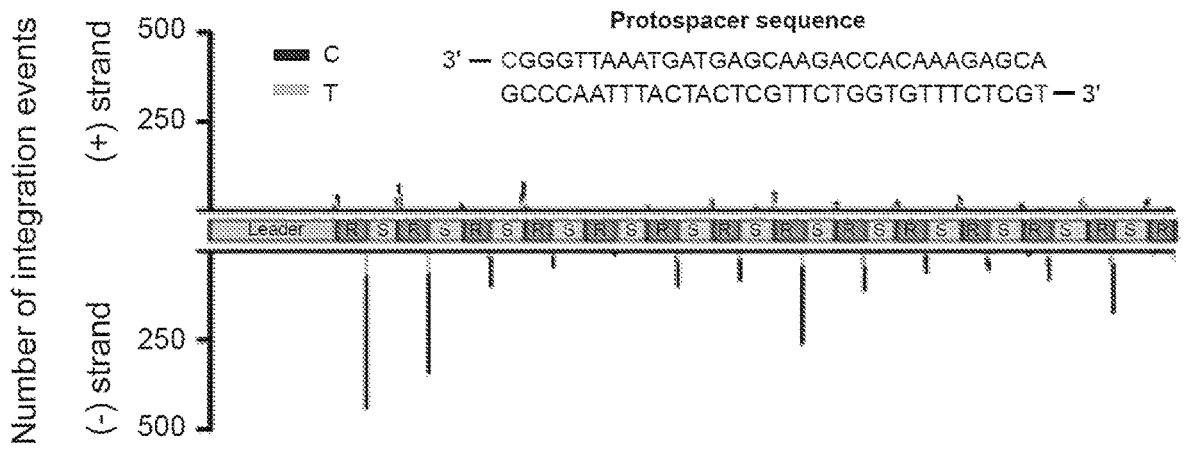
Figure 4:
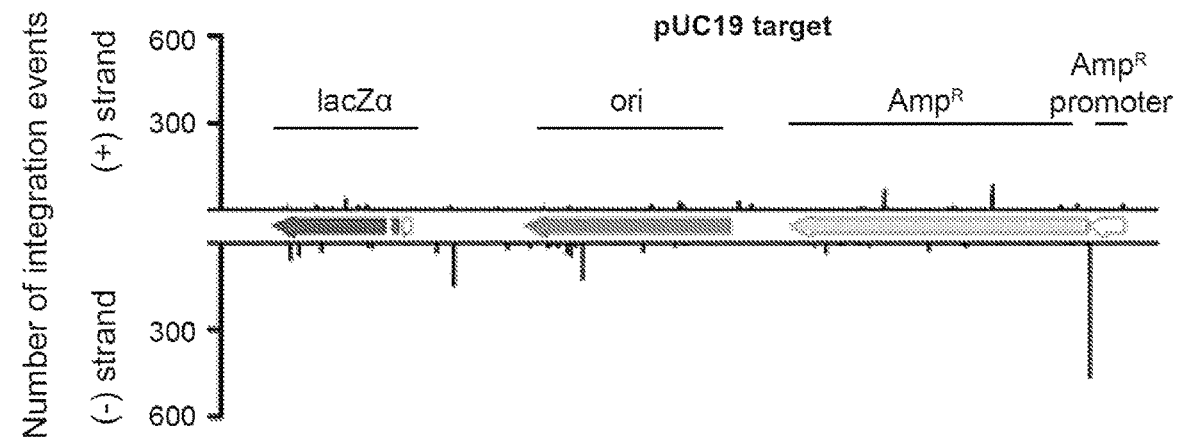
Figure 4:
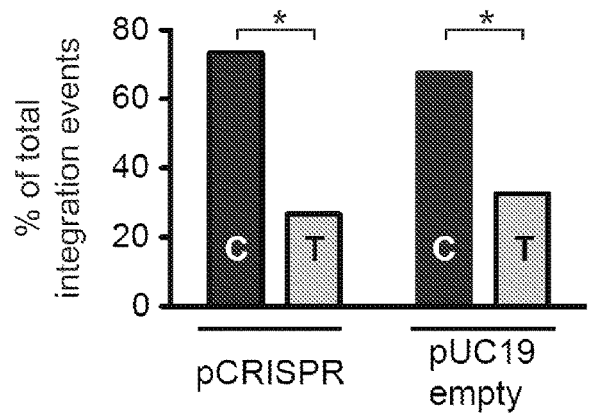
Figure 4:
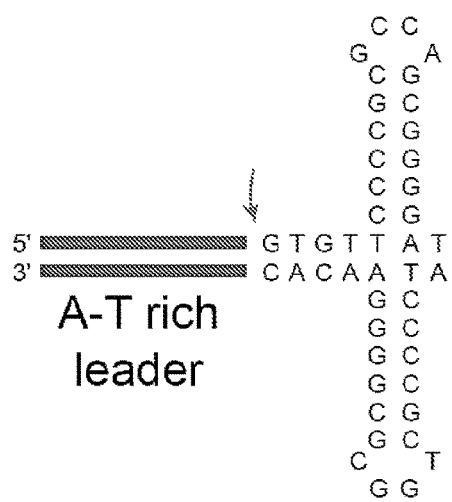
Figure 4:
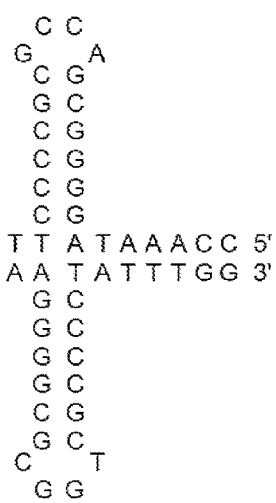
Figure 5:
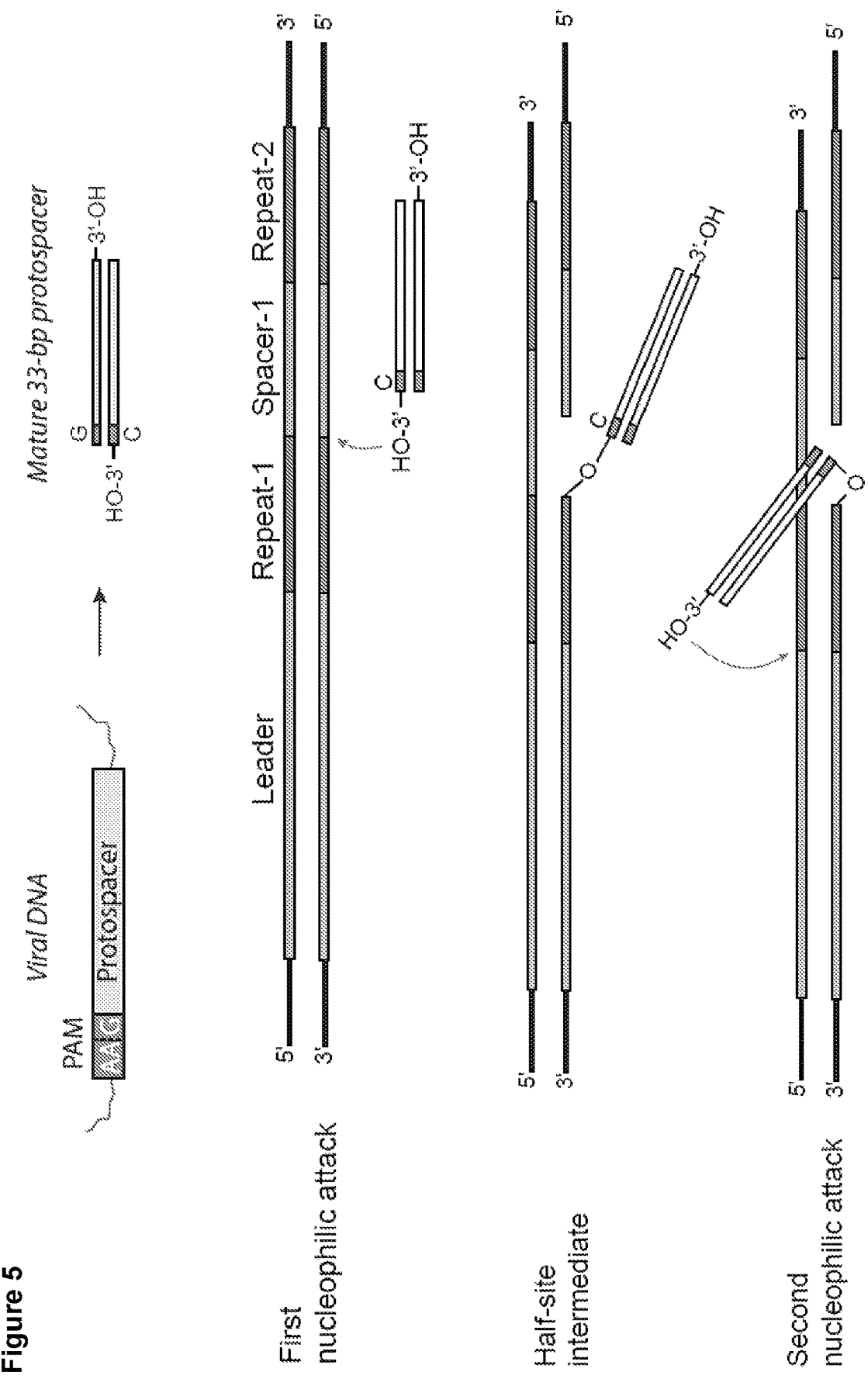
FIG. 5 provides a schematic of a model of protospacer integration during CRISPR-Cas adaptive immunity.
Figure 5:
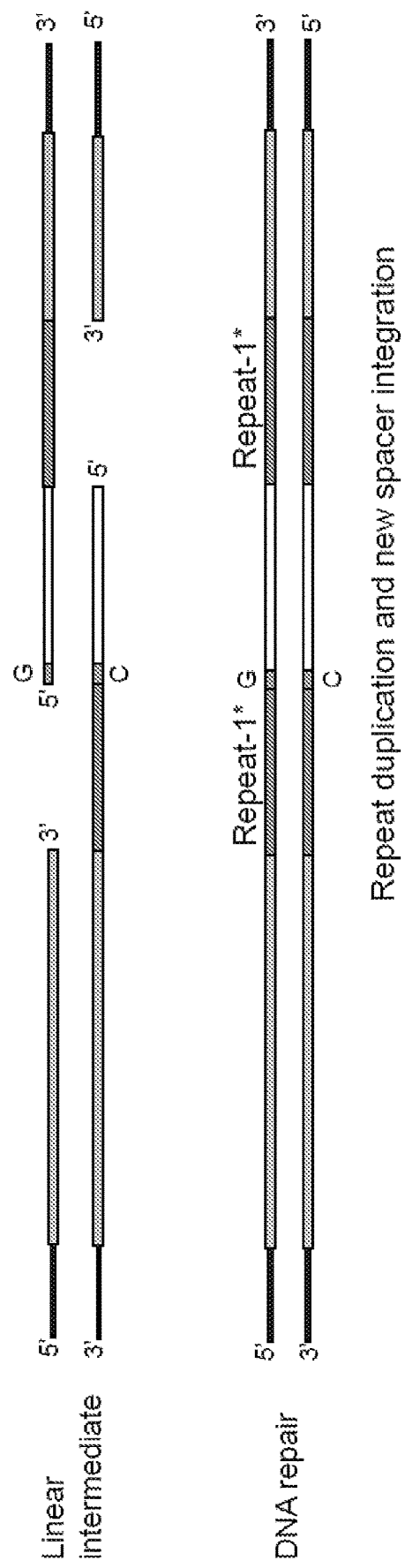

FIG. 4. Protospacers are specifically integrated into the CRISPR locus. a, Mapped integration sites along pCRISPR. b, Magnified view of the integration sites along the ~1 kb CRISPR locus. The cyan peaks represent positions where the 3' T of the protospacer DNA was integrated whereas the black peaks represent the C 3'-OH integration events. The protospacer sequence is depicted above the plot. c, Mapped integration sites along pUC19 empty vector. d, Comparison of C 3'-OH or T 3'-OH selection in the total reads from pCRISPR and pUC19 empty targets (Chi-square test, *p<0.0001). e, Schematic of DNA cruciform formation of the repeat sequences. The orange arrows depict the cleavage site on the plus and minus strands, based on the integration sites in (b).

FIG. 5. Model of protospacer integration during CRISPR-Cas adaptive immunity. The first nucleophilic attack occurs on the minus strand of the first repeat, distal to the leader, by the C 3'-OH end of the protospacer. After half-site intermediate formation, the second integration event occurs on the opposite strand at the leader-repeat border. The resulting single-stranded DNA gaps are repaired by yet uncharacterized mechanisms and the protospacer is fully integrated with the G as the first nucleotide at its 5' end. The asterisk denotes the duplication of the first repeat, as previously observed in vivo (refs 13-15).

Figure 13:
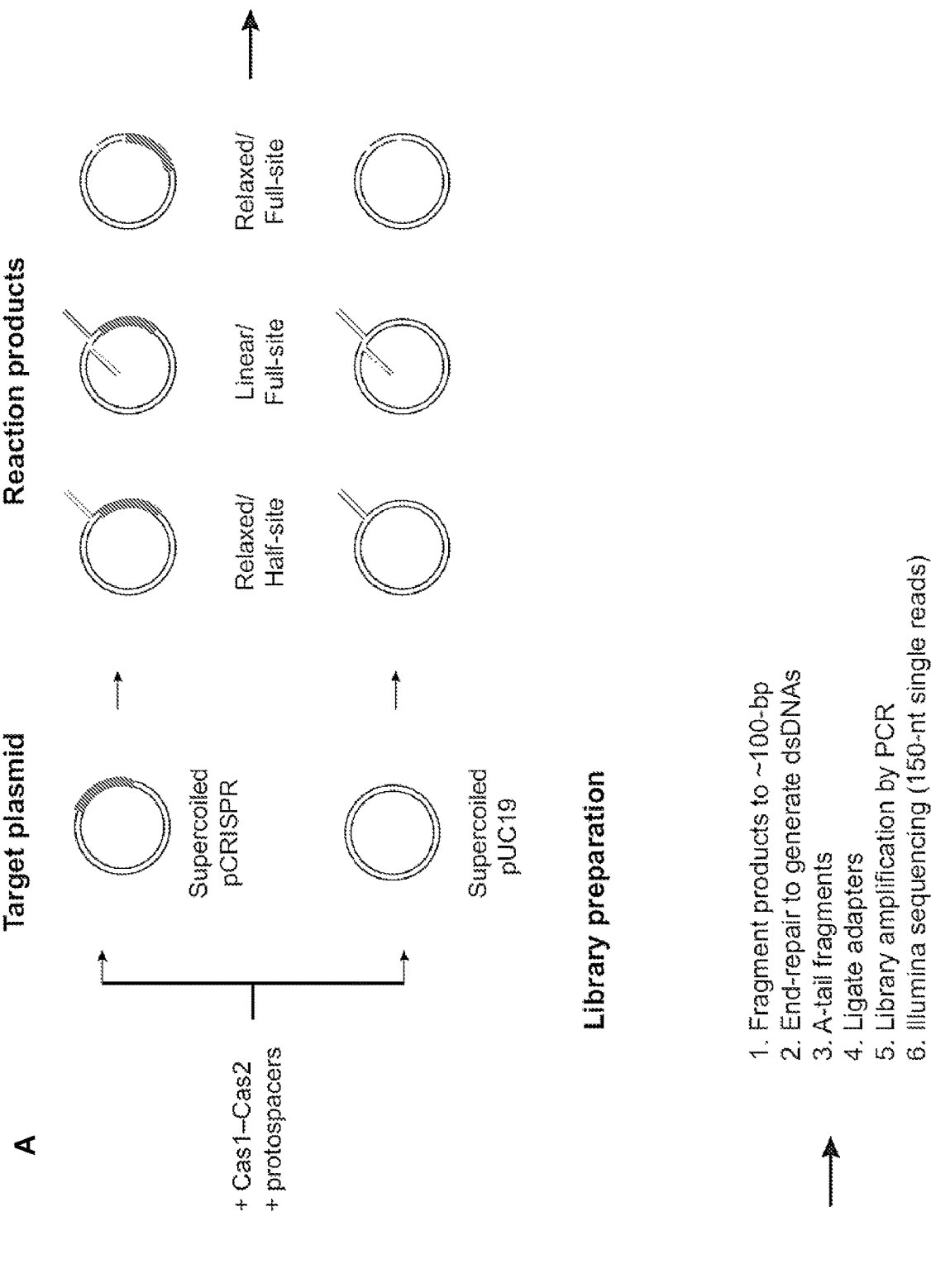
FIGS. 13A-H provide evidence related to high-throughput sequencing of integration products revealing sequence-specific integration.
Figure 13:
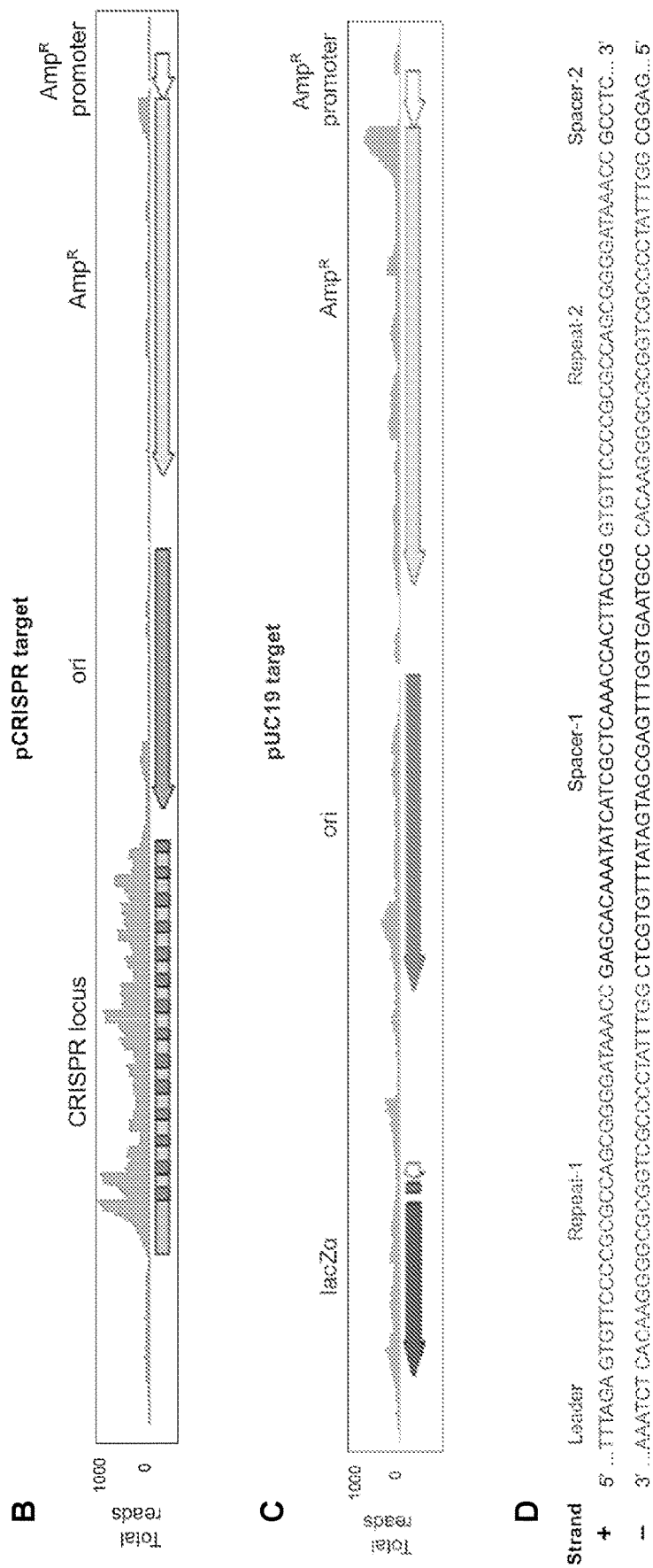
Figure 13:
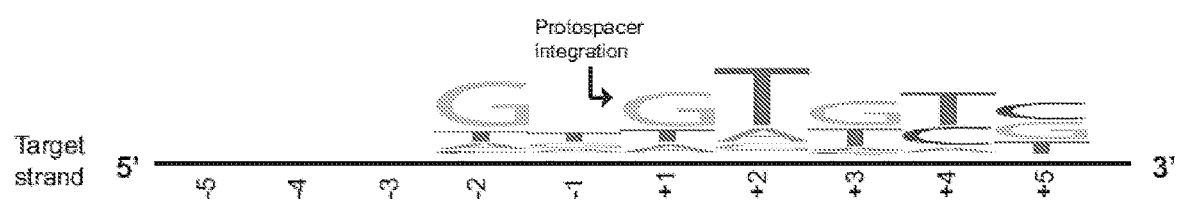
Figure 13:
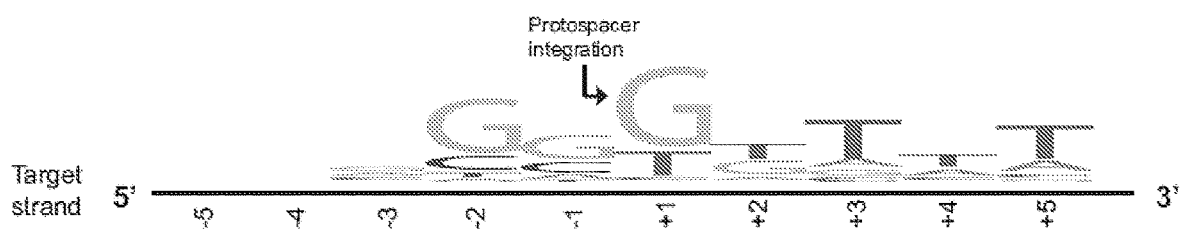
Figure 13:
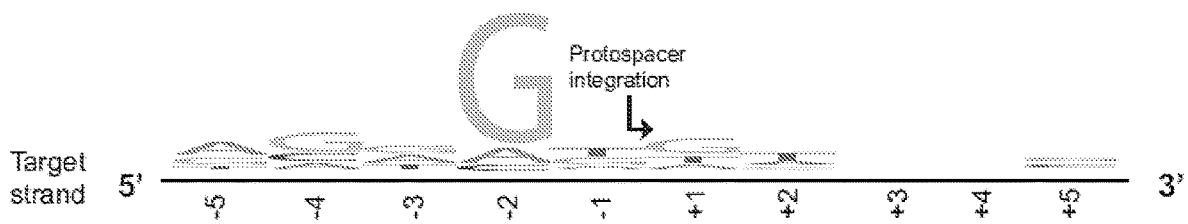
Figure 13:
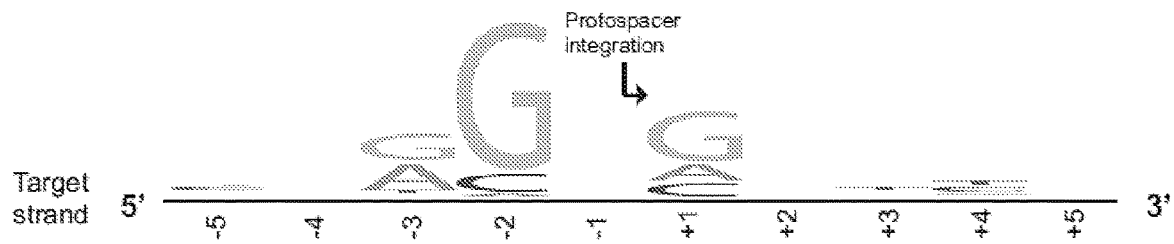

FIG. 13 High-throughput sequencing of integration products reveals sequence-specific integration. a, Schematic of the workflow for high-throughput sequencing analysis of the integration sites. b, Raw map of the total reads along pCRISPR before collapsing into single peaks of protospacer-pCRISPR junctions depicted in FIG. 4. c, Same as b, except for the pUC19 target. d, Sequence of the leader-end of the CRISPR locus in E. coli. e,f, WebLogo analysis from the −5 to +5 positions surrounding the protospacer integration sites on the (e) plus and (f) minus of pCRISPR. The arrow points to the nucleotide that is covalently joined to the protospacer. g, h, Same as e,f, except for the pUC19 target.

FIG. 14. Cas1–Cas2 correctly orients the protospacer DNA during integration. Mapped integration sites along the CRISPR locus of pCRISPR when using protospacer DNA with nucleotide ends (a) "wild type" 3' C and 3' T, (c) 3' A and 3' T, and (e) 3' C and 3' C. The red arrow in c and e points to the nucleotide change in the protospacer DNA compared to the "wild type" sequence in a. The protospacer DNA 3' nucleotide and the CRISPR locus strand biases in a, c, e are plotted in b, d and f, respectively, as percentages of integration events within the CRISPR locus. The black and clear bars represent the (−) and (+) strands of the CRISPR locus, respectively. NS corresponds to not significant and *p<0.0001 by Chi-square test.

Mechanism of Protospacer Integration During CRISPR-Cas Immunity

Figure 15:
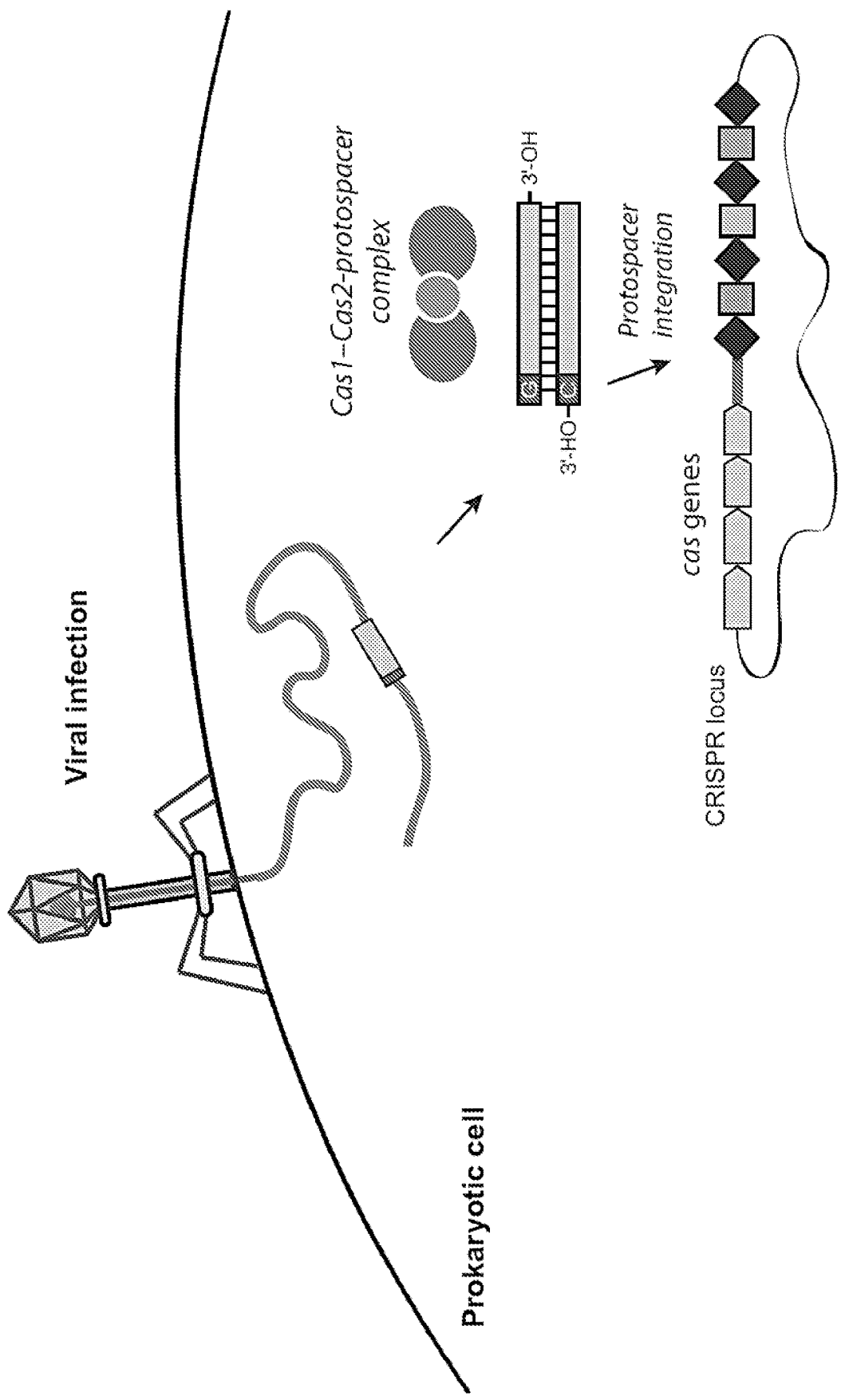
FIG. 15 provides a schematic model of the CRISPR-Cas adaptive immunity pathway in *E. coli*.

The results presented here explain the mechanistic basis for foreign DNA acquisition during CRISPR-Cas adaptive immunity (FIG. 5). The Cas1–Cas2 complex catalyzes integration of protospacers preferentially at the leader-end of the CRISPR locus. Intriguingly, the experiments herein show that Cas1–Cas2 also functions to select the terminal C 3'-OH as the attacking nucleophile to preferentially target the minus strand of CRISPR repeats, resulting in the 5' G on the opposite strand of the protospacer becoming the first nucleotide of the newly integrated spacer. This orientation bias, previously observed in vivo[39], is a key step during immunity for productive downstream foreign DNA targeting by the Cascade complex and Cas3 effector nuclease (FIG. 15). Interestingly, the presence of the complete AAG PAM in the protospacer is not required for in vitro integration, suggesting that a highly specific selection or processing step occurs in vivo to exclude the AA nucleotides from the mature protospacer prior to integration.

FIG. 15. Model of the CRISPR-Cas adaptive immunity pathway in E. coli. Mature double-stranded protospacers bearing a 3' C—OH are site-specifically integrated into the leader-end of the CRISPR locus. Correct protospacer integration (left) results in the 5'G/3'C as the first nucleotide of the spacer, proximal to the leader. After transcription of the CRISPR locus and subsequent crRNA processing, foreign DNA destruction is initiated by strand-specific recognition of the 3'-TTC-5' PAM sequence in the target strand by the crRNA-guided Cascade complex. Incorrect protospacer integration (right) cannot initiate foreign DNA destruction due to the inability for the crRNA to recognize the strand with the 3'-TTC-5' PAM. Thus, foreign DNA interference during CRISPR-Cas adaptive immunity relies on the Cas1–Cas2 complex for correctly orienting the protospacer during integration.

A two-step integration mechanism is suggested during spacer acquisition, in which the C 3'-OH first attacks the minus strand of the CRISPR repeat to produce a half-site intermediate (FIG. 5). The 3'-OH on the opposite strand of the integrating DNA then attacks the target DNA 28 bp away on the opposite side of the repeat on the plus strand, leading to full integration of the protospacer (FIG. 5). As evidenced by agarose gel electrophoresis and high throughput sequencing, most of the in vitro products are half-site integration intermediates. The conclusion is that the in vitro system predominantly traps the first step of a two-step integration mechanism. We posit that the second nucleophilic attack is greatly accelerated in vivo in the presence of cellular factors and high Cas1–Cas2 concentrations. This model is consistent with spacer integration intermediates that are observed in vivo, in which protospacers are integrated such that staggered cleavage at each end of the repeat generates single-stranded gaps that ensure repeat duplication[34].

The results highlight the fundamental role of repeat sequences at multiple stages of CRISPR-Cas adaptive immunity. In addition to their role in creating structures within nascent CRISPR transcripts that ensure correct RNA processing during crRNA maturation[45], the repeats also operate at the DNA level to recruit the Cas1–Cas2 complex for sequence- and structure-specific protospacer integration. This recruitment involves transient DNA cruciform formation within the CRISPR inverted repeats that occurs as a function of target DNA supercoiling[46].

REFERENCES

1 Barrangou, R. et al. CRISPR provides acquired resistance against viruses in prokaryotes. Science 315, 1709-1712, doi:10.1126/science.1138140 (2007).
2 van der Oost, J., Westra, E. R., Jackson, R. N. & Wiedenheft, B. Unravelling the structural and mechanistic basis of CRISPR-Cas systems. Nature reviews. Microbiology 12, 479-492, doi:10.1038/nrmicro3279 (2014).
3 Mojica, F. J., Diez-Villasenor, C., Garcia-Martinez, J. & Soria, E. Intervening sequences of regularly spaced prokaryotic repeats derive from foreign genetic elements. Journal of molecular evolution 60, 174-182, doi:10.1007/s00239-004-0046-3 (2005).
4 Bolotin, A., Quinquis, B., Sorokin, A. & Ehrlich, S. D. Clustered regularly interspaced short palindrome repeats (CRISPRs) have spacers of extrachromosomal origin. Microbiology 151, 2551-2561, doi:10.1099/mic.0.28048-0 (2005).
5 Pourcel, C., Salvignol, G. & Vergnaud, G. CRISPR elements in *Yersinia pestis* acquire new repeats by preferential uptake of bacteriophage DNA, and provide additional tools for evolutionary studies. Microbiology 151, 653-663, doi:10.1099/mic.0.27437-0 (2005).
6 Stern, A., Keren, L., Wurtzel, O., Amitai, G. & Sorek, R. Self-targeting by CRISPR: gene regulation or autoimmunity? Trends in genetics: TIG 26, 335-340, doi:10.1016/j.tig.2010.05.008 (2010).
7 Carte, J., Wang, R., Li, H., Terns, R. M. & Terns, M. P. Cas6 is an endoribonuclease that generates guide RNAs for invader defense in prokaryotes. Genes & development 22, 3489-3496, doi:10.1101/gad.1742908 (2008).
8 Haurwitz, R. E., Jinek, M., Wiedenheft, B., Zhou, K. & Doudna, J. A. Sequence- and structure-specific RNA processing by a CRISPR endonuclease. Science 329, 1355-1358, doi:10.1126/science.1192272 (2010).
9 Deltcheva, E. et al. CRISPR RNA maturation by trans-encoded small RNA and host factor RNase III. Nature 471, 602-607, doi:10.1038/nature09886 (2011).
10 Brouns, S. J. et al. Small CRISPR RNAs guide antiviral defense in prokaryotes. Science 321, 960-964, doi:10.1126/science.1159689 (2008).
11 Garneau, J. E. et al. The CRISPR/Cas bacterial immune system cleaves bacteriophage and plasmid DNA. Nature 468, 67-71, doi:10.1038/nature09523 (2010).
12 Jinek, M. et al. A programmable dual-RNA-guided DNA endonuclease in adaptive bacterial immunity. Science 337, 816-821, doi:10.1126/science.1225829 (2012).
13 Yosef, I., Goren, M. G. & Qimron, U. Proteins and DNA elements essential for the CRISPR adaptation process in *Escherichia coli*. Nucleic acids research 40, 5569-5576, doi:10.1093/nar/gks216 (2012).
14 Datsenko, K. A. et al. Molecular memory of prior infections activates the CRISPR/Cas adaptive bacterial immunity system. Nature communications 3, 945, doi:10.1038/ncomms1937 (2012).
15 Swarts, D. C., Mosterd, C., van Passel, M. W. & Brouns, S. J. CRISPR interference directs strand specific spacer acquisition. PloS one 7, e35888, doi:10.1371/journal.pone.0035888 (2012).
16 Nunez, J. K. et al. Cas1–Cas2 complex formation mediates spacer acquisition during CRISPR-Cas adaptive immunity. Nature structural & molecular biology 21, 528-534, doi:10.1038/nsmb.2820 (2014).
17 Wiedenheft, B. et al. Structural basis for DNase activity of a conserved protein implicated in CRISPR-mediated genome defense. Structure 17, 904-912, doi:10.1016/j.str.2009.03.019 (2009).
18 Babu, M. et al. A dual function of the CRISPR-Cas system in bacterial antivirus immunity and DNA repair. Molecular microbiology 79, 484-502, doi:10.1111/j.1365-2958.2010.07465.x (2011).
19 Kim, T Y., Shin, M., Huynh Thi Yen, L. & Kim, J S Crystal structure of Cas1 from *Archaeoglobus fulgidus* and characterization of its nucleolytic activity. Biochemical and biophysical research communications, doi:10.1016/j.bbrc.2013.10.122 (2013).
20 Beloglazova, N. et al. A novel family of sequence-specific endoribonucleases associated with the clustered regularly interspaced short palindromic repeats. The Journal of biological chemistry 283, 20361-20371, doi:10.1074/jbc.M803225200 (2008).
21 Samai, P., Smith, P. & Shuman, S. Structure of a CRISPR-associated protein Cas2 from *Desulfovibrio vulgaris*. Acta crystallographica. Section F, Structural biology and crystallization communications 66, 1552-1556, doi:10.1107/S1744309110039801 (2010).
22 Nam, K. H. et al. Double-stranded endonuclease activity in *Bacillus halodurans* clustered regularly interspaced short palindromic repeats (CRISPR)-associated Cas2 protein. The Journal of biological chemistry 287, 35943-35952, doi:10.1074/jbc.M112.382598 (2012).
23 Li, M. & Craigie, R. Processing of viral DNA ends channels the HIV-1 integration reaction to concerted integration. The Journal of biological chemistry 280, 29334-29339, doi:10.1074/jbc.M505367200 (2005).
24 Cherepanov, P. LEDGF/p75 interacts with divergent lentiviral integrases and modulates their enzymatic activity in vitro. Nucleic acids research 35, 113-124, doi:10.1093/nar/gkl885 (2007).
25 Hare, S. et al. A novel co-crystal structure affords the design of gain-of-function lentiviral integrase mutants in the presence of modified PSIP1/LEDGF/p75. PLoS pathogens 5, e1000259, doi:10.1371/journal.ppat.1000259 (2009).
26 Yang, J. Y., Jayaram, M. & Harshey, R. M. Positional information within the Mu transposase tetramer: catalytic contributions of individual monomers. Cell 85, 447-455 (1996).
27 DiNardo, S., Voelkel, K. A., Sternglanz, R., Reynolds, A. E. & Wright, A. *Escherichia coli* DNA topoisomerase I mutants have compensatory mutations in DNA gyrase genes. Cell 31, 43-51 (1982).
28 Pruss, G. J., Manes, S. H. & Drlica, K. *Escherichia coli* DNA topoisomerase I mutants: increased supercoiling is corrected by mutations near gyrase genes. Cell 31, 35-42 (1982).
29 Chow, S. A., Vincent, K. A., Ellison, V. & Brown, P. O. Reversal of integration and DNA splicing mediated by integrase of human immunodeficiency virus. Science 255, 723-726 (1992).
30 Au, T. K., Pathania, S. & Harshey, R. M. True reversal of Mu integration. The EMBO journal 23, 3408-3420, doi:10.1038/sj.emboj.7600344 (2004).
31 Engelman, A., Mizuuchi, K. & Craigie, R. HIV-1 DNA integration: mechanism of viral DNA cleavage and DNA strand transfer. Cell 67, 1211-1221 (1991).
32 Mizuuchi, K. & Adzuma, K. Inversion of the phosphate chirality at the target site of Mu DNA strand transfer: evidence for a one-step transesterification mechanism. Cell 66, 129-140 (1991).
33 Curcio, M. J. & Derbyshire, K. M. The outs and ins of transposition: from mu to kangaroo. Nature reviews. Molecular cell biology 4, 865-877, doi:10.1038/nrm1241 (2003).
34 Arslan, Z., Hermanns, V., Wurm, R., Wagner, R. & Pul, U. Detection and characterization of spacer integration intermediates in type I-E CRISPR-Cas system. Nucleic acids research 42, 7884-7893, doi:10.1093/nar/gku510 (2014).

35 Tyson, G. W. & Banfield, J. F. Rapidly evolving CRISPRs implicated in acquired resistance of microorganisms to viruses. Environmental microbiology 10, 200-207, doi: 10.1111/j.1462-2920.2007.01444.x (2008).
36 Sheflin, L. G. & Kowalski, D. Altered DNA conformations detected by mung bean nuclease occur in promoter and terminator regions of supercoiled pBR322 DNA. Nucleic acids research 13, 6137-6154 (1985).
37 Goren, M. G., Yosef, I., Auster, 0. & Qimron, U. Experimental definition of a clustered regularly interspaced short palindromic duplicon in *Escherichia coli*. Journal of molecular biology 423, 14-16, doi:10.1016/j.jmb.2012.06.037 (2012).
38 Savitskaya, E., Semenova, E., Dedkov, V., Metlitskaya, A. & Severinov, K. High-throughput analysis of type I-E CRISPR/Cas spacer acquisition in *E. coli*. RNA biology 10, 716-725, doi:10.4161/rna.24325 (2013).
39 Shmakov, S. et al. Pervasive generation of oppositely oriented spacers during CRISPR adaptation. Nucleic acids research 42, 5907-5916, doi:10.1093/nar/gku226 (2014).
40 Deveau, H. et al. Phage response to CRISPR-encoded resistance in *Streptococcus thermophilus*. Journal of bacteriology 190, 1390-1400, doi:10.1128/JB.01412-07 (2008).
41 Semenova, E. et al. Interference by clustered regularly interspaced short palindromic repeat (CRISPR) RNA is governed by a seed sequence. Proceedings of the National Academy of Sciences of the United States of America 108, 10098-10103, doi:10.1073/pnas.1104144108 (2011).
42 Westra, E. R. et al. Type I-E CRISPR-cas systems discriminate target from non-target DNA through base pairing-independent PAM recognition. PLoS genetics 9, e1003742, doi:10.1371/journal.pgen.1003742 (2013).
43 Craigie, R. & Bushman, F. D. HIV DNA integration. Cold Spring Harbor perspectives in medicine 2, a006890, doi:10.1101/cshperspect.a006890 (2012).
44 Nowotny, M. Retroviral integrase superfamily: the structural perspective. EMBO reports 10, 144-151, doi: 10.1038/embor.2008.256 (2009).
45 Hochstrasser, M. L. & Doudna, J. A. Cutting it close: CRISPR-associated endoribonuclease structure and function. Trends in Biochemical Sciences (2014).
46 Palecek, E. Local supercoil-stabilized DNA structures. Critical reviews in biochemistry and molecular biology 26, 151-226, doi:10.3109/10409239109081126 (1991).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of nucleic acid integration, the method comprising: contacting in vitro a target supercoiled DNA molecule with: (1) a double stranded donor DNA molecule and a Cas1 protein, or (2) the double stranded donor DNA molecule, the Cas1 protein, and a Cas2 protein;

wherein:
(a) the target supercoiled DNA molecule comprises an AT-rich region upstream of a region that forms a DNA cruciform structure; and
(b) the double stranded donor DNA molecule is linear and comprises a 3'-OH overhang with a length of from 1 to 5 nucleotides, wherein at least one 3' most nucleotide of the double stranded donor DNA molecule is a C,
wherein said contacting is not in a bacterial or archaeal cell, and wherein the Cas1 protein, or the Cas1 protein complexed with the Cas2 protein, catalyzes preferentially full integration of the C 3'-OH double stranded donor DNA molecule into the target strand of DNA molecule that runs 5'-to-3'.

2. The method according to claim 1, wherein the method comprises contacting the target DNA molecule with the double stranded donor DNA molecule, the Cas1 protein, and the Cas2 protein.

3. The method according to claim 1, wherein the in vitro contacting is outside of a cell outside of a cell.

4. The method according to claim 1, wherein said contacting comprises:
a) introducing into a target cell: (i) the Cas1 protein, or a nucleic acid comprising a nucleotide sequence that encodes the Cas1 protein; and (ii) the linear double stranded donor DNA molecule, wherein the target cell comprises the target DNA molecule; or
b) introducing into a target cell: i) the Cas1 protein; ii) the Cas2 protein; or iii) the Cas1 protein and the Cas2 protein.

5. The method according to claim 4, wherein the Cas1 protein and the linear double stranded donor DNA molecule are introduced into the target cell as a targeting composition comprising the Cas1 protein and the linear double stranded donor DNA molecule.

6. The method according to claim 1, wherein said contacting is performed in the presence of an integration host factor (IHF) protein.

7. The method according to claim 6, wherein the method comprises introducing into the target cell an IHF protein, or a nucleic acid comprising nucleotides that encode an IHF protein.

8. The method according to claim 4, wherein the target cell is a eukaryotic cell.

9. The method according to claim 1, wherein the target DNA molecule does not contain a leader sequence or a CRISPR repeat sequence from a naturally existing CRISPR locus.

10. The method according to claim 1, wherein the target DNA molecule does not contain a naturally existing CRISPR locus.

11. The method according to claim 1, wherein the AT-rich region is positioned 5' and within 50 nucleotides of the region that forms a DNA cruciform structure.

12. The method according to claim 11, wherein the length of an upper and lower stem of the DNA cruciform structure is in a range of from 5 to 30 base pairs.

13. The method according to claim 1, wherein the linear double stranded donor DNA molecule has a length in a range of from 10 to 500 nucleotides (nt).

14. The method according to claim 2, wherein one or more of: the Cas1 protein and the Cas2 protein:
 a) is a fusion protein comprising one or more heterologous fusion partners; or
 b) comprises one or more nuclear localization signals (NLSs).

15. The method of claim 8, wherein the eukaryotic cell is a plant cell, a single-celled eukaryotic organism, a fungal cell, an animal cell, a frog cell, or a fish cell.

16. The method of claim 15, wherein the cell is a mammalian cell.

* * * * *

SEQUENCE LISTING

```
<160> NUMBER OF SEQ ID NOS: 256

<210> SEQ ID NO 1
<211> LENGTH: 33
<212> TYPE: DNA
<213> ORGANISM: Artificial sequence
<220> FEATURE:
<223> OTHER INFORMATION: Synthetic nucleic acid sequence

<400> SEQUENCE: 1
gcccaattta ctactcgttc tggtgtttct cgt                                    33

<210> SEQ ID NO 2
<211> LENGTH: 33
<212> TYPE: DNA
<213> ORGANISM: Artificial sequence
<220> FEATURE:
<223> OTHER INFORMATION: Synthetic nucleic acid sequence

<400> SEQUENCE: 2
acgagaaaca ccagaacgag tagtaaattg ggc                                    33

<210> SEQ ID NO 3
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 3
ggccccagtg ctgcaatgat                                                   20

<210> SEQ ID NO 4
<211> LENGTH: 40
<212> TYPE: DNA
<213> ORGANISM: Artificial sequence
```

```
<220> FEATURE:
<223> OTHER INFORMATION: Synthetic nucleic acid sequence

<400> SEQUENCE: 4
gtgagcgtgg gtctcgcggt atcattgcag cactggggcc                           40

<210> SEQ ID NO 5
<211> LENGTH: 53
<212> TYPE: DNA
<213> ORGANISM: Artificial sequence
<220> FEATURE:
<223> OTHER INFORMATION: Synthetic nucleic acid sequence

<400> SEQUENCE: 5
gcccaattta ctactcgttc tggtgtttct cgtaccgcga gacccacgct cac            53

<210> SEQ ID NO 6
<211> LENGTH: 33
<212> TYPE: DNA
<213> ORGANISM: Artificial sequence
<220> FEATURE:
<223> OTHER INFORMATION: Synthetic nucleic acid sequence

<400> SEQUENCE: 6
acgagaaaca ccagaacgag tagtaaattg ggc                                  33

<210> SEQ ID NO 7
<211> LENGTH: 58
<212> TYPE: DNA
<213> ORGANISM: Artificial sequence
<220> FEATURE:
<223> OTHER INFORMATION: Synthetic nucleic acid sequence

<400> SEQUENCE: 7
aatgatacgg cgaccaccga gatctacact ctttccctac acgacgctct tccgatct       58

<210> SEQ ID NO 8
<211> LENGTH: 57
<212> TYPE: DNA
<213> ORGANISM: Artificial sequence
<220> FEATURE:
<223> OTHER INFORMATION: Synthetic nucleic acid sequence

<400> SEQUENCE: 8
gatcggaaga gcacacgtct gaactccagt cacatctcgt atgccgtctt ctgcttg        57

<210> SEQ ID NO 9
<211> LENGTH: 44
<212> TYPE: DNA
<213> ORGANISM: Artificial sequence
<220> FEATURE:
<223> OTHER INFORMATION: Synthetic nucleic acid sequence

<400> SEQUENCE: 9
aatgatacgg cgaccaccga gatctacact ctttccctac acga                      44

<210> SEQ ID NO 10
<211> LENGTH: 24
<212> TYPE: DNA
<213> ORGANISM: Artificial sequence
<220> FEATURE:
<223> OTHER INFORMATION: Synthetic nucleic acid sequence

<400> SEQUENCE: 10
caagcagaag acggcatacg agat                                            24
```

```
<210> SEQ ID NO 11
<211> LENGTH: 33
<212> TYPE: DNA
<213> ORGANISM: Artificial sequence
<220> FEATURE:
<223> OTHER INFORMATION: Synthetic nucleic acid sequence

<400> SEQUENCE: 11
acgagaaaca ccagaacgag tagtaaattg ggc                              33

<210> SEQ ID NO 12
<211> LENGTH: 33
<212> TYPE: DNA
<213> ORGANISM: Artificial sequence
<220> FEATURE:
<223> OTHER INFORMATION: Synthetic nucleic acid sequence

<400> SEQUENCE: 12
gcccaattta ctactcgttc tggtgtttct cgt                              33

<210> SEQ ID NO 13
<211> LENGTH: 56
<212> TYPE: DNA
<213> ORGANISM: Artificial sequence
<220> FEATURE:
<223> OTHER INFORMATION: Synthetic nucleic acid sequence

<400> SEQUENCE: 13
gtgttccccg cgccagcggg gataaaccgt gttccccgcg ccagcgggga taaacc     56

<210> SEQ ID NO 14
<211> LENGTH: 56
<212> TYPE: DNA
<213> ORGANISM: Artificial sequence
<220> FEATURE:
<223> OTHER INFORMATION: Synthetic nucleic acid sequence

<400> SEQUENCE: 14
ggtttatccc cgctggcgcg gggaacacgg tttatccccg ctggcgcggg gaacac     56

<210> SEQ ID NO 15
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 15
ggccccagtg ctgcaatgat                                             20

<210> SEQ ID NO 16
<211> LENGTH: 40
<212> TYPE: DNA
<213> ORGANISM: Artificial sequence
<220> FEATURE:
<223> OTHER INFORMATION: Synthetic nucleic acid sequence

<400> SEQUENCE: 16
gtgagcgtgg gtctcgcggt atcattgcag cactggggcc                       40

<210> SEQ ID NO 17
<211> LENGTH: 53
<212> TYPE: DNA
<213> ORGANISM: Artificial sequence
<220> FEATURE:
<223> OTHER INFORMATION: Synthetic nucleic acid sequence
```

<400> SEQUENCE: 17
gcccaattta ctactcgttc tggtgtttct cgtaccgcga gacccacgct cac        53

<210> SEQ ID NO 18
<211> LENGTH: 33
<212> TYPE: DNA
<213> ORGANISM: Artificial sequence
<220> FEATURE:
<223> OTHER INFORMATION: Synthetic nucleic acid sequence

<400> SEQUENCE: 18
acgagaaaca ccagaacgag tagtaaattg ggc        33

<210> SEQ ID NO 19
<211> LENGTH: 40
<212> TYPE: DNA
<213> ORGANISM: Artificial sequence
<220> FEATURE:
<223> OTHER INFORMATION: Synthetic nucleic acid sequence

<400> SEQUENCE: 19
ggccccagtg ctgcaatgat accgcgagac ccacgctcac        40

<210> SEQ ID NO 20
<211> LENGTH: 33
<212> TYPE: DNA
<213> ORGANISM: Artificial sequence
<220> FEATURE:
<223> OTHER INFORMATION: Synthetic nucleic acid sequence

<400> SEQUENCE: 20
gcccaattta ctactcgttc tggtgtttct cgt        33

<210> SEQ ID NO 21
<211> LENGTH: 108
<212> TYPE: PRT
<213> ORGANISM: E. coli

<400> SEQUENCE: 21

Glu Pro Ala Pro Ala Arg Arg Ser Val Glu Gln Leu Arg Gly Ile Glu
1               5                   10                  15

Gly Ser Arg Val Arg Ala Thr Tyr Ala Leu Leu Ala Lys Gln Tyr Gly
            20                  25                  30

Val Thr Trp Asn Gly Arg Arg Tyr Asp Asp Thr Ile Asn Gln Cys Ile
        35                  40                  45

Ser Ala Ala Thr Ser Cys Leu Tyr Gly Val Thr Glu Ala Ala Ile Leu
    50                  55                  60

Ala Ala Gly Tyr Ala Pro Ala Ile Gly Phe Val His Thr Gly Lys Pro
65                  70                  75                  80

Leu Ser Phe Val Tyr Asp Ile Ala Asp Ile Ile Lys Phe Asp Thr Val
                85                  90                  95

Val Pro Lys Ala Phe Glu Ile Ala Arg Arg Asn Pro
            100                 105

<210> SEQ ID NO 22
<211> LENGTH: 133
<212> TYPE: PRT
<213> ORGANISM: T. maritima

```
<400> SEQUENCE: 22

Arg Val Lys Arg Ala Asp Ser Leu Thr Arg Tyr Lys Lys Ala Glu
1               5                   10                  15

Glu Ala Ser Asn Val Ser Glu Leu Met Gly Ile Glu Gly Asn Ala Arg
                20                  25                  30

Glu Glu Tyr Tyr Ser Met Ile Asp Ser Leu Val Ser Asp Glu Arg Arg
            35                  40                  45

Pro Pro Lys Asn Phe Ala Asn Thr Leu Ile Ser Phe Gly Asn Ser Leu
        50                  55                  60

Leu Tyr Thr Thr Val Leu Ser Leu Ile Tyr Gln Thr His Leu Asp Pro
65                  70                  75                  80

Arg Ile Gly Tyr Leu His Glu Thr Asn Phe Arg Arg Phe Ser Leu Asn
                85                  90                  95

Leu Asp Ile Ala Glu Leu Phe Lys Pro Ala Val Val Asp Arg Leu Phe
            100                 105                 110

Leu Asn Leu Val Asn Thr Arg Gln Ile Asn Glu Lys His Phe Asp Glu
        115                 120                 125

Ile Ser Glu Gly Leu
        130

<210> SEQ ID NO 23
<211> LENGTH: 126
<212> TYPE: PRT
<213> ORGANISM: P. horikoshii

<400> SEQUENCE: 23

Trp Gly Ile Lys Ala Lys Leu Ser Asp Tyr Leu Asp Glu Leu Asn Asp
1               5                   10                  15

Ala Arg Lys Ile Thr Glu Ile Met Asn Val Glu Ala Arg Ile Arg Gln
                20                  25                  30

Glu Tyr Tyr Ala Lys Trp Asp Glu Asn Leu Pro Lys Asn Glu Met Asn
            35                  40                  45

Ala Leu Ile Ser Phe Leu Asn Ser Arg Leu Tyr Ala Thr Ile Ile Thr
        50                  55                  60

Glu Ile Tyr Asn Thr Gln Leu Ala Pro Thr Ile Ser Tyr Leu His Glu
65                  70                  75                  80

Pro Ser Glu Arg Arg Phe Ser Leu Ser Leu Asp Leu Ser Glu Ile Phe
                85                  90                  95

Lys Pro Ile Ile Ala Asp Arg Val Ala Asn Arg Leu Val Lys Lys Gly
            100                 105                 110

Ser Leu Lys Lys Glu His Phe Arg Glu Asp Leu Asn Gly Val
        115                 120                 125

<210> SEQ ID NO 24
<211> LENGTH: 125
<212> TYPE: PRT
<213> ORGANISM: P. aeolicus

<400> SEQUENCE: 24

Ser Ala Asp Thr Tyr Leu Asn Lys Val Lys Glu Thr Asn Ser Ile Pro
1               5                   10                  15

Glu Leu Met Ser Val Glu Ala Glu Phe Arg Lys Leu Cys Tyr Lys Lys
                20                  25                  30

Leu Glu Glu Val Thr Gly Trp Glu Leu Glu Pro Pro Gln Asn Pro Leu
            35                  40                  45
```

Asn Ala Leu Ile Ser Phe Gly Asn Ser Leu Thr Tyr Ala Lys Val Leu
 50                  55                  60

Gly Glu Ile Tyr Lys Thr Gln Leu Asn Pro Thr Val Ser Tyr Leu His
 65                  70                  75                  80

Glu Pro Ser Arg Phe Ser Leu Ser Leu Asp Val Ala Glu Val Phe Lys
                 85                  90                  95

Pro Ile Phe Val Asp Asn Leu Ile Ile Arg Leu Ile Gln Glu Asn Lys
             100                 105                 110

Ile Asp Lys Thr His Phe Ser Thr Glu Leu Asn Met Thr
         115                 120                 125

<210> SEQ ID NO 25
<211> LENGTH: 136
<212> TYPE: PRT
<213> ORGANISM: P. aeruginosa

<400> SEQUENCE: 25

Arg Val Leu Arg Asp Ala Gly Phe Ala Val Asp Ala Thr Ala Leu Ala
  1               5                  10                  15

Val Ala Val Glu Asp Ser Ala Arg Ala Leu Glu Gln Ala Pro Asn His
             20                  25                  30

Glu His Leu Leu Thr Glu Glu Ala Arg Leu Ser Lys Arg Leu Phe Lys
         35                  40                  45

Leu Ala Ala Gln Ala Thr Arg Tyr Gly Glu Phe Val Arg Ala Lys Arg
 50                  55                  60

Gly Ser Gly Gly Asp Pro Ala Asn Arg Phe Leu Asp His Gly Asn Tyr
 65                  70                  75                  80

Leu Ala Tyr Gly Leu Ala Ala Thr Ala Thr Trp Val Leu Gly Ile Pro
                 85                  90                  95

His Gly Leu Ala Val Leu His Gly Lys Thr Arg Arg Gly Gly Leu Val
             100                 105                 110

Phe Asp Val Ala Asp Leu Ile Lys Asp Ser Leu Ile Leu Pro Gln Ala
         115                 120                 125

Phe Leu Ser Ala Met Arg Gly Asp
 130                 135

<210> SEQ ID NO 26
<211> LENGTH: 100
<212> TYPE: DNA
<213> ORGANISM: Artificial sequence
<220> FEATURE:
<223> OTHER INFORMATION: Synthetic nucleic acid sequence

<400> SEQUENCE: 26
tttagagtgt tccccgcgcc agcggggata aaccgagcac aaatatcatc gctcaaacca      60
cttacgggtg ttccccgcgc cagcggggat aaaccgcctc                           100

<210> SEQ ID NO 27
<211> LENGTH: 100
<212> TYPE: DNA
<213> ORGANISM: Artificial sequence
<220> FEATURE:
<223> OTHER INFORMATION: Synthetic nucleic acid sequence

<400> SEQUENCE: 27
gaggcggttt atccccgctg gcgcggggaa caccgtaag tggtttgagc gatgatattt       60
gtgctcggtt tatccccgct ggcgcgggga acactctaaa                          100

<210> SEQ ID NO 28
<211> LENGTH: 316
<212> TYPE: PRT
<213> ORGANISM: Aquifex aeolicus

<400> SEQUENCE: 28

Met Gly Arg Val Tyr Tyr Ile Asn Ser His Gly Thr Leu Ser Arg His
1               5                   10                  15

Glu Asn Thr Leu Arg Phe Glu Asn Ala Glu Val Lys Lys Asp Ile Pro
            20                  25                  30

Val Glu Asp Val Glu Glu Ile Phe Val Phe Ala Glu Leu Ser Leu Asn
        35                  40                  45

Thr Lys Leu Leu Asn Phe Leu Ala Ser Lys Gly Ile Pro Leu His Phe
50                  55                  60

Phe Asn Tyr Tyr Gly Tyr Tyr Thr Gly Thr Phe Tyr Pro Arg Glu Ser
65                  70                  75                  80

Ser Val Ser Gly His Leu Leu Ile Lys Gln Val Glu His Tyr Leu Asp
                85                  90                  95

Ala Gln Lys Arg Leu Tyr Leu Ala Lys Ser Phe Val Ile Gly Ser Ile
            100                 105                 110

Leu Asn Leu Glu Tyr Val Tyr Lys Ile Ser Ala Asp Thr Tyr Leu Asn
        115                 120                 125

Lys Val Lys Glu Thr Asn Ser Ile Pro Glu Leu Met Ser Val Glu Ala
130                 135                 140

Glu Phe Arg Lys Leu Cys Tyr Lys Lys Leu Glu Glu Val Thr Gly Trp
145                 150                 155                 160

Glu Leu Glu Lys Arg Thr Lys Arg Pro Pro Gln Asn Pro Leu Asn Ala
                165                 170                 175

Leu Ile Ser Phe Gly Asn Ser Leu Thr Tyr Ala Lys Val Leu Gly Glu
            180                 185                 190

Ile Tyr Lys Thr Gln Leu Asn Pro Thr Val Ser Tyr Leu His Glu Pro
        195                 200                 205

Ser Thr Lys Arg Phe Ser Leu Ser Leu Asp Val Ala Glu Val Phe Lys
210                 215                 220

Pro Ile Phe Val Asp Asn Leu Ile Ile Arg Leu Ile Gln Glu Asn Lys
225                 230                 235                 240

Ile Asp Lys Thr His Phe Ser Thr Glu Leu Asn Met Thr Phe Leu Asn
                245                 250                 255

Glu Ile Gly Arg Lys Val Phe Leu Lys Ala Phe Asn Glu Leu Leu Glu
            260                 265                 270

Thr Thr Ile Phe Tyr Pro Lys Leu Asn Arg Lys Val Ser His Arg Thr
        275                 280                 285

Leu Ile Lys Leu Glu Leu Tyr Lys Leu Ile Lys His Leu Leu Glu Glu
290                 295                 300

Glu Val Tyr Leu Pro Leu Asn Tyr Gly Gly Leu Lys
305                 310                 315

<210> SEQ ID NO 29
<211> LENGTH: 345
<212> TYPE: PRT
<213> ORGANISM: Archaeoglobus fulgidus

<400> SEQUENCE: 29

```
Met Arg Leu Val Val Asp Gly Phe Gly Lys Tyr Leu Gly Ile Glu Asn
1               5                   10                  15

Gly Leu Ile Val Val Lys Glu Lys Gly Lys Ala Leu Arg Lys Val Arg
            20                  25                  30

Pro Glu Asp Leu Lys Gln Val Leu Ile Ile Gly Lys Ala Ala Ile Ser
        35                  40                  45

Ser Asp Ala Ile Lys Leu Leu Lys Asn Arg Val Asp Val Val Phe
    50                  55                  60

Leu Asp Phe Asn Gly Glu Ile Leu Gly Arg Leu Ser His Pro Leu Ile
65                  70                  75                  80

Gly Thr Ala Lys Thr Arg Arg Glu Gln Tyr Leu Ala Tyr Gly Asp Lys
                85                  90                  95

Arg Gly Val His Leu Ala Lys Glu Phe Ile Lys Ala Lys Met Ala Asn
            100                 105                 110

Gln Met Ala Ile Leu Thr Asn Leu Ala Lys Ala Arg Lys Asp Ser Asn
        115                 120                 125

Pro Glu Val Ala Glu Ser Leu Leu Lys Ala Lys Lys Glu Ile Asp Ala
    130                 135                 140

Cys Leu Asn Glu Leu Asp Gly Val Glu Ala Glu Met Ile Asp Lys Val
145                 150                 155                 160

Arg Glu Arg Leu Leu Gly Ile Glu Gly Lys Ala Ser Lys His Tyr Trp
                165                 170                 175

Asp Ala Ile Ser Leu Val Ile Pro Glu Glu Tyr Arg Phe Asn Gly Arg
            180                 185                 190

Arg Gly Ile Glu Ile Gly Ser Pro Arg Tyr Ala Lys Asp Ile Val Asn
        195                 200                 205

Ala Met Leu Asn Tyr Gly Tyr Ser Ile Leu Leu Ala Glu Cys Val Lys
    210                 215                 220

Ala Val Glu Leu Ala Gly Leu Asp Pro Tyr Ala Gly Phe Leu His Val
225                 230                 235                 240

Asp Val Ser Gly Arg Ser Ser Leu Ala Ile Asp Leu Met Glu Asn Phe
                245                 250                 255

Arg Gln Gln Val Val Asp Arg Val Leu Arg Leu Ile Ser Tyr Arg
            260                 265                 270

Gln Ile Lys Pro Glu Asp Cys Glu Lys Arg Asn Met Val Cys Gln Leu
        275                 280                 285

Ser Asp Asn Ala Arg Arg Leu Leu Leu Ala Ser Leu Leu Glu Arg Leu
    290                 295                 300

Asp Ser Lys Thr Gln Tyr Arg Gly Arg Asn Leu Ala Tyr Ser Ser Ile
305                 310                 315                 320

Ile Leu Leu His Ala Arg Asp Val Val Ala Phe Leu Arg Gly Glu Arg
                325                 330                 335

Arg Tyr Glu Gly Phe Val Gln Lys Trp
            340                 345
```

<210> SEQ ID NO 30
<211> LENGTH: 322
<212> TYPE: PRT
<213> ORGANISM: Archaeoglobus fulgidus

<400> SEQUENCE: 30

```
Met Arg Lys Lys Asn Tyr Tyr Leu Val Ser Asp Gly Lys Leu Arg Arg
1               5                   10                  15

His Glu Asn Thr Ile Tyr Phe Glu Asn Glu Asp Gly Lys Arg Pro Ile
            20                  25                  30

Pro Ile Asn Ser Ile Tyr Ala Ile Tyr Ala Leu Gly Ser Leu Ser Ile
        35                  40                  45

Thr Ser Lys Ala Ile Ser Leu Leu Ala Lys Glu Gly Val Cys Ile His
    50                  55                  60

Phe Phe Asn Arg Tyr Gly Tyr Tyr Ile Gly Ser Phe Tyr Pro Arg Glu
65                  70                  75                  80

Ser Leu Val Ser Gly Glu Val Val Leu Arg Gln Ala Glu His His Leu
                85                  90                  95

Asp Ser Glu Lys Arg Leu His Leu Ala Arg Ala Phe Val Glu Gly Ala
            100                 105                 110

Ile Leu Asn Met Ala Arg Val Leu Lys Lys Ala Glu Gln Asp Asp Ser
        115                 120                 125

Asp Val Ile Ala Ser Leu Gln His Leu Ser Ser Ala Lys Ser Ile Val
    130                 135                 140

Glu Leu Met Gly Ala Glu Ala Ala Arg Asn Ala Tyr Tyr Thr Lys
145                 150                 155                 160

Phe Asp Glu Ile Leu Lys Asn Phe Glu Phe Gly Lys Arg Ser Arg Met
                165                 170                 175

Pro Pro Glu Asn Glu Val Asn Ala Met Ile Ser Phe Gly Asn Ser Leu
            180                 185                 190

Leu Tyr Ser Ala Val Leu Ser Glu Ile Tyr His Thr Gln Leu Asn Pro
        195                 200                 205

Ala Ile Ser Tyr Leu His Glu Pro Ser Glu Arg Arg Phe Ser Leu Ala
    210                 215                 220

Leu Asp Ile Ala Glu Leu Phe Lys Pro Val Ile Val Asp Arg Leu Ile
225                 230                 235                 240

Phe Tyr Leu Val Asn Asn Gly Ile Val Thr Glu Ser Asp Phe Asp Ser
                245                 250                 255

Arg Leu Gly Gly Ile Leu Leu Ser Glu Gly Lys Lys Lys Phe Val
            260                 265                 270

Arg His Phe Asn Glu Arg Leu Glu Lys Thr Val Lys His Arg Lys Leu
        275                 280                 285

Asn Arg Lys Val Ser Tyr Gln Arg Leu Ile Arg Leu Glu Cys Tyr Lys
    290                 295                 300

Leu Val Lys His Phe Thr Ala Val Glu Lys Tyr Ser Pro Phe Val Met
305                 310                 315                 320

Trp Trp
```

<210> SEQ ID NO 31
<211> LENGTH: 296
<212> TYPE: PRT
<213> ORGANISM: Campylobacter jejuni

<400> SEQUENCE: 31

```
Met Ser Tyr Asp Glu Ala Phe Lys Thr Leu Leu Ile Ser Ser Asn Ala
1               5                   10                  15

Lys Leu Asn Leu Glu Leu Asn His Leu Val Ile Lys Gln Asp Glu Asn
            20                  25                  30
```

```
Ile Ala Lys Leu Phe Leu Lys Asp Ile Asn Ile Ile Val Leu Glu Ser
         35                  40                  45

Leu Gln Val Ser Ile Ser Ser Ala Leu Phe Asn Ala Phe Ala Arg His
 50                  55                  60

Lys Ile Ile Leu Leu Thr Cys Asp Glu Thr His Ser Ile Asn Gly Val
 65                  70                  75                  80

Phe Thr Pro Phe Leu Gly His Phe Gln Ser Ala Lys Ile Ala Lys Glu
                 85                  90                  95

Gln Met Asn Val Ser Ala Gln Lys Lys Ala Ile Leu Trp Gln Lys Ile
                100                 105                 110

Ile Lys Asn Lys Ile Leu Asn Gln Ala Phe Ile Leu Lys Lys Tyr Asn
            115                 120                 125

Lys Ile Glu Gln Ser Asn Glu Leu Ile Asn Leu Ala Lys Lys Val Ser
        130                 135                 140

Leu Asn Asp Ser Lys Asn Ile Glu Ala Val Ala Ala Leu Tyr Phe
145                 150                 155                 160

Lys Thr Leu Phe Gly Thr Ser Phe Ser Arg Asp Glu Leu Cys Phe Glu
                165                 170                 175

Asn Ser Ala Leu Asn Tyr Gly Tyr Ala Ile Ile Arg Ala Cys Ile Ile
                180                 185                 190

Arg Ala Val Cys Ile Ser Gly Leu Leu Pro Trp Leu Gly Ile Lys His
        195                 200                 205

Asp Asn Ile Tyr Asn Ser Phe Ala Leu Cys Asp Asp Leu Ile Glu Val
    210                 215                 220

Phe Arg Ala Ser Val Asp Asp Cys Val Leu Lys Leu Lys Gly Glu Ser
225                 230                 235                 240

Glu Phe Leu Ser Lys Asp Asp Lys Arg Ala Leu Ile Gly Asn Leu Gln
                245                 250                 255

Ser Lys Ile Asn Phe Asp Gly Gln Asn Tyr Pro Leu Asn Arg Ala Ile
                260                 265                 270

Asn His Tyr Val Ala Asn Phe Lys Asn Ala Leu Leu Tyr Glu Asp Glu
            275                 280                 285

Leu Lys Ile Val Lys Phe Asp Asp
    290                 295

<210> SEQ ID NO 32
<211> LENGTH: 296
<212> TYPE: PRT
<213> ORGANISM: Chlorobium tepidum

<400> SEQUENCE: 32

Met Lys Ser Asn Thr Leu Gly Asp Glu Gly Asn Pro Ala Arg Leu Leu
 1               5                  10                  15

Ile Lys Val Thr Arg Glu Thr Leu Pro Gln Val Lys Glu Lys Tyr Pro
                 20                  25                  30

Phe Leu Tyr Leu Glu Lys Gly Arg Ile Glu Ile Asp Asp Ser Ser Ile
             35                  40                  45

Lys Trp Ile Asp Cys Asp Cys Asn Val Val Arg Leu Pro Val Ala Met
 50                  55                  60

Leu Asn Cys Ile Leu Leu Gly Pro Gly Thr Thr Val Thr His Glu Ala
 65                  70                  75                  80

Val Lys Val Met Ala Ala Ala Asn Cys Gly Ile Cys Trp Val Gly Asp
                 85                  90                  95

Asp Ser Leu Met Phe Tyr Ala Ser Gly Gln Thr Pro Thr Ser Asn Thr
                100                 105                 110
```

```
Arg Asn Met Thr His Gln Met Lys Leu Ala Ala Asn Pro Ala Lys Ala
            115                 120                 125

Leu Glu Val Ala Arg Arg Leu Phe Ala Tyr Arg Phe Pro Asp Ala Asn
        130                 135                 140

Leu Glu Asn Lys Thr Leu Pro Gln Met Met Gly Met Glu Gly Leu Arg
145                 150                 155                 160

Val Arg Lys Leu Tyr Glu Met Ala Val Lys Tyr Lys Val Gly Trp
                165                 170                 175

Lys Gly Arg Arg Phe Glu Pro Gly Lys Phe Glu Met Ser Asp Thr Thr
            180                 185                 190

Asn Lys Ile Leu Thr Ala Ser Asn Ala Ala Leu Tyr Ser Ile Ile Leu
        195                 200                 205

Ser Ala Val His Ser Met Gly Tyr Ser Pro His Ile Gly Phe Ile His
        210                 215                 220

Ser Gly Ser Pro Leu Pro Phe Ile Tyr Asp Leu Ala Asp Leu Tyr Lys
225                 230                 235                 240

Gln Gln Val Ser Ile Asp Leu Ala Phe Ser Leu Thr Ala Asp Met Ala
                245                 250                 255

Gly Tyr Tyr Asp Arg His Lys Ile Ala Ser Glu Phe Arg Lys Arg Val
            260                 265                 270

Ile Glu Ile Asp Leu Leu Gly Lys Ile Gly Pro Asp Ile Glu Thr Ile
        275                 280                 285

Leu Gly Lys Lys Gln Cys Ser Ser
        290                 295

<210> SEQ ID NO 33
<211> LENGTH: 343
<212> TYPE: PRT
<213> ORGANISM: Chlorobium tepidum

<400> SEQUENCE: 33

Met Lys Lys His Leu Asn Thr Leu Phe Val Thr Thr Gln Gly Ser Tyr
1               5                   10                  15

Leu Ser Lys Glu Gly Glu Cys Val Leu Ile Ser Ile Asp Arg Val Glu
            20                  25                  30

Lys Thr Arg Ile Pro Leu His Met Leu Asn Gly Ile Val Cys Phe Gly
        35                  40                  45

Gln Val Ser Cys Ser Pro Phe Leu Leu Gly His Cys Ala Gln Leu Gly
    50                  55                  60

Val Ala Val Thr Phe Leu Thr Glu His Gly Arg Phe Leu Cys Gln Met
65                  70                  75                  80

Gln Gly Pro Val Lys Gly Asn Ile Leu Leu Arg Arg Ala Gln Tyr Arg
                85                  90                  95

Met Ala Asp Asn Tyr Asp Gln Thr Ala Thr Leu Ala Arg Leu Phe Val
            100                 105                 110

Ile Gly Lys Ile Gly Asn Ala Arg Val Thr Leu Ala Arg Ala Leu Arg
        115                 120                 125

Asp His Pro Glu Lys Thr Asp Gly Glu Lys Leu Lys Asn Ala Gln His
    130                 135                 140

Val Leu Ala Gly Cys Ile Arg Arg Leu Gln Glu Ala Thr Asp Gln Glu
145                 150                 155                 160

Leu Ile Arg Gly Ile Glu Gly Glu Ala Ala Lys Ala Tyr Phe Ser Val
                165                 170                 175

Phe Asp Glu Cys Ile Thr Ala Asp Pro Ala Phe Arg Phe Glu Gly
            180                 185                 190
```

```
Arg Ser Arg Arg Pro Pro Leu Asp Arg Val Asn Cys Leu Ser Phe
            195                 200                 205
Val Tyr Thr Leu Met Thr His Asp Ile Arg Ser Ala Leu Glu Ser Cys
210                 215                 220
Gly Leu Asp Pro Ala Ala Gly Phe Leu His Lys Asp Arg Pro Gly Arg
225                 230                 235                 240
Pro Ser Leu Ala Leu Asp Met Leu Glu Glu Phe Arg Ser Tyr Ile Gly
                245                 250                 255
Asp Arg Leu Val Leu Ser Leu Ile Asn Arg Gly Gln Ile His Ala Lys
                260                 265                 270
Asp Phe Asp Ile Ser Glu Thr Gly Ala Val Ala Met Lys Asp Asp Ala
            275                 280                 285
Arg Lys Thr Leu Ile Thr Ala Tyr Gln Gln Arg Lys Gln Glu Glu Ile
            290                 295                 300
Glu His Pro Phe Val Gly Glu Lys Met Ala Val Gly Leu Leu Trp His
305                 310                 315                 320
Met Gln Ala Met Leu Leu Ala Arg Tyr Ile Arg Gly Asp Ile Asp Met
                325                 330                 335
Tyr Pro Pro Phe Val Trp Arg
                340

<210> SEQ ID NO 34
<211> LENGTH: 330
<212> TYPE: PRT
<213> ORGANISM: Clostridium perfringens

<400> SEQUENCE: 34

Met Gly Arg Asp Tyr Tyr Ile Phe Ser Asn Gly Arg Ile Lys Arg Lys
1               5                   10                  15
Glu Asn Thr Ile Tyr Phe Glu Asp Phe Glu Gly Asn Lys Lys Gly Leu
                20                  25                  30
Pro Ile Glu Asp Ile Glu Arg Leu His Ile Phe Gly Glu Val Asp Leu
            35                  40                  45
Asn Thr Lys Phe Leu Asn Tyr Ile Ser Arg Tyr Ser Val Leu Ile Ser
50                  55                  60
Ile Tyr Asn Tyr Tyr Gly Phe Tyr Ser Gly Ser Tyr Tyr Ser Lys Lys
65                  70                  75                  80
Lys Asn Val Ser Gly Val Leu Leu Val Asn Gln Ala Leu Ala Tyr Asp
                85                  90                  95
Asn Tyr Glu Phe Arg Val Ala Ile Ala Lys Thr Phe Ile Asp Ser Ala
                100                 105                 110
Met His His Ile Leu Arg Asn Leu Arg Arg Tyr Lys Glu Lys Thr Ser
            115                 120                 125
Glu Phe Val Lys Ala Ile Glu Asn Glu Arg Lys Ile Met Lys Glu Ala
130                 135                 140
Lys Thr Ile Glu Glu Val Met Gly Ala Glu Gly Arg Ala Arg Lys Lys
145                 150                 155                 160
Tyr Tyr Glu Ser Tyr Asn Ala Phe Leu Lys Phe Leu Lys Asn Asp Phe
                165                 170                 175
His Phe Asn Lys Arg Glu Lys Lys Pro Pro Asn Asp Pro Ile Asn Ala
                180                 185                 190
Leu Ile Ser Phe Gly Asn Ser Met Met Tyr Thr Thr Val Leu Gly Glu
            195                 200                 205
Ile Tyr Lys Thr Gln Leu Asp Pro Thr Ile Ser Tyr Leu His Glu Pro
210                 215                 220
```

```
Ser Thr Lys Arg Phe Ser Leu Ser Leu Asp Leu Ala Glu Ile Phe Lys
225                 230                 235                 240

Pro Leu Ile Val Asp Ser Val Ile Phe Asn Met Ile Asn Lys Gly Met
            245                 250                 255

Ile Lys Lys Ser Asp Phe Asp Thr Asp Glu Gly Ile Cys Tyr Leu Asn
        260                 265                 270

Glu Asn Gly Arg Lys Lys Phe Ile Lys Glu Tyr Glu Asn Lys Leu Ser
    275                 280                 285

Thr Thr Val Arg His Arg Thr Leu Asn Arg Asn Val Ser Tyr Arg Glu
290                 295                 300

Leu Ile Arg Leu Glu Cys Tyr Lys Leu Ile Lys Met Leu Leu Gly Asp
305                 310                 315                 320

Glu Asp Tyr Lys Pro Leu Lys Ala Trp Trp
                325                 330

<210> SEQ ID NO 35
<211> LENGTH: 301
<212> TYPE: PRT
<213> ORGANISM: Clostridium sp.

<400> SEQUENCE: 35

Met Pro Arg Ile Ser Asp Arg Val Thr Tyr Ile Tyr Val Glu His Ser
1               5                   10                  15

Lys Ile Asn Arg Val Asp Gly Ser Ile Thr Val Ala Glu Ser Arg Gly
            20                  25                  30

Ile Val Arg Ile Pro Ala Ser Met Ile Gly Ile Leu Leu Leu Gly Pro
        35                  40                  45

Gly Thr Asp Ile Ser His Arg Ala Met Glu Leu Leu Gly Asp Ser Gly
    50                  55                  60

Thr Ser Val Ala Trp Val Gly Glu Gln Gly Val Arg Asn Tyr Ala His
65                  70                  75                  80

Gly Arg Ser Leu Ser His Thr Ser Arg Phe Leu Glu Leu Gln Ala Lys
                85                  90                  95

Leu Val Ser Asn Thr Arg Ser Arg Leu Gln Val Ala Arg Lys Met Tyr
            100                 105                 110

Gln Met Arg Phe Pro Glu Glu Asp Val Ser Ser Leu Thr Met Gln Gln
        115                 120                 125

Leu Arg Ala Lys Glu Gly Ala Arg Ile Arg Lys Ile Tyr Arg Lys Met
    130                 135                 140

Ser Ala Glu Tyr Gly Val Asp Trp Asn Gly Arg Thr Tyr Asp Pro Asp
145                 150                 155                 160

Asp Phe Glu Gly Gly Asp Pro Val Asn Gln Ala Leu Ser Ala Ala Asn
                165                 170                 175

Val Ala Leu Tyr Gly Leu Ala Tyr Ser Ala Ile Ala Ala Met Gly Leu
            180                 185                 190

Ala Thr Gly Leu Gly Phe Val His Thr Gly His Asp Leu Ser Phe Val
        195                 200                 205

Tyr Asp Ile Ala Asp Leu Tyr Lys Ala Asp Ile Thr Val Pro Val Ala
    210                 215                 220

Phe Glu Ile Ala Ser Glu Tyr Glu Glu Gly Asp Asn Val Gly Lys Ile
225                 230                 235                 240

Ser Arg Gln Lys Val Arg Asp Lys Phe Ile Gly Gly Lys Leu Phe Ala
                245                 250                 255

Thr Ile Val Arg Asp Ile Gln Leu Leu Phe Gly Ile Lys Glu Glu Glu
            260                 265                 270
```

```
Gln Leu Asn Val Glu Pro Leu Ser Leu Trp Asp Asn Arg Glu Gly Asn
            275                 280                 285
Ile Lys Tyr Gly Ile Asn Tyr Ser Asn Glu Asn Glu Asp
        290                 295                 300

<210> SEQ ID NO 36
<211> LENGTH: 343
<212> TYPE: PRT
<213> ORGANISM: Desulfovibrio vulgaris

<400> SEQUENCE: 36

Met Lys Lys Leu Leu Asn Thr Leu Tyr Val Thr Thr Gln Gly Thr Tyr
1               5                   10                  15
Leu Ala Lys Glu Gly Glu Cys Ile Val Val Arg Val Gly Asp Glu Val
                20                  25                  30
Arg Leu Arg Val Pro Val His Ser Leu Gly Gly Val Val Cys Phe Gly
            35                  40                  45
Gln Val Ser Cys Ser Pro Phe Leu Met Gly Phe Ala Ala Glu Arg Gly
        50                  55                  60
Leu Gly Phe Ser Phe Leu Thr Glu His Gly Arg Phe Leu Ala Arg Val
65                  70                  75                  80
Gln Gly Pro Val Ser Gly Asn Val Leu Leu Arg Arg Glu Gln Tyr Arg
                85                  90                  95
Arg Ala Asp Ser Pro Glu Ala Ser Ala Glu Val Ala Arg Ser Ile Val
            100                 105                 110
Ser Ala Lys Val Val Asn Ala Arg Gly Val Leu Gln Arg Ala Met Arg
        115                 120                 125
Asp His Gly Asp Lys Val Asp Gly Val Ala Leu Glu Ala Glu Val Leu
130                 135                 140
His Leu Arg Ala Cys Leu Met Arg Leu Gln Gln Pro Ala Gly Leu Asp
145                 150                 155                 160
Ala Val Arg Gly Ile Glu Gly Glu Ala Ala Lys Gly Tyr Phe Ser Val
                165                 170                 175
Phe Asp Asn Leu Ile Leu Thr Arg Glu Ala Ala Phe Arg Phe Glu Gly
            180                 185                 190
Arg Ser Arg Arg Pro Pro Leu Asp Arg Val Asn Cys Leu Leu Ser Phe
        195                 200                 205
Ile Tyr Thr Leu Leu Gly His Asp Val Arg Ser Ala Leu Glu Gly Val
210                 215                 220
Gly Leu Asp Ser Ala Val Gly Phe Leu His Arg Asp Arg Pro Gly Arg
225                 230                 235                 240
His Gly Leu Ala Leu Asp Val Met Glu Glu Phe Arg Ala Val Val Ala
                245                 250                 255
Asp Arg Leu Ala Leu Ser Leu Ile Asn Leu Gly Lys Leu Lys Lys Ser
            260                 265                 270
Asp Phe Glu Ile Gln Glu Thr Gly Ala Val Arg Met Thr Asp Asp Ala
        275                 280                 285
Arg Lys Ala Leu Leu Val Ala Tyr Gln Lys Arg Lys Gln Asp Glu Ile
        290                 295                 300
Val His Pro Phe Leu Asn Glu Arg Ile Pro Leu Gly Leu Val Phe His
305                 310                 315                 320
Val Gln Ala Met Leu Met Ala Arg Trp Leu Arg Gly Asp Leu Asp Gly
                325                 330                 335
Tyr Pro Pro Phe Val Trp Lys
            340
```

```
<210> SEQ ID NO 37
<211> LENGTH: 305
<212> TYPE: PRT
<213> ORGANISM: Escherichia coli

<400> SEQUENCE: 37

Met Thr Trp Leu Pro Leu Asn Pro Ile Pro Leu Lys Asp Arg Val Ser
 1               5                  10                  15

Met Ile Phe Leu Gln Tyr Gly Gln Ile Asp Val Ile Asp Gly Ala Phe
                20                  25                  30

Val Leu Ile Asp Lys Thr Gly Ile Arg Thr His Ile Pro Val Gly Ser
            35                  40                  45

Val Ala Cys Ile Met Leu Glu Pro Gly Thr Arg Val Ser His Ala Ala
        50                  55                  60

Val Arg Leu Ala Ala Gln Val Gly Thr Leu Leu Val Trp Val Gly Glu
 65                  70                  75                  80

Ala Gly Val Arg Val Tyr Ala Ser Gly Gln Pro Gly Gly Ala Arg Ser
                85                  90                  95

Asp Lys Leu Leu Tyr Gln Ala Lys Leu Ala Leu Asp Glu Asp Leu Arg
            100                 105                 110

Leu Lys Val Val Arg Lys Met Phe Glu Leu Arg Phe Gly Glu Pro Ala
        115                 120                 125

Pro Ala Arg Arg Ser Val Glu Gln Leu Arg Gly Ile Glu Gly Ser Arg
130                 135                 140

Val Arg Ala Thr Tyr Ala Leu Leu Ala Lys Gln Tyr Gly Val Thr Trp
145                 150                 155                 160

Asn Gly Arg Arg Tyr Asp Pro Lys Asp Trp Glu Lys Gly Asp Thr Ile
                165                 170                 175

Asn Gln Cys Ile Ser Ala Ala Thr Ser Cys Leu Tyr Gly Val Thr Glu
            180                 185                 190

Ala Ala Ile Leu Ala Ala Gly Tyr Ala Pro Ala Ile Gly Phe Val His
        195                 200                 205

Thr Gly Lys Pro Leu Ser Phe Val Tyr Asp Ile Ala Asp Ile Ile Lys
210                 215                 220

Phe Asp Thr Val Val Pro Lys Ala Phe Glu Ile Ala Arg Arg Asn Pro
225                 230                 235                 240

Gly Glu Pro Asp Arg Glu Val Arg Leu Ala Cys Arg Asp Ile Phe Arg
                245                 250                 255

Ser Ser Lys Thr Leu Ala Lys Leu Ile Pro Leu Ile Glu Asp Val Leu
            260                 265                 270

Ala Ala Gly Glu Ile Gln Pro Pro Ala Pro Glu Asp Ala Gln Pro
        275                 280                 285

Val Ala Ile Pro Leu Pro Val Ser Leu Gly Asp Ala Gly His Arg Ser
    290                 295                 300

Ser
305

<210> SEQ ID NO 38
<211> LENGTH: 305
<212> TYPE: PRT
<213> ORGANISM: Escherichia coli
```

<400> SEQUENCE: 38

Met Thr Trp Leu Pro Leu Asn Pro Ile Pro Leu Lys Asp Arg Val Ser
1               5                   10                  15

Met Ile Phe Leu Gln Tyr Gly Gln Ile Asp Val Ile Asp Gly Ala Phe
            20                  25                  30

Val Leu Ile Asp Lys Thr Gly Ile Arg Thr His Ile Pro Val Gly Ser
        35                  40                  45

Val Ala Cys Ile Met Leu Glu Pro Gly Thr Arg Val Ser His Ala Ala
    50                  55                  60

Val Arg Leu Ala Ala Gln Val Gly Thr Leu Leu Val Trp Val Gly Glu
65                  70                  75                  80

Ala Gly Val Arg Val Tyr Ala Ser Gly Gln Pro Gly Gly Ala Arg Ser
                85                  90                  95

Asp Lys Leu Leu Tyr Gln Ala Lys Leu Ala Leu Asp Glu Asp Leu Arg
            100                 105                 110

Leu Lys Val Val Arg Lys Met Phe Glu Leu Arg Phe Gly Glu Pro Ala
        115                 120                 125

Pro Ala Arg Arg Ser Val Glu Gln Leu Arg Gly Ile Glu Gly Ser Arg
    130                 135                 140

Val Arg Ala Thr Tyr Ala Leu Leu Ala Lys Gln Tyr Gly Val Thr Trp
145                 150                 155                 160

Asn Gly Arg Arg Tyr Asp Pro Lys Asp Trp Glu Lys Gly Asp Thr Ile
                165                 170                 175

Asn Gln Cys Ile Ser Ala Ala Thr Ser Cys Leu Tyr Gly Val Thr Glu
            180                 185                 190

Ala Ala Ile Leu Ala Ala Gly Tyr Ala Pro Ala Ile Gly Phe Val His
        195                 200                 205

Thr Gly Lys Pro Leu Ser Phe Val Tyr Asp Ile Ala Asp Ile Ile Lys
    210                 215                 220

Phe Asp Thr Val Val Pro Lys Ala Phe Glu Ile Ala Arg Arg Asn Pro
225                 230                 235                 240

Gly Glu Pro Asp Arg Glu Val Arg Leu Ala Cys Arg Asp Ile Phe Arg
                245                 250                 255

Ser Ser Lys Thr Leu Ala Lys Leu Ile Pro Leu Ile Glu Asp Val Leu
            260                 265                 270

Ala Ala Gly Glu Ile Gln Pro Pro Ala Pro Pro Glu Asp Ala Gln Pro
        275                 280                 285

Val Ala Ile Pro Leu Pro Val Ser Leu Gly Asp Ala Gly His Arg Ser
    290                 295                 300

Ser
305

<210> SEQ ID NO 39
<211> LENGTH: 244
<212> TYPE: PRT
<213> ORGANISM: Francisella novicida

<400> SEQUENCE: 39

Met Leu Val Gly Ala Asn Gln His Ala Val Val Gln Ala Arg Ile Asn
1               5                   10                  15

Gln Tyr Arg Tyr Ile His Glu Asn Ala Leu Ala Leu Ser Thr Lys Leu
            20                  25                  30

Ile Ile Ala Lys Ile Lys Asn Gln Arg Ala Thr Leu Ser Tyr Phe Asn
        35                  40                  45

```
Lys His His Lys Ser Val Asn Leu Leu Asn Ala Ile Glu Glu Leu Lys
    50                  55                  60

Arg Ile Ala Gln Leu Ile Lys Asn Ala Lys Thr Leu Asn Asp Val Leu
 65                  70                  75                  80

Gly Tyr Glu Gly Tyr Ala Ala Asn Ile Tyr Phe Ser Ser Leu Ala Arg
                 85                  90                  95

Asp Lys Phe Leu Ser Glu Ser Phe Ala Asn Arg Glu Gly Arg Gly Ser
            100                 105                 110

Gln Glu Ile Ala Asn Ser Met Leu Asn Phe Gly Tyr Ala Ile Leu Ser
            115                 120                 125

Ser Tyr Ile Leu Asn Ala Val Thr Asn Ala Gly Leu Glu Pro Tyr Leu
130                 135                 140

Gly Phe Leu His Gln Lys Arg Pro Gly Lys Met Ser Leu Val Leu Asp
145                 150                 155                 160

Leu Met Glu Glu Tyr Arg Ala Trp Val Val Asp Arg Val Val Ile Lys
                165                 170                 175

Leu Arg Glu Gln Tyr Lys Asn Lys Lys Ser Ile Asp Pro Lys Leu Lys
            180                 185                 190

Ser Ala Leu Ile Ser Glu Ile Gln Ala Thr Ile Ala Lys Lys Tyr Ile
            195                 200                 205

Tyr Asn Gly Lys Lys Leu Lys Leu Glu His Ile Ile Gln Arg Gln Val
210                 215                 220

Tyr Arg Leu Ser Gly Glu Phe Ala Gly Glu His Asn Tyr Lys Pro Tyr
225                 230                 235                 240

Ile Phe Lys Trp

<210> SEQ ID NO 40
<211> LENGTH: 338
<212> TYPE: PRT
<213> ORGANISM: Fusobacterium nucleatum subsp. nucleatum

<400> SEQUENCE: 40

Met Phe Cys Ile Gly Gly Val Asn Met Lys Arg Ser Phe Phe Leu Tyr
 1               5                  10                  15

Ser Asn Gly Thr Leu Lys Arg Lys Asp Asn Thr Ile Thr Phe Ile Asn
             20                  25                  30

Glu Lys Asp Glu Lys Arg Asp Ile Pro Ile Glu Met Val Asp Asp Phe
         35                  40                  45

Tyr Val Met Ser Glu Met Asn Phe Asn Thr Lys Phe Ile Asn Tyr Ile
 50                  55                  60

Ser Gln Phe Gly Ile Pro Ile His Phe Phe Asn Tyr Tyr Thr Phe Tyr
 65                  70                  75                  80

Thr Gly Ser Phe Tyr Pro Arg Glu Met Asn Ile Ser Gly Gln Leu Leu
                 85                  90                  95

Val Lys Gln Val Glu His Tyr Thr Asn Glu Gln Lys Arg Val Glu Ile
            100                 105                 110

Ala Arg Glu Phe Ile Glu Gly Ala Ser Phe Asn Ile Tyr Arg Asn Leu
            115                 120                 125

Arg Tyr Tyr Asn Gly Arg Gly Lys Asp Leu Lys Leu Tyr Met Asp Gln
130                 135                 140

Ile Glu Glu Leu Arg Lys His Leu Lys Glu Val Asn Asn Val Glu Glu
145                 150                 155                 160

Leu Met Gly Tyr Glu Gly Asn Ile Arg Lys Ile Tyr Tyr Glu Ala Trp
                165                 170                 175
```

```
Asn Ile Ile Val Asn Gln Glu Ile Asp Phe Glu Lys Arg Val Lys Asn
                180                 185                 190

Pro Pro Asp Asn Met Ile Asn Ser Leu Ile Ser Phe Val Asn Thr Leu
            195                 200                 205

Phe Tyr Thr Lys Val Leu Gly Glu Ile Tyr Lys Thr Gln Leu Asn Pro
        210                 215                 220

Thr Val Ser Tyr Leu His Gln Pro Ser Thr Arg Arg Phe Ser Leu Ser
225                 230                 235                 240

Leu Asp Ile Ser Glu Val Phe Lys Pro Leu Ile Val Asp Arg Leu Ile
                245                 250                 255

Phe Ser Leu Leu Asn Lys Asn Gln Ile Thr Glu Lys Ser Phe Val Lys
            260                 265                 270

Asp Phe Glu Tyr Leu Arg Leu Lys Glu Asp Val Ser Lys Leu Ile Val
        275                 280                 285

Gln Glu Phe Glu Asp Arg Leu Lys Gln Ile Ile Thr His Lys Asp Leu
290                 295                 300

Asn Arg Lys Ile Ser Tyr Gln Tyr Leu Val Arg Leu Glu Cys Tyr Lys
305                 310                 315                 320

Leu Ile Lys His Leu Leu Gly Glu Lys Lys Tyr Lys Ser Phe Gln Met
                325                 330                 335

Trp Trp

<210> SEQ ID NO 41
<211> LENGTH: 306
<212> TYPE: PRT
<213> ORGANISM: Geobacter sulfurreducens

<400> SEQUENCE: 41

Met Gln Pro Gln Leu Pro Pro Leu Lys Pro Ile Pro Ile Lys Asp Arg
1               5                   10                  15

Ile Ser Val Leu Tyr Val Glu Arg Gly Asn Leu Asp Val Leu Asp Gly
                20                  25                  30

Ala Phe Val Val Asp Lys Thr Gly Val Arg Thr His Leu Pro Val
            35                  40                  45

Gly Gly Val Ala Cys Leu Met Leu Glu Pro Gly Thr Arg Val Ser His
        50                  55                  60

Ala Ala Val Thr Leu Ala Ser Arg Ile Gly Cys Leu Leu Val Trp Ile
65                  70                  75                  80

Gly Glu Ala Gly Val Arg Leu Tyr Ala Ser Gly Gln Pro Gly Gly Ala
                85                  90                  95

Arg Ala Asp Arg Leu Leu Tyr Gln Ala Lys Leu Ala Leu Asp Asp Ser
            100                 105                 110

Ala Arg Leu Lys Val Val Arg Lys Met Tyr Ala Leu Arg Phe Arg Glu
        115                 120                 125

Glu Pro Pro Glu Arg Arg Ser Val Glu Gln Leu Arg Gly Ile Glu Gly
    130                 135                 140

Val Arg Val Arg Lys Met Tyr Glu Leu Leu Ala Arg Gln His Gly Val
145                 150                 155                 160

Ala Trp Lys Ala Arg Asn Tyr Asp His Thr Gln Trp Glu Ser Gly Asp
                165                 170                 175

Val Pro Asn Arg Cys Leu Ser Ser Ala Thr Ala Cys Leu Tyr Gly Ile
            180                 185                 190

Cys Glu Ala Ala Ile Leu Ala Ala Gly Tyr Ala Pro Val Gly Phe
        195                 200                 205
```

```
Ile His Thr Gly Lys Pro Gln Ser Phe Val Tyr Asp Ile Ala Asp Ile
210                 215                 220

Phe Lys Phe Glu Thr Val Val Pro Val Ala Phe Arg Ile Ala Ala Lys
225                 230                 235                 240

Lys Pro Arg Asp Pro Glu Arg Glu Val Arg Leu Ala Cys Arg Asp Ala
            245                 250                 255

Phe Arg Gln Ser Lys Ile Leu His Arg Ile Ile Pro Thr Ile Glu Gln
            260                 265                 270

Val Leu Ala Ala Gly Gly Met Asp Val Pro Thr Pro Pro Glu Ser
                275                 280                 285

Val Glu Ala Val Ile Pro Asn Lys Glu Gly Ile Gly Asp Ala Gly His
290                 295                 300

Arg Gly
305

<210> SEQ ID NO 42
<211> LENGTH: 331
<212> TYPE: PRT
<213> ORGANISM: Haloarcula hispanica

<400> SEQUENCE: 42

Met Asp Arg Asn Tyr His Val Phe Ser Asp Gly Arg Leu Glu Arg Ser
1               5                   10                  15

Asp Asp Thr Leu Arg Leu Val Pro Asp Asp Ala Gly Asp Lys Gln Tyr
            20                  25                  30

Ile Pro Ile Glu Asn Ala Glu Ala Phe Phe Leu His Gly Gln Ile Asp
        35                  40                  45

Phe Asn Thr Arg Leu Met Ser Phe Leu Asn Asp Arg Thr Val Ala Leu
50                  55                  60

His Ile Phe Gly Trp Glu Asp Tyr Tyr Ala Gly Ser Val Met Pro Lys
65                  70                  75                  80

Arg Gly Gln Thr Ser Gly Lys Thr Val Val Asn Gln Val Arg Ala Tyr
                85                  90                  95

Glu Asp Ser Gln His Arg Arg Gln Leu Ala Ala Ala Ile Val Lys Gly
            100                 105                 110

Ser Ile His Asn Met Arg Thr Asn Val Val Tyr Tyr Asn Gly Arg Asp
        115                 120                 125

His Asp Leu Asp Ser Val Ile Glu Asp Leu Ala Ala Ala Thr Arg
    130                 135                 140

Val Asp Glu Ser Leu Pro Ile Asp Glu Leu Met Gly Ile Glu Ala Thr
145                 150                 155                 160

Ala Lys Lys Ala Tyr Tyr Arg Ser Phe Asn Gln Ile Leu Pro Ser Glu
                165                 170                 175

Phe Gln Leu Ser Gln Arg Glu Tyr Asn Pro Pro Asn Glu Ile Asn
            180                 185                 190

Ser Leu Ile Ser Phe Gly Asn Ser Met Val Tyr Ala Asn Cys Val Ser
        195                 200                 205

Ala Ile Arg Ala Thr Ala Leu Asp Pro Thr Ile Ser Tyr Leu His Glu
    210                 215                 220

Pro Gly Glu Arg Arg Tyr Ser Leu Ser Leu Asp Ile Ala Asp Leu Phe
225                 230                 235                 240

Lys Pro Val Leu Ala Asp Arg Val Leu Phe Arg Leu Val Asn Arg Asn
                245                 250                 255

Gln Ile Ser Glu Ser Asp Phe Glu Thr Glu Leu Gly Ser Cys Leu Leu
            260                 265                 270
```

Asn Glu Ala Gly Arg Lys Thr Tyr Thr Lys Ala Phe Glu Glu Met Leu
            275                 280                 285

Glu Arg Thr Val Glu His Pro Thr Leu Asn Arg Lys Val Ser Tyr Gln
            290                 295                 300

Tyr Leu Met Arg Leu Glu Ala Tyr Lys Leu Lys Lys His Leu Leu Thr
305                 310                 315                 320

Gly Glu Ala Tyr Asp Ser Phe Gln Arg Trp Trp
            325                 330

<210> SEQ ID NO 43
<211> LENGTH: 331
<212> TYPE: PRT
<213> ORGANISM: Hyperthermus butylicus

<400> SEQUENCE: 43

Met Pro Glu Val Leu Leu Val Ala Thr Pro Gly Thr Arg Ile Tyr Val
1               5                   10                  15

Arg Arg Gly Val Val Tyr Ala Glu Ala Pro Ser Gly Glu Lys Ala Val
                20                  25                  30

Val Thr Ala Asp Thr Glu Leu Val Leu Ala Thr Gly Ser Val Ser
            35                  40                  45

Val Ser Gly Arg Ala Leu Arg Arg Leu Ala Glu Leu Gly Val Arg Leu
50                  55                  60

Val Val Leu Gly Gln Arg Gly Gln Val Val Ala Glu His Arg Pro Val
65                  70                  75                  80

Asp Arg Val Asn Arg Thr Ile Glu Ala Arg Met Glu Gln Tyr Arg Val
                85                  90                  95

Lys Ala Thr Gly Glu Ala Leu Tyr Tyr Ala Ala Glu Met Val Tyr Ala
                100                 105                 110

Lys Ile Val Asn Gln Ala Lys Leu Leu Arg Tyr Leu Ala Lys Ser Arg
                115                 120                 125

Arg Glu Pro Trp Leu Arg Asp Ala Gly Tyr Arg Val Glu Gly His Ala
                130                 135                 140

Asp Arg Leu Arg Gln Ile Ile Glu Asn Glu Glu Pro Thr Thr Pro Glu
145                 150                 155                 160

Val Ile Arg Ser Ile Glu Ala Gln Ala Ala Arg Asp Tyr Trp Asp Ala
                165                 170                 175

Ile Ala Gln Ile Ala Pro Thr Pro Phe Pro Gly Arg Gln Pro Arg Gly
                180                 185                 190

Glu Asp His Leu Asn Met Ala Leu Ser Tyr Gly Tyr Ala Ile Leu Tyr
                195                 200                 205

Ser Ile Ala His Asp Ala Leu Thr Val Ala Gly Leu Asp Pro Tyr Ala
                210                 215                 220

Gly Phe Leu His Ala Asp Arg Ser Gly Arg Pro Ser Leu Thr Tyr Asp
225                 230                 235                 240

Tyr Ala Asp Thr Tyr Lys Pro Ile Ala Val Asp Lys Pro Leu Leu Thr
                245                 250                 255

Ala Pro Arg Lys Thr Asp Cys Leu Asp Thr Tyr Met Gly Ala Leu Thr
                260                 265                 270

Tyr Asn Ala Arg Arg Cys Ile Ala Thr Leu Val Leu Glu Asn Ile Tyr
                275                 280                 285

Lys Thr Pro Tyr Pro Asp Ser Arg Gly Arg Lys Lys Thr Leu Arg Asp
                290                 295                 300

His Ile Tyr Thr Tyr Ala Trp Asn Leu Ala Ala Ile Arg Gln His
305                 310                 315                 320

Lys Pro Tyr Lys Pro Phe Ile Val Gly Arg Leu
            325                 330

<210> SEQ ID NO 44
<211> LENGTH: 341
<212> TYPE: PRT
<213> ORGANISM: Korarchaeum cryptofilum

<400> SEQUENCE: 44

Met Glu Thr Thr Gln Tyr Gly His Leu Leu Ile Asp Gly Phe Gly Val
1               5                   10                  15

Ser Leu Arg Lys Arg Gly Arg Ile Leu Ile Leu Ser Lys Gly Glu
            20                  25                  30

Lys Lys Glu Ile Pro Met Lys Ser Val Lys Glu Val Ile Ile Gly
            35                  40                  45

Lys Ala Ala Leu Ser Ser Glu Leu Leu Lys Ala Leu Ala Gln Ser Gly
50                  55                  60

Thr Asp Leu Leu Ile Ala Thr Pro Thr Gly Arg Pro Val Ala Arg Leu
65                  70                  75                  80

Ile Pro Ala Lys Ala Gly Gly Thr Ala Arg Asn Arg Tyr Glu Gln Tyr
                85                  90                  95

Lys Ser Leu Glu Asp Arg Arg Gly Ile Glu Ile Ala Arg Ala Val Ile
            100                 105                 110

Val Gly Lys Ile Arg Asn Gln Ala Ser Asn Leu Ser Tyr Tyr Ser Lys
            115                 120                 125

Ala Arg Arg Met Asp Glu Glu Leu Ser Ser Glu Leu Tyr Asp Ala Ala
            130                 135                 140

Gln Gln Leu Lys Arg Glu Met Glu Glu Leu Lys Asn Glu Glu Phe Pro
145                 150                 155                 160

Asp Ile Asp Glu Ala Arg Lys Arg Ile Met Ala Arg Glu Ser Lys Cys
                165                 170                 175

Ala Asn Ile Tyr Trp Glu Lys Ile Ala Ser Ile Met Glu Glu Trp Lys
            180                 185                 190

Phe Arg Gly Arg Glu Lys Arg Thr Asp Leu Glu Gly Asn Val Ile Asp
            195                 200                 205

Pro Val Asn Leu Cys Leu Asn Val Cys Tyr Asn Leu Leu Ser Ala Gln
            210                 215                 220

Ile Trp Lys Asn Val Leu Arg Phe Gly Leu Asp Pro Phe Leu Gly Tyr
225                 230                 235                 240

Leu His Val Glu Arg Pro Gly Arg Ile Ser Leu Val Tyr Asp Leu Met
                245                 250                 255

Glu Pro Phe Arg Pro Met Val Asp Arg Phe Val Phe Ser Tyr Leu Arg
            260                 265                 270

Gly Met Ser Pro Ser Leu Phe Ser Ser Asn Ile Val Ser Gly Thr Ile
            275                 280                 285

Ala Ser Leu Arg Ser Arg Phe Phe Ser Asp Phe Met Asn Trp Arg Leu
            290                 295                 300

Asp Tyr Lys Gly Arg Lys Leu Gly Met Glu Thr Ile Met Phe Leu Tyr
305                 310                 315                 320

Val Arg Asp Ile Val Ser Phe Leu Arg Gly Gly Lys Glu Pro Thr Met
                325                 330                 335

Pro Tyr Ile Pro Trp
            340

<210> SEQ ID NO 45
<211> LENGTH: 254
<212> TYPE: PRT
<213> ORGANISM: Leptospira interrogans serogroup Icterohaemorrhagiae serovar Lai

<400> SEQUENCE: 45

```
Met Ile Arg Lys Ala Gln Phe Lys Lys Ser Glu Ile Glu Lys Phe Arg
1               5                   10                  15

Leu Glu Ile Ala Arg Ser Ile Val Ala Gly Lys Leu Gln Asn Cys Arg
            20                  25                  30

Ser Val Leu Ser Arg Thr Ala Arg Lys Ser Lys Asn Glu Ser Glu Lys
        35                  40                  45

Gln Asp Ile Lys Glu Ala Ile Gly Lys Ile Glu Lys Asn Ile Ser Leu
    50                  55                  60

Leu Glu Lys Ala Glu Ser Ile Glu Ser Ile Arg Gly Tyr Glu Gly Ala
65                  70                  75                  80

Ser Ala Lys Thr Tyr Phe Ser Val Phe Asp Tyr Cys Ile Ile Gln Gln
                85                  90                  95

Lys Glu Asp Phe Gln Phe His Lys Arg Thr Arg Arg Pro Pro Arg Ser
            100                 105                 110

Arg Thr Asn Ala Leu Leu Ser Phe Leu Tyr Ser Leu Leu Thr Asn Asp
        115                 120                 125

Cys Ile Ala Val Cys Gln Ala Val Gly Leu Asp Pro Tyr Ile Gly Phe
    130                 135                 140

Leu His Asp Glu Arg Pro Gly Arg Pro Ser Leu Ala Leu Asp Met Met
145                 150                 155                 160

Glu Glu Phe Arg Pro Phe Ile Asp Arg Leu Val Phe Thr Leu Ile Asn
                165                 170                 175

Arg Lys Gln Ile Gln Val Ser Asp Phe Leu Glu Lys Pro Gly Ser Val
            180                 185                 190

Phe Phe Ile Asn Asp Asp Ser Arg Lys Glu Leu Ile Lys Ser Tyr Gln
        195                 200                 205

Glu Arg Lys Lys Glu Glu Ile Phe His Pro Trp Leu Asn Ile Lys Ser
    210                 215                 220

Thr Val Gly Glu Leu Pro Tyr Leu Gln Ala Arg Ile Phe Ala Arg Thr
225                 230                 235                 240

Leu Arg Gly Asp Leu Lys Tyr Tyr Ile Pro Phe Ile Trp Lys
                245                 250
```

<210> SEQ ID NO 46
<211> LENGTH: 322
<212> TYPE: PRT
<213> ORGANISM: Methanobrevibacter ruminantium

<400> SEQUENCE: 46

```
Met Ser Lys Lys Asn Tyr Tyr Leu Leu Ser Glu Gly Ile Leu Lys Arg
1               5                   10                  15

Lys Glu Asn Thr Ile Tyr Phe Val Asn Glu Lys Gly Ser Lys Pro Leu
            20                  25                  30

Pro Ile Asn Lys Ile Tyr Ser Met Tyr Ala Tyr Gly Gln Ile Thr Ile
        35                  40                  45

Ser Ser Gln Val Ile Ser Leu Phe Ala Lys Glu Gly Ile Pro Ile His
    50                  55                  60

Phe Phe Asn Tyr Tyr Gly Tyr Tyr Asn Gly Ser Phe Tyr Pro Arg Glu
65                  70                  75                  80
```

Ser Leu Leu Ser Gly Asp Leu Leu Ile Lys Gln Ala Glu His Asn Ile
                85                  90                  95

Asp Phe Ser Lys Arg Leu Lys Leu Ala Lys Leu Phe Val Glu Gly Ala
            100                 105                 110

Ala Lys Asn Ile Leu Lys Val Leu Ala Tyr Tyr Lys Ile Glu Asn Asn
        115                 120                 125

Ile Lys Asn Thr Leu Thr Glu Leu Asn Glu Ser Ser Lys Ile Thr Glu
    130                 135                 140

Val Met Asn Val Glu Gly Arg Ile Arg Ala Glu Tyr Tyr Gln Tyr Phe
145                 150                 155                 160

Asp Asp Ile Leu Pro Asp Glu Phe Lys Met Glu Gly Arg Ser Arg Gln
                165                 170                 175

Pro Pro Thr Asn Met Ile Asn Ser Leu Ile Ser Phe Gly Asn Ser Met
            180                 185                 190

Met Tyr Ala Ser Val Ile Thr Glu Leu Tyr Asn Thr Gln Leu Asn Pro
        195                 200                 205

Thr Ile Ser Tyr Leu His Glu Pro Ala Glu Arg Arg Phe Ser Leu Ala
    210                 215                 220

Leu Asp Leu Ser Glu Ile Phe Lys Pro Ile Ile Val Asp Arg Val Ile
225                 230                 235                 240

Phe Tyr Leu Val Asn Lys Lys Met Ile Thr Glu Lys Asp Phe Asn Gln
                245                 250                 255

Asp Leu Asn Cys Cys Leu Leu Asn Asp Lys Gly Arg Ala Thr Phe Val
            260                 265                 270

Lys Glu Tyr Asn Lys Arg Leu Glu Thr Thr Ile Lys His Lys Asp Leu
        275                 280                 285

Gly Arg Lys Val Ser Tyr Gln Arg Leu Ile Arg Leu Glu Ala Tyr Lys
    290                 295                 300

Leu Lys Lys His Val Phe Gly Met Lys Glu Tyr Asp Pro Phe Val Ile
305                 310                 315                 320

Trp Trp

<210> SEQ ID NO 47
<211> LENGTH: 334
<212> TYPE: PRT
<213> ORGANISM: Methanobrevibacter ruminantium

<400> SEQUENCE: 47

Met Lys Leu Val Val Asp Gly Phe Gly Lys Ser Val Ala Lys Arg Asp
1               5                   10                  15

Asn Gln Ile Val Ile Lys Glu Asn Gly Lys Glu Ile Asn Tyr Tyr Leu
            20                  25                  30

Ala Lys Asp Ile Ser Gln Ile Leu Leu Thr Gly Lys Gly Ser Ile Thr
        35                  40                  45

Phe Asp Ala Leu Thr Leu Leu Ala Glu Asn Asp Val Asp Cys Val Ser
    50                  55                  60

Ile Asn Trp Lys Gly His Val Asp Tyr Arg Leu Ser Ala Pro Asp Arg
65                  70                  75                  80

Lys Asn Ala Ile Val Lys Lys Glu Gln Tyr Phe Ala Leu Thr Asp Ser
                85                  90                  95

Arg Ser Gly Tyr Leu Ala Lys Ala Phe Val Arg Ala Lys Ile Glu Asn
            100                 105                 110

Gln Lys Ala Val Leu Gly Thr Leu Ala Lys Ser Arg Glu Glu Lys Asp
        115                 120                 125

```
Tyr Ile Ile Glu Gln Arg Glu Lys Val Ser Glu His Ile Gly Lys Ile
        130                 135                 140

Glu Lys Leu Ser Asn Ile Asn Ser Asp Asn Ile Arg Asn Asn Ile Leu
145                 150                 155                 160

Gly Ile Glu Gly Gln Ala Ser His Glu Tyr Trp Ser Ala Phe Ala Ser
                165                 170                 175

Val Leu Asp Glu Lys Trp Glu Phe Phe Gly Arg Ser Gly Arg Gly Ala
                180                 185                 190

Lys Asp Pro Val Asn Ser Leu Asn Tyr Gly Tyr Ala Val Ile Glu
                195                 200                 205

Ser Glu Ile Trp Lys Ser Ile Tyr Leu Ala Gly Leu Asp Pro Tyr Cys
    210                 215                 220

Gly Phe Leu His Ser Glu Arg Tyr Gly Arg Ala Ser Leu Val Tyr Asp
225                 230                 235                 240

Leu Ile Glu Glu Phe Arg Gln Gln Ile Val Asp Lys Thr Val Leu Ser
                245                 250                 255

Ile Val Asn Arg Asn Gln Ile Thr Pro Asp Asp Phe Glu Glu Asp Gly
                260                 265                 270

Asn Tyr Ile Lys Ile His Glu Arg Ala Arg Leu Leu Ile Ala Lys
    275                 280                 285

Ile Leu Asp Lys Leu Asn Ser Lys Ile Met Phe His Ser Lys Asn Ile
    290                 295                 300

Ser Tyr Ser Asp Ile Ile Leu Tyr Gln Gly Lys Leu Met Ala Asp Tyr
305                 310                 315                 320

Leu Thr Asn Gly Val Pro Tyr Glu Gly Phe Ser Leu Arg Trp
                325                 330

<210> SEQ ID NO 48
<211> LENGTH: 334
<212> TYPE: PRT
<213> ORGANISM: Methanobrevibacter ruminantium

<400> SEQUENCE: 48

Met Lys Ile Leu Ile Glu Gly Tyr Asn Lys Ser Ile His Lys Arg Asp
1               5                   10                  15

Asn Gln Ile Leu Ile Met Glu Lys Glu Gly Leu Glu Lys Ile Asn
                20                  25                  30

Ile Lys Lys Ile Asp Asp Ile Thr Ile Gly Lys Gly Ser Ile Thr
            35                  40                  45

Phe Asp Ala Leu Arg Leu Ile Ser Glu Asn Asn Val Arg Leu Met Ser
    50                  55                  60

Ile Asp Tyr Phe Gly Lys Ile Asn Tyr Thr Leu Glu Tyr Pro Ser Asn
65                  70                  75                  80

Glu Asn Ile Phe Leu Arg Lys Gln Gln Tyr Lys Thr Ser Glu Asn His
                85                  90                  95

Lys Gly Leu Ile Ile Ala Arg Glu Met Ile Met Ser Lys Met Ile Asn
            100                 105                 110

Gln Lys Ser Thr Ile Lys Thr Leu Asn Lys Asn Lys Leu Glu Asn
    115                 120                 125

Val Lys Ile Phe Glu Arg Asn Ile Asn Glu Ala Ile Lys Gln Ile Gly
130                 135                 140

Ser Leu Arg Phe Gly Glu Arg Thr Asp Ile Glu Lys Ser Lys Met Lys
145                 150                 155                 160

Met Met Gly Ile Glu Gly Ser Ala Ser Val Asp Tyr Trp Leu Ala Val
                165                 170                 175
```

```
Asn Glu Leu Leu Pro Lys Glu Ile Gly Phe Phe Ser Arg Asn Asn Arg
            180                 185                 190

His Pro Asn Asp Ile Thr Asn Ala Ser Leu Asn Tyr Ala Tyr Ala Ile
        195                 200                 205

Leu Ala Ser Glu Val Asn Lys Ala Leu Val Ile Asn Gly Leu Asp Ser
    210                 215                 220

Tyr Cys Gly Phe Leu His Phe Asp Arg Gln Lys Arg Thr Ser Leu Thr
225                 230                 235                 240

Phe Asp Leu Met Glu Glu Phe Arg Gln Gln Leu Val Asp Lys Val Val
                245                 250                 255

Phe Ser Leu Val Asn Thr Lys Gln Ile Ser Asn Asp Asp Leu Asp Lys
            260                 265                 270

Arg Asn Asn Ser Ile Ser Leu Asp Val Arg Lys Leu Ile Ile Gly Arg
        275                 280                 285

Val Leu Asp Lys Val Asn Ser Asn Ile Asn Tyr Glu Gly Glu Asn Leu
    290                 295                 300

Ser Tyr Ala Gln Ile Ile Asp Lys Gln Ala Lys Lys Ile Val Asn Tyr
305                 310                 315                 320

Leu Ile Asn Gly Glu Lys Tyr Thr Gly Phe Ser Leu Arg Trp
                325                 330
```

<210> SEQ ID NO 49
<211> LENGTH: 322
<212> TYPE: PRT
<213> ORGANISM: Methanocaldococcus jannaschii

<400> SEQUENCE: 49

```
Met Arg Lys Lys Ser Leu Thr Leu Leu Ser Asp Gly Tyr Leu Phe Arg
1               5                   10                  15

Lys Glu Asn Thr Ile Tyr Phe Glu Asn Ala Arg Gly Lys Lys Pro Leu
            20                  25                  30

Ala Ile Glu Gly Ile Tyr Asp Ile Tyr Ile Tyr Gly Lys Val Ser Ile
        35                  40                  45

Ser Ser Gln Ala Leu His Tyr Leu Ala Gln Lys Gly Ile Ala Leu His
    50                  55                  60

Phe Phe Asn His Tyr Gly Tyr Asp Gly Ser Phe Tyr Pro Arg Glu
65                  70                  75                  80

Ser Leu His Ser Gly Tyr Leu Val Val Asn Gln Val Glu His Tyr Leu
                85                  90                  95

Asp Lys Asp Lys Arg Leu Glu Leu Ala Lys Leu Phe Ile Ile Gly Gly
            100                 105                 110

Ile Lys Asn Met Glu Trp Asn Leu Leu Lys Phe Lys Asn Lys Thr Lys
        115                 120                 125

Phe Ser Ser Tyr Ile Glu Glu Leu Asn Asn Cys Asn Lys Ile Thr Glu
    130                 135                 140

Val Met Asn Val Glu Gly Arg Val Arg Thr Glu Tyr Tyr Arg Leu Trp
145                 150                 155                 160

Asp Glu Thr Leu Pro Asp Asp Phe Lys Ile Val Lys Arg Thr Arg Arg
                165                 170                 175

Pro Pro Lys Asn Glu Met Asn Ala Leu Ile Ser Phe Leu Asn Ser Arg
            180                 185                 190

Leu Tyr Pro Ala Ile Ile Thr Glu Leu Tyr Asn Thr Gln Leu Thr Pro
        195                 200                 205

Thr Val Ser Tyr Leu His Glu Pro His Glu Arg Arg Phe Ser Leu Ala
    210                 215                 220
```

```
Leu Asp Leu Ser Glu Ile Phe Lys Pro Met Ile Ala Asp Arg Leu Ala
225                 230                 235                 240

Asn Arg Leu Val Lys Gln Gly Ile Ile Gln Lys Lys His Phe Arg Asp
            245                 250                 255

Asp Leu Asn Gly Val Leu Leu Asn Lys Glu Gly Met Lys Val Val Leu
            260                 265                 270

Glu His Phe Asn Lys Glu Met Asp Lys Thr Val Asn His Lys Lys Leu
        275                 280                 285

Lys Lys Asn Val Ser Lys Arg Arg Leu Ile Arg Leu Glu Ala Tyr Lys
        290                 295                 300

Leu Val Lys His Leu Val Gly Gln Lys Arg Tyr Glu Pro Leu Val Ala
305                 310                 315                 320

Trp Phe

<210> SEQ ID NO 50
<211> LENGTH: 331
<212> TYPE: PRT
<213> ORGANISM: Methanopyrus kandleri

<400> SEQUENCE: 50

Met Gly Ala Pro Asn Asp Thr Val Ile Phe Leu Arg Arg Gly Lys Ile
1               5                   10                  15

Glu Arg Arg Glu Asp Ala Phe Arg Ile Gly Lys Ser Lys Tyr Ser Ala
            20                  25                  30

Val Arg Thr Thr Gly Ile Ile Ile Ala Gly Ala Gln Ile Thr Thr
        35                  40                  45

Gln Ala Val Arg Leu Ala Leu Arg Asn Glu Val Pro Ile Val Tyr Leu
    50                  55                  60

Gly Gly Asn Arg Ile Leu Gly Val Thr Val Pro Phe Ser Glu Arg Tyr
65                  70                  75                  80

Ala Thr Leu Arg Leu Lys Gln Tyr Glu Ile Ala Ser Gln Pro Ser Ala
                85                  90                  95

Arg Leu Ala Phe Ala Arg Pro Leu Ile Ala Ser Ser Ile Leu Ala Arg
            100                 105                 110

Ala Ala Val Leu Glu Phe Leu Ala Asn Glu Thr Gly Ile Thr Gly Leu
        115                 120                 125

Glu Asp Ala Ala Asp Glu Val Arg Ser Glu Ala Glu Arg Ala Leu Asn
130                 135                 140

Ala Gly Ser Thr Asp Ala Leu Arg Gly Tyr Glu Gly Arg Ala Ala Cys
145                 150                 155                 160

Arg Tyr Phe Arg Ala Leu Ala Glu Val Leu Pro Asp Trp Ala Phe Ser
                165                 170                 175

Gly Arg Arg Thr Arg Arg Pro Pro Arg Asp Pro Phe Asn Ala Ala Ile
            180                 185                 190

Ser Phe Gly Tyr Ala Gly Val Leu Leu Pro Val Leu Leu Ser Arg Thr
        195                 200                 205

Val Ala Ala Gly Leu Glu Pro Phe Leu Gly Phe Leu His Gly Pro Arg
210                 215                 220

Gly Arg Arg Pro Gly Leu Ile Leu Asp Leu Met Glu Gly Trp Arg Ala
225                 230                 235                 240

Leu Ala Val Asp Val Pro Val Leu Arg Arg Phe Leu Asp Gly Ser Leu
                245                 250                 255

Ser Arg Glu Met Phe Arg Trp Lys Gly Asp Ala Val Leu Leu Arg Asp
            260                 265                 270
```

```
Leu Asp Ala Val Ser Ala Pro Val Leu Thr Val Leu Ser Arg Val Arg
            275                 280                 285

Gly Gly Leu Leu Glu Ala Val Asp Arg Arg Ile Arg Glu Val Arg Asp
290                 295                 300

Gly Val Ser Arg Gln Ser Pro Pro Glu Pro Leu Glu Phe Asp Pro Glu
305                 310                 315                 320

Asp Val Gly Val Val Trp Asp Ala Leu Glu Val
                325                 330

<210> SEQ ID NO 51
<211> LENGTH: 299
<212> TYPE: PRT
<213> ORGANISM: Methanospirillum hungatei JF-1

<400> SEQUENCE: 51

Met Thr Pro Thr Leu Pro Asp Ile Lys Pro Ile Pro Ile Lys Glu Arg
1               5                   10                  15

Ser Ser Val Val Phe Leu Gly Arg Gly Glu Leu Asp Val Ile Asp Gly
                20                  25                  30

Ala Phe Val Leu Val Asp Thr Asn Gly Ile Arg Met Gln Ile Pro Val
            35                  40                  45

Gly Gly Leu Ala Ser Leu Met Leu Glu Pro Gly Ser Arg Val Ser His
        50                  55                  60

Ala Ala Val Ser Leu Ala Ser Lys Val Gly Cys Leu Leu Val Phe Val
65                  70                  75                  80

Gly Glu Gly Gly Val Arg Leu Tyr Ser Val Gly His Pro Gly Gly Ala
                85                  90                  95

Arg Ser Asp Arg Leu Leu Tyr Gln Ala Arg Leu Ala Leu Asp Glu Val
                100                 105                 110

Leu Arg Leu Lys Val Val Lys Lys Met Phe Ser Leu Arg Phe Gly Glu
            115                 120                 125

Asp Phe Ser Asp Ala Tyr Ser Val Glu Gln Leu Arg Gly Leu Glu Gly
        130                 135                 140

Val Arg Val Arg Glu Gly Tyr Arg Lys Ile Ala Arg Asp Thr Gly Val
145                 150                 155                 160

Ile Trp Asn Gly Arg Arg Tyr Asp Pro His Ser Trp Gly Ser Ala Asp
                165                 170                 175

Leu Pro Asn Arg Cys Leu Ser Ala Ala Thr Ala Ser Leu Tyr Gly Ile
                180                 185                 190

Cys Glu Ala Ala Val Leu Ala Ala Gly Tyr Ser Pro Ser Ile Gly Phe
            195                 200                 205

Leu His Thr Gly Lys Pro Leu Ser Phe Val Tyr Asp Ile Ala Asp Leu
        210                 215                 220

Phe Lys Phe Glu Thr Val Val Pro Ala Ala Phe Lys Thr Ala Ala Leu
225                 230                 235                 240

Asn Pro Arg Glu Pro Glu Arg Glu Val Arg Tyr Ala Cys Arg Asp Leu
                245                 250                 255

Phe Arg Glu Thr Gln Leu Leu Lys Arg Ile Ile Pro Thr Ile Glu Glu
                260                 265                 270

Val Leu Thr Ala Gly Gly Ile Ser Ala Pro Ala Pro Pro Asp Trp Val
            275                 280                 285

Val Pro Pro Ala Ile Pro Val Asp Glu Glu Gly
        290                 295
```

```
<210> SEQ ID NO 52
<211> LENGTH: 347
<212> TYPE: PRT
<213> ORGANISM: Methanospirillum hungatei JF-1

<400> SEQUENCE: 52
```

| | | | | | | | | | | | | | | | |
|---|---|---|---|---|---|---|---|---|---|---|---|---|---|---|---|
| Met | Asn | Ile | Glu | Asn | Glu | Val | His | Ile | Glu | Asn | Ala | Ser | Glu | Ser | Lys |
| 1 | | | | 5 | | | | | 10 | | | | | 15 | |
| Arg | Glu | Pro | Lys | Pro | Glu | Gly | Leu | Leu | Glu | Asp | Asp | Thr | Ile | Tyr | |
| | | | 20 | | | | | 25 | | | | | 30 | | |
| Ile | Thr | Thr | Pro | Tyr | Gly | Lys | Ile | Ser | Leu | Asp | Gly | Gly | Arg | Ile | Gln |
| | | | 35 | | | | | 40 | | | | | 45 | | |
| Val | Lys | Asp | Ser | Asp | Gly | Glu | Ile | Val | Ala | Ser | Phe | Pro | Leu | Glu | Lys |
| 50 | | | | | 55 | | | | | 60 | | | | | |
| Val | Cys | Thr | Met | Asn | Val | Phe | Gly | Ser | Ala | Ser | Val | Ser | Thr | Pro | Leu |
| 65 | | | | | 70 | | | | | 75 | | | | | 80 |
| Leu | Lys | His | Cys | Ser | Asp | Lys | Glu | Val | Val | Ile | Asn | Tyr | Phe | Thr | Asn |
| | | | | 85 | | | | | 90 | | | | | 95 | |
| Phe | Gly | Lys | Tyr | Phe | Gly | Ser | Phe | Val | Pro | Ser | Arg | Asn | Thr | Ile | Ala |
| | | | 100 | | | | | 105 | | | | | 110 | | |
| Leu | Val | Arg | Arg | His | Gln | Ala | Gly | Ile | Thr | Lys | Glu | Lys | Ser | Leu | Ala |
| | | | 115 | | | | | 120 | | | | | 125 | | |
| Ile | Cys | Arg | Glu | Ile | Ile | His | Ala | Lys | Leu | Gln | Asn | Ser | Cys | Val | Phe |
| 130 | | | | | 135 | | | | | 140 | | | | | |
| Leu | Ala | Arg | Lys | Arg | Val | Glu | Val | Pro | Ser | Leu | Leu | Lys | Glu | Leu | Arg |
| 145 | | | | | 150 | | | | | 155 | | | | | 160 |
| Asp | Arg | Ser | Leu | His | Ala | Val | Ser | Val | Asp | Ser | Leu | Arg | Gly | Ile | Glu |
| | | | | 165 | | | | | 170 | | | | | 175 | |
| Gly | Glu | Ala | Ala | Ser | Ile | Tyr | Phe | Pro | Met | Leu | Ser | Ser | Ser | Leu | Pro |
| | | | 180 | | | | | 185 | | | | | 190 | | |
| Asp | Glu | Trp | Arg | Ser | Asp | Lys | Arg | Thr | Arg | Arg | Pro | Pro | Arg | Asp | Glu |
| | | | 195 | | | | | 200 | | | | | 205 | | |
| Leu | Asn | Ala | Leu | Leu | Ser | Leu | Thr | Tyr | Thr | Met | Val | Asn | Thr | Glu | Val |
| 210 | | | | | 215 | | | | | 220 | | | | | |
| Ile | Ser | Ala | Leu | Arg | Gln | Tyr | Asn | Leu | Asp | Pro | Phe | Ile | Gly | Val | Met |
| 225 | | | | | 230 | | | | | 235 | | | | | 240 |
| His | Val | Asp | Arg | His | Gly | Lys | Pro | Ala | Leu | Ala | Leu | Asp | Leu | Leu | Glu |
| | | | | 245 | | | | | 250 | | | | | 255 | |
| Glu | Phe | Arg | Pro | Val | Phe | Cys | Asp | Ala | Phe | Val | Ala | Arg | Leu | Ile | Asn |
| | | | 260 | | | | | 265 | | | | | 270 | | |
| Lys | Arg | Met | Ile | Thr | Lys | Asp | Asp | Phe | Thr | Gln | Gly | Ser | Arg | Leu | Asn |
| | | | 275 | | | | | 280 | | | | | 285 | | |
| Asp | Thr | Ala | Phe | Lys | Lys | Tyr | Leu | Gly | Phe | Tyr | His | Asp | Phe | Met | Glu |
| | | | 290 | | | | | 295 | | | | | 300 | | |
| Glu | Ser | Leu | Lys | His | Pro | Arg | Phe | Lys | Tyr | Ser | Val | Ser | Arg | Lys | Lys |
| 305 | | | | | 310 | | | | | 315 | | | | | 320 |
| Ala | Ile | Gln | Ile | Gln | Ala | Ile | Ile | Phe | Arg | Lys | Ala | Ile | Cys | Gly | Glu |
| | | | | 325 | | | | | 330 | | | | | 335 | |
| Leu | Lys | Gly | Tyr | Tyr | Pro | Phe | Ile | Tyr | Ala | Arg | | | | | |
| | | | 340 | | | | | 345 | | | | | | | |

```
<210> SEQ ID NO 53
<211> LENGTH: 331
<212> TYPE: PRT
<213> ORGANISM: Methanospirillum hungatei JF-1
```

<400> SEQUENCE: 53

| Met | Asn | Ser | Val | Leu | Ile | Thr | Gly | Ala | Gly | Tyr | Arg | Ile | Arg | Lys | Arg |
|---|---|---|---|---|---|---|---|---|---|---|---|---|---|---|---|
| 1 | | | | 5 | | | | | 10 | | | | | 15 | |

Gly Asp Val Leu Thr Ile Glu Thr Gly Lys Asp Ser Asp Thr Ala Glu
                20                  25                  30

Pro Pro Arg Thr Leu Ser Pro Leu Gly Leu Asp Leu Leu Ala Ile Ala
            35                  40                  45

Gly Asp His Ser Ile Ser Thr Ala Ala Val Arg Leu Val Thr Ser His
50                  55                  60

Gly Gly Ala Ile Ala Leu Met Asp Gly Leu Gly Asn Pro Phe Gly His
65                  70                  75                  80

Phe Leu Pro Leu Gly Arg Ser Ala Leu Ile Glu Gln Tyr Glu Ala Gln
                85                  90                  95

Ala Ser Ala Pro Glu Glu Arg Arg Leu Glu Ile Ala Arg Ser Ile Cys
            100                 105                 110

Thr Gly Ala Leu Glu Asn Lys Arg Thr Leu Leu Ser Asn Leu Glu Arg
        115                 120                 125

Ile Arg Gly Phe Asp Leu Ser Arg Glu Ile Arg Leu Val Glu Asp Ala
130                 135                 140

Gln Asp Lys Ala Leu Glu Cys Gln Ser Leu Asp Ser Leu Arg Gly Val
145                 150                 155                 160

Glu Gly Ser Gly Ala His Ala Tyr Phe Gln Gly Phe Ser Leu Ala Phe
                165                 170                 175

Asp Glu Glu Trp Gly Phe Leu Gly Arg Ser Gln Asn Pro Ala Thr Asp
            180                 185                 190

Pro Val Asn Ser Leu Leu Ser Tyr Gly Tyr Gly Met Leu Tyr Ile Gln
        195                 200                 205

Ala Arg Gln Ala Leu Val Leu Ser Gly Tyr Ser Pro Tyr Tyr Gly Ala
210                 215                 220

Tyr His Glu Thr Tyr Lys Lys Gln Glu Ala Leu Val Tyr Asp Leu Val
225                 230                 235                 240

Glu Glu Phe Arg Gln Pro Val Val Asp Arg Thr Val Val Thr Phe Leu
                245                 250                 255

Ala Lys His Met Ala Thr Pro Asp Phe Thr Tyr Pro Asp Glu Gly
            260                 265                 270

Gly Cys Met Ile Gly Thr Met Ala Lys Lys Tyr Ala Ala Val
        275                 280                 285

Leu Thr Arg Ile His Gly Lys Val Lys Tyr Glu Glu Gln Thr Phe Gln
290                 295                 300

Asp Ile Phe Lys Arg Gln Ala Glu Arg Ile Gly Lys Ala Leu Thr Glu
305                 310                 315                 320

Gly Asp Glu Tyr Val Pro Tyr Arg Tyr Arg Thr
                325                 330

<210> SEQ ID NO 54
<211> LENGTH: 303
<212> TYPE: PRT
<213> ORGANISM: Methanospirillum hungatei JF-1

<400> SEQUENCE: 54

Met Gly Gly Phe Gly Ala His Ile Lys Ser Asn Arg Thr Glu Ile Thr
1               5                   10                  15

Ile Gln His Lys Gly Lys Ile Thr Asp Ile Pro Ile Lys Asp Leu Ser
            20                  25                  30

His Phe Leu Leu Ile Gly Gly His Thr Ile Gln Thr Ser Thr Ile Thr
            35                  40                  45

Ser Leu Val Lys Glu Gly Val Phe Ile Ser Phe Cys Glu Ser Asp Gly
 50                  55                  60

Glu Pro Val Gly Tyr Ile Ser Pro Tyr Asp Tyr Ser Leu Phe Lys Glu
 65                  70                  75                  80

Ile Gln Asn Leu Gln Lys Thr Ala Ala Pro Tyr Ser Tyr Ala Leu Ala
                85                  90                  95

Cys Ala Asn Glu Ser Ile Lys Ser Arg Ile Leu Ala Ile Glu Lys Tyr
            100                 105                 110

Ala Glu Glu Ile Gly Pro Glu Ile Leu Phe Ser Gly Glu Leu Asp Ile
        115                 120                 125

Leu Thr Gly Tyr Ala Lys Glu Leu Glu Asn Met Val Leu Ile Glu Glu
130                 135                 140

Leu Arg Arg Ile Glu Gln Leu Val Arg Asp Met Tyr Tyr Glu Ile Leu
145                 150                 155                 160

Gly Arg Leu Ile Ser Pro Thr Tyr Leu Phe Lys Arg Arg Thr Ser Arg
                165                 170                 175

Pro Tyr Leu Asp Pro Val Asn Ala Ile Phe Ser Phe Gly Tyr Gly Met
            180                 185                 190

Leu Ser Ser Ala Cys Thr Arg Ala Val Ile Gly Gly His Leu Asp Pro
        195                 200                 205

Gly His Gly Tyr Leu Asn Arg Gly Asn Gln Ala Leu Val Gln Asp Leu
210                 215                 220

Met Asn Cys Trp Lys Pro Lys Met Ile Asp Asn His Ala Ile Gly Phe
225                 230                 235                 240

Leu Arg Ser Gly Arg Leu His Gln Asn Gly Tyr Glu Arg Thr Lys Asp
                245                 250                 255

Arg Cys Ile Leu His Asp Glu Val Ile Glu Leu Ile His Leu Phe
            260                 265                 270

Ser Lys Ser Ile Gln Glu Glu Leu Ile Asn Thr Gln Ile Asp Val Leu
        275                 280                 285

Ile Gln Ser Leu Arg Gly Glu Ala Gln Phe Ser Ile Ile Lys Pro
290                 295                 300

<210> SEQ ID NO 55
<211> LENGTH: 334
<212> TYPE: PRT
<213> ORGANISM: Methanothermobacter thermautotrophicus

<400> SEQUENCE: 55

Met Asn Ser Ala Gly Leu Glu Gln Cys Gly Met Ile Met Thr Arg Lys
 1               5                  10                  15

Asn Tyr Tyr Ile Thr Thr Asp Gly Leu Leu Lys Arg Asn Glu Asn Thr
                20                  25                  30

Leu Tyr Phe Ile Asn Lys Asp Leu Lys Arg Pro Ile Pro Ile Asn Lys
            35                  40                  45

Ile Tyr Ser Ile Tyr Ser Tyr Gly Ala Leu Thr Ile Ser Ser Gln Ala
 50                  55                  60

Leu Asn Leu Leu Ser Lys Glu Gly Ile Pro Ile His Phe Phe Asn Arg
 65                  70                  75                  80

Tyr Gly Phe Tyr Ser Gly Ser Phe Tyr Pro Arg Glu Thr Leu Leu Ser
                85                  90                  95

Gly Asp Val Ile Ile Lys Gln Ala Glu His Val Ile Asp His Asp Lys
            100                 105                 110

```
Arg Ile Glu Leu Ala Arg Ser Phe Val Arg Gly Ala Ala Leu Asn Met
            115                 120                 125

Arg Arg Val Leu Ser Tyr Tyr Gly Ile Glu Asn Gly Ile Ser Asp Thr
130                 135                 140

Leu Met Asp Leu Asp Ser Ser Asn Ser Val Thr Asp Val Met Asn Val
145                 150                 155                 160

Glu Gly Arg Ile Arg Ser Asp Tyr Tyr Asn Ala Ile Asp Ser Ile Leu
                165                 170                 175

Pro Glu Gly Phe Arg Ile Gly Lys Arg Thr Arg Arg Pro Pro Glu Asn
                180                 185                 190

Met Thr Asn Ala Met Ile Ser Phe Gly Asn Ser Leu Leu Tyr Ser Thr
                195                 200                 205

Val Ile Thr Glu Leu Tyr Asn Thr Gln Leu Asn Pro Thr Ile Ser Tyr
            210                 215                 220

Leu His Glu Pro Phe Glu Arg Arg Tyr Ser Leu Ala Leu Asp Leu Ser
225                 230                 235                 240

Glu Ile Phe Lys Pro Thr Leu Ile Asp Arg Met Ile Ile Ser Leu Ile
                245                 250                 255

Lys Lys Lys Ala Ile Lys Ala Glu Asp Phe Glu His Gly Met Asn His
                260                 265                 270

Cys Leu Leu Asn Asn Ser Gly Lys Arg Lys Phe Leu Ala Glu Tyr Asp
            275                 280                 285

Arg Arg Leu Gly Lys Thr Val Lys His Arg Glu Leu Gly Arg Lys Val
290                 295                 300

Ser Tyr Arg Arg Leu Ile Arg Leu Glu Ala Tyr Lys Leu Ile Lys His
305                 310                 315                 320

Leu Ile Gly Gln Lys Ser Tyr Glu Pro Phe Val Met Trp Trp
                325                 330

<210> SEQ ID NO 56
<211> LENGTH: 343
<212> TYPE: PRT
<213> ORGANISM: Moorella thermoacetica

<400> SEQUENCE: 56

Met His Ile Leu Leu Asn Thr Leu Tyr Leu Met Thr Pro Arg Thr Leu
1               5                   10                  15

Val Arg Leu Asp His Glu Thr Val Lys Ile Glu Val Glu Gly Glu Leu
                20                  25                  30

Lys Met Gln Ile Pro Leu His His Leu Gly Ser Ile Val Cys Phe Gly
            35                  40                  45

Asp Val Thr Leu Thr Thr Pro Leu Ile Met Arg Cys Ala Glu Asp Lys
50                  55                  60

Arg Leu Ile Val Phe His Asp Gln His Gly Arg Phe Lys Ala Arg Val
65                  70                  75                  80

Glu Gly Pro Val Ser Gly Asn Val Phe Leu Arg His Ala Gln His Glu
                85                  90                  95

Ala Leu Ser Asp Ser Lys Lys Thr Thr Ala Ile Ala Arg Asn Ile Val
            100                 105                 110

Ala Gly Lys Ile Arg Asn Thr Arg Gln Val Val Leu Arg Gly Ala Arg
            115                 120                 125

Glu Ala Asp Asn Glu Asp Asp Arg Lys Ala Leu Gln Glu Thr Ala Arg
130                 135                 140

Glu Leu Ala His Gly Leu Asp Ala Leu Ser Arg Ser Pro Asp Leu Glu
145                 150                 155                 160
```

-continued

```
Gln Ile Arg Gly Ile Glu Gly Asn Ala Ala Arg His Tyr Phe Ala Thr
            165                 170                 175

Leu Asp Arg Met Val Arg Val Asn Arg Glu Ala Phe Lys Ile Thr His
        180                 185                 190

Arg Asn Arg Arg Pro Pro Leu Asp Arg Met Asn Ala Leu Leu Ser Tyr
    195                 200                 205

Ile Tyr Ala Leu Leu Asn Asp Cys Leu Ser Ala Ala Glu Gly Val
210                 215                 220

Gly Leu Asp Pro Gln Ile Gly Tyr Leu His Val Leu Arg Ser Gly Arg
225                 230                 235                 240

Pro Ala Leu Ala Leu Asp Leu Met Glu Glu Phe Arg Ala Ile Leu Ala
                245                 250                 255

Asp Arg Leu Ala Leu Thr Leu Val Asn Arg Arg Gln Ile Asp Glu Arg
            260                 265                 270

Asp Phe Val Glu Arg Pro Gly Gly Ala Val His Ile Asn Asp Asn Ala
        275                 280                 285

Arg Lys Glu Ile Ala Ile Ala Tyr Gln Lys Arg Lys Gln Glu Glu Val
    290                 295                 300

Leu His Pro Val Leu Asn Arg Lys Val Pro Leu Gly Leu Val Pro His
305                 310                 315                 320

Ile Gln Ala Arg Leu Leu Ala Arg Val Leu Arg Gly Asp Ala Glu Glu
                325                 330                 335

Tyr Leu Pro Phe Met Tyr Arg
            340

<210> SEQ ID NO 57
<211> LENGTH: 321
<212> TYPE: PRT
<213> ORGANISM: Moorella thermoacetica

<400> SEQUENCE: 57

Met Arg Thr Tyr Tyr Ile Phe Ser Ser Gly Arg Leu Arg Arg Met Asp
1               5                   10                  15

Asn Thr Leu Ala Leu Glu Leu Glu Thr Glu Arg Arg Val Val Pro Val
            20                  25                  30

Glu Asp Ile Asp His Ile Tyr Cys Phe Ser Glu Leu Asp Leu Asn Thr
        35                  40                  45

Arg Leu Leu Asp Phe Leu Ala Gln Lys Gln Ile Cys Leu His Phe Phe
    50                  55                  60

Asn Tyr Tyr Gly His Tyr Ser Gly Ser Phe Ile Pro Arg Glu Ser Gln
65                  70                  75                  80

Leu Ser Gly Phe Leu Leu Val Arg Gln Val Glu His Tyr Leu Asp Gln
                85                  90                  95

Ala Lys Arg Leu Glu Leu Ala Arg Thr Phe Val Glu Gly Ala Leu His
            100                 105                 110

Asn Ile Arg Arg Asn Leu Glu Lys Arg Glu Tyr Asp Asp Ile Cys Ser
        115                 120                 125

Lys Leu Asp Glu Ile Arg Glu Gly Ile Gly Lys Thr Ala Ser Ile Glu
    130                 135                 140

Glu Leu Met Ser Leu Glu Ala His Ala Arg Lys Ala Tyr Tyr Asp Thr
145                 150                 155                 160

Trp Glu Glu Ile Thr Gly Trp Glu Phe Gly Ser Arg Ser Lys Arg Pro
                165                 170                 175

Pro Ala Asn Ala Leu Asn Ala Leu Ile Ser Phe Gly Asn Ala Met Met
            180                 185                 190
```

```
Tyr Thr Val Val Leu Lys Glu Ile Tyr Arg Thr Ala Leu Asn Pro Thr
            195                 200                 205

Ile Ser Tyr Leu His Glu Pro Ser Glu Arg Arg Tyr Ser Leu Ala Leu
    210                 215                 220

Asp Val Ala Glu Ile Phe Lys Pro Val Phe Val Asp Arg Leu Ile Phe
225                 230                 235                 240

Arg Leu Ile Asn Leu Asn Met Leu Lys Glu Thr His Phe Asp Thr Asn
                245                 250                 255

Val Asn Phe Val Tyr Leu Thr Glu Gly Arg Lys Val Phe Val Lys
            260                 265                 270

Glu Phe Glu Glu Thr Leu Glu Lys Thr Ile Leu His Arg Lys Leu Lys
            275                 280                 285

Arg Asn Ile Arg Tyr Lys Ser Leu Val Arg Leu Asp Leu Tyr Lys Leu
            290                 295                 300

Ile Lys His Leu Leu Gly Glu Glu Lys Tyr Ser Pro Met Lys Val Trp
305                 310                 315                 320

Trp

<210> SEQ ID NO 58
<211> LENGTH: 338
<212> TYPE: PRT
<213> ORGANISM: Mycobacterium tuberculosis

<400> SEQUENCE: 58

Met Val Gln Leu Tyr Val Ser Asp Ser Val Ser Arg Ile Ser Phe Ala
1               5                   10                  15

Asp Gly Arg Val Ile Val Trp Ser Glu Leu Gly Glu Ser Gln Tyr
            20                  25                  30

Pro Ile Glu Thr Leu Asp Gly Ile Thr Leu Phe Gly Arg Pro Thr Met
            35                  40                  45

Thr Thr Pro Phe Ile Val Glu Met Leu Lys Arg Glu Arg Asp Ile Gln
    50                  55                  60

Leu Phe Thr Thr Asp Gly His Tyr Gln Gly Arg Ile Ser Thr Pro Asp
65                  70                  75                  80

Val Ser Tyr Ala Pro Arg Leu Arg Gln Gln Val His Arg Thr Asp Asp
                85                  90                  95

Pro Ala Phe Cys Leu Ser Leu Ser Lys Arg Ile Val Ser Arg Lys Ile
            100                 105                 110

Leu Asn Gln Gln Ala Leu Ile Arg Ala His Thr Ser Gly Gln Asp Val
            115                 120                 125

Ala Glu Ser Ile Arg Thr Met Lys His Ser Leu Ala Trp Val Asp Arg
130                 135                 140

Ser Gly Ser Leu Ala Glu Leu Asn Gly Phe Glu Gly Asn Ala Ala Lys
145                 150                 155                 160

Ala Tyr Phe Thr Ala Leu Gly His Leu Val Pro Gln Glu Phe Ala Phe
                165                 170                 175

Gln Gly Arg Ser Thr Arg Pro Pro Leu Asp Ala Phe Asn Ser Met Val
            180                 185                 190

Ser Leu Gly Tyr Ser Leu Leu Tyr Lys Asn Ile Ile Gly Ala Ile Glu
            195                 200                 205

Arg His Ser Leu Asn Ala Tyr Ile Gly Phe Leu His Gln Asp Ser Arg
            210                 215                 220

Gly His Ala Thr Leu Ala Ser Asp Leu Met Glu Val Trp Arg Ala Pro
225                 230                 235                 240
```

```
Ile Ile Asp Asp Thr Val Leu Arg Leu Ile Ala Asp Gly Val Val Asp
            245                 250                 255

Thr Arg Ala Phe Ser Lys Asn Ser Asp Thr Gly Ala Val Phe Ala Thr
            260                 265                 270

Arg Glu Ala Thr Arg Ser Ile Ala Arg Ala Phe Gly Asn Arg Ile Ala
            275                 280                 285

Arg Thr Ala Thr Tyr Ile Lys Gly Asp Pro His Arg Tyr Thr Phe Gln
            290                 295                 300

Tyr Ala Leu Asp Leu Gln Leu Gln Ser Leu Val Arg Val Ile Glu Ala
305                 310                 315                 320

Gly His Pro Ser Arg Leu Val Asp Ile Asp Ile Thr Ser Glu Pro Ser
            325                 330                 335

Gly Ala

<210> SEQ ID NO 59
<211> LENGTH: 338
<212> TYPE: PRT
<213> ORGANISM: Mycobacterium tuberculosis

<400> SEQUENCE: 59

Met Val Gln Leu Tyr Val Ser Asp Ser Val Ser Arg Ile Ser Phe Ala
1               5                   10                  15

Asp Gly Arg Val Ile Val Trp Ser Glu Glu Leu Gly Glu Ser Gln Tyr
            20                  25                  30

Pro Ile Glu Thr Leu Asp Gly Ile Thr Leu Phe Gly Arg Pro Thr Met
            35                  40                  45

Thr Thr Pro Phe Ile Val Glu Met Leu Lys Arg Glu Arg Asp Ile Gln
        50                  55                  60

Leu Phe Thr Thr Asp Gly His Tyr Gln Gly Arg Ile Ser Thr Pro Asp
65                  70                  75                  80

Val Ser Tyr Ala Pro Arg Leu Arg Gln Gln Val His Arg Thr Asp Asp
                85                  90                  95

Pro Ala Phe Cys Leu Ser Leu Ser Lys Arg Ile Val Ser Arg Lys Ile
            100                 105                 110

Leu Asn Gln Gln Ala Leu Ile Arg Ala His Thr Ser Gly Gln Asp Val
            115                 120                 125

Ala Glu Ser Ile Arg Thr Met Lys His Ser Leu Ala Trp Val Asp Arg
        130                 135                 140

Ser Gly Ser Leu Ala Glu Leu Asn Gly Phe Glu Gly Asn Ala Ala Lys
145                 150                 155                 160

Ala Tyr Phe Thr Ala Leu Gly His Leu Val Pro Gln Glu Phe Ala Phe
                165                 170                 175

Gln Gly Arg Ser Thr Arg Pro Pro Leu Asp Ala Phe Asn Ser Met Val
            180                 185                 190

Ser Leu Gly Tyr Ser Leu Leu Tyr Lys Asn Ile Ile Gly Ala Ile Glu
            195                 200                 205

Arg His Ser Leu Asn Ala Tyr Ile Gly Phe Leu His Gln Asp Ser Arg
        210                 215                 220

Gly His Ala Thr Leu Ala Ser Asp Leu Met Glu Val Trp Arg Ala Pro
225                 230                 235                 240

Ile Ile Asp Asp Thr Val Leu Arg Leu Ile Ala Asp Gly Val Val Asp
                245                 250                 255

Thr Arg Ala Phe Ser Lys Asn Ser Asp Thr Gly Ala Val Phe Ala Thr
            260                 265                 270
```

```
Arg Glu Ala Thr Arg Ser Ile Ala Arg Ala Phe Gly Asn Arg Ile Ala
            275                 280                 285

Arg Thr Ala Thr Tyr Ile Lys Gly Asp Pro His Arg Tyr Thr Phe Gln
        290                 295                 300

Tyr Ala Leu Asp Leu Gln Leu Gln Ser Leu Val Arg Val Ile Glu Ala
305                 310                 315                 320

Gly His Pro Ser Arg Leu Val Asp Ile Asp Ile Thr Ser Glu Pro Ser
                325                 330                 335

Gly Ala

<210> SEQ ID NO 60
<211> LENGTH: 333
<212> TYPE: PRT
<213> ORGANISM: Nanoarchaeum equitans

<400> SEQUENCE: 60

Met Lys Thr Ile Tyr Ile Leu Ser Ile Gly Lys Leu Tyr Arg Gly Lys
1               5                   10                  15

Asn Gly Leu Tyr Phe Ile Asn Lys Asp Lys Lys Ser Pro Ile Pro
            20                  25                  30

Leu Glu Ser Ile Lys Glu Ile Phe Ile Leu Asn Lys Val Ser Val Thr
        35                  40                  45

Tyr Asn Ala Leu Lys Leu Leu Ala Asp Arg Asn Ile Pro Ile His Phe
    50                  55                  60

Phe Tyr Glu Asn Thr Lys Lys Gly Ile Ser Tyr Tyr Leu Gly Ser Phe
65                  70                  75                  80

Leu Pro Arg Gln Lys Thr Lys Ser Gly Leu Val Leu Val Lys Gln Val
                85                  90                  95

Glu Ala Tyr Lys Asp Ile Glu Lys Arg Thr Glu Ile Ala Leu Glu Ile
            100                 105                 110

Val Asp Ala Ile Arg Tyr Asn Cys Ile Lys Val Leu Glu Lys Tyr His
        115                 120                 125

Ile Asp Glu Val Lys Glu Leu Arg Lys Ile Asp Val Trp Lys Met Phe
    130                 135                 140

Glu Glu Ser Leu Asn Asp Trp Lys Asp Ala Ile Asn Ile Ile Arg Gly
145                 150                 155                 160

Ile Glu Ser Asn Ile Trp Asn Leu Phe Tyr Gln Gly Leu Asp Lys Ile
                165                 170                 175

Leu Lys Leu Tyr Lys Leu Glu Arg Arg Thr Arg Arg Pro Pro Lys Asn
            180                 185                 190

Glu Ala Asn Thr Ile Val Ser Phe Ala Asn Thr Leu Leu Tyr Gly Val
        195                 200                 205

Thr Leu Thr Glu Ile Tyr Lys Thr His Leu Asp Pro Thr Ile Ser Phe
    210                 215                 220

Leu His Glu Leu Arg Asp Thr Arg Tyr Ser Leu Ala Leu Asp Leu Ser
225                 230                 235                 240

Glu Asn Phe Lys Pro Ile Ile Thr Phe Arg Ile Leu Ile Trp Leu Val
                245                 250                 255

Asn Gln Gly Ile Ile Lys Asp Thr His Phe Val Lys Gly Leu Asn Gly
            260                 265                 270

Val Leu Leu Asn Glu Gln Gly Lys Lys Leu Val Ile Lys Glu Phe Asn
        275                 280                 285
```

```
Lys Arg Leu Asp Glu Thr Ile Lys Leu Lys Ser Gly Leu Lys Arg Ser
290                 295                 300

Met Arg Trp Tyr Ile Lys Ala Gln Ala Tyr Asn Leu Glu Arg Phe Leu
305                 310                 315                 320

Leu Asp Gly Arg Lys Phe Lys Ala Phe Arg Leu Ile Tyr
                325                 330
```

<210> SEQ ID NO 61
<211> LENGTH: 304
<212> TYPE: PRT
<213> ORGANISM: Neisseria meningitidis

<400> SEQUENCE: 61

```
Met Thr Trp Arg Ser Leu Leu Ile Gln Asn Gly Gly Lys Leu Ser Leu
1               5                   10                  15

Gln Arg Arg Gln Leu Leu Ile Gln Asn Gly Glu Ser His Thr Val
                20                  25                  30

Pro Leu Glu Asp Ile Ala Val Ile Ile Glu Asn Arg Glu Thr Leu
                35                  40                  45

Ile Thr Ala Pro Leu Leu Ser Ala Leu Ala Glu His Gly Ala Thr Leu
50                  55                  60

Leu Thr Cys Asp Glu Gln Phe Leu Pro Cys Gly Gln Trp Leu Pro Tyr
65                  70                  75                  80

Ala Gln Tyr His Arg Gln Leu Lys Ile Leu Lys Leu Gln Leu Asn Ile
                85                  90                  95

Ser Glu Pro Leu Lys Lys Gln Leu Trp Gln His Ile Val Arg Gln Lys
                100                 105                 110

Ile Leu Asn Gln Ala Phe Val Ala Asp Glu Thr Gly Asn Asp Leu Ala
                115                 120                 125

Ala Lys Arg Leu Arg Thr Leu Ala Ser Glu Val Arg Ser Gly Asp Thr
130                 135                 140

Gly Asn Arg Glu Ala Gln Ala Ala Leu Tyr Phe Gln Ala Leu Phe
145                 150                 155                 160

Gly Glu Lys Phe Thr Arg Asn Asp Asn Asn Ala Val Asn Ala Ala Leu
                165                 170                 175

Asn Tyr Thr Tyr Ala Val Leu Arg Ala Ala Val Ala Arg Thr Leu Thr
                180                 185                 190

Leu Tyr Gly Trp Leu Pro Ala Leu Gly Leu Phe His Arg Ser Glu Leu
                195                 200                 205

Asn Pro Phe Asn Leu Ala Asp Asp Phe Ile Glu Pro Leu Arg Pro Leu
210                 215                 220

Ala Asp Leu Thr Val Ile His Leu Tyr Glu Gln Gly Arg Leu Lys Ala
225                 230                 235                 240

Glu Leu Thr Pro Gly Ile Lys Gln His Leu Ile Lys Thr Leu His Tyr
                245                 250                 255

Gln Ile Ser Ile Glu Arg Gln His Phe Ser Thr Leu Ala Ala Ile Asp
                260                 265                 270

Lys Met Val Ser Ser Phe Gln Ala Gly Val Thr Asp Lys Asn Ala Lys
                275                 280                 285

Gln Leu Lys Leu Pro Glu Ile Leu Pro Leu Lys Glu Tyr Gln Tyr Glu
                290                 295                 300
```

<210> SEQ ID NO 62
<211> LENGTH: 304
<212> TYPE: PRT
<213> ORGANISM: Neisseria meningitidis serogroup C

<400> SEQUENCE: 62

Met Thr Trp Arg Ser Leu Leu Ile Gln Asn Gly Gly Lys Leu Ser Leu
1               5                   10                  15

Gln Arg Arg Gln Leu Leu Ile Gln Gln Asn Gly Glu Ser His Thr Val
            20                  25                  30

Pro Leu Glu Asp Ile Ala Val Ile Ile Glu Asn Arg Glu Thr Leu
        35                  40                  45

Ile Thr Ala Pro Leu Leu Ser Ala Leu Ala Glu His Gly Ala Thr Leu
50                  55                  60

Leu Thr Cys Asp Glu Gln Phe Leu Pro Cys Gly Gln Trp Leu Pro Tyr
65                  70                  75                  80

Ala Gln Tyr His Arg Gln Leu Lys Ile Leu Lys Leu Gln Leu Asn Ile
                85                  90                  95

Ser Glu Pro Leu Lys Lys Gln Leu Trp Gln His Ile Val Arg Gln Lys
            100                 105                 110

Ile Leu Asn Gln Ala Phe Val Ala Asp Glu Thr Gly Asn Asp Leu Ala
        115                 120                 125

Ala Lys Arg Leu Arg Thr Leu Ala Ser Glu Val Arg Ser Gly Asp Thr
130                 135                 140

Gly Asn Arg Glu Ala Gln Ala Ala Leu Tyr Phe Gln Ala Leu Phe
145                 150                 155                 160

Gly Glu Lys Phe Thr Arg Asn Asp Asn Ala Val Asn Ala Ala Leu
                165                 170                 175

Asn Tyr Thr Tyr Ala Val Leu Arg Ala Ala Val Ala Arg Thr Leu Thr
            180                 185                 190

Leu Tyr Gly Trp Leu Pro Ala Leu Gly Leu Phe His Arg Ser Glu Leu
        195                 200                 205

Asn Pro Phe Asn Leu Ala Asp Asp Phe Ile Glu Pro Leu Arg Pro Leu
210                 215                 220

Ala Asp Leu Thr Val Ile His Leu Tyr Glu Gln Gly Arg Leu Lys Ala
225                 230                 235                 240

Glu Leu Thr Pro Gly Ile Lys Gln His Leu Ile Lys Thr Leu His Tyr
                245                 250                 255

Gln Ile Ser Ile Glu Arg Gln His Phe Ser Thr Leu Ala Ala Ile Asp
            260                 265                 270

Lys Met Val Ser Ser Phe Gln Ala Gly Val Thr Asp Lys Asn Ala Lys
        275                 280                 285

Gln Leu Lys Leu Pro Glu Ile Leu Pro Leu Lys Glu Tyr Gln Tyr Glu
290                 295                 300

<210> SEQ ID NO 63
<211> LENGTH: 326
<212> TYPE: PRT
<213> ORGANISM: Pectobacterium atrosepticum

<400> SEQUENCE: 63

Met Asp Asn Ala Phe Ser Pro Ser Asp Leu Lys Thr Ile Leu His Ser
1               5                   10                  15

Lys Arg Ala Asn Val Tyr Tyr Leu Gln His Cys Arg Ile Leu Val Asn
            20                  25                  30

Gly Gly Arg Val Glu Tyr Val Thr Glu Glu Gly Asn Gln Ser Leu Tyr
        35                  40                  45

Trp Asn Ile Pro Ile Ala Asn Thr Ser Val Val Met Leu Gly Thr Gly
50                  55                  60

```
Thr Ser Val Thr Gln Ala Ala Met Arg Glu Phe Ala Arg Ala Gly Val
 65                  70                  75                  80

Met Ile Gly Phe Cys Gly Gly Gly Thr Pro Leu Phe Ala Ala Asn
                 85                  90                  95

Glu Ala Glu Val Ala Val Ser Trp Leu Ser Pro Gln Ser Glu Tyr Arg
                100                 105                 110

Pro Thr Glu Tyr Leu Gln Asp Trp Val Ser Phe Trp Phe Asp Asp Glu
                115                 120                 125

Lys Arg Leu Ala Ala Ala Ile Ala Phe Gln Gln Val Arg Ile Thr Gln
            130                 135                 140

Ile Arg Gln His Trp Leu Gly Ser Arg Leu Ser Arg Glu Ser Arg Phe
145                 150                 155                 160

Thr Phe Lys Ser Glu His Leu Gln Ala Leu Leu Asp Arg Tyr Gln Lys
                165                 170                 175

Gly Leu Thr Asp Cys Arg Thr Ser Asn Asp Val Leu Val Gln Glu Ala
                180                 185                 190

Met Met Thr Lys Ala Leu Tyr Arg Leu Ala Ala Asn Ala Val Ser Tyr
            195                 200                 205

Gly Asp Phe Thr Arg Ala Lys Arg Gly Gly Thr Asp Leu Ala Asn
210                 215                 220

Arg Phe Leu Asp His Gly Asn Tyr Leu Ala Tyr Gly Leu Ala Ala Val
225                 230                 235                 240

Ser Thr Trp Val Leu Gly Leu Pro His Gly Leu Ala Val Leu His Gly
                245                 250                 255

Lys Thr Arg Arg Gly Gly Leu Val Phe Asp Val Ala Asp Leu Ile Lys
                260                 265                 270

Asp Ala Leu Val Leu Pro Gln Ala Phe Ile Ala Ala Met Glu Gly Glu
            275                 280                 285

Asp Glu Gln Glu Phe Arg Gln Arg Cys Leu Thr Ala Phe Gln Gln Ser
                290                 295                 300

Glu Ala Leu Asp Val Met Ile Gly Ser Leu Gln Asp Val Ala Ser Lys
305                 310                 315                 320

Leu Ser Gln Val Val Arg
                325

<210> SEQ ID NO 64
<211> LENGTH: 324
<212> TYPE: PRT
<213> ORGANISM: Pseudomonas aeruginosa

<400> SEQUENCE: 64

Met Asp Asp Ile Ser Pro Ser Glu Leu Lys Thr Ile Leu His Ser Lys
  1               5                  10                  15

Arg Ala Asn Leu Tyr Tyr Leu Gln His Cys Arg Val Leu Val Asn Gly
                 20                  25                  30

Gly Arg Val Glu Tyr Val Thr Asp Glu Gly Arg His Ser His Tyr Trp
             35                  40                  45

Asn Ile Pro Ile Ala Asn Thr Ser Leu Leu Gly Thr Gly Thr
 50                  55                  60

Ser Ile Thr Gln Ala Ala Met Arg Glu Leu Ala Arg Ala Gly Val Leu
 65                  70                  75                  80

Val Gly Phe Cys Gly Gly Gly Thr Pro Leu Phe Ser Ala Asn Glu
                 85                  90                  95

Val Asp Val Glu Val Ser Trp Leu Thr Pro Gln Ser Glu Tyr Arg Pro
                100                 105                 110
```

```
Thr Glu Tyr Leu Gln Arg Trp Val Gly Phe Trp Phe Asp Glu Glu Lys
            115                 120                 125

Arg Leu Val Ala Ala Arg His Phe Gln Arg Ala Arg Leu Glu Arg Ile
130                 135                 140

Arg His Ser Trp Leu Glu Asp Arg Val Leu Arg Asp Ala Gly Phe Ala
145                 150                 155                 160

Val Asp Ala Thr Ala Leu Ala Val Ala Val Glu Asp Ser Ala Arg Ala
                165                 170                 175

Leu Glu Gln Ala Pro Asn His Glu His Leu Leu Thr Glu Glu Ala Arg
            180                 185                 190

Leu Ser Lys Arg Leu Phe Lys Leu Ala Ala Gln Ala Thr Arg Tyr Gly
        195                 200                 205

Glu Phe Val Arg Ala Lys Arg Gly Ser Gly Gly Asp Pro Ala Asn Arg
    210                 215                 220

Phe Leu Asp His Gly Asn Tyr Leu Ala Tyr Gly Leu Ala Ala Thr Ala
225                 230                 235                 240

Thr Trp Val Leu Gly Ile Pro His Gly Leu Ala Val Leu His Gly Lys
                245                 250                 255

Thr Arg Arg Gly Gly Leu Val Phe Asp Val Ala Asp Leu Ile Lys Asp
            260                 265                 270

Ser Leu Ile Leu Pro Gln Ala Phe Leu Ser Ala Met Arg Gly Asp Glu
        275                 280                 285

Glu Gln Asp Phe Arg Gln Ala Cys Leu Asp Asn Leu Ser Arg Ala Gln
    290                 295                 300

Ala Leu Asp Phe Met Ile Asp Thr Leu Lys Asp Val Ala Gln Arg Ser
305                 310                 315                 320

Thr Val Ser Ala

<210> SEQ ID NO 65
<211> LENGTH: 324
<212> TYPE: PRT
<213> ORGANISM: Pseudomonas aeruginosa

<400> SEQUENCE: 65

Met Asp Asp Ile Ser Pro Ser Glu Leu Lys Thr Ile Leu His Ser Lys
1               5                   10                  15

Arg Ala Asn Leu Tyr Tyr Leu Gln His Cys Arg Val Leu Val Asn Gly
            20                  25                  30

Gly Arg Val Glu Tyr Val Thr Asp Glu Gly Arg His Ser His Tyr Trp
        35                  40                  45

Asn Ile Pro Ile Ala Asn Thr Thr Ser Leu Leu Leu Gly Thr Gly Thr
    50                  55                  60

Ser Ile Thr Gln Ala Ala Met Arg Glu Leu Ala Arg Ala Gly Val Leu
65                  70                  75                  80

Val Gly Phe Cys Gly Gly Gly Thr Pro Leu Phe Ser Ala Asn Glu
                85                  90                  95

Val Asp Val Glu Val Ser Trp Leu Thr Pro Gln Ser Glu Tyr Arg Pro
            100                 105                 110

Thr Glu Tyr Leu Gln Leu Trp Val Gly Phe Trp Phe Asp Glu Glu Lys
        115                 120                 125

Arg Leu Glu Ala Ala Arg His Phe Gln Arg Val Arg Leu Glu Arg Ile
    130                 135                 140

Arg His Ser Trp Leu Glu Asp Arg Val Leu Arg Asp Ala Gly Phe Ala
145                 150                 155                 160
```

```
Val Asp Ala Thr Ala Leu Ala Val Ala Val Glu Asp Ser Ala Arg Ala
                165                 170                 175

Leu Glu Gln Ala Pro Asn His Glu His Leu Leu Thr Glu Glu Ala Arg
            180                 185                 190

Leu Ser Lys Arg Leu Phe Lys Leu Ala Ala Gln Ala Thr Arg Tyr Gly
        195                 200                 205

Glu Phe Val Arg Ala Lys Arg Gly Ser Gly Gly Asp Pro Ala Asn Arg
    210                 215                 220

Phe Leu Asp His Gly Asn Tyr Leu Ala Tyr Gly Leu Ala Ala Thr Ala
225                 230                 235                 240

Thr Trp Val Leu Gly Ile Pro His Gly Leu Ala Val Leu His Gly Lys
                245                 250                 255

Thr Arg Arg Gly Gly Leu Val Phe Asp Val Ala Asp Leu Ile Lys Asp
            260                 265                 270

Ser Leu Ile Leu Pro Gln Ala Phe Leu Ser Ala Met Arg Gly Asp Glu
        275                 280                 285

Glu Gln Asp Phe Arg Gln Ala Cys Leu Asp Asn Leu Ser Arg Ala Gln
    290                 295                 300

Ala Leu Asp Phe Met Ile Asp Thr Leu Lys Asp Val Ala Gln Arg Ser
305                 310                 315                 320

Thr Val Ser Ala
```

<210> SEQ ID NO 66
<211> LENGTH: 302
<212> TYPE: PRT
<213> ORGANISM: Pyrobaculum aerophilum

<400> SEQUENCE: 66

```
Met Glu Val Val Lys Asp Trp Gly Val Ser Leu Gly Tyr Ser Arg
1               5                   10                  15

Gly Ala Leu Val Ile Lys Lys Arg Gly Gly Val Asp Arg Ile Pro Leu
            20                  25                  30

Phe Gln Val Asp Arg Ile Trp Ile Leu Thr Gly Gly Val Ser Ile Ser
        35                  40                  45

Ser Arg Leu Val Arg Ala Leu Ser His His Phe Ile Asp Val Val Phe
    50                  55                  60

Phe Asp Ala Lys Gly Asn Pro Val Ala Arg Leu Phe Pro Pro Glu Ala
65                  70                  75                  80

Asn Gly Thr Val Thr His Arg Arg Ala Gln Tyr Glu Ala Tyr Leu Thr
                85                  90                  95

Gly Arg Gly Phe Glu Leu Ala Lys Leu Val Thr Tyr Gly Lys Leu Ile
            100                 105                 110

Asn Gln Ala Arg Ala Leu Arg Arg Leu Gly Gln Trp Lys Arg Glu His
        115                 120                 125

Tyr Gly Ala Leu Ala Glu Ala Ala Ser Lys Ile Ala Asp Leu Ala Gly
    130                 135                 140

Arg Ile Pro Ser Cys Ala Asp Val Gln Cys Val Leu Gly His Glu Gly
145                 150                 155                 160

Ala Ala Ala Ser Leu Tyr Trp Asp Ala Val Ser Lys Thr Thr Gly Leu
                165                 170                 175

Pro Gly Arg Asn Pro Glu Ala Ala Asp Pro Leu Asn Leu Ala Leu Asn
            180                 185                 190

Tyr Gly Tyr Gly Val Leu Lys Tyr Ala Val Trp Arg Gln Ala Val Ile
        195                 200                 205
```

His Gly Leu Asp Pro Tyr Ala Gly Tyr Ile His Ala Asp Lys Ser Gly
    210                 215                 220

Arg Pro Ser Leu Val Leu Asp Leu Met Glu Glu Phe Arg Pro His Val
225                 230                 235                 240

Asp Leu Leu Val Ile Arg Leu Arg Pro Ser Ala Asp Trp Ala Asp Gly
                245                 250                 255

Gly Val Leu Lys Arg Glu Ile Arg Ala Met Leu Val Glu Glu Trp Thr
                260                 265                 270

Gly Glu Arg Leu Glu Pro Val Ile Ala Arg Gln Val Gly Leu Ala Val
                275                 280                 285

Ala His Leu His Gly Gln Arg Ala Tyr Thr Pro His Gln Leu
                290                 295                 300

<210> SEQ ID NO 67
<211> LENGTH: 295
<212> TYPE: PRT
<213> ORGANISM: Pyrobaculum aerophilum

<400> SEQUENCE: 67

Met Gln Ile Val Val Ala Ser Tyr Gly Ala Arg Ile Arg Ala Lys Lys
1               5                   10                  15

Gly Leu Leu Ile Val Glu Gly Arg Glu Gly Arg Arg Glu Tyr Pro Leu
                20                  25                  30

His Gln Val Asp Glu Val Leu Leu Leu Thr Gly Gly Ile Ser Ile Ser
            35                  40                  45

Thr Arg Ala Leu Arg Ala Leu Leu Arg Ala Gly Ala Val Val Ala Val
    50                  55                  60

Phe Asp Gln Arg Gly Glu Pro Leu Gly Ile Phe Met Lys Pro Val Gly
65                  70                  75                  80

Asp Ala Thr Gly Ala Lys Arg Leu Cys Gln Tyr Ala Ala Ala Thr Asp
                85                  90                  95

Gly Arg Gly Leu Gln Leu Ala Lys Lys Trp Val Trp Leu Lys Ile Arg
                100                 105                 110

Gly Gln Leu Glu Asn Leu Lys Arg Trp Arg Arg Leu Gly Lys Tyr
                115                 120                 125

Gly Thr Tyr Ala Glu Ser Ile Ser Lys Ala Ile Asn Ala Leu Ala Ser
    130                 135                 140

Ala Ala Thr Pro Arg Glu Val Met Glu Ala Glu Ala Ala Ala Glu
145                 150                 155                 160

Ala Tyr Trp Ala Ala Tyr Arg Glu Ile Thr Gly Phe Pro Gly Arg Asp
                165                 170                 175

Gln Glu Gly Arg Asp Pro Val Asn Ala Gly Leu Asn Tyr Gly Tyr Gly
                180                 185                 190

Ile Leu Lys Ala Leu Cys Phe Lys Ser Ile Leu Leu Ala Gly Leu Asp
                195                 200                 205

Pro Tyr Val Gly Phe Leu His Ala Asp Lys Ser Gly Arg Pro Ser Leu
    210                 215                 220

Val Leu Asp Phe Met Glu Gln Trp Arg Pro Arg Val Asp Ala Val Val
225                 230                 235                 240

Ala Gln Leu Ala Glu Glu Leu Glu Ala Glu Asn Gly Leu Leu Thr His
                245                 250                 255

Lys Ser Arg Leu Arg Leu Ala Ala Ala Val Leu Glu Glu Phe Asn Ala
                260                 265                 270

```
Thr Gly Arg Pro Leu Ser Ala Glu Ile His Arg Glu Ala Arg Ser Ile
        275                 280                 285
Ala Lys Ala Leu Cys Thr Ser
290                 295

<210> SEQ ID NO 68
<211> LENGTH: 290
<212> TYPE: PRT
<213> ORGANISM: Pyrobaculum neutrophilum

<400> SEQUENCE: 68

Met Ala Ala Tyr Gly Ala Arg Ile Arg Ala Arg Lys Gly Leu Leu Leu
1               5                   10                  15
Val Glu Thr Lys Glu Gly Ala Arg Glu Tyr Pro Leu His Glu Val Asp
            20                  25                  30
Glu Val Leu Leu Leu Thr Gly Gly Ile Ser Ile Thr Thr Arg Ala Leu
        35                  40                  45
Arg Ala Leu Leu Ala Ala Gly Ala Thr Val Ala Val Phe Ser Pro Arg
    50                  55                  60
Gly Glu Pro Leu Gly Ile Phe Met Lys Pro Ile Gly Asp Ala Thr Gly
65                  70                  75                  80
Ala Lys Arg Arg Cys Gln Tyr Lys Ala Ala Glu Asp Gly Arg Gly Leu
                85                  90                  95
Gln Tyr Ala Lys Ser Trp Val Phe Lys Lys Met Leu Gly Gln Arg Asp
            100                 105                 110
Asn Ile Lys Ala Trp Arg Arg Leu Arg Gly Tyr Ser Gln Tyr Ala
        115                 120                 125
Glu Ser Leu Ala Lys Ala Leu Gln Ala Leu Arg Asp Ala Ala Ser Pro
    130                 135                 140
His Ala Val Leu Glu Ala Glu Ala Ala Glu Ala Tyr Trp Ala
145                 150                 155                 160
Ala Tyr Arg Glu Val Thr Gly Phe Pro Gly Arg Asp Gln Glu Gly Arg
                165                 170                 175
Asp Pro Val Asn Ala Gly Leu Asn Tyr Gly Tyr Gly Ile Leu Lys Ala
            180                 185                 190
Leu Val Tyr Lys Ser Leu Ile Leu Ala Gly Leu Asp Pro Tyr Val Gly
        195                 200                 205
Phe Leu His Val Asp Lys Ser Gly Arg Pro Ser Leu Ala Leu Asp Phe
    210                 215                 220
Met Glu Gln Trp Arg Pro Arg Val Asp Ala Val Val Ala Lys Met Ala
225                 230                 235                 240
Asp Lys Leu Glu Ser Glu Gly Gly Leu Leu Thr Arg Arg Ser Arg Leu
                245                 250                 255
Glu Leu Ala Ala Ala Val Leu Glu Glu Leu His Ala Lys Arg Pro
            260                 265                 270
Leu Ser Ala Glu Ile His Arg Glu Ala Arg Ala Leu Ala Arg Ser Ile
        275                 280                 285
Cys Thr
290

<210> SEQ ID NO 69
<211> LENGTH: 322
<212> TYPE: PRT
<213> ORGANISM: Pyrococcus horikoshii
```

<400> SEQUENCE: 69

Met Arg Lys Lys Pro Leu Thr Ile Phe Ser Asp Gly Thr Leu Thr Arg
1               5                   10                  15

Arg Glu Asn Thr Leu Tyr Phe Glu Ser Ala Lys Gly Arg Lys Pro Leu
                20                  25                  30

Ala Ile Glu Gly Ile Tyr Asp Ile Tyr Ile Tyr Gly His Val Asn Ile
            35                  40                  45

Thr Ser Gln Ala Leu His Tyr Ile Ala Gln Lys Gly Ile Leu Ile His
        50                  55                  60

Phe Phe Asn His Tyr Gly Tyr Tyr Asp Gly Thr Phe Tyr Pro Arg Glu
65                  70                  75                  80

Thr Leu Leu Ser Gly Asp Leu Ile Ile Arg Gln Ala Glu His Tyr Leu
                85                  90                  95

Asn Lys Glu Lys Arg Leu Phe Leu Ala Lys Ser Phe Val Thr Gly Gly
                100                 105                 110

Thr Lys Asn Met Glu Arg Asn Leu Lys Asn Trp Gly Ile Lys Ala Lys
            115                 120                 125

Leu Ser Asp Tyr Leu Asp Glu Leu Asn Asp Ala Arg Lys Ile Thr Glu
        130                 135                 140

Ile Met Asn Val Glu Ala Arg Ile Arg Gln Glu Tyr Tyr Ala Lys Trp
145                 150                 155                 160

Asp Glu Asn Leu Pro Glu Glu Phe Lys Ile Val Lys Arg Thr Arg Arg
                165                 170                 175

Pro Pro Lys Asn Glu Met Asn Ala Leu Ile Ser Phe Leu Asn Ser Arg
                180                 185                 190

Leu Tyr Ala Thr Ile Ile Thr Glu Ile Tyr Asn Thr Gln Leu Ala Pro
            195                 200                 205

Thr Ile Ser Tyr Leu His Glu Pro Ser Glu Arg Arg Phe Ser Leu Ser
210                 215                 220

Leu Asp Leu Ser Glu Ile Phe Lys Pro Ile Ile Ala Asp Arg Val Ala
225                 230                 235                 240

Asn Arg Leu Val Lys Lys Gly Ser Leu Lys Lys Glu His Phe Arg Glu
                245                 250                 255

Asp Leu Asn Gly Val Leu Leu Thr Glu Glu Gly Met Lys Ile Val Thr
            260                 265                 270

Lys Ala Tyr Asn Glu Glu Leu Gln Lys Ser Val Lys His Pro Lys Ile
        275                 280                 285

Gly Ser Asn Val Thr Arg Gln Arg Leu Ile Arg Leu Glu Ala Tyr Lys
290                 295                 300

Leu Ile Lys His Leu Val Gly Val Glu Gly Tyr Lys Pro Leu Val Ala
305                 310                 315                 320

Trp Phe

<210> SEQ ID NO 70
<211> LENGTH: 313
<212> TYPE: PRT
<213> ORGANISM: Rhodospirillum rubrum

<400> SEQUENCE: 70

Met Ala Asp Pro Ala Phe Val Pro Leu Arg Pro Ile Ala Ile Lys Asp
1               5                   10                  15

Arg Ser Ser Ile Val Phe Leu Gln Arg Gly Gln Leu Asp Val Val Asp
                20                  25                  30

Gly Ala Phe Val Leu Ile Asp Gln Glu Gly Val Arg Val Gln Ile Pro
            35                  40                  45

Val Gly Gly Leu Ala Cys Leu Met Leu Glu Pro Gly Thr Arg Ile Thr
 50                  55                  60

His Ala Ala Ile Val Leu Cys Ala Arg Val Gly Cys Leu Val Ile Trp
 65                  70                  75                  80

Val Gly Glu Arg Gly Thr Arg Leu Tyr Ala Ala Gly Gln Pro Gly Gly
                85                  90                  95

Ala Arg Ala Asp Arg Leu Leu Phe Gln Ala Arg Asn Ala Leu Asp Glu
            100                 105                 110

Thr Ala Arg Leu Asn Val Val Arg Glu Met Tyr Arg Arg Arg Phe Asp
            115                 120                 125

Asp Asp Pro Pro Ala Arg Arg Ser Val Asp Gln Leu Arg Gly Met Glu
            130                 135                 140

Gly Val Arg Val Arg Glu Ile Tyr Arg Leu Leu Ala Lys Lys Tyr Ala
145                 150                 155                 160

Val Asp Trp Asn Ala Arg Arg Tyr Asp His Asn Asp Trp Asp Gly Ala
                165                 170                 175

Asp Ile Pro Asn Arg Cys Leu Ser Ala Ala Thr Ala Cys Leu Tyr Gly
            180                 185                 190

Leu Cys Glu Ala Ala Ile Leu Ala Ala Gly Tyr Ala Pro Ala Ile Gly
            195                 200                 205

Phe Leu His Arg Gly Lys Pro Gln Ser Phe Val Tyr Asp Val Ala Asp
            210                 215                 220

Leu Tyr Lys Val Glu Thr Val Val Pro Thr Ala Phe Ser Ile Ala Ala
225                 230                 235                 240

Lys Ile Ala Ala Gly Lys Gly Asp Ser Pro Pro Glu Arg Gln Val
                245                 250                 255

Arg Ile Ala Cys Arg Asp Gln Phe Arg Lys Ser Gly Leu Leu Glu Lys
            260                 265                 270

Ile Ile Pro Asp Ile Glu Glu Ile Leu Arg Ala Gly Gly Leu Glu Pro
            275                 280                 285

Pro Leu Asp Ala Pro Glu Ala Val Asp Pro Val Ile Pro Pro Glu Glu
            290                 295                 300

Pro Ser Gly Asp Asp Gly His Arg Gly
305                 310

<210> SEQ ID NO 71
<211> LENGTH: 344
<212> TYPE: PRT
<213> ORGANISM: Rhodospirillum rubrum

<400> SEQUENCE: 71

Met Lys Lys Leu Leu Asn Thr Val Tyr Val Thr Thr Glu Gly Thr Gly
 1               5                  10                  15

Leu Arg Lys Asp Gly Glu Asn Leu Val Ala Glu Leu Asp Gly Val Gln
            20                  25                  30

Lys Gly Arg Val Pro Leu His Met Val Gly Ser Val Val Phe Gly
            35                  40                  45

Gly Thr Tyr Val Ser Pro Gly Leu Met Gly Ala Cys Ala Ala His Gly
 50                  55                  60

Ile Thr Ile Val Leu Leu Asp Arg Val Gly Arg Phe Gln Ala Arg Val
 65                  70                  75                  80

Glu Gly Pro Val Ala Gly Asn Val Leu Leu Arg Arg Ala Gln Tyr Lys
                85                  90                  95

Ala Ser Glu Ala Pro Glu Asp Ile Val Lys Ser Leu Ile Leu Gly Lys
              100                 105                 110

Val Ser Asn Gln Arg Ala Val Leu Leu Arg Ala Leu Arg Asp His Gly
        115                 120                 125

Ala Asp Phe Pro Ala Ala Glu Ala Leu Ala Val Lys Asp Ala Ile Asp
    130                 135                 140

Arg Met Ala His Ile Leu Arg Lys Val Gly Ala Ser Ala Glu Asp Ala
145                 150                 155                 160

Asp His Leu Arg Gly Ala Glu Gly Glu Ala Ser Leu Tyr Phe Gly
                165                 170                 175

Val Phe Gly Gln Leu Ile Arg Ser Pro Asp Gly Asp Phe Ala Phe Arg
        180                 185                 190

Gly Arg Ser Arg Arg Pro Pro Leu Asp Pro Thr Asn Ala Leu Leu Ser
        195                 200                 205

Phe Leu Tyr Thr Leu Leu Thr His Asp Cys Arg Ser Ala Cys Glu Ser
    210                 215                 220

Val Gly Leu Asp Pro Ala Val Gly Phe Leu His Arg Asp Arg Pro Gly
225                 230                 235                 240

Arg Pro Ser Leu Ala Leu Asp Leu Met Glu Glu Leu Arg Pro Val Leu
                245                 250                 255

Val Asp Arg Leu Ala Leu Ser Leu Ile Asn Arg Arg Gln Leu Arg Ala
        260                 265                 270

Thr Asp Phe Gln Arg Leu Asp Gly Ala Val Leu Leu Thr Asp Glu
        275                 280                 285

Ala Arg Lys Thr Val Leu Ser Ala Trp Gln Glu Arg Lys Lys Gln Glu
290                 295                 300

Arg Arg His Pro Phe Leu Glu Glu Ser Ala Pro Leu Gly Leu Val Pro
305                 310                 315                 320

Tyr Leu Gln Ala Gln Met Leu Ala Arg His Leu Arg Gly Asp Leu Asp
                325                 330                 335

Ala Tyr Pro Pro Trp Phe Trp Lys
                340

<210> SEQ ID NO 72
<211> LENGTH: 371
<212> TYPE: PRT
<213> ORGANISM: Rhodospirillum rubrum

<400> SEQUENCE: 72

Met Val Gly Ser Gly Thr Gly Ala Pro Pro Arg Ser Ser Pro
1               5                   10                  15

Met Thr Thr Leu Tyr Val Thr Gln Pro Gly Ser Val Val Arg Ser Glu
            20                  25                  30

Gly Gly Ser Leu Thr Val Trp Val Glu Thr Glu Ala Asp Asp Pro Gly
        35                  40                  45

Pro Asn Asp Ser Pro Val Arg Arg Lys Arg Leu Ala Ser Val Glu Pro
    50                  55                  60

His Arg Leu Glu Ser Leu Val Leu Leu Gly Phe Thr Thr Ile Thr Ala
65              70                  75                  80

Asn Ala Met Arg Leu Cys Met Ala Asn Lys Ile Ala Val Ser Leu Leu
                85                  90                  95

Asp Gly Gly Gly Gly Leu Ala Ala Arg Val Val Pro Glu Ala Arg
            100                 105                 110

Ser Ala Asp Leu Arg Leu His Gln Tyr Ala Leu His Leu Asp Pro Pro
        115                 120                 125

Glu Arg Leu Ile Arg Ala Arg Ala Val Val Thr Ala Lys Leu Arg Asn
130                 135                 140

Ala Ala Ala Val Leu Arg Gly Ile Arg Ser Asn Gln Ala Ser Ser Ala
145                 150                 155                 160

Ala Leu Ala Ser Ala Ile Thr Gln Thr Glu Ala Ser Ala Glu Ala Ala
            165                 170                 175

Ala Ala Ala Val Ser Ala Glu Ser Leu Leu Gly Ile Glu Gly Asn Gly
        180                 185                 190

Ala His Gln Tyr Phe Ala Gly Leu Arg Thr Ala Phe Val Gly Gly Ile
    195                 200                 205

Pro Phe Leu Gly Arg Ala Gln Arg Pro Pro Asp Pro Ala Asn Ser
210                 215                 220

Leu Leu Ser Phe Gly Tyr Val Leu Leu Gly Asn Arg Leu Thr Gly Leu
225                 230                 235                 240

Leu Glu Ala Arg Gly Val Asp Pro Cys Leu Gly Phe Phe His Asp Leu
                245                 250                 255

Arg Pro Gly Arg Pro Ser Leu Ala Leu Asp Leu Leu Glu Glu Leu Arg
            260                 265                 270

His Pro Val Val Asp Arg Leu Ala Leu Arg Ile Cys Asn Leu Arg Lys
        275                 280                 285

Ile Gln Pro Gln His Phe Glu Pro Asp Ala Glu Arg Pro Gly Gly Val
    290                 295                 300

Lys Leu Thr Val Asp Gly Arg Lys Ile Phe Leu Glu Glu Trp Glu Gly
305                 310                 315                 320

His Leu Ala Arg Pro Leu Arg Glu Pro Gly Val Ala Ala Glu His Arg
                325                 330                 335

Leu Asp Val His Arg Leu Leu Gln Arg Gln Val Asp Arg Leu Val Ser
            340                 345                 350

Asp Leu Arg Gly Gly Glu Pro Tyr Arg Pro Phe Arg Phe Gly Thr Ser
        355                 360                 365

Arg Pro Gly
    370

<210> SEQ ID NO 73
<211> LENGTH: 301
<212> TYPE: PRT
<213> ORGANISM: Staphylococcus epidermidis

<400> SEQUENCE: 73

Met Lys Asp Val Ile Tyr Val Glu Asn His Tyr Phe Val Thr Ala Lys
1               5                   10                  15

Glu Asn Ser Ile Lys Phe Arg Asn Val Ile Asp Lys Ser Glu Lys Phe
                20                  25                  30

Tyr Leu Phe Glu Glu Ile Glu Ala Ile Ile Phe Asp His Tyr Lys Ser
            35                  40                  45

Tyr Phe Ser His Lys Leu Val Ile Lys Cys Ile Glu Asn Asp Ile Ala
        50                  55                  60

Ile Ile Phe Cys Asp Lys Lys His Ser Pro Val Thr Gln Leu Ile Ser
65                  70                  75                  80

Ser Tyr Gly Met Val Asn Arg Leu Lys Arg Ile Gln Ser Gln Phe Gln
                85                  90                  95

Leu Ser Gly Arg Thr Lys Asp Arg Ile Trp Lys Lys Ile Val Ile Asn
            100                 105                 110

Lys Ile Phe Asn Gln Thr Arg Cys Leu Glu Asn Asn Leu His Asn Glu
        115                 120                 125

```
Asn Val Lys Leu Met Leu Gly Phe Ala Lys Glu Val Ser Ser Gly Asp
    130                 135                 140

Lys Ser Asn Lys Glu Ala His Ala Thr Arg Ile Tyr Phe Lys Asp Leu
145                 150                 155                 160

Phe Gly Lys Gln Phe Lys Arg Gly Arg Tyr Asn Asp Val Ile Asn Ser
                165                 170                 175

Gly Leu Asn Tyr Gly Tyr Ser Ile Leu Arg Ser Phe Ile Asn Lys Glu
            180                 185                 190

Leu Ala Ile His Gly Phe Glu Met Ser Leu Gly Ile Lys His Gln Ser
        195                 200                 205

Lys Glu Asn Pro Phe Asn Leu Ala Asp Asp Ile Ile Glu Val Phe Arg
    210                 215                 220

Pro Phe Val Asp Asn Ile Val Tyr Glu Ile Val Phe Lys Lys Asn Ile
225                 230                 235                 240

Asp Thr Phe Asp Ile Asn Glu Lys Lys Leu Leu Asn Val Leu Tyr
                245                 250                 255

Glu Arg Cys Ile Ile Asp Lys Lys Val Val Arg Leu Leu Asp Ser Val
            260                 265                 270

Lys Ile Val Ile Gln Ser Leu Ile Arg Cys Tyr Glu Glu Asn Thr Pro
    275                 280                 285

Thr Tyr Leu Leu Leu Pro Lys Met Ile Glu Val Gly Asn
    290                 295                 300

<210> SEQ ID NO 74
<211> LENGTH: 289
<212> TYPE: PRT
<213> ORGANISM: Streptococcus pyogenes

<400> SEQUENCE: 74

Met Ala Gly Trp Arg Thr Val Val Asn Thr His Ser Lys Leu Ser
1               5                   10                  15

Tyr Lys Asn Asn His Leu Ile Phe Lys Asp Ala Tyr Lys Thr Glu Leu
            20                  25                  30

Ile His Leu Ser Glu Ile Asp Ile Leu Leu Glu Thr Thr Asp Ile
        35                  40                  45

Val Leu Ser Thr Met Leu Val Lys Arg Leu Val Asp Glu Asn Val Leu
    50                  55                  60

Val Ile Phe Cys Asp Asp Lys Arg Leu Pro Thr Ala Met Leu Met Pro
65                  70                  75                  80

Phe Tyr Gly Arg His Asp Ser Ser Leu Gln Leu Gly Lys Gln Met Ser
                85                  90                  95

Trp Ser Glu Thr Val Lys Ser Gln Val Trp Thr Thr Ile Ile Ala Gln
            100                 105                 110

Lys Ile Leu Asn Gln Ser Cys Tyr Leu Gly Ala Cys Ser Tyr Phe Glu
        115                 120                 125

Lys Ser Gln Ser Ile Met Asp Leu Tyr His Gly Leu Glu Asn Phe Asp
    130                 135                 140

Pro Ser Asn Arg Glu Gly His Ala Ala Arg Ile Tyr Phe Asn Thr Leu
145                 150                 155                 160

Phe Gly Asn Asp Phe Ser Arg Asp Leu Glu His Pro Thr Asn Ala Gly
                165                 170                 175

Leu Asp Tyr Gly Tyr Thr Leu Leu Ser Met Phe Ala Arg Glu Val
            180                 185                 190

Val Val Ser Gly Cys Met Thr Gln Phe Gly Leu Lys His Ala Asn Gln
        195                 200                 205
```

```
Phe Asn Gln Phe Asn Phe Ala Ser Asp Ile Met Glu Pro Phe Arg Pro
    210                 215                 220

Leu Val Asp Lys Ile Val Tyr Glu Asn Arg Asn Gln Pro Phe Pro Lys
225                 230                 235                 240

Ile Lys Arg Glu Leu Phe Thr Leu Phe Ser Asp Thr Phe Ser Tyr Asn
                245                 250                 255

Gly Lys Glu Met Tyr Leu Thr Asn Ile Ile Ser Asp Tyr Thr Lys Lys
            260                 265                 270

Val Val Lys Ala Leu Asn Asn Glu Gly Lys Gly Val Pro Glu Phe Arg
        275                 280                 285

Ile

<210> SEQ ID NO 75
<211> LENGTH: 289
<212> TYPE: PRT
<213> ORGANISM: Streptococcus thermophilus GN

<400> SEQUENCE: 75

Met Ala Gly Trp Arg Thr Val Val Asn Ile His Ser Lys Leu Ser
1               5                   10                  15

Tyr Lys Asn Asn His Leu Ile Phe Arg Asn Ser Tyr Lys Thr Glu Met
                20                  25                  30

Ile His Leu Ser Glu Ile Asp Ile Leu Leu Glu Thr Thr Asp Ile
            35                  40                  45

Val Leu Thr Thr Met Leu Val Lys Arg Leu Val Asp Glu Asn Ile Leu
        50                  55                  60

Val Ile Phe Cys Asp Asp Lys Arg Leu Pro Thr Ala Phe Leu Thr Pro
65                  70                  75                  80

Tyr Tyr Ala Arg His Asp Ser Ser Leu Gln Ile Ala Arg Gln Ile Ala
                85                  90                  95

Trp Lys Glu Asn Val Lys Cys Glu Val Trp Thr Ala Ile Ile Ala Gln
            100                 105                 110

Lys Ile Leu Asn Gln Ser Tyr Tyr Leu Gly Glu Cys Ser Phe Phe Glu
        115                 120                 125

Lys Ser Gln Ser Ile Met Glu Leu Tyr His Gly Leu Glu Arg Phe Asp
130                 135                 140

Pro Ser Asn Arg Glu Gly His Ser Ala Arg Ile Tyr Phe Asn Thr Leu
145                 150                 155                 160

Phe Gly Asn Asp Phe Thr Arg Glu Ser Asp Asn Asp Ile Asn Ala Ala
                165                 170                 175

Leu Asp Tyr Gly Tyr Thr Leu Leu Leu Ser Met Phe Ala Arg Glu Val
            180                 185                 190

Val Val Cys Gly Cys Met Thr Gln Ile Gly Leu Lys His Ala Asn Gln
        195                 200                 205

Phe Asn Gln Phe Asn Leu Ala Ser Asp Ile Met Glu Pro Phe Arg Pro
    210                 215                 220

Ile Ile Asp Arg Ile Val Tyr Gln Asn Arg His Asn Asn Phe Val Lys
225                 230                 235                 240

Ile Lys Lys Glu Leu Phe Ser Ile Phe Ser Glu Thr Tyr Leu Tyr Asn
                245                 250                 255

Gly Lys Glu Met Tyr Leu Ser Asn Ile Val Ser Asp Tyr Thr Lys Lys
            260                 265                 270
```

-continued

Val Ile Lys Ala Leu Asn Gln Leu Gly Glu Glu Ile Pro Glu Phe Arg
                275                 280                 285
Ile

<210> SEQ ID NO 76
<211> LENGTH: 304
<212> TYPE: PRT
<213> ORGANISM: Sulfolobus islandicus

<400> SEQUENCE: 76

Met Arg Thr Leu Val Ile Ser Glu Tyr Gly Ala Tyr Ile Tyr Val Lys
1               5                   10                  15

Lys Asn Met Leu Val Ile Lys Lys Gly Asp Asn Lys Val Glu Ile Ser
                20                  25                  30

Pro Ser Glu Val Asp Glu Ile Leu Ile Thr Ala Ser Cys Ser Ile Ser
            35                  40                  45

Thr Ser Ala Leu Ser Leu Ala Leu Thr His Gly Ile Ser Val Met Phe
        50                  55                  60

Leu Asn Ser Arg Asp Thr Pro Trp Gly Ile Leu Leu Pro Ser Val Ile
65                  70                  75                  80

Thr Glu Thr Val Lys Thr Lys Lys Ala Gln Tyr Glu Thr Ile Val Ala
                85                  90                  95

Lys Lys Asp Ile Arg Tyr Gly Glu Glu Ile Ile Ser Ser Lys Ile Tyr
            100                 105                 110

Asn Gln Ser Val His Leu Lys Tyr Trp Thr Arg Leu Thr Gly Thr Arg
        115                 120                 125

Asn Asp Tyr Lys Glu Leu Leu Gly Lys Asp Glu Pro Thr Ala Ala Arg
    130                 135                 140

Ile Tyr Trp Arg Asn Ile Ser Gln Leu Leu Pro Lys Asp Ile Gly Phe
145                 150                 155                 160

Asp Gly Arg Asp Val Asp Gly Val Asp Gln Phe Asn Met Ala Leu Asn
                165                 170                 175

Tyr Ser Tyr Ala Ile Leu Tyr Asn Thr Ile Phe Lys Tyr Leu Val Ile
            180                 185                 190

Ala Gly Leu Asp Pro Tyr Leu Gly Phe Ile His Lys Asp Arg Pro Gly
        195                 200                 205

Asn Glu Ser Leu Val Tyr Asp Phe Ser Glu Met Phe Lys Pro Tyr Ile
    210                 215                 220

Asp Phe Leu Leu Val Arg Ala Leu Arg Ser Gly Phe Arg Leu Lys Val
225                 230                 235                 240

Lys Asp Gly Leu Ile Glu Glu Asn Ser Arg Gly Asp Leu Ala Lys Leu
                245                 250                 255

Ile Arg Lys Gly Met Glu Glu Lys Val Lys Glu Glu Ser Asp His Asn
            260                 265                 270

Pro Lys Thr Leu Ile Gln Ala Ile Arg Ala His Ala Val Lys Leu Ala
        275                 280                 285

Ser Ser Ile Arg Glu Gly Lys Glu Tyr Lys Gly Phe Lys Leu Val Met
    290                 295                 300

<210> SEQ ID NO 77
<211> LENGTH: 352
<212> TYPE: PRT
<213> ORGANISM: Sulfolobus solfataricus

<400> SEQUENCE: 77

```
Met Val His Lys Val Ser Gln Arg Glu Phe Ser Arg Cys Tyr Lys Arg
1               5                   10                  15

Asn Cys Asp Cys Ile Cys Arg Lys Pro Lys Gln Arg Arg Asn Val Tyr
            20                  25                  30

Leu Asn Tyr Ser Leu Glu Leu Leu Ile Thr Ile Phe Lys Glu Val Ile
        35                  40                  45

Pro Asn Leu Pro Met Asp Lys Lys Ile Ala Phe Val Lys Asp Tyr Gly
    50                  55                  60

Ala Tyr Leu Lys Val Glu Lys Gly Leu Ile Thr Cys Lys Ile Lys Asn
65                  70                  75                  80

Gln Val Lys Trp Ser Ile Ala Pro Thr Glu Leu His Ser Ile Val Val
                85                  90                  95

Leu Thr Asn Ser Ser Ile Ser Ser Glu Val Val Lys Val Ala Asn Glu
            100                 105                 110

Tyr Gly Ile Glu Ile Val Phe Phe Asn Lys His Glu Pro Tyr Ala Lys
        115                 120                 125

Leu Ile Pro Ala Lys Tyr Ala Gly Ser Phe Lys Val Trp Leu Lys Gln
    130                 135                 140

Leu Thr Ala Trp Lys Arg Arg Lys Val Glu Phe Ala Lys Ala Phe Ile
145                 150                 155                 160

Tyr Gly Lys Val His Asn Gln Trp Val Thr Leu Arg Tyr Tyr Glu Arg
                165                 170                 175

Lys Tyr Gly Tyr Asn Leu Thr Ser Gln Glu Leu Asp Arg Leu Ala Arg
            180                 185                 190

Glu Ile Thr Phe Val Asn Thr Ala Glu Glu Val Met Gln Lys Glu Ala
        195                 200                 205

Glu Ala Ala Lys Val Tyr Trp Arg Gly Val Lys Ser Leu Leu Pro Lys
    210                 215                 220

Ser Leu Gly Phe Lys Gly Arg Met Lys Arg Val Ser Asp Asn Leu Asp
225                 230                 235                 240

Pro Phe Asn Arg Ala Leu Asn Ile Gly Tyr Gly Met Leu Arg Lys Val
                245                 250                 255

Val Trp Gly Ala Val Ile Ser Val Gly Leu Asn Pro Tyr Ile Gly Phe
            260                 265                 270

Leu His Lys Phe Arg Ser Gly Arg Ile Ser Leu Val Phe Asp Leu Met
        275                 280                 285

Glu Glu Phe Arg Ser Pro Phe Val Asp Arg Lys Leu Ile Gly Leu Ala
    290                 295                 300

Arg Glu Ser Ala Asp Lys Val Thr Asp Leu Lys Thr Val Tyr Ser Leu
305                 310                 315                 320

Phe Ser Asp Val Lys Glu Asp Glu Ile Tyr Thr Gln Ala Arg Arg Leu
                325                 330                 335

Val Asn Ala Ile Leu Asn Asp Glu Glu Tyr Arg Pro Tyr Leu Ala Lys
            340                 345                 350
```

<210> SEQ ID NO 78
<211> LENGTH: 307
<212> TYPE: PRT
<213> ORGANISM: Sulfolobus solfataricus

<400> SEQUENCE: 78

```
Met Ile Ser Val Arg Thr Leu Val Ile Ser Glu Tyr Gly Ala Tyr Val
1               5                   10                  15

Tyr Val Lys Lys Asn Met Leu Val Ile Lys Lys Gly Asp Lys Lys Val
            20                  25                  30

Glu Ile Ser Pro Ser Glu Val Asp Glu Ile Leu Ile Thr Val Ser Cys
        35                  40                  45

Ser Ile Ser Thr Ser Ala Leu Ser Leu Ala Leu Thr His Gly Ile Ser
    50                  55                  60

Val Met Phe Leu Asn Ser Arg Glu Thr Pro Trp Gly Ile Leu Leu Pro
65                  70                  75                  80

Ser Ile Val Thr Glu Thr Val Lys Thr Lys Lys Ala Gln Tyr Glu Ala
                85                  90                  95

Ile Val Val Arg Lys Asp Asn Arg Tyr Gly Glu Ile Ile Ser Ser
            100                 105                 110

Lys Ile Tyr Asn Gln Ser Val His Leu Lys Tyr Trp Ala Arg Val Thr
        115                 120                 125

Gly Thr Lys Asn Asp Tyr Lys Glu Leu Leu Asp Lys Asp Glu Pro Ala
130                 135                 140

Ala Ala Arg Val Tyr Trp Gln Asn Ile Ser Gln Leu Leu Pro Lys Asp
145                 150                 155                 160

Ile Gly Phe Asp Gly Arg Asp Val Asp Gly Thr Asp Gln Phe Asn Met
                165                 170                 175

Ala Leu Asn Tyr Ser Tyr Ala Ile Leu Tyr Asn Thr Ile Phe Lys Tyr
            180                 185                 190

Leu Val Ile Ala Gly Leu Asp Pro Tyr Leu Gly Phe Ile His Lys Asp
        195                 200                 205

Arg Pro Gly Asn Glu Ser Leu Val Tyr Asp Phe Ser Glu Met Phe Lys
210                 215                 220

Pro Tyr Ile Asp Phe Leu Leu Val Arg Ala Leu Arg Ser Gly Phe Arg
225                 230                 235                 240

Leu Lys Val Lys Gly Gly Leu Ile Glu Glu Asn Ser Arg Gly Asp Leu
                245                 250                 255

Ala Lys Leu Ile Arg Lys Gly Met Glu Glu Asn Val Lys Glu Ser
            260                 265                 270

Asp His Asn Pro Lys Thr Leu Ile Gln Ala Ile Arg Ala His Ala Val
        275                 280                 285

Lys Leu Ala Ser Ser Ile Arg Glu Gly Lys Glu Tyr Arg Gly Phe Lys
290                 295                 300

Leu Val Met
305
```

<210> SEQ ID NO 79
<211> LENGTH: 326
<212> TYPE: PRT
<213> ORGANISM: Thermococcus kodakaraensis

<400> SEQUENCE: 79

```
Met Arg Lys Arg Ser Leu Thr Leu Phe Ser Asp Gly Asn Leu Phe Arg
1               5                   10                  15

Arg Glu Asn Thr Leu Tyr Phe Glu Asn Ala Gln Gly Arg Lys Pro Leu
            20                  25                  30

Ala Val Glu Gly Ile Tyr Asp Ile Tyr Val Tyr Gly His Val Asn Ile
        35                  40                  45
```

```
Ser Ser Gln Ala Leu His Phe Leu Ala Gln Lys Gly Ile Pro Val His
    50                  55                  60

Phe Phe Asn His Tyr Gly His Tyr Asp Gly Ser Phe Tyr Pro Arg Glu
 65                  70                  75                  80

Ser Leu Leu Ser Gly Asp Leu Ile Ile Lys Gln Ala Lys His Tyr Leu
                85                  90                  95

Asp Gln Glu Lys Arg Leu Ile Leu Ala Lys Leu Phe Val Arg Gly Ser
            100                 105                 110

Ala Leu Asn Met Glu Lys Asn Leu Lys Arg Trp Lys Val Ala Asp Gly
            115                 120                 125

Phe Ser Gly Leu Leu Asp Glu Leu Phe Glu Glu Leu Glu Ser Ala Arg
130                 135                 140

Lys Ile Thr Glu Val Met Asn Val Glu Ala Arg Ile Arg Gly Glu Tyr
145                 150                 155                 160

Tyr Thr Arg Trp Asp Asn Ala Leu Pro Glu Gly Phe Lys Ile Val Lys
                165                 170                 175

Arg Thr Arg Arg Pro Pro Glu Asn Glu Met Asn Ala Leu Ile Ser Phe
            180                 185                 190

Leu Asn Ser Arg Leu Tyr Ala Thr Ile Val Ser Glu Leu Tyr Asn Thr
        195                 200                 205

Gln Leu Ala Pro Thr Val Ser Tyr Leu His Glu Pro Gly Glu Arg Arg
210                 215                 220

Phe Ser Leu Ala Leu Asp Leu Ser Glu Ile Phe Lys Pro Ile Ile Ala
225                 230                 235                 240

Asp Arg Ile Ala Asn Arg Leu Val Lys Gln Gly Ile Ile Lys Arg Glu
                245                 250                 255

His Phe Arg Gly Glu Leu Asn Gly Val Leu Leu Thr Lys Glu Gly Met
            260                 265                 270

Lys Val Val Leu Lys Ala Tyr Asn Glu Glu Leu Gly Arg Ser Val Lys
        275                 280                 285

His Pro Gly Leu Lys Lys Asn Val Thr Lys Gln Arg Leu Ile Arg Leu
290                 295                 300

Glu Ala Tyr Lys Leu Ile Lys His Leu Val Gly Val Lys Asp Tyr Glu
305                 310                 315                 320

Pro Leu Val Ala Trp Phe
                325

<210> SEQ ID NO 80
<211> LENGTH: 318
<212> TYPE: PRT
<213> ORGANISM: Thermodesulfovibrio yellowstonii

<400> SEQUENCE: 80

Met Ser Thr Val Phe Ile Asp Arg Lys Asp Ile Glu Ile Arg Val Asp
  1               5                  10                  15

Gly Asn Ser Ile Ser Phe Tyr Ala Lys Gly Lys Lys Asp Gly Ser Leu
                 20                  25                  30

Pro Leu Ser Pro Leu Lys Arg Val Ile Val Gly Asn Val Lys Ile
             35                  40                  45

Glu Thr Ser Val Leu Tyr Lys Leu Val Asn His Gly Ile Thr Val Leu
     50                  55                  60

Phe Leu Thr Gly Lys Leu Lys Tyr Ser Gly Ile Leu Asn Gly Pro Leu
 65                  70                  75                  80

His Asn Asn Gly Leu Leu Arg Val Lys Gln Tyr Gln Lys Ser Leu Ser
                 85                  90                  95
```

```
Gly Phe Ser Leu Lys Phe Ala Lys Glu Leu Ile Lys Arg Lys Ile Val
                100                 105                 110

Ser Gln Arg Asp Phe Leu Ser Glu Ile Arg Glu Ile Lys Lys Ala Leu
            115                 120                 125

Ala Met Gln Ala Asp Arg Ala Ile Glu Ile Leu Asn Lys Ala Ile Ser
        130                 135                 140

Asn Ile Glu Val Thr Pro Ile Ser Ile Asp Ser Leu Arg Gly Ile Glu
145                 150                 155                 160

Gly Ala Ala Ser Ser Ile Tyr Phe Ile Thr Tyr Ser Lys Ile Phe Pro
                165                 170                 175

Asn Ser Leu Lys Phe Val Arg Arg Ile Lys Arg Pro Pro Lys Asp Pro
            180                 185                 190

Val Asn Ala Met Leu Ser Leu Cys Tyr Thr Leu Leu His Tyr Glu Ile
        195                 200                 205

Val Arg Glu Ile Gln Leu Ile Gly Leu Asp Pro Thr Ile Gly Phe Tyr
210                 215                 220

His Gln Phe Glu Tyr Gly Arg Glu Ser Leu Ala Cys Asp Leu Val Glu
225                 230                 235                 240

Leu Phe Arg Val Asn Val Asp Arg Phe Val Tyr Glu Leu Phe Lys Ala
                245                 250                 255

Lys His Leu Gly Asn Arg Asp Phe Met Lys Asp Glu Glu Ser Gly Gly
            260                 265                 270

Val Tyr Leu Lys Lys Thr Gly Arg Lys Lys Phe Tyr Pro Leu Tyr Glu
        275                 280                 285

Gln Trp Val Gln Gln Arg Thr Ile Trp Arg Gly Glu Val Gln Gly
290                 295                 300

Phe Ala Arg Arg Ile Leu Glu Glu Lys Asp Ile Ile Ser Gly
305                 310                 315

<210> SEQ ID NO 81
<211> LENGTH: 327
<212> TYPE: PRT
<213> ORGANISM: Thermofilum pendens

<400> SEQUENCE: 81

Met Arg Leu Leu Val Leu Arg Gly Val Asp Glu Val Thr Val Ser Ser
1               5                   10                  15

Arg Ser Thr Val Val Ile Lys Ser Gly Asn Arg Val Phe Glu Arg Ala
                20                  25                  30

Leu Arg Asp Val Asp Ala Val Leu Val Gly Ser Gly Ile Lys Ile
            35                  40                  45

Ser Ser Ser Leu Pro Pro Val Leu Ala Leu His Gly Ile Pro Leu Ser
50                  55                  60

Ile Leu Ala Lys Gly His Val Ala Val Leu Leu Asn Pro Val Gly Thr
65                  70                  75                  80

Lys Tyr Asn Asn Tyr Arg Ala Leu Gln Tyr Thr Leu Pro Lys Asn Lys
                85                  90                  95

Ala Leu Ala Ile Ala Leu Glu Tyr Leu Lys Ser Arg Val Arg Gly Met
            100                 105                 110

Ala Ser Ile Ile Arg Asn Arg Gly Gly Arg Leu Pro Ala Leu Pro Glu
        115                 120                 125

Pro Pro Asp Pro Ala Leu Tyr Glu Asp Pro Ala Arg Leu Glu Ser Asp
    130                 135                 140

Ile Arg Ser Trp Glu Ala Ala Ser Asn Thr Leu Trp Asp Glu Val
145                 150                 155                 160
```

```
Phe Lys Leu Leu Asp Pro Ser Ala Ala Arg Glu Leu Arg Glu Arg Tyr
                165                 170                 175

Gly Phe Ala Gly Arg Lys Pro Gly His Pro Asp Pro Leu Asn Lys Ala
            180                 185                 190

Ile Ser Ala Met Tyr Ala Val Leu Tyr Thr Leu Ser Thr Lys Ala Leu
        195                 200                 205

Val Ala Ala Gly Leu Asp Pro Thr Tyr Gly Phe Leu His Arg Thr Gln
    210                 215                 220

Tyr Ser Val Pro Leu Ala Phe Asp Tyr Ala Glu Ala Phe Lys Pro Leu
225                 230                 235                 240

Ala Val Glu Ala Ala Leu Asp Leu Val Asn Glu Glu Gly Leu Pro Thr
                245                 250                 255

Leu Ser Glu Asp Gly Asp Leu Asp Lys Asp Ser Leu Asn Lys Ala Met
            260                 265                 270

Lys Arg Leu Tyr Arg Tyr Leu Ser Ala Lys His Arg Glu Thr Gly Lys
        275                 280                 285

Thr Pro Tyr Gln Gln Ile His Leu Lys Ala Phe Cys Leu Ala Lys His
    290                 295                 300

Leu Glu Gly Lys Cys Ser Arg Glu Lys Leu Ala Phe Thr Trp Asp Lys
305                 310                 315                 320

Lys Arg Tyr Ile Ile His Glu
                325

<210> SEQ ID NO 82
<211> LENGTH: 327
<212> TYPE: PRT
<213> ORGANISM: Thermofilum pendens

<400> SEQUENCE: 82

Met Arg Leu Leu Val Leu Arg Gly Val Asp Glu Val Thr Val Ser Ser
1               5                   10                  15

Arg Ser Thr Val Val Ile Lys Ser Gly Asn Arg Val Phe Glu Arg Ala
                20                  25                  30

Leu Arg Asp Val Asp Ala Val Leu Val Gly Ser Gly Ile Lys Ile
            35                  40                  45

Ser Ser Ser Leu Pro Pro Val Leu Ala Leu His Gly Ile Pro Leu Ser
        50                  55                  60

Ile Leu Ala Lys Gly His Val Ala Val Leu Leu Asn Pro Val Gly Thr
65                  70                  75                  80

Lys Tyr Asn Asn Tyr Arg Ala Leu Gln Tyr Thr Leu Pro Lys Asn Lys
                85                  90                  95

Ala Leu Ala Ile Ala Leu Glu Tyr Leu Lys Ser Arg Val Arg Gly Met
            100                 105                 110

Ala Ser Ile Ile Arg Asn Arg Gly Gly Arg Leu Pro Ala Leu Pro Glu
        115                 120                 125

Pro Pro Asp Pro Ala Leu Tyr Glu Asp Pro Ala Arg Leu Glu Ser Asp
    130                 135                 140

Ile Arg Ser Trp Glu Ala Ala Ala Ser Asn Thr Leu Trp Asp Glu Val
145                 150                 155                 160

Phe Lys Leu Leu Asp Pro Ser Ala Ala Arg Glu Leu Arg Glu Arg Tyr
                165                 170                 175

Gly Phe Ala Gly Arg Lys Pro Gly His Pro Asp Pro Leu Asn Lys Ala
            180                 185                 190

Ile Ser Ala Met Tyr Ala Val Leu Tyr Thr Leu Ser Thr Lys Ala Leu
        195                 200                 205
```

```
Val Ala Ala Gly Leu Asp Pro Thr Tyr Gly Phe Leu His Arg Thr Gln
            210                 215                 220

Tyr Ser Val Pro Leu Ala Phe Asp Tyr Ala Glu Ala Phe Lys Pro Leu
225                 230                 235                 240

Ala Val Glu Ala Ala Leu Asp Leu Val Asn Glu Glu Gly Leu Pro Thr
                245                 250                 255

Leu Ser Glu Asp Gly Asp Leu Asp Lys Asp Ser Leu Asn Lys Ala Met
                260                 265                 270

Lys Arg Leu Tyr Arg Tyr Leu Ser Ala Lys His Arg Glu Thr Gly Lys
                275                 280                 285

Thr Pro Tyr Gln Gln Ile His Leu Lys Ala Phe Cys Leu Ala Lys His
290                 295                 300

Leu Glu Gly Lys Cys Ser Arg Glu Lys Leu Ala Phe Thr Trp Asp Lys
305                 310                 315                 320

Lys Arg Tyr Ile Ile His Glu
                325

<210> SEQ ID NO 83
<211> LENGTH: 319
<212> TYPE: PRT
<213> ORGANISM: Thermotoga maritima

<400> SEQUENCE: 83

Met Glu Ser Val Tyr Leu Phe Ser Ser Gly Thr Leu Lys Arg Lys Ala
1               5                   10                  15

Asn Thr Ile Cys Leu Glu Thr Glu Ser Gly Arg Lys Tyr Ile Pro Val
                20                  25                  30

Glu Asn Val Met Asp Ile Lys Val Phe Gly Glu Val Asp Leu Asn Lys
                35                  40                  45

Arg Phe Leu Glu Phe Leu Ser Gln Lys Arg Ile Pro Ile His Phe Phe
    50                  55                  60

Asn Arg Glu Gly Tyr Tyr Val Gly Thr Phe Tyr Pro Arg Glu Tyr Leu
65                  70                  75                  80

Asn Ser Gly Phe Leu Ile Leu Lys Gln Ala Glu His Tyr Ile Asn Gln
                85                  90                  95

Glu Lys Arg Met Leu Ile Ala Arg Glu Ile Val Ser Arg Ser Phe Gln
                100                 105                 110

Asn Met Val Asp Phe Leu Lys Lys Arg Lys Val Arg Ala Asp Ser Leu
            115                 120                 125

Thr Arg Tyr Lys Lys Lys Ala Glu Glu Ala Ser Asn Val Ser Glu Leu
        130                 135                 140

Met Gly Ile Glu Gly Asn Ala Arg Glu Tyr Tyr Ser Met Ile Asp
145                 150                 155                 160

Ser Leu Val Ser Asp Glu Arg Phe Arg Ile Glu Lys Arg Thr Arg Arg
                165                 170                 175

Pro Pro Lys Asn Phe Ala Asn Thr Leu Ile Ser Phe Gly Asn Ser Leu
                180                 185                 190

Leu Tyr Thr Thr Val Leu Ser Leu Ile Tyr Gln Thr His Leu Asp Pro
            195                 200                 205

Arg Ile Gly Tyr Leu His Glu Thr Asn Phe Arg Arg Phe Ser Leu Asn
        210                 215                 220

Leu Asp Ile Ala Glu Leu Phe Lys Pro Ala Val Val Asp Arg Leu Phe
225                 230                 235                 240

Leu Asn Leu Val Asn Thr Arg Gln Ile Asn Glu Lys His Phe Asp Glu
                245                 250                 255
```

```
Ile Ser Glu Gly Leu Met Leu Asn Asp Glu Gly Lys Ser Leu Phe Val
            260                 265                 270

Lys Asn Tyr Glu Gln Ala Leu Arg Glu Thr Val Phe His Lys Lys Leu
            275                 280                 285

Asn Arg Tyr Val Ser Met Arg Ser Leu Ile Lys Met Glu Leu His Lys
            290                 295                 300

Leu Glu Lys His Leu Ile Gly Glu Gln Val Phe Gly Ser Glu Glu
305                 310                 315

<210> SEQ ID NO 84
<211> LENGTH: 315
<212> TYPE: PRT
<213> ORGANISM: Thermus thermophilus

<400> SEQUENCE: 84

Met Thr Leu His Leu Thr Arg Gln Gly Ala Thr Leu Arg Leu Arg Gln
1               5                   10                  15

Gly Arg Leu Leu Leu Glu Glu Glu Gly Arg Glu Val Ala Gly Phe Pro
            20                  25                  30

Ala Arg Gln Val Arg Ser Val Ala Leu Trp Gly Asn Val Arg Leu Ser
        35                  40                  45

Thr Pro Ala Leu Val Phe Leu Leu Arg Gln Gly Val Pro Val Phe Phe
50                  55                  60

Tyr Ser Leu Glu Gly Phe Leu His Gly Val Ala Gly Ala Tyr Pro Asp
65                  70                  75                  80

Pro His Pro Ala His Leu Arg Ala Gln Phe Ala Ala Glu Gly Leu Pro
                85                  90                  95

Leu Ala Arg Ala Phe Val Val Gly Lys Leu Arg Ser Ala Leu Ala Leu
            100                 105                 110

Leu Glu Arg His Arg Leu Pro Glu Ala Gly Val Val Glu Ala Leu
        115                 120                 125

Ala Arg Ala Glu Gly Ala Ser Glu Leu Glu Arg Leu Arg Gly Ala Glu
130                 135                 140

Gly Glu Gly Ser Arg Val Tyr Phe Gln Gly Leu Ala Arg Leu Leu Gly
145                 150                 155                 160

Pro Tyr Gly Phe Gly Gly Arg Thr Arg Arg Pro Pro Arg Asp Pro Val
                165                 170                 175

Asn Ala Ala Leu Ser Tyr Gly Tyr Ala Leu Leu Leu Gly Arg Val Leu
            180                 185                 190

Val Ala Val Arg Leu Ala Gly Leu His Pro Glu Val Gly Phe Leu His
        195                 200                 205

Ala Glu Gly Arg Arg Ser Pro Ala Leu Ala Leu Asp Leu Met Glu Glu
210                 215                 220

Phe Arg Val Pro Val Val Asp Gln Val Val Leu Ser Ala Phe Arg Arg
225                 230                 235                 240

Gly Leu Leu Thr Pro Ser His Ala Glu Val Arg Glu Gly Gly Val Tyr
                245                 250                 255

Leu Asn Glu Glu Gly Arg Arg Leu Ile Gln Leu Phe Glu Glu Arg
            260                 265                 270

Leu Leu Glu Gly Val Ser His Pro Leu Gly Phe Arg Lys Pro Leu Gly
        275                 280                 285

Glu Thr Ile Glu Val Gln Ala Gln Arg Leu Lys Ala Ala Leu Leu Gly
    290                 295                 300

Arg Gly Arg Tyr Thr Pro Phe Tyr Leu Trp Arg
305                 310                 315
```

<210> SEQ ID NO 85
<211> LENGTH: 325
<212> TYPE: PRT
<213> ORGANISM: Thermus thermophilus

<400> SEQUENCE: 85

Met Pro Pro Val Ser Ser Ala Arg Asn Leu Lys Glu Leu Pro Lys Phe
1               5                   10                  15

Arg Asp Gly Leu Ser Tyr Leu Tyr Val Glu His Ala Val Val Glu Arg
            20                  25                  30

Glu Ala Gly Gly Ile Gly Ile Tyr Asp Gln Glu Gly Leu Thr Leu Ala
        35                  40                  45

Pro Val Ala Gly Leu Gly Val Leu Phe Leu Gly Pro Gly Thr Arg Ile
    50                  55                  60

Thr His Ala Ala Val Arg Leu Leu Ala Glu Asn Gly Cys Thr Val Ala
65                  70                  75                  80

Trp Val Gly Glu Gly Met Ala Arg Phe Tyr Ala Gln Gly Leu Gly Asp
                85                  90                  95

Thr Arg Ser Ala Ala Arg Phe Tyr Arg Gln Ala Arg Ala Trp Ala Asp
            100                 105                 110

Pro Ala Leu His Leu Glu Val Val Met Arg Leu Tyr Arg Met Arg Phe
        115                 120                 125

Ser Glu Pro Leu Pro Glu Gly Leu Thr Leu Glu Gln Val Arg Gly Leu
    130                 135                 140

Glu Gly Val Arg Val Arg Asn Ala Tyr Ala Arg Trp Ser Arg Glu Thr
145                 150                 155                 160

Gly Val Pro Trp Tyr Gly Arg Ser Tyr Asp Arg Gly Asn Trp Arg Ala
                165                 170                 175

Ala Asp Pro Val Asn Arg Ala Leu Ser Ala Gly Ala Ser Tyr Leu Tyr
            180                 185                 190

Gly Leu Ala His Ala Ala Ile Val Ser Leu Gly Phe Ser Pro Ala Leu
        195                 200                 205

Gly Phe Ile His Thr Gly Lys Leu Leu Ser Phe Val Tyr Asp Ile Ala
    210                 215                 220

Asp Leu Tyr Lys Ala Asp Tyr Leu Val Pro Ala Ala Phe Arg Thr Val
225                 230                 235                 240

Ala Glu Ser Glu Glu Ala Val Glu Arg Arg Val Arg Arg Ala Leu Arg
                245                 250                 255

Glu Ala Ile Gln Glu Gly Arg Leu Leu Glu Arg Met Ala Glu Asp Leu
            260                 265                 270

Leu Asn Leu Phe Arg Gly Leu Gly Leu Pro Glu Glu Glu Asp Pro Val
        275                 280                 285

Glu Glu Asp Pro Thr Arg Pro Gly Gly Leu Trp Asp Leu Glu Gly Glu
    290                 295                 300

Val Glu Gly Gly Val Ala Tyr Gly Gly Asp Asp Pro Gly Glu Gly Ala
305                 310                 315                 320

Glu Glu Pro Glu Gly
                325

<210> SEQ ID NO 86
<211> LENGTH: 332
<212> TYPE: PRT
<213> ORGANISM: Thermus thermophilus

```
<400> SEQUENCE: 86

Met Ala Glu Gly Gly Gly Val Gly Val Val Tyr Val Leu Glu Asn
1               5                   10                  15

Glu Ala Tyr Leu Ser Lys Glu Gly Thr Leu Lys Val Ser Arg Arg
                20                  25                  30

Ala Gly Arg Glu Val Leu Leu Gln Lys Pro Leu Ile Ala Val Glu Glu
            35                  40                  45

Ile Val Ile Leu Gly Asn Ala Val Val Thr Pro Ala Leu Leu Lys His
    50                  55                  60

Cys Ala Gln Glu Gly Val Gly Ile His Tyr Leu Ser Pro Thr Gly Thr
65                  70                  75                  80

Tyr Tyr Ala Gly Leu Thr Arg Thr Pro Ser Lys Asn Ala Pro Ala Arg
                85                  90                  95

Val Ala Gln Phe Lys Ala Tyr Leu Glu Pro Thr Trp Lys Leu Ala Leu
            100                 105                 110

Ala Gln Arg Phe Val Leu Gly Lys Ile Arg Asn Gly Leu Val Phe Leu
        115                 120                 125

Arg Arg Asn Gly Ala Glu Gly Trp Glu Arg Leu Lys Glu Ala Leu Leu
130                 135                 140

Glu Ala Glu Arg Ala Gln Asp Glu Glu Ala Leu Arg Gly Ala Glu Gly
145                 150                 155                 160

Arg Ala Ala Asp Leu Tyr Phe Arg Ala Phe Ala Glu Leu Leu Pro Glu
                165                 170                 175

Glu Phe Ala Phe Gly Glu Arg Ser Arg Arg Pro Pro Arg Asp Pro Ala
            180                 185                 190

Asn Ser Leu Leu Ser Leu Ala Tyr Thr Leu Leu Ala Lys Glu Cys Glu
        195                 200                 205

Ser Ala Leu Leu Val Ala Gly Leu Asp Pro Tyr Val Gly Tyr Leu His
210                 215                 220

Glu Val Arg Tyr Gly Arg Pro Ser Leu Ala Leu Asp Leu Met Glu Glu
225                 230                 235                 240

Phe Arg Ser Val Leu Ala Asp Ser Val Val Leu Ser Leu Leu Asn Asn
                245                 250                 255

Arg Arg Val Thr Leu Glu Asp Phe Asp Asp Ser Glu Gly Phe Pro Arg
            260                 265                 270

Leu Arg Lys Glu Ala Trp Pro Lys Phe Leu Arg Ala Trp Glu Gly Arg
        275                 280                 285

Leu Asn Glu Arg Ile Gln His Pro Leu Leu Gly Lys Arg Leu Ala Tyr
290                 295                 300

Arg Glu Ile Leu Leu Ala Gln Ala Arg Ile Leu Val Lys His Leu Leu
305                 310                 315                 320

Gly Glu Leu Pro Arg Tyr Glu Pro Phe Ala Val Arg
                325                 330

<210> SEQ ID NO 87
<211> LENGTH: 108
<212> TYPE: PRT
<213> ORGANISM: Acidovorax avenae

<400> SEQUENCE: 87

Met Leu Thr Gly Tyr Arg Leu Met Trp Met Val Met Phe Asp Leu
1               5                   10                  15

Pro Val Ile Thr Lys Ala Glu Arg Lys Ala Ala Thr Gly Phe Arg Asn
                20                  25                  30
```

```
Ala Leu Leu Asp Val Gly Phe Gln Met Ser Gln Phe Ser Val Tyr Leu
            35                  40                  45

Arg Phe Cys Thr Ser Gln Ala Gln Val Asp Thr Leu Cys Arg Gln Val
 50                  55                  60

Glu Gln Ala Leu Pro Ala Gly Gly Lys Val His Ile Phe Gln Phe Thr
 65                  70                  75                  80

Asp Lys Gln Tyr Glu Arg Ala Ile Ser Phe His Gly Arg Ser Arg Gln
                85                  90                  95

Pro Ala Gln Lys Ala Pro Asp Gln Phe Asp Leu Phe
                100                 105

<210> SEQ ID NO 88
<211> LENGTH: 102
<212> TYPE: PRT
<213> ORGANISM: Acidovorax ebreus

<400> SEQUENCE: 88

Met Arg Met Leu Val Phe Phe Asp Leu Pro Val Val Ser Lys Ala Asp
  1               5                  10                  15

Arg Arg Ala Tyr Thr Val Phe Arg Arg Phe Leu Leu Asn Asp Gly Tyr
                 20                  25                  30

Asp Met Ile Gln Phe Ser Val Tyr Gly Arg Ile Leu Asn Gly Thr Asp
            35                  40                  45

Ala Ala Gln Lys His Met Gln Arg Leu Leu Ala Asn Leu Pro Ser Glu
 50                  55                  60

Gly Ser Val Arg Val Leu Thr Val Thr Glu Lys Gln Phe Ala Ser Met
 65                  70                  75                  80

Lys Leu Leu Val Gly Leu Pro Leu Phe Gln Glu Lys Val Asn Ala
                 85                  90                  95

Ala Gln Ile Ala Leu Phe
            100

<210> SEQ ID NO 89
<211> LENGTH: 92
<212> TYPE: PRT
<213> ORGANISM: Aeropyrum pernix

<400> SEQUENCE: 89

Met Val Tyr Val Leu Ile Ala Tyr Asp Ile Ser Asn Asp Ser Lys Arg
  1               5                  10                  15

Leu Lys Ala Ala Gln Lys Leu Leu Gln Met Gly Phe Ala Arg Val Gln
                 20                  25                  30

Lys Ser Val Tyr Ile Ala Lys Gly Gly Arg Ser Leu Ala Lys Glu Ala
            35                  40                  45

Tyr Arg Ala Leu Gln Arg Leu Ala Asp Ser Gly Lys Asp Lys Ile Met
 50                  55                  60

Val Met Val Ile Pro Gly Asp Ser Val Arg Asp Ala Tyr Gly Leu Gly
 65                  70                  75                  80

Gly Ser Leu Glu Asp Gly Lys Arg Val Val Val
                 85                  90

<210> SEQ ID NO 90
<211> LENGTH: 94
<212> TYPE: PRT
<213> ORGANISM: Allochromatium vinosum
```

```
<400> SEQUENCE: 90

Met Ser Ser Arg Leu Ala Val Phe Ala Tyr Asp Ile Arg Asp Asp Arg
1               5                   10                  15

Val Arg Arg His Ala Leu Lys Thr Leu Arg Glu Trp Arg Leu Asp Gly
            20                  25                  30

Gln Leu Ser Val His Glu Cys Gln Val Asp Ala Ile Gln Ala Arg Arg
        35                  40                  45

Leu Phe Glu Gln Leu Gly Asp Glu Leu Asp Pro Ala Thr Asp Ala Trp
50                  55                  60

Leu Phe Thr Trp Val Glu Gly His Arg Ala Val Leu Ala Arg Gly Lys
65                  70                  75                  80

Gly Arg Thr Thr Ala Leu Gln Asp Gly Leu Leu Leu Ala Ala
                85                  90

<210> SEQ ID NO 91
<211> LENGTH: 96
<212> TYPE: PRT
<213> ORGANISM: Bacillus halodurans

<400> SEQUENCE: 91

Met Leu Val Leu Ile Thr Tyr Asp Val Gln Thr Ser Ser Met Gly Gly
1               5                   10                  15

Thr Lys Arg Leu Arg Lys Val Ala Lys Ala Cys Gln Asn Tyr Gly Gln
            20                  25                  30

Arg Val Gln Asn Ser Val Phe Glu Cys Ile Val Asp Ser Thr Gln Leu
        35                  40                  45

Thr Ser Leu Lys Leu Glu Leu Thr Ser Leu Ile Asp Glu Glu Lys Asp
50                  55                  60

Ser Leu Arg Ile Tyr Arg Leu Gly Asn Asn Tyr Lys Thr Lys Val Glu
65                  70                  75                  80

His Ile Gly Ala Lys Pro Ser Ile Asp Leu Glu Asp Pro Leu Ile Phe
                85                  90                  95

<210> SEQ ID NO 92
<211> LENGTH: 143
<212> TYPE: PRT
<213> ORGANISM: Campylobacter jejuni

<400> SEQUENCE: 92

Met Ile Glu Asp Lys Phe Met Arg Val Leu Leu Met Phe Asp Val Pro
1               5                   10                  15

Thr Lys Ser Lys Lys Glu Gln Lys Leu Ala Ser Lys Phe Arg Asn Asn
            20                  25                  30

Leu Ile Lys Leu Gly Tyr Phe Met Leu Gln Phe Ser Val Tyr Met Arg
        35                  40                  45

Ile Cys Lys Gly Leu Ser Ser Ala Lys Ser Ser Ile Glu Asn Val Lys
50                  55                  60

Lys Ile Leu Pro Pro Tyr Gly Asn Val Arg Ala Leu Ile Ile Thr Glu
65                  70                  75                  80

Lys Gln Phe Asp Lys Met Glu Leu Leu Leu Gly Gly Ile Val Phe Asn
                85                  90                  95

Glu Lys Val Asn Asn Glu Thr Asn Leu Thr Leu Phe Asp Ile Asp Ser
                100                 105                 110
```

```
His Gly Glu Phe Lys Tyr Lys Asn Ser Asn Asn Glu Glu Ile Gln Ile
            115                 120                 125

Asn Lys Lys Gln Glu Lys Tyr His Gln Gln Asn Leu Phe Glu Phe
        130                 135                 140

<210> SEQ ID NO 93
<211> LENGTH: 143
<212> TYPE: PRT
<213> ORGANISM: Campylobacter jejuni

<400> SEQUENCE: 93

Met Ile Glu Asp Lys Phe Met Arg Val Leu Leu Met Phe Asp Val Pro
1               5                   10                  15

Thr Lys Ser Lys Lys Glu Gln Lys Leu Ala Ser Lys Phe Arg Asn Asn
            20                  25                  30

Leu Ile Lys Leu Gly Tyr Phe Met Leu Gln Phe Ser Val Tyr Met Arg
        35                  40                  45

Ile Cys Lys Gly Leu Ser Ser Ala Lys Ser Ser Ile Glu Asn Val Lys
    50                  55                  60

Lys Ile Leu Pro Pro Tyr Gly Asn Val Arg Ala Leu Ile Ile Thr Glu
65                  70                  75                  80

Lys Gln Phe Asp Lys Met Glu Leu Leu Leu Gly Gly Ile Val Phe Asn
                85                  90                  95

Glu Lys Val Asn Asn Glu Thr Asn Leu Thr Leu Phe Asp Ile Asp Ser
            100                 105                 110

His Gly Glu Phe Lys Tyr Lys Asn Ser Asn Asn Glu Glu Ile Gln Leu
        115                 120                 125

Asn Lys Lys Gln Glu Lys Tyr His Gln Gln Asn Leu Phe Glu Phe
    130                 135                 140

<210> SEQ ID NO 94
<211> LENGTH: 101
<212> TYPE: PRT
<213> ORGANISM: Capnocytophaga canimorsus

<400> SEQUENCE: 94

Met Trp Val Met Val Leu Tyr Asp Leu Pro Thr Glu Thr Lys Ala Met
1               5                   10                  15

Gln Lys Ala Ala Asn Leu Phe Arg Lys Arg Leu Glu Asp Asp Gly Phe
            20                  25                  30

Ser Leu Phe Gln Phe Ser Ile Tyr Leu Arg His Cys Pro Ser Arg Glu
        35                  40                  45

Asn Ala Glu Val His Lys Lys Arg Val Lys Met Met Leu Pro Lys Tyr
    50                  55                  60

Gly Lys Val Ala Val Met Thr Ile Thr Asp Lys Gln Phe Gly Asp Met
65                  70                  75                  80

Glu Ile Phe His Ser Lys Val Arg Glu Asp Pro Pro Thr Tyr Gln
                85                  90                  95

Gln Leu Glu Leu Phe
            100

<210> SEQ ID NO 95
<211> LENGTH: 96
<212> TYPE: PRT
<213> ORGANISM: Chlorobium tepidum
```

```
<400> SEQUENCE: 95

Met Leu Val Leu Val Thr Tyr Asp Val Asn Thr Glu Thr Pro Ala Gly
1               5                   10                  15

Arg Arg Arg Leu Arg Arg Ile Ala Lys Thr Cys Gln Asn Tyr Gly Gln
            20                  25                  30

Arg Val Gln Phe Ser Val Phe Glu Cys Asn Val Asp Pro Ala Gln Trp
        35                  40                  45

Val Lys Leu Arg Ser Lys Leu Leu Asn Glu Met Asp Pro Lys Leu Asp
    50                  55                  60

Ser Leu Arg Phe Tyr Phe Leu Gly Ser Asn Trp Gln Gly Arg Val Glu
65                  70                  75                  80

His Glu Gly Ala Lys Glu Pro Arg Asp Leu Glu Gly Thr Leu Ile Leu
                85                  90                  95

<210> SEQ ID NO 96
<211> LENGTH: 93
<212> TYPE: PRT
<213> ORGANISM: Chloroflexus aurantiacus

<400> SEQUENCE: 96

Met Phe Tyr Leu Ile Ser Tyr Asp Ile Ser Val Asp Gln Arg Arg Leu
1               5                   10                  15

Lys Ile Ala Lys Leu Leu Glu Gly Tyr Gly Gln Arg Val Leu Glu Ser
            20                  25                  30

Val Phe Glu Cys Asp Leu Glu Leu Pro Ala Tyr Arg Gln Leu Arg Gln
        35                  40                  45

Lys Leu Asn Arg Leu Ile Lys Asp Glu Glu Gly Asp Arg Leu Arg Ile
    50                  55                  60

Tyr Arg Leu Cys Ala Ser Cys Arg Glu Gln Ile Glu Ile Ile Gly Asp
65                  70                  75                  80

Gly Pro Pro Pro Glu Thr Ser Gln Asp Ile Tyr Ile Ile
                85                  90

<210> SEQ ID NO 97
<211> LENGTH: 85
<212> TYPE: PRT
<213> ORGANISM: Chloroflexus aurantiacus

<400> SEQUENCE: 97

Met Gln Cys Leu Val Ile Tyr Asp Ile Pro Asn Asp Arg Ala Arg Gln
1               5                   10                  15

Arg Val Ala Asp Ala Cys Leu Asp Tyr Gly Leu Gln Arg Ile Gln Tyr
            20                  25                  30

Ser Ala Phe Ala Gly Asn Leu Ser Arg Thr His Gln Arg Ala Leu Phe
        35                  40                  45

Gly Glu Ile Thr Arg Arg Val Lys Gly His Thr Ala Asn Val Gln Leu
    50                  55                  60

Phe Val Phe Asp Ser Lys Thr Trp Ser Asp Arg Arg Ile Leu Glu Gln
65                  70                  75                  80

Gln Tyr Asp Asp Ala
                85

<210> SEQ ID NO 98
<211> LENGTH: 93
<212> TYPE: PRT
<213> ORGANISM: Chloroflexus aurantiacus
```

<400> SEQUENCE: 98

Met Lys Met Phe Thr Val Ile Ser Tyr Asp Ile Val Asp Gln Arg
1               5                   10                  15

Arg Thr Ser Val Met Lys Val Leu Lys Gly Tyr Gly Val Arg Val Gln
            20                  25                  30

Tyr Ser Val Phe Glu Ala Ile Leu Asp Ala Arg Glu Phe His Asp Leu
        35                  40                  45

Ser Asn Gln Leu Arg Lys Ile Ile Asp Pro Gly Gln Asp Ser Ile Arg
    50                  55                  60

Cys Tyr Arg Leu Asp Gln Val Ala Ala Gln Arg Thr Val Ile Tyr Gly
65                  70                  75                  80

Ile Gly Leu Thr Thr Thr Asp Pro Thr His Tyr Met Val
                85                  90

<210> SEQ ID NO 99
<211> LENGTH: 106
<212> TYPE: PRT
<213> ORGANISM: Desulforudis audaxviator

<400> SEQUENCE: 99

Met Lys Thr Leu Val Ser Tyr Asp Ile Val Glu Asp Lys Val Arg Arg
1               5                   10                  15

Lys Val Phe Glu Ala Cys Lys Asp Tyr Gly Leu Thr Asn Val Gln Tyr
            20                  25                  30

Ser Leu Phe Phe Gly Asp Met Thr His Asn Arg Arg Glu Glu Leu Phe
        35                  40                  45

Gln Arg Leu Arg Arg Ile Ile Gly Arg Gln Glu Gly Lys Val Leu Ile
    50                  55                  60

Cys Pro Val Cys Asp Lys Asp Leu Arg Leu Ser Lys Ala Ile Glu Val
65                  70                  75                  80

Ser Ala Gly Met Pro Glu Glu Ala Ala Glu Ala Ala Val Ser Tyr Pro
                85                  90                  95

Gly Arg Ser Arg Lys Lys Ala Arg Ala Gly
            100                 105

<210> SEQ ID NO 100
<211> LENGTH: 102
<212> TYPE: PRT
<213> ORGANISM: Desulfovibrio vulgaris

<400> SEQUENCE: 100

Met Tyr Gly Asn Asp Ala Met Leu Val Leu Ile Ser Tyr Asp Val Ser
1               5                   10                  15

Phe Glu Asp Pro Gly Gly Gln Arg Arg Leu Arg Arg Ile Ala Lys Ala
            20                  25                  30

Cys Gln Asp Tyr Gly Gln Arg Val Gln Tyr Ser Val Phe Glu Cys Val
        35                  40                  45

Val Asp Pro Ala Gln Trp Ala Lys Leu Lys His Arg Leu Leu Ser Glu
    50                  55                  60

Met Asp Lys Glu Lys Asp Cys Leu Arg Phe Tyr Tyr Leu Gly Ala Asn
65                  70                  75                  80

Trp Arg Asn Lys Val Glu His Val Gly Ala Lys Pro Ala Tyr Asp Pro
                85                  90                  95

Glu Gly Pro Leu Ile Leu
            100

```
<210> SEQ ID NO 101
<211> LENGTH: 96
<212> TYPE: PRT
<213> ORGANISM: Desulfovibrio vulgaris

<400> SEQUENCE: 101

Met Leu Val Leu Ile Ser Tyr Asp Val Ser Phe Glu Asp Pro Gly Gly
1               5                   10                  15

Gln Arg Arg Leu Arg Arg Ile Ala Lys Ala Cys Gln Asp Tyr Gly Gln
                20                  25                  30

Arg Val Gln Tyr Ser Val Phe Glu Cys Val Val Asp Pro Ala Gln Trp
            35                  40                  45

Ala Lys Leu Lys His Arg Leu Leu Ser Glu Met Asp Lys Glu Lys Asp
        50                  55                  60

Cys Leu Arg Phe Tyr Tyr Leu Gly Ala Asn Trp Arg Asn Lys Val Glu
65                  70                  75                  80

His Val Gly Ala Lys Pro Ala Tyr Asp Pro Glu Gly Pro Leu Ile Leu
                85                  90                  95

<210> SEQ ID NO 102
<211> LENGTH: 87
<212> TYPE: PRT
<213> ORGANISM: Dictyoglomus turgidum

<400> SEQUENCE: 102

Met Tyr Val Ile Met Val Tyr Asp Val Asn Gln Arg Arg Ile Asn Lys
1               5                   10                  15

Val Leu Asn Thr Ala Arg Lys Tyr Leu Glu Trp Ile Gln Asn Ser Val
                20                  25                  30

Leu Glu Gly Glu Ile Thr Glu Ala Lys Phe Glu Met Leu Lys Arg Glu
            35                  40                  45

Ile Glu Ile Ile Ile Asn Glu Glu Asp Ser Val Ile Phe Tyr Ile
        50                  55                  60

Met Arg Thr Thr Lys Tyr Ser Glu Arg Gln Ile Leu Gly Ile Glu Lys
65                  70                  75                  80

Asn Lys Arg Glu Gln Ile Leu
                85

<210> SEQ ID NO 103
<211> LENGTH: 94
<212> TYPE: PRT
<213> ORGANISM: Escherichia coli

<400> SEQUENCE: 103

Met Ser Met Leu Val Val Thr Glu Asn Val Pro Pro Arg Leu Arg
1               5                   10                  15

Gly Arg Leu Ala Ile Trp Leu Leu Glu Val Arg Ala Gly Val Tyr Val
                20                  25                  30

Gly Asp Val Ser Ala Lys Ile Arg Glu Met Ile Trp Glu Gln Ile Ala
            35                  40                  45

Gly Leu Ala Glu Glu Gly Asn Val Val Met Ala Trp Ala Thr Asn Thr
        50                  55                  60

Glu Thr Gly Phe Glu Phe Gln Thr Phe Gly Leu Asn Arg Arg Thr Pro
65                  70                  75                  80

Val Asp Leu Asp Gly Leu Arg Leu Val Ser Phe Leu Pro Val
                85                  90
```

```
<210> SEQ ID NO 104
<211> LENGTH: 94
<212> TYPE: PRT
<213> ORGANISM: Escherichia coli

<400> SEQUENCE: 104

Met Ser Met Leu Val Val Thr Glu Asn Val Pro Pro Arg Leu Arg
1               5                   10                  15

Gly Arg Leu Ala Ile Trp Leu Leu Glu Val Arg Ala Gly Val Tyr Val
                20                  25                  30

Gly Asp Val Ser Ala Lys Ile Arg Glu Met Ile Trp Glu Gln Ile Ala
            35                  40                  45

Gly Leu Ala Glu Glu Gly Asn Val Val Met Ala Trp Ala Thr Asn Thr
    50                  55                  60

Glu Thr Gly Phe Glu Phe Gln Thr Phe Gly Leu Asn Arg Arg Thr Pro
65                  70                  75                  80

Val Asp Leu Asp Gly Leu Arg Leu Val Ser Phe Leu Pro Val
                85                  90

<210> SEQ ID NO 105
<211> LENGTH: 101
<212> TYPE: PRT
<213> ORGANISM: Filifactor alocis

<400> SEQUENCE: 105

Met Arg Ile Ile Val Phe Phe Asp Leu Pro Thr Ile Thr Leu Glu Asp
1               5                   10                  15

Lys Arg Asp Tyr Arg Asp Phe Arg Lys Phe Leu Ile Lys Lys Gly Phe
                20                  25                  30

Leu Met Met Gln Glu Ser Val Tyr Cys Lys Leu Val Leu Asn Gln Thr
            35                  40                  45

Val Ala Ser Ser Val Leu Ser Ser Ile Arg Lys His Lys Pro Lys Ser
    50                  55                  60

Gly Leu Val Gln Met Ile Met Val Thr Glu Lys Gln Phe Ala Lys Met
65                  70                  75                  80

Glu Tyr Leu Cys Gly Glu Lys Arg Ser Asn Val Val Asp Ser Asp
                85                  90                  95

Arg Leu Val Ile Leu
            100

<210> SEQ ID NO 106
<211> LENGTH: 115
<212> TYPE: PRT
<213> ORGANISM: Flavobacterium psychrophilum

<400> SEQUENCE: 106

Met Tyr Asp Glu His Tyr Thr Arg Leu Asn Gln Tyr Arg Ser Leu Trp
1               5                   10                  15

Ile Leu Val Phe Phe Asp Leu Pro Thr Glu Thr Arg Lys Glu Arg Lys
                20                  25                  30

Ile Ala Ser Glu Phe Arg Lys Lys Leu Leu Asp Asp Gly Phe Ser Met
            35                  40                  45

Phe Gln Phe Ser Ile Tyr Ile Arg Phe Cys Ala Ser Arg Glu Asn Ala
    50                  55                  60

Glu Val His Thr Lys Arg Ile Arg Asn Ser Leu Pro Glu His Gly Lys
65                  70                  75                  80

Ile Gly Val Met Gln Ile Thr Asp Lys Gln Phe Gly Met Met Glu Leu
                85                  90                  95
```

```
Phe Tyr Gly Lys Lys Pro Val Glu Thr Asp Lys Pro Ser Gln Gln Leu
            100                 105                 110

Glu Leu Phe
        115

<210> SEQ ID NO 107
<211> LENGTH: 113
<212> TYPE: PRT
<213> ORGANISM: Francisella novicida

<400> SEQUENCE: 107

Met Ser Tyr Arg Tyr Met Arg Met Ile Leu Met Phe Asp Met Pro Thr
1               5                   10                  15

Asp Thr Ala Glu Glu Arg Lys Ala Tyr Arg Lys Phe Arg Lys Phe Leu
            20                  25                  30

Leu Ser Glu Gly Phe Ile Met His Gln Phe Ser Ile Tyr Ser Lys Leu
        35                  40                  45

Leu Leu Asn Asn Thr Ala Asn Asn Ala Met Ile Gly Arg Leu Arg Glu
    50                  55                  60

His Asn Pro Asn Lys Gly Asn Ile Thr Leu Leu Thr Val Thr Glu Lys
65                  70                  75                  80

Gln Phe Ala Arg Met Ile Tyr Leu His Gly Glu Arg Asn Asn Cys Ile
                85                  90                  95

Ala Asn Ser Asp Glu Arg Leu Val Phe Leu Gly Glu Ala Phe Asp Glu
            100                 105                 110

Ser

<210> SEQ ID NO 108
<211> LENGTH: 87
<212> TYPE: PRT
<213> ORGANISM: Frankia alni

<400> SEQUENCE: 108

Met Phe Val Val Leu Val Tyr Asp Thr Ala Ala Glu Arg Asn Pro Asn
1               5                   10                  15

Ala Leu Arg Thr Cys Arg Lys Tyr Leu His Trp Val Gln Arg Ser Val
            20                  25                  30

Phe Glu Gly Glu Leu Ser Ala Ala Gln Tyr Arg Ala Leu Met Thr Thr
        35                  40                  45

Leu Arg Asp Gln Leu Asp Leu Thr Tyr Asp Ser Ile Arg Val Tyr Arg
    50                  55                  60

Thr Arg Ser Pro Ala Leu Val Glu Thr Glu Trp Leu Gly Val Pro Leu
65                  70                  75                  80

Gly Asn Gln Asp Ser Val Leu
                85

<210> SEQ ID NO 109
<211> LENGTH: 106
<212> TYPE: PRT
<213> ORGANISM: Fusobacterium nucleatum subsp. nucleatum

<400> SEQUENCE: 109

Met Lys Arg Asn Ile Asn Leu Phe Lys Cys Gly Gly Asp Lys Met Tyr
1               5                   10                  15

Val Val Val Val Tyr Asp Ile Ser Leu Asp Glu Lys Gly Ser Arg Asn
            20                  25                  30

Trp Arg Lys Ile Phe Gly Ile Cys Lys Arg Tyr Leu His Ile Gln
        35                  40                  45
```

```
Asn Ser Val Phe Glu Gly Glu Leu Ser Glu Val Asp Ile Gln Arg Leu
    50                  55                  60

Lys Tyr Glu Val Ser Lys Tyr Ile Arg Asp Asp Leu Asp Ser Phe Ile
 65                  70                  75                  80

Ile Phe Lys Ser Arg Asn Glu Arg Trp Met Glu Lys Glu Met Leu Gly
                 85                  90                  95

Leu Gln Glu Asp Lys Thr Asp Asn Phe Leu
                100                 105
```

<210> SEQ ID NO 110
<211> LENGTH: 95
<212> TYPE: PRT
<213> ORGANISM: Geobacter sulfurreducens

<400> SEQUENCE: 110

```
Met Glu His Leu Tyr Ile Val Ser Tyr Asp Ile Arg Asn Gln Arg Arg
  1               5                  10                  15

Trp Arg Arg Leu Phe Lys Thr Met His Gly Phe Gly Cys Trp Leu Gln
                 20                  25                  30

Leu Ser Val Phe Gln Cys Arg Leu Asp Arg Ile Arg Ile Ile Lys Met
             35                  40                  45

Glu Ala Ala Ile Asn Glu Ile Val Asn His Ala Glu Asp His Val Leu
    50                  55                  60

Ile Leu Asp Leu Gly Pro Ala Glu Asn Val Lys Pro Lys Val Ser Ser
 65                  70                  75                  80

Ile Gly Lys Thr Phe Asp Pro Ile Leu Arg Gln Ala Val Ile Val
                 85                  90                  95
```

<210> SEQ ID NO 111
<211> LENGTH: 86
<212> TYPE: PRT
<213> ORGANISM: Haloarcula hispanica

<400> SEQUENCE: 111

```
Met Tyr Val Val Met Val Tyr Asp Leu Glu Ala Asp Arg Thr Gln Lys
  1               5                  10                  15

Ala Leu Lys Ile Gly Arg Arg Tyr Leu Thr His Val Gln Asn Ser Val
                 20                  25                  30

Leu Glu Gly Glu Ile Ser Glu Gly Asp Leu Ser Asn Leu Lys Asn Glu
             35                  40                  45

Ile Asp Asp Leu Leu Lys Pro Gly Glu Ser Thr Ile Ile Tyr Glu Leu
    50                  55                  60

Ser Ser Asp Thr Leu Leu Asn Arg Thr Val Tyr Gly Asp Asp Pro Thr
 65                  70                  75                  80

Glu Asp Gln Arg Phe Leu
                 85
```

<210> SEQ ID NO 112
<211> LENGTH: 95
<212> TYPE: PRT
<213> ORGANISM: Hyperthermus butylicus

<400> SEQUENCE: 112

```
Met Pro Tyr Val Val Phe Tyr Asp Val Ser Asp Asn Lys Arg Arg
  1               5                  10                  15

Asp Leu Leu Ala Lys Thr Leu Gln Ser Leu Gly Leu Val Arg Val Gln
                 20                  25                  30
```

Arg Ser Val Phe Met Gly Arg Gly Tyr Thr Lys Ala Lys Glu Ala
            35                  40                  45

Ile Arg Ala Ala Ser Arg Ile Val Asp Ala Arg Thr Asp Ser Val Val
 50                  55                  60

Ala Leu Val Val Pro Glu Asp Tyr Ala Arg Arg Met Leu Val Tyr Gly
 65                  70                  75                  80

Gly Ile Met Ser Asp Pro Lys Gln Lys Gln Ala Val Arg Val Val
                85                  90                  95

<210> SEQ ID NO 113
<211> LENGTH: 93
<212> TYPE: PRT
<213> ORGANISM: Korarchaeum cryptofilum

<400> SEQUENCE: 113

Met Arg Gly Gly Asn Leu Lys Val Leu Val Tyr Asp Ile Thr Asp
 1               5                  10                  15

Asp Ser Leu Arg Leu Lys Val Ala Glu Ile Leu Lys Asp Leu Gly Leu
                20                  25                  30

Phe Arg Ile Gln Lys Ser Ala Phe Ile Gly Glu Met Thr Ser Gln Glu
            35                  40                  45

Arg Glu Asn Met Glu Glu Ile Leu Arg Arg Gln Asn Leu Gly Pro Ser
 50                  55                  60

Asp Arg Ile Asp Val Phe Pro Ile Cys Asp Arg Asp Leu Lys Met His
 65                  70                  75                  80

Ser Gln Ile Gly Arg Gly Lys Phe Gly Arg Gly Pro Pro
                85                  90

<210> SEQ ID NO 114
<211> LENGTH: 101
<212> TYPE: PRT
<213> ORGANISM: Lactobacillus rhamnosus

<400> SEQUENCE: 114

Met Arg Leu Met Ile Met Phe Asp Leu Pro Val Ala Thr Ser Lys Asp
 1               5                  10                  15

Arg Arg Asn Tyr Arg Arg Phe Arg Arg Ala Leu Ile Asp Glu Gly Phe
                20                  25                  30

Leu Met Ile Gln Tyr Ser Val Tyr Val Arg Val Cys Lys Thr Lys Lys
            35                  40                  45

Ser Ala Ala Tyr Met Glu Gln Arg Ile Ala Thr Val Lys Pro Pro Thr
 50                  55                  60

Gly Ile Val Gln Thr Leu Met Val Thr Glu Ala Gln Tyr Gln Ser Met
 65                  70                  75                  80

His Phe Met Val Gly Thr Glu Lys Gln Asp Ile Arg Asn Ser Ala Asp
                85                  90                  95

Arg Thr Val Met Ile
            100

<210> SEQ ID NO 115
<211> LENGTH: 101
<212> TYPE: PRT
<213> ORGANISM: Lactobacillus salivarius

<400> SEQUENCE: 115

Met Arg Leu Met Ile Ile Phe Asp Leu Pro Val Glu Thr Ser Glu Glu
1               5                   10                  15

Arg Lys Glu Tyr Arg Lys Phe Arg Lys Asn Leu Ile Asn Glu Gly Phe
            20                  25                  30

Ile Met Ile Gln Tyr Ser Val Tyr Val Arg Val Cys Val Asn Lys Lys
        35                  40                  45

Ser Ala Glu Phe Thr Glu Lys Arg Ile Glu Ser Phe Leu Pro Ser Lys
    50                  55                  60

Gly Val Val Gln Ser Leu Ile Leu Thr Glu Lys Gln Tyr Asn Asp Met
65                  70                  75                  80

His Phe Leu Leu Gly Lys Lys Ile Lys Glu Val Arg Asn Ser Ala Glu
                85                  90                  95

Arg Thr Ile Ile Leu
            100

<210> SEQ ID NO 116
<211> LENGTH: 94
<212> TYPE: PRT
<213> ORGANISM: Leptospira interrogans serogroup Icterohaemorrhagiae
      serovar Lai

<400> SEQUENCE: 116

Met Lys His Trp Arg Leu Val Ser Tyr Asp Ile Arg Glu Pro Lys Arg
1               5                   10                  15

Leu Arg Arg Val Ala Lys Ile Met Glu Gly Phe Gly Arg Ile Gln
            20                  25                  30

Tyr Ser Val Phe Arg Ile Tyr Ser Thr Asp Lys Glu Leu Glu Lys Leu
        35                  40                  45

Arg Trp Lys Leu Ala Lys Val Thr Glu Glu Asp Asn Ile Phe Tyr
    50                  55                  60

Leu Thr Leu Cys Thr Lys Cys Ala Ser Gly Ala His Thr Gln Glu Lys
65                  70                  75                  80

Lys Ser Ala Trp Pro Glu Ala Pro Lys Thr Leu Lys Ile Leu
                85                  90

<210> SEQ ID NO 117
<211> LENGTH: 91
<212> TYPE: PRT
<213> ORGANISM: Methanobrevibacter ruminantium

<400> SEQUENCE: 117

Met Lys Val Leu Val Ser Phe Glu Ile Lys Phe Lys Thr Asn Lys Glu
1               5                   10                  15

Lys Ile Ile Ser Ile Leu Lys His Phe Gly Phe Arg Arg Met Gln Glu
            20                  25                  30

Asn Leu Tyr Phe Gly Asp Val Glu Tyr Asp Glu Leu Tyr Ala Met Gln
        35                  40                  45

Ser Asp Ile Met Glu Asn Ile Arg Glu Tyr Asp Ser Ile Leu Thr Ile
    50                  55                  60

Pro Ile Cys Lys Ser Cys Tyr Leu Lys Leu Asn Val Phe Gly Arg Asn
65                  70                  75                  80

Leu Ser Phe Lys Asp Glu Leu Tyr Lys Ile Phe
                85                  90

```
<210> SEQ ID NO 118
<211> LENGTH: 114
<212> TYPE: PRT
<213> ORGANISM: Methanocaldococcus jannaschii

<400> SEQUENCE: 118

Met Leu Lys Lys Glu Trp Asp Tyr Val Asn Lys Ile Leu Lys Lys Ile
1               5                   10                  15

Lys Asn Ile Arg Asn Leu Leu Gln Asp Glu Ser Met Tyr Val Ile Ile
            20                  25                  30

Val Tyr Asp Val Asn Val Ser Arg Val Asn Lys Ile Lys Ser Phe Leu
        35                  40                  45

Arg Lys His Leu Asn Trp Val Gln Asn Ser Val Phe Glu Gly Glu Val
    50                  55                  60

Thr Lys Ala Glu Phe Glu Arg Ile Lys Asp Gly Ile Leu Arg Ile Ile
65                  70                  75                  80

Asp Glu Asp Glu Asp Ser Val Ile Ile Tyr Gln Phe Pro Leu Asn Phe
                85                  90                  95

Met Pro Lys Arg Glu Ile Leu Gly Leu Glu Lys Asn Pro Ile Asp Asp
            100                 105                 110

Ile Ile

<210> SEQ ID NO 119
<211> LENGTH: 101
<212> TYPE: PRT
<213> ORGANISM: Methanopyrus kandleri

<400> SEQUENCE: 119

Met Gly Val Leu Gly Gly Pro Ser Pro Arg Leu Arg Leu Tyr Val Tyr
1               5                   10                  15

Asp Phe Lys Glu Pro Gly Gly Glu Ala Glu Arg Arg Lys Leu Arg Glu
            20                  25                  30

Leu Leu Glu Ser His Gly Ala Phe Arg Leu Gln Tyr Ser Thr Tyr Ala
        35                  40                  45

Leu Leu Ala Glu Pro Glu Val His Ala Arg Val Leu Arg Arg Val Val
    50                  55                  60

Ala Arg Val Asp Phe Glu Glu Gly Asp Ser Leu Ile Val Val Pro Met
65                  70                  75                  80

Cys Arg Arg Cys Leu Arg Val Ala Arg Trp Val Asp Ala Glu Gly Val
                85                  90                  95

Arg Gly Leu Arg Phe
            100

<210> SEQ ID NO 120
<211> LENGTH: 87
<212> TYPE: PRT
<213> ORGANISM: Methanosarcina acetivorans

<400> SEQUENCE: 120

Met Tyr Val Val Ile Val Tyr Asp Val Gly Val Glu Arg Val Asn Lys
1               5                   10                  15

Val Arg Ser Phe Leu Arg Glu Tyr Met Asn Trp Val Gln Asn Ser Val
            20                  25                  30

Phe Glu Gly Glu Leu Thr Lys Ala Glu Phe Leu Lys Ile Lys Ser Arg
        35                  40                  45

Leu Lys Glu Leu Ile Gln Glu Ser Ser Asp His Ile Ile Phe Tyr Ser
    50                  55                  60
```

Ser Arg Asp Arg Lys Tyr Leu Gly Ile Glu Asp Leu Gly Thr Pro Lys
65                  70                  75                  80

Ala Asp Thr Ser Asn Ile Ile
                85

<210> SEQ ID NO 121
<211> LENGTH: 95
<212> TYPE: PRT
<213> ORGANISM: Methanospirillum hungatei JF-1

<400> SEQUENCE: 121

Met Thr Val Lys His Leu Ile Val Cys Tyr Asp Val Glu Lys Thr Lys
1               5                   10                  15

Asp Arg Asn Lys Val Ile Lys Val Leu Glu Tyr Tyr Gly Leu Ile Arg
                20                  25                  30

Val Gln Tyr Ser Val Phe Met Gly Ser Leu Thr Glu Thr Arg Leu His
            35                  40                  45

Gln Met Asn Ala Arg Ile Lys Arg Glu Phe Thr Lys Pro Ser Ile Lys
50                  55                  60

Ile Leu Val Ile Glu Val Cys Asn Ala Cys Met Glu Arg Ala Leu Leu
65                  70                  75                  80

Val His Glu Glu Leu Pro Lys Val Asn Arg Gln Phe Glu Val Ile
                85                  90                  95

<210> SEQ ID NO 122
<211> LENGTH: 89
<212> TYPE: PRT
<213> ORGANISM: Methanospirillum hungatei JF-1

<400> SEQUENCE: 122

Met Val Arg Leu Val Ile Thr Tyr Asp Ile Arg Lys Asp Lys Ile Arg
1               5                   10                  15

Asn Lys Leu Phe Arg Leu Leu Glu Arg Tyr Gly Ala Trp Lys Gln Tyr
                20                  25                  30

Ser Val Phe Glu Leu Glu Ile Asn Pro Val His Lys Val Glu Leu Phe
            35                  40                  45

His Ser Ile Ala Asp Leu Ile Glu Asp Thr Asp Arg Val Arg Ile Tyr
50                  55                  60

Asp Leu Cys Glu Arg Cys Gln Gly Lys Ile Thr Glu Leu Gly Glu Val
65                  70                  75                  80

Ser Pro Asp Lys Met Gln Val Val Ile
                85

<210> SEQ ID NO 123
<211> LENGTH: 91
<212> TYPE: PRT
<213> ORGANISM: Methanothermobacter thermautotrophicus

<400> SEQUENCE: 123

Met Val Val Thr Val Tyr Leu Leu Ile Val Tyr Asp Val Gly Val Glu
1               5                   10                  15

Arg Val Asn Arg Val Lys Ser Tyr Leu Arg Thr Glu Leu His Trp Val
                20                  25                  30

Gln Asn Ser Val Phe Glu Gly Glu Val Thr Glu Ser Gln Phe Arg Arg
            35                  40                  45

Ile Glu Thr Asn Leu Glu Arg Ile Glu Asp Arg Glu Arg Asp Ser Val
50                  55                  60

```
Ile Ile Tyr Ser Phe Arg Ser Glu Arg Ala Met Asn Arg Asn Val Leu
 65                  70                  75                  80

Gly Leu Glu Lys Ser Pro Leu Asp Val Ile Leu
                 85                  90

<210> SEQ ID NO 124
<211> LENGTH: 95
<212> TYPE: PRT
<213> ORGANISM: Methylobacterium extorquens

<400> SEQUENCE: 124

Met Ala Val Phe Leu Ile Ala Tyr Asp Leu Val Asn Glu Arg Arg Gly
1               5                   10                  15

Thr His Asp Tyr Gln Pro Leu Trp Asp Glu Leu Lys Arg Leu Gly Ala
                20                  25                  30

His Arg Thr Gln Phe Ser Leu Trp Leu Val Ser Ala Asn Asn Thr Thr
            35                  40                  45

Ala Glu Val Arg Gln His Phe Gln Gln Phe Val Asp Ser Asn Asp Arg
        50                  55                  60

Ile Trp Val Thr Arg Leu Arg Lys Ser Gln Tyr Asp Tyr Ala Asn Ala
 65                  70                  75                  80

Ile Gly Gly Thr Asn Asn Trp Leu Ser Asn Asn Pro Pro Glu Ala
                 85                  90                  95

<210> SEQ ID NO 125
<211> LENGTH: 95
<212> TYPE: PRT
<213> ORGANISM: Methylobacterium extorquens

<400> SEQUENCE: 125

Met Ala Val Phe Leu Ile Ala Tyr Asp Leu Val Asn Glu Arg Arg Gly
1               5                   10                  15

Thr His Asp Tyr Gln Pro Leu Trp Asp Glu Leu Lys Arg Leu Gly Ala
                20                  25                  30

His Arg Thr Gln Phe Ser Leu Trp Leu Val Ser Ala Asn Asn Thr Thr
            35                  40                  45

Ala Glu Val Arg Gln His Phe Gln Gln Phe Val Asp Ser Asn Asp Arg
        50                  55                  60

Ile Trp Val Thr Arg Leu Arg Lys Ser Gln Tyr Asp Tyr Ala Asn Ala
 65                  70                  75                  80

Ile Gly Gly Thr Asn Asn Trp Leu Ser Asn Asn Pro Pro Glu Ala
                 85                  90                  95

<210> SEQ ID NO 126
<211> LENGTH: 91
<212> TYPE: PRT
<213> ORGANISM: Moorella thermoacetica

<400> SEQUENCE: 126

Met Ile Leu Ile Tyr Asp Ile Asn Thr Glu Asp Asn Asp Gly Lys Arg
1               5                   10                  15

Arg Leu Val Lys Ile Met Lys Thr Ser Arg Lys Tyr Leu Ser His Val
                20                  25                  30

Gln Lys Ser Val Phe Glu Gly Asp Ile Thr Glu Gly Gln Ile Ser Leu
            35                  40                  45

Leu Lys Lys Glu Ile Met Ala Ile Val Asn Met Lys Lys Asp Phe Val
        50                  55                  60
```

Ile Ile Tyr Ser Leu Arg Asp Gly Val Lys Leu Asn Arg Glu Ile Leu
65                  70                  75                  80

Thr Asp Thr Pro Asp Pro Thr Asp Asn Phe Leu
                85                  90

<210> SEQ ID NO 127
<211> LENGTH: 96
<212> TYPE: PRT
<213> ORGANISM: Moorella thermoacetica

<400> SEQUENCE: 127

Met Tyr Ile Leu Ile Thr Tyr Asp Val Ser Thr Glu Thr Glu Ala Gly
1               5                   10                  15

Lys Lys Arg Leu Arg Lys Val Ala Gln Val Cys Lys Asp Phe Gly Gln
                20                  25                  30

Arg Val Gln Lys Ser Val Phe Glu Cys Ser Val Asn Glu Ala Gln Phe
            35                  40                  45

Glu Gln Leu Lys His Arg Leu Leu Gln Cys Ile Asp Glu Lys Ser Asp
        50                  55                  60

Ser Leu Arg Ile Tyr Arg Leu Arg Glu Pro Ala Lys Lys Tyr Ile Gln
65                  70                  75                  80

Glu Tyr Gly Val Asn Leu Thr Ile Asp Phe Asp Ala Pro Leu Val Leu
                85                  90                  95

<210> SEQ ID NO 128
<211> LENGTH: 113
<212> TYPE: PRT
<213> ORGANISM: Mycobacterium tuberculosis

<400> SEQUENCE: 128

Met Pro Thr Arg Ser Arg Glu Glu Tyr Phe Asn Leu Pro Leu Lys Val
1               5                   10                  15

Asp Glu Ser Ser Gly Thr Ile Gly Lys Met Phe Val Leu Val Ile Tyr
                20                  25                  30

Asp Ile Ser Asp Asn Arg Arg Arg Ala Ser Leu Ala Lys Ile Leu Ala
            35                  40                  45

Gly Phe Gly Tyr Arg Val Gln Glu Ser Ala Phe Glu Ala Met Leu Thr
        50                  55                  60

Lys Gly Gln Leu Ala Lys Leu Val Ala Arg Ile Asp Arg Phe Ala Ile
65                  70                  75                  80

Asp Cys Asp Asn Ile Arg Ile Tyr Lys Ile Arg Gly Val Ala Ala Val
                85                  90                  95

Thr Phe Tyr Gly Arg Gly Arg Leu Val Ser Ala Glu Glu Phe Val Phe
                100                 105                 110

Phe

<210> SEQ ID NO 129
<211> LENGTH: 113
<212> TYPE: PRT
<213> ORGANISM: Mycobacterium tuberculosis

<400> SEQUENCE: 129

Met Pro Thr Arg Ser Arg Glu Glu Tyr Phe Asn Leu Pro Leu Lys Val
1               5                   10                  15

Asp Glu Ser Ser Gly Thr Ile Gly Lys Met Phe Val Leu Val Ile Tyr
                20                  25                  30

Asp Ile Ser Asp Asn Arg Arg Arg Ala Ser Leu Ala Lys Ile Leu Ala
            35                  40                  45

```
Gly Phe Gly Tyr Arg Val Gln Glu Ser Ala Phe Glu Ala Met Leu Thr
        50                  55                  60

Lys Gly Gln Leu Ala Lys Leu Val Ala Arg Ile Asp Arg Phe Ala Ile
 65                  70                  75                  80

Asp Cys Asp Asn Ile Arg Ile Tyr Lys Ile Arg Gly Val Ala Ala Val
                    85                  90                  95

Thr Phe Tyr Gly Arg Gly Arg Leu Val Ser Ala Glu Glu Phe Val Phe
                100                 105                 110

Phe
```

<210> SEQ ID NO 130
<211> LENGTH: 97
<212> TYPE: PRT
<213> ORGANISM: Myxococcus xanthus

<400> SEQUENCE: 130

```
Met Ala Glu Pro Arg Arg Trp Tyr Leu Ile Thr Tyr Asp Ile Arg Asp
  1               5                  10                  15

Pro Lys Arg Trp Arg Lys Val His Ala Leu Leu Lys Gly Tyr Gly Glu
                 20                  25                  30

Trp Leu Gln Leu Ser Val Phe Arg Cys Ser Leu Thr Asp Arg Asp Arg
             35                  40                  45

Glu Lys Leu Arg Trp Glu Leu Ser Arg Arg Met Asp Ala Val Asp Thr
         50                  55                  60

Leu Leu Val Ile Gly Leu Cys Gly Gly Cys Val Glu Arg Val Arg Ala
 65                  70                  75                  80

Ile Asn Ala Lys Glu Asp Trp Pro Glu Glu Pro Ala Pro Phe Lys Val
                 85                  90                  95

Leu
```

<210> SEQ ID NO 131
<211> LENGTH: 91
<212> TYPE: PRT
<213> ORGANISM: Nanoarchaeum equitans

<400> SEQUENCE: 131

```
Met Gln Tyr Lys Ile Asn Met Tyr Ala Ile Val Val Tyr Asp Val Asn
  1               5                  10                  15

Val Ser Arg Gln Asn Gln Ile Arg Glu Phe Leu Arg Lys Tyr Leu Tyr
                 20                  25                  30

His Val Gln Arg Ser Val Phe Glu Gly Glu Ile Ser Pro Ser Ser Leu
             35                  40                  45

Tyr Tyr Met Lys Lys Ile Leu Gln Ser Tyr Ile Gly Glu Thr Asp Ser
         50                  55                  60

Leu Ile Ile Tyr Val Leu Arg Asp Lys Ser Cys Leu Met Asp Lys Ile
 65                  70                  75                  80

Val Leu Gly Glu Asp Lys Asp Leu Gln Ile Tyr
                 85                  90
```

<210> SEQ ID NO 132
<211> LENGTH: 108
<212> TYPE: PRT
<213> ORGANISM: Neisseria meningitidis -continued

<400> SEQUENCE: 132

Met Ser Glu Ala Lys Phe Met Arg Ile Ile Val Phe Phe Asp Leu Pro
1               5                   10                  15

Val Ile Thr Ala Ala Lys Arg Lys Ala Ala Asn Gln Phe Arg Gln Phe
            20                  25                  30

Leu Leu Lys Asp Gly Tyr Gln Met Leu Gln Leu Ser Val Tyr Ser Arg
        35                  40                  45

Ile Val Lys Gly Arg Asp Ser Leu Gln Lys His His Asn Arg Leu Cys
    50                  55                  60

Ala Asn Leu Pro Gln Glu Gly Ser Ile Arg Cys Leu Glu Ile Thr Glu
65                  70                  75                  80

Lys Gln Tyr Ala Ala Met Lys Leu Leu Leu Gly Glu Leu Lys Thr Gln
                85                  90                  95

Glu Lys Lys Val Asn Ser Asp Gln Leu Leu Leu Phe
            100                 105

<210> SEQ ID NO 133
<211> LENGTH: 108
<212> TYPE: PRT
<213> ORGANISM: Neisseria meningitidis

<400> SEQUENCE: 133

Met Ser Glu Ala Lys Phe Met Arg Ile Ile Val Phe Phe Asp Leu Pro
1               5                   10                  15

Val Ile Thr Ala Ala Lys Arg Lys Ala Ala Asn Gln Phe Arg Gln Phe
            20                  25                  30

Leu Leu Lys Asp Gly Tyr Gln Met Leu Gln Leu Ser Val Tyr Ser Arg
        35                  40                  45

Ile Val Lys Gly Arg Asp Ser Leu Gln Lys His His Asn Arg Leu Cys
    50                  55                  60

Ala Asn Leu Pro Gln Glu Gly Ser Ile Arg Cys Leu Glu Ile Thr Glu
65                  70                  75                  80

Lys Gln Tyr Ala Ala Met Lys Leu Leu Leu Gly Glu Leu Lys Thr Gln
                85                  90                  95

Glu Lys Lys Val Asn Ser Asp Gln Leu Leu Leu Phe
            100                 105

<210> SEQ ID NO 134
<211> LENGTH: 101
<212> TYPE: PRT
<213> ORGANISM: Parvibaculum lavamentivorans

<400> SEQUENCE: 134

Met Trp Val Ile Ala Met Phe Asp Leu Pro Thr Asp Thr Pro Lys Ala
1               5                   10                  15

Arg Lys Ala Tyr Ala Arg Phe Arg Lys Asp Leu Leu Glu Asp Gly Phe
            20                  25                  30

Thr Met Met Gln Tyr Ser Val Tyr Ser Arg His Cys Ala Ser Ile Glu
        35                  40                  45

Asn Ala Glu Val His Val Lys Arg Met Gly Ala Val Pro Ala Gln
    50                  55                  60

Gly Glu Val Arg Phe Leu Thr Ile Thr Asp Asn Gln Phe Gly Arg Ile
65                  70                  75                  80

```
Lys Val Tyr Val Gly Lys Lys Arg Gln Pro Thr Thr Gln Ser Pro Ser
                85                  90                  95

Gln Leu Gln Leu Phe
            100

<210> SEQ ID NO 135
<211> LENGTH: 95
<212> TYPE: PRT
<213> ORGANISM: Pyrobaculum aerophilum

<400> SEQUENCE: 135

Met Ile Trp Leu Ala Val Tyr Asp Ile Glu Asp Gly Glu Arg Ala
1               5                   10                  15

Lys Ala Ser Ala Ile Leu Gln Ala Trp Gly Phe Val Arg Val Gln Arg
                20                  25                  30

Ser Phe Tyr Val Gly Arg Met Pro Arg Gly Lys Ala Ala Asp Leu Leu
                35                  40                  45

Lys Ile Leu Gln Arg His Val Lys Ser Gly His Ile Ala Leu Ile Pro
65              50              55              60

Ile Thr Asp Glu Leu Leu Ala Lys Ala Leu Glu Leu Gly Arg Pro Pro
65                  70                  75                  80

Tyr Ala Pro Leu Lys Pro Pro Lys Tyr Ala Gln Ile Tyr Val Val
                85                  90                  95

<210> SEQ ID NO 136
<211> LENGTH: 91
<212> TYPE: PRT
<213> ORGANISM: Pyrobaculum aerophilum

<400> SEQUENCE: 136

Met Tyr Val Val Ala Tyr Asp Ile Thr Glu Asp Glu Val Arg Asn
1               5                   10                  15

Lys Val Ala Asp Ala Leu Lys Ala Tyr Gly Leu Glu Arg Ile Gln Arg
                20                  25                  30

Ser Val Phe Val Gly Arg Ile Asn Pro Ala Leu Leu Lys Asp Leu Val
                35                  40                  45

Glu Arg Leu Lys Arg Ile Thr Lys Gly Ala Asn Ala Asp Ile Thr Ile
                50                  55                  60

Phe Lys Val Asp Arg Arg Ala Ile Asp Thr Ala Ile Arg Ile Gly Pro
65                  70                  75                  80

Pro Pro Pro Ala Arg Lys Asn Val Asp Leu Tyr
                85                  90

<210> SEQ ID NO 137
<211> LENGTH: 90
<212> TYPE: PRT
<213> ORGANISM: Pyrobaculum neutrophilum

<400> SEQUENCE: 137

Met Tyr Ile Ile Val Val Tyr Asp Ile Thr Glu Asn Asp Val Arg Ala
1               5                   10                  15

Lys Val Ala Asp Ile Leu Arg Ala Tyr Gly Leu Ala Arg Ile Gln Arg
                20                  25                  30

Ser Ala Tyr Val Gly Arg Leu Pro Pro Ala Leu Val Lys Glu Leu Ala
                35                  40                  45

Glu Arg Leu Ala Arg Ala Val Lys Gly Ala Asn Ala Asp Ile Ala Ile
                50                  55                  60
```

Phe Lys Val Asp Lys Arg Ala Ile Glu Thr Ala Leu Arg Ile Pro Pro
65                  70                  75                  80

Arg Pro Pro Ala Gly His Ala Ala Leu His
                85                  90

<210> SEQ ID NO 138
<211> LENGTH: 85
<212> TYPE: PRT
<213> ORGANISM: Pyrococcus furiosus

<400> SEQUENCE: 138

Met Tyr Ile Val Val Tyr Asp Val Gly Val Glu Arg Val Asn Lys
1               5                   10                  15

Val Lys Lys Phe Leu Arg Met His Leu Asn Trp Val Gln Asn Ser Val
                20                  25                  30

Phe Glu Gly Glu Val Thr Leu Ala Glu Phe Glu Arg Ile Lys Glu Gly
            35                  40                  45

Leu Lys Lys Ile Ile Asp Glu Asn Ser Asp Ser Val Ile Ile Tyr Lys
        50                  55                  60

Leu Arg Ser Met Pro Pro Arg Glu Thr Leu Gly Ile Glu Lys Asn Pro
65                  70                  75                  80

Ile Glu Glu Ile Ile
                85

<210> SEQ ID NO 139
<211> LENGTH: 102
<212> TYPE: PRT
<213> ORGANISM: Rhodospirillum rubrum

<400> SEQUENCE: 139

Met Gly Thr Arg Arg Ser Asn Ala Glu His Ala Tyr Val Val Ala Tyr
1               5                   10                  15

Asp Ile Ala Asp Pro Lys Arg Trp Arg Gln Val Phe Lys Thr Met Lys
                20                  25                  30

Gly Tyr Gly Gln Trp Val Gln Leu Ser Val Phe Gln Cys Arg Leu Asp
            35                  40                  45

Gly Gly Arg Arg Ile Ala Met Ala Ser Ile Leu Glu Ser Leu Ile Asp
        50                  55                  60

Arg Glu Thr Asp His Val Leu Met Leu Asp Leu Gly Pro Ala Glu Asp
65                  70                  75                  80

Val Asp Leu Ala Val Glu Ser Leu Gly Lys Ala Phe Glu Thr Leu Glu
                85                  90                  95

Arg Gln Ala Met Ile Ile
            100

<210> SEQ ID NO 140
<211> LENGTH: 95
<212> TYPE: PRT
<213> ORGANISM: Rhodospirillum rubrum

<400> SEQUENCE: 140

Met Ile Leu Val Thr Tyr Asp Val Asn Thr Val Glu Pro Gly Gly Arg
1               5                   10                  15

Arg Arg Leu Arg Gln Val Ala Lys Ala Cys Gln Asp Tyr Gly Gln Arg
                20                  25                  30

Val Gln Asn Ser Val Phe Glu Val Glu Val Asp Pro Ala Arg Trp Val
            35                  40                  45

```
Ala Leu Lys Ala Arg Leu Glu Ala Ile Ile Asp Pro Ala Leu Asp Ser
 50                  55                  60

Leu Arg Tyr Tyr Asp Leu Gly Ala Asn Trp Gln Arg Arg Val Asp His
 65                  70                  75                  80

Val Gly Ala Lys Pro Ala Val Asp Leu His Gly Pro Leu Ile Leu
             85                  90                  95
```

<210> SEQ ID NO 141
<211> LENGTH: 124
<212> TYPE: PRT
<213> ORGANISM: Rhodospirillum rubrum

<400> SEQUENCE: 141

```
Met Val Trp Trp Asp Asp Pro Asp Asp Ala Phe Cys Glu Asp Pro Phe
 1               5                  10                  15

Asp Pro Glu Gly Asp Tyr Gly Ala Leu Gln Val Gly Lys Gln Pro Met
             20                  25                  30

Asn Arg Tyr Val Ile Cys Tyr Asp Ile Val Asp Asp Lys Arg Arg Leu
         35                  40                  45

Lys Val Ala Lys Cys Leu Asp Ser Tyr Gly Ser Arg Val Gln Phe Ser
 50                  55                  60

Val Phe Glu Val Leu Val Ser Lys Pro Leu Met Thr Arg Met Val Arg
 65                  70                  75                  80

Glu Leu Gly Ala Leu Ile Asn Ala Lys Thr Asp Arg Ile Ser Ile Tyr
             85                  90                  95

Pro Gln Cys Ala Thr Cys Asp Ala Arg Arg Thr Asp Leu Gly Ala Thr
        100                 105                 110

Val Glu Lys Pro Val His Glu Pro Trp Ile Ile Val
        115                 120
```

<210> SEQ ID NO 142
<211> LENGTH: 112
<212> TYPE: PRT
<213> ORGANISM: Rhodospirillum rubrum

<400> SEQUENCE: 142

```
Met Pro Asp Gly Trp Arg Lys Met Gly Val Leu Val Phe Tyr Asp Leu
 1               5                  10                  15

Pro Val Val Ser Pro Glu Gln Arg Leu Ala Ala Val Arg Phe His Lys
             20                  25                  30

Phe Leu Leu Ala Asp Gly Phe Glu Arg Met His Tyr Ser Ile Tyr Ala
         35                  40                  45

Arg Tyr Cys Gly Ser Met Glu Arg Ala Ala Thr Tyr Glu Arg Arg Val
 50                  55                  60

Glu Gln Ala Leu Pro Ala Val Gly His Val Asn Leu Leu Lys Leu Thr
 65                  70                  75                  80

Asp Arg Gln Met Val Gly Met Arg Lys Trp Ile Arg Gly Asn Tyr Arg
             85                  90                  95

Ala Pro Glu Asn Ala Glu Phe Val Pro Pro Ala Gln Tyr Gln Leu Phe
        100                 105                 110
```

<210> SEQ ID NO 143
<211> LENGTH: 101
<212> TYPE: PRT
<213> ORGANISM: Staphylococcus epidermidis

<400> SEQUENCE: 143

Met Tyr Leu Leu Val Ser Phe Asp Leu Pro Arg Asp Thr Lys Leu Glu
1               5                   10                  15

Arg Arg Ile Ala Ser Lys Tyr Arg Leu Arg Leu Ile Glu Leu Gly Phe
            20                  25                  30

Ser Met Lys Gln Phe Ser Leu Tyr Glu Arg Tyr Val Ser Asn Val Gln
        35                  40                  45

Lys Lys Asp Lys Ile Leu Glu Ile Leu Lys Gln Glu Ile Pro Asp Thr
50                  55                  60

Gly Ser Ile Thr Leu Tyr Ile Leu Pro Asp Glu Val Asn Ser Asn Gln
65                  70                  75                  80

Ile Thr Ile Leu Gly Lys Glu Val Lys Leu Ala Val Asn Lys Glu Pro
                85                  90                  95

Lys Leu Ile Phe Ile
            100

<210> SEQ ID NO 144
<211> LENGTH: 109
<212> TYPE: PRT
<213> ORGANISM: Streptococcus gallolyticus

<400> SEQUENCE: 144

Met Arg Met Ile Leu Met Phe Asp Met Pro Thr Glu Thr Ala Glu Glu
1               5                   10                  15

Arg Lys Ala Tyr Arg Lys Phe Arg Lys Phe Leu Leu Ser Glu Gly Phe
            20                  25                  30

Ile Met His Gln Phe Ser Val Tyr Ser Lys Leu Leu Leu Asn Asn Ser
        35                  40                  45

Ala Asn Lys Ala Met Ile Asp Arg Leu Gln Ala Asn Asn Pro Lys Lys
    50                  55                  60

Gly Ser Ile Thr Leu Leu Thr Val Thr Glu Lys Gln Phe Ala Arg Met
65                  70                  75                  80

Ile Tyr Leu Asn Gly Glu Arg Asn Thr Ser Val Ala Asn Ser Asp Arg
                85                  90                  95

Arg Leu Val Phe Leu Gly Glu Asp Tyr Ser Asp Glu Asn
            100                 105

<210> SEQ ID NO 145
<211> LENGTH: 109
<212> TYPE: PRT
<213> ORGANISM: Streptococcus mutans serotype c

<400> SEQUENCE: 145

Met Arg Met Ile Leu Met Phe Asp Met Pro Thr Asp Thr Ala Glu Glu
1               5                   10                  15

Arg Lys Ala Tyr Arg Lys Phe Arg Lys Phe Leu Leu Ser Glu Gly Phe
            20                  25                  30

Ile Met His Gln Phe Ser Val Tyr Ser Lys Leu Leu Leu Asn Asn Ser
        35                  40                  45

Ala Asn Thr Ala Met Ile Ala Arg Leu Lys Glu Asn Asn Pro Lys Lys
    50                  55                  60

Gly Asn Ile Thr Leu Leu Thr Val Thr Glu Lys Gln Phe Ala Arg Met
65                  70                  75                  80

```
Ile Tyr Leu Asn Gly Glu Arg Asp Thr Ser Ile Ala Asn Ser Asp Ser
            85                  90                  95

Arg Leu Val Phe Leu Gly Glu Ala Phe Pro Asp Glu Thr
        100                 105

<210> SEQ ID NO 146
<211> LENGTH: 107
<212> TYPE: PRT
<213> ORGANISM: Streptococcus mutans serotype c

<400> SEQUENCE: 146

Met Ile Leu Met Phe Asp Met Pro Thr Asp Thr Ala Glu Glu Arg Lys
1               5                   10                  15

Ala Tyr Arg Lys Phe Arg Lys Phe Leu Leu Ser Glu Gly Phe Ile Met
            20                  25                  30

His Gln Phe Ser Val Tyr Ser Lys Leu Leu Leu Asn Asn Ser Ala Asn
        35                  40                  45

Thr Ala Met Ile Ala Arg Leu Lys Glu Asn Pro Lys Lys Gly Asn
    50                  55                  60

Ile Thr Leu Leu Thr Val Thr Glu Lys Gln Phe Ala Arg Met Ile Tyr
65                  70                  75                  80

Leu Asn Gly Glu Arg Asp Thr Ser Ile Ala Asn Ser Asp Ser Arg Leu
                85                  90                  95

Val Phe Leu Gly Glu Ala Phe Pro Asp Glu Thr
            100                 105

<210> SEQ ID NO 147
<211> LENGTH: 113
<212> TYPE: PRT
<213> ORGANISM: Streptococcus pyogenes

<400> SEQUENCE: 147

Met Ser Tyr Arg Tyr Met Arg Met Ile Leu Met Phe Asp Met Pro Thr
1               5                   10                  15

Asp Thr Ala Glu Glu Arg Lys Ala Tyr Arg Lys Phe Arg Lys Phe Leu
            20                  25                  30

Leu Ser Glu Gly Phe Ile Met His Gln Phe Ser Ile Tyr Ser Lys Leu
        35                  40                  45

Leu Leu Asn Asn Thr Ala Asn Asn Ala Met Ile Gly Arg Leu Arg Glu
    50                  55                  60

His Asn Pro Asn Lys Gly Asn Ile Thr Leu Leu Thr Val Thr Glu Lys
65                  70                  75                  80

Gln Phe Ala Arg Met Ile Tyr Leu His Gly Glu Arg Asn Asn Cys Ile
                85                  90                  95

Ala Asn Ser Asp Glu Arg Leu Val Phe Leu Gly Glu Ala Phe Asp Glu
            100                 105                 110

Ser

<210> SEQ ID NO 148
<211> LENGTH: 114
<212> TYPE: PRT
<213> ORGANISM: Streptococcus thermophilus GN

<400> SEQUENCE: 148

Met Ser Tyr Arg Tyr Met Arg Met Ile Leu Met Phe Asp Met Pro Thr
1               5                   10                  15

Asp Thr Ala Glu Glu Arg Lys Ala Tyr Arg Lys Phe Arg Lys Phe Leu
            20                  25                  30
```

```
Leu Ser Glu Gly Phe Ile Met His Gln Phe Ser Val Tyr Ser Lys Leu
            35                  40                  45

Leu Leu Asn His Thr Ala Asn Thr Ala Met Val Gly Arg Leu Lys Ala
 50                  55                  60

Asn Asn Pro Lys Lys Gly Asn Ile Thr Ile Leu Thr Val Thr Glu Lys
65                  70                  75                  80

Gln Phe Ala Arg Met Ile Tyr Leu Tyr Gly Asp Lys Asn Thr Ser Ile
            85                  90                  95

Ala Asn Ser Glu Glu Arg Leu Val Phe Leu Gly Asp Asn Tyr Cys Asp
                100                 105                 110

Glu Asp

<210> SEQ ID NO 149
<211> LENGTH: 88
<212> TYPE: PRT
<213> ORGANISM: Sulfolobus islandicus

<400> SEQUENCE: 149

Met Lys Leu Leu Val Val Tyr Asp Val Ser Asp Ser Lys Arg Ser
1               5                   10                  15

Lys Leu Ala Asn Asn Leu Lys Lys Leu Gly Leu Glu Arg Ile Gln Arg
            20                  25                  30

Ser Ala Phe Glu Gly Asp Ile Asp Ser Gln Arg Val Lys Asp Leu Ile
            35                  40                  45

Arg Val Val Arg Leu Ile Val Asp Thr Ser Thr Asp Ile Val His Ile
 50                  55                  60

Ile Pro Leu Gly Val Arg Asp Trp Glu Arg Arg Ile Val Ile Gly Lys
65                  70                  75                  80

Glu Gly Leu Glu Glu Trp Leu Val
            85

<210> SEQ ID NO 150
<211> LENGTH: 94
<212> TYPE: PRT
<213> ORGANISM: Synechocystis sp.

<400> SEQUENCE: 150

Met Leu Tyr Leu Ile Ile Tyr Asp Val Pro Ala Thr Lys Ala Gly Asn
1               5                   10                  15

Lys Arg Arg Thr Arg Leu Phe Asp Leu Leu Ser Gly Tyr Gly Lys Trp
            20                  25                  30

Arg Gln Phe Ser Val Phe Glu Cys Phe Leu Ser Val Lys Gln Phe Ala
            35                  40                  45

Lys Leu Gln Thr Ala Met Glu Lys Leu Ile Lys Leu Asp Glu Asp Ala
 50                  55                  60

Val Cys Ile Tyr Val Leu Asp Glu Asn Thr Val Gln Arg Thr Ile Thr
65                  70                  75                  80

Tyr Gly Thr Pro Gln Pro Glu Lys Pro Gly Ser Ile Ile Ile
            85                  90

<210> SEQ ID NO 151
<211> LENGTH: 92
<212> TYPE: PRT
<213> ORGANISM: Synechocystis sp.
```

<400> SEQUENCE: 151

Met Phe Leu Tyr Val Ile Ala Tyr Asp Ile Pro Asp Arg Arg Arg
1               5                   10                  15

Lys Lys Met Ala Asp Leu Leu Glu Gly Tyr Gly Gln Arg Val Gln Tyr
            20                  25                  30

Ser Val Phe Glu Cys Thr Leu Ser Lys Ser Lys Phe Asn Glu Leu Gln
            35                  40                  45

Lys Arg Leu Arg Lys Ile Tyr Gln Ser Glu Asp Ser Leu Arg Phe
    50                  55                  60

Tyr Pro Leu Ser Gly His Thr Leu Thr Gln Val Asp Ile Trp Gly Glu
65                  70                  75                  80

Pro Pro Leu Thr Lys Pro Pro Gly Ser Val Ile Val
                85                  90

<210> SEQ ID NO 152
<211> LENGTH: 93
<212> TYPE: PRT
<213> ORGANISM: Synechocystis sp.

<400> SEQUENCE: 152

Met Asp Phe Trp Leu Val Cys Tyr Asp Val Arg Asp Lys Arg Arg
1               5                   10                  15

Arg Lys Leu Ala Lys Leu Leu Glu Gln Arg Cys Gln Arg Val Gln Tyr
            20                  25                  30

Ser Val Phe Glu Cys Pro Leu Pro Glu Lys Val Leu Thr Asp Leu Leu
            35                  40                  45

His Arg Arg Trp Leu Lys Glu Leu Asn Leu Lys Glu Asp Ser Leu Arg
    50                  55                  60

Ala Tyr Pro Leu Gln Arg Gln Ser Arg Ser Gln Ala Lys Ile Phe Gly
65                  70                  75                  80

Ser Pro Asp Leu Tyr Glu Pro Pro Asp Phe Leu Ile Leu
                85                  90

<210> SEQ ID NO 153
<211> LENGTH: 85
<212> TYPE: PRT
<213> ORGANISM: Thermococcus kodakaraensis

<400> SEQUENCE: 153

Met Tyr Ile Ile Val Val Tyr Asp Val Ser Val Glu Arg Val Asn Arg
1               5                   10                  15

Val Lys Lys Phe Leu Arg Gln His Leu His Trp Val Gln Asn Ser Val
            20                  25                  30

Phe Glu Gly Glu Val Thr Leu Ala Glu Phe Glu Arg Ile Lys Ala Gly
            35                  40                  45

Ile Gly Glu Leu Ile Asp Gly Asp Glu Asp Ser Val Val Ile Tyr Lys
    50                  55                  60

Leu Arg Ser Met Pro Lys Arg Glu Val Met Gly Val Glu Lys Asn Pro
65                  70                  75                  80

Ile Glu Asp Ile Ile
                85

<210> SEQ ID NO 154
<211> LENGTH: 92
<212> TYPE: PRT
<213> ORGANISM: Thermodesulfovibrio yellowstonii -continued

<400> SEQUENCE: 154

Met Arg Val Leu Tyr Ile Ile Ala Tyr Asp Ile Thr Asp Ala Arg Arg
1               5                   10                  15

Leu Gly Gln Ile Arg Tyr Phe Leu Lys Gly Tyr Ser Thr Gly Gly Gln
                20                  25                  30

Lys Ser Val Tyr Glu Cys Phe Leu Glu Arg Glu Leu Lys Phe Ile
            35                  40                  45

Ile Ser Lys Ile Lys Arg Leu Ile Asn Pro Asn Glu Asp Arg Val His
50                  55                  60

Ile Phe Arg Ile Asp Gly Arg Ser Lys Val Ile Thr Leu Gly Ile Ala
65                  70                  75                  80

Val Pro Pro Ile Asp Pro Glu Tyr Phe Tyr Ile Gly
                85                  90

<210> SEQ ID NO 155
<211> LENGTH: 91
<212> TYPE: PRT
<213> ORGANISM: Thermodesulfovibrio yellowstonii

<400> SEQUENCE: 155

Met Arg Leu Pro Tyr Leu Val Cys Tyr Asp Ile Ser Asp Glu Gly Arg
1               5                   10                  15

Leu Asn Arg Val Tyr Arg Phe Met Lys Gly Lys Gly Phe His Ile Gln
                20                  25                  30

Tyr Ser Val Phe Tyr Cys Ile Leu Thr Asp Val Glu Leu Lys Glu Met
            35                  40                  45

Lys Ala Glu Ile Leu Lys Leu Ile His Ser Arg Tyr Asp Asp Val Arg
50                  55                  60

Ile Tyr Pro Leu Pro Asn Asn Ser Leu Val Ala Val Leu Gly Val Gly
65                  70                  75                  80

Asp Arg Ile Pro Asp Gly Val Glu Val Phe Tyr
                85                  90

<210> SEQ ID NO 156
<211> LENGTH: 88
<212> TYPE: PRT
<213> ORGANISM: Thermodesulfovibrio yellowstonii

<400> SEQUENCE: 156

Met Pro Tyr Leu Ile Val Thr Tyr Asp Ile Ala Glu Glu Arg Val Asn
1               5                   10                  15

Lys Val Arg Lys Ile Leu Lys Lys Tyr Phe Met Trp Val Gln Asn Ser
                20                  25                  30

Val Phe Glu Gly Glu Ile Thr Glu Gly Lys Leu Leu Lys Cys Lys Leu
            35                  40                  45

Glu Leu Glu Lys Val Ile Asp Lys Glu Val Asp Ser Val Tyr Phe Tyr
50                  55                  60

Ser Leu Glu Asn Arg Leu Asn Tyr Arg Lys Thr Val Leu Gly Ile Glu
65                  70                  75                  80

Lys Glu Ile Thr Gly Asn Ile Leu
                85

<210> SEQ ID NO 157
<211> LENGTH: 93
<212> TYPE: PRT
<213> ORGANISM: Thermofilum pendens -continued

<400> SEQUENCE: 157

Met Ile Val Ile Val Ala Tyr Asp Ile Ser Asp Glu Asp Arg Arg Gly
1               5                   10                  15

Arg Leu Arg Arg Tyr Leu Arg Arg Leu Gly Leu Ala Arg Val Asn Arg
            20                  25                  30

Ser Val Tyr Ala Gly Pro Gly Thr Ala Thr Thr Ala Glu Leu Val Ala
        35                  40                  45

Glu Arg Ala Lys Glu Ile Val Glu Glu Gly Asp Ser Val Phe Val Ile
    50                  55                  60

Val Val Arg Glu Asp Glu Tyr Gln Arg Ala His Val Phe Asp Gly Arg
65                  70                  75                  80

Asp Tyr Tyr Ile Val Ser Glu Arg Lys Tyr Glu Val Tyr
                85                  90

<210> SEQ ID NO 158
<211> LENGTH: 93
<212> TYPE: PRT
<213> ORGANISM: Thermofilum pendens

<400> SEQUENCE: 158

Met Ile Val Ile Val Ala Tyr Asp Ile Ser Asp Glu Asp Arg Arg Gly
1               5                   10                  15

Arg Leu Arg Arg Tyr Leu Arg Arg Leu Gly Leu Ala Arg Val Asn Arg
            20                  25                  30

Ser Val Tyr Ala Gly Pro Gly Thr Ala Thr Thr Ala Glu Leu Val Ala
        35                  40                  45

Glu Arg Ala Lys Glu Ile Val Glu Glu Gly Asp Ser Val Phe Val Ile
    50                  55                  60

Val Val Arg Glu Asp Glu Tyr Gln Arg Ala His Val Phe Asp Gly Arg
65                  70                  75                  80

Asp Tyr Tyr Ile Val Ser Glu Arg Lys Tyr Glu Val Tyr
                85                  90

<210> SEQ ID NO 159
<211> LENGTH: 87
<212> TYPE: PRT
<213> ORGANISM: Thermotoga maritima

<400> SEQUENCE: 159

Met Tyr Val Ile Met Val Tyr Asp Val Asn Glu Lys Arg Val Ala Lys
1               5                   10                  15

Ile Leu Lys Ile Ala Arg Lys Tyr Leu Lys Trp Val Gln Asn Ser Val
            20                  25                  30

Leu Glu Gly Glu Leu Ser Pro Gly Lys Tyr Glu Lys Leu Lys Leu Glu
        35                  40                  45

Val Ser Arg Leu Ile Asp Glu Lys Glu Asp Ser Val Arg Phe Tyr Val
    50                  55                  60

Met Asp Ser Gln Lys Val Phe Asn Leu Glu Thr Leu Gly Val Glu Lys
65                  70                  75                  80

Gly Glu Asp Gly Phe Ile Phe
                85

<210> SEQ ID NO 160
<211> LENGTH: 94
<212> TYPE: PRT
<213> ORGANISM: Thermus thermophilus

```
<400> SEQUENCE: 160

Met Arg Glu Leu Tyr Leu Val Ile Ala Tyr Asp Thr Pro Asp Asp Arg
1               5                   10                  15

Arg Arg Ala Arg Leu Ala Lys Leu Leu Lys Gly Phe Gly Glu Arg Arg
            20                  25                  30

Gln Tyr Ser Val Phe Glu Ala Arg Leu Thr Arg Glu Gln Trp Ala His
        35                  40                  45

Leu Lys Gly Lys Leu Glu Ala Leu Val Asn Lys Glu Glu Asp Val Leu
    50                  55                  60

Ala Val Tyr Phe Leu Pro Pro Glu Ala Val Gly Arg Thr Trp Arg Ile
65                  70                  75                  80

Gly His Glu Gly Leu Lys Arg Leu Glu Asp Pro Asp Phe Val
                85                  90

<210> SEQ ID NO 161
<211> LENGTH: 101
<212> TYPE: PRT
<213> ORGANISM: Treponema denticola

<400> SEQUENCE: 161

Met Arg Val Ile Val Phe Phe Asp Leu Pro Val Ile Thr Pro Glu Asn
1               5                   10                  15

Arg His Asn Tyr Ser Val Phe Arg Lys Tyr Leu Ile Lys Ser Gly Phe
            20                  25                  30

Ile Met Gln Gln Lys Ser Val Tyr Ser Lys Leu Val Leu Asn Leu Thr
        35                  40                  45

Asn Arg Asp Ser Ile Val Lys Ser Ile Glu Lys Asn Lys Pro Pro Glu
    50                  55                  60

Gly Leu Val Glu Val Leu Thr Val Thr Glu Lys Gln Tyr Ala Lys Met
65                  70                  75                  80

Glu Ile Ile Ile Gly Glu Ser Lys Thr Glu Tyr Leu Asn Thr Asp Glu
                85                  90                  95

Arg Leu Val Val Leu
            100

<210> SEQ ID NO 162
<211> LENGTH: 262
<212> TYPE: PRT
<213> ORGANISM: Thermoproteus tenax

<400> SEQUENCE: 162

Met Asp Glu Val Leu Leu Leu Thr Gly Gly Ile Ser Ile Thr Thr Arg
1               5                   10                  15

Ala Leu Arg Ala Leu Leu Ala Thr Gly Ala Thr Val Ala Val Phe Ser
            20                  25                  30

Pro Arg Gly Glu Pro Leu Gly Ile Phe Met Arg Pro Val Gly Asp Ala
        35                  40                  45

Thr Gly Ala Lys Arg Arg Cys Gln Tyr Lys Ala Ala Glu Asp Gly Arg
    50                  55                  60

Gly Leu Gln Tyr Ala Lys Ser Trp Val Phe Lys Lys Ile Leu Gly Gln
65                  70                  75                  80

Arg Asp Asn Ile Lys Ala Trp Arg Arg Leu Arg Gly Tyr Ser Gln
                85                  90                  95

Tyr Ala Glu Ser Leu Ala Lys Ala Leu Pro Gly Ala Gly Leu His Gly
            100                 105                 110
```

```
Ala Met Glu Thr Pro Arg Arg Arg Arg Gly Gln Asp Gly Gly Gln
            115                 120                 125
Ala Gly Val Arg Gly Arg Pro Thr His Pro Val Pro Pro Gly Ala
        130                 135                 140
Gly Arg Arg Ser Pro Gly Gly Ala Pro Arg Gly Gln Glu Ala Ser Leu
145                 150                 155                 160
Arg Arg Asp Pro Gln Arg Gly Gln Ser Ser Gly Ala Leu His Met Tyr
                165                 170                 175
Val Ile Val Val Tyr Asp Ile Thr Glu Asn Asp Val Arg Ala Lys Val
            180                 185                 190
Ala Asp Ile Leu Arg Ala Tyr Gly Leu Ala Arg Ile Gln Arg Ser Ala
        195                 200                 205
Tyr Val Gly Arg Leu Pro Pro Ala Leu Val Lys Glu Leu Ala Glu Arg
    210                 215                 220
Leu Ala Arg Ala Val Arg Gly Ala Asn Ala Asp Ile Ala Ile Phe Lys
225                 230                 235                 240
Val Asp Lys Arg Thr Ile Asp Thr Ser Leu Arg Ile Pro Pro Arg Pro
                245                 250                 255
Pro Ala Gly His Val Ala
            260
```

<210> SEQ ID NO 163
<211> LENGTH: 100
<212> TYPE: DNA
<213> ORGANISM: Thermoproteus tenax

<400> SEQUENCE: 163
caaaactgct atcatgccac ctcaagagtc cgccgagatc aacgtcagtc tcgtgagaaa    60
aaagcttaaa agctcgtaga aacaaagaca acaatacccg    100

<210> SEQ ID NO 164
<211> LENGTH: 100
<212> TYPE: DNA
<213> ORGANISM: Thermoproteus tenax

<400> SEQUENCE: 164
agaggaatat atgaatgtaa atgggcgttt gaaggcgacc gccgggcggg cggaggatct    60
gggcaaaatt taaatagccg gggccgcaat cgacgtgggc    100

<210> SEQ ID NO 165
<211> LENGTH: 100
<212> TYPE: DNA
<213> ORGANISM: Thermoproteus tenax

<400> SEQUENCE: 165
ggagaatgtg tgaatgtaaa gggcagcgga aaagcggccg ccgggcgggc ggaggatctg    60
ggcaaaattt aaatacccga ggccgcagtc aacgtgggcg    100

<210> SEQ ID NO 166
<211> LENGTH: 100
<212> TYPE: DNA
<213> ORGANISM: Thermoproteus tenax

<400> SEQUENCE: 166
aaagccctcc ccggggcaac acaaggtcgc gccgggacta cacaaagac ccacagagga    60 aaacttaaaa atcggcaaaa actaaagacc agaaggcccg    100

-continued

```
<210> SEQ ID NO 167
<211> LENGTH: 100
<212> TYPE: DNA
<213> ORGANISM: Thermoproteus tenax

<400> SEQUENCE: 167
aaagccctcc ccggggcaac acaaggtcgc gccgggacca agacaaagac ccgcagagga    60
aaacttaaaa atcggcagaa actaaagacc aggaggcccg                         100

<210> SEQ ID NO 168
<211> LENGTH: 100
<212> TYPE: DNA
<213> ORGANISM: Thermoproteus tenax

<400> SEQUENCE: 168
gcagtccggg gagagctatc tcaagaacac gctgcaatca acgcaaaacc caccagagaa    60
aaacttaaaa acagccaaaa accaaaaccc agaaggcccg                         100

<210> SEQ ID NO 169
<211> LENGTH: 100
<212> TYPE: DNA
<213> ORGANISM: Thermoproteus tenax

<400> SEQUENCE: 169
aaccccaccc cttagccaac acgagaacac gccagaacta acacaaaacc caccagagaa    60
aaacttaaaa acagccaaaa gccaaaaccc agaaggcccg                         100

<210> SEQ ID NO 170
<211> LENGTH: 100
<212> TYPE: DNA
<213> ORGANISM: Haloarcula hispanica

<400> SEQUENCE: 170
aggtgaatcg acaattatct acgagctgtc ttctgataca ctgctcaacc ggacagtcta    60
cggcgacgat ccaactgagg atcagcggtt tctatagtcg                         100

<210> SEQ ID NO 171
<211> LENGTH: 200
<212> TYPE: DNA
<213> ORGANISM: Desulfovibrio vulgaris

<400> SEQUENCE: 171
agaaggcccc ctgattctgt agcgcgaacc ccaagcgacc ctgttttttcc cggcaggttc    60 gcgaacatga caatgacctg ttttcattga attgcgtaac ctttaatgca ggctggtcac   120
acatcttggc ggtgctgctg gcccggttcg cggaaccctc gtcgcaaggt caatactgcc   180
aacgtgtttg atggccgaca                                              200

<210> SEQ ID NO 172
<211> LENGTH: 200
<212> TYPE: DNA
<213> ORGANISM: Thermofilum pendens

<400> SEQUENCE: 172
ccgtaggtgt ctgcgcgtag gctggagaaa cgggcgccga gaggttcggg aaccgctcct    60
cgcatcgtca gtctaggata aggttgaggc agttttagcg gaaagattgg gctctaaaaa   120
ttgattgaat tgatcgtttt tctaaacttt tcacgatttt tcgaacaaga atattagaga   180 atgcaaccctc ttctgttacc                                             200
```

```
<210> SEQ ID NO 173
<211> LENGTH: 100
<212> TYPE: DNA
<213> ORGANISM: Escherichia coli

<400> SEQUENCE: 173
actctttaac ataatggatg tgttgtttgt gtgatactat aaagttggta gattgtgact      60
ggcttaaaaa atcattaatt aataataggt tatgtttaga                          100

<210> SEQ ID NO 174
<211> LENGTH: 100
<212> TYPE: DNA
<213> ORGANISM: Escherichia coli

<400> SEQUENCE: 174
aagaattagc tgatctttaa taataaggaa atgttacatt aaggttggtg ggttgttttt      60
atgggaaaaa atgctttaag aacaaatgta tacttttaga                          100

<210> SEQ ID NO 175
<211> LENGTH: 100
<212> TYPE: DNA
<213> ORGANISM: Pseudomonas aeruginosa

<400> SEQUENCE: 175
tataaatcag caagttacga gacctcgaaa aaagagggt tctggcagga aaaactcggt       60
atttcctttt ccttcaaatg gttataggtt ttcggggcta                          100

<210> SEQ ID NO 176
<211> LENGTH: 100
<212> TYPE: DNA
<213> ORGANISM: Pseudomonas aeruginosa

<400> SEQUENCE: 176
ttttagatca aagggttaga gatcgctgca aaaagagggt ttttccgggc tttggcgctg      60
gagcccttgg agcttggaag gttgatggtt tttgggtcta                          100

<210> SEQ ID NO 177
<211> LENGTH: 100
<212> TYPE: DNA
<213> ORGANISM: Pseudomonas aeruginosa

<400> SEQUENCE: 177
tagctccgaa aacctataac catttgaagg aaaaagaaat accgagtttt tcccgccaga      60
aaccctcttt tttcgaggtc tcgtaacttg ctgatttata                          100

<210> SEQ ID NO 178
<211> LENGTH: 100
<212> TYPE: DNA
<213> ORGANISM: Campylobacter jejuni

<400> SEQUENCE: 178
agatatttac cagataatga aaatttcggg gttttttcat gaaaaatagc aaaaattatg      60
ctataatctc ataagaaatt taaaaaggga ctaaaataaa                          100

<210> SEQ ID NO 179
<211> LENGTH: 100
<212> TYPE: DNA
<213> ORGANISM: Campylobacter jejuni
```

```
<400> SEQUENCE: 179
agatatttac cagataatga aaatttcggg gttttttcat gaaaaatagc aaaaattatg     60
ctataatctc ataagaaatt taaaaaggga ctaaaataaa                          100

<210> SEQ ID NO 180
<211> LENGTH: 100
<212> TYPE: DNA
<213> ORGANISM: Streptococcus pyogenes

<400> SEQUENCE: 180
ctcttaataa atgcagtaat acagggcttt tcaagactg aagtctagct gagacaaata      60
gtgcgattac gaaatttttt agacaaaaat agtctacgag                         100

<210> SEQ ID NO 181
<211> LENGTH: 100
<212> TYPE: DNA
<213> ORGANISM: Streptococcus pyogenes

<400> SEQUENCE: 181
aacattgccg atgataactt gagaaagagg gttcatacca gcagtcggat acctttctat    60
tcttcctgtt aaaacgtttt catgttataa taggcaaaag                         100

<210> SEQ ID NO 182
<211> LENGTH: 100
<212> TYPE: DNA
<213> ORGANISM: Francisella novicida

<400> SEQUENCE: 182
ttgaattgat attttgctat ataactattt tagcggttat attatctgat atactttacc    60
cagatagaaa cttctaaata ttattcgtaa aattaattaa                         100

<210> SEQ ID NO 183
<211> LENGTH: 100
<212> TYPE: DNA
<213> ORGANISM: Francisella novicida

<400> SEQUENCE: 183
agccaagaca aacctagagt ttgcaaggct ttgagagaat tatttgctgg tgttttttcg    60
caaacatcct acttgtaaaa aaatgtagac attttgcgaa                         100

<210> SEQ ID NO 184
<211> LENGTH: 100
<212> TYPE: DNA
<213> ORGANISM: Neisseria meningitides

<400> SEQUENCE: 184
aaaaaaggtc aattcagacc aattattgtt attttaagcc cattttttca taacaaataa    60
aacgggaaac ccttatgaaa taaggatttc ccgtcgaagt                         100

<210> SEQ ID NO 185
<211> LENGTH: 100
<212> TYPE: DNA
<213> ORGANISM: Staphylococcus epidermidis

<400> SEQUENCE: 185
tttctacata ataacatctt tcatttttc catcccctag aaattaatca atgcgtattt     60
tattcaaaat ctacaatttt ttagagtgtt gttagattta                         100
```

```
<210> SEQ ID NO 186
<211> LENGTH: 100
<212> TYPE: DNA
<213> ORGANISM: Staphylococcus epidermidis

<400> SEQUENCE: 186
gatactttaa caaatgccat cacaactata tttcaagcat cattttttgct gtcaaaaaat    60 atgacaatca ctagtacaag attatatgat atgtcacttt                         100

<210> SEQ ID NO 187
<211> LENGTH: 100
<212> TYPE: DNA
<213> ORGANISM: Sulfolobus islandicus

<400> SEQUENCE: 187
tcttattcga tataaacgta cttatatcta ttaggacttc gtcttttccc atacggcttc    60
cctagattta gatttcaaac aagtcataga atatagtata                         100

<210> SEQ ID NO 188
<211> LENGTH: 100
<212> TYPE: DNA
<213> ORGANISM: Sulfolobus islandicus

<400> SEQUENCE: 188
tgagggttta ttacttttta tctaatatct tgttctctct tcgttattta taagctttac    60
tctgtattat cttttcaatt tttctcctca tcctttcact                         100

<210> SEQ ID NO 189
<211> LENGTH: 24
<212> TYPE: DNA
<213> ORGANISM: Thermoproteus tenax

<400> SEQUENCE: 189
gaatctcaga tagagatttg aagg                                           24

<210> SEQ ID NO 190
<211> LENGTH: 26
<212> TYPE: DNA
<213> ORGANISM: Thermoproteus tenax

<400> SEQUENCE: 190
agtggaaatc aaaagatagt agaaac                                         26

<210> SEQ ID NO 191
<211> LENGTH: 25
<212> TYPE: DNA
<213> ORGANISM: Thermoproteus tenax

<400> SEQUENCE: 191
gtggaaatca aagatagta gaaag                                           25

<210> SEQ ID NO 192
<211> LENGTH: 24
<212> TYPE: DNA
<213> ORGANISM: Thermoproteus tenax

<400> SEQUENCE: 192
gaatctcaaa gagaggattg aaag                                           24
```

```
<210> SEQ ID NO 193
<211> LENGTH: 24
<212> TYPE: DNA
<213> ORGANISM: Thermoproteus tenax

<400> SEQUENCE: 193
gaatctcaaa gagaggattg aaag                                          24

<210> SEQ ID NO 194
<211> LENGTH: 24
<212> TYPE: DNA
<213> ORGANISM: Thermoproteus tenax

<400> SEQUENCE: 194
gaatctcaaa aagaggattg aaag                                          24

<210> SEQ ID NO 195
<211> LENGTH: 24
<212> TYPE: DNA
<213> ORGANISM: Thermoproteus tenax

<400> SEQUENCE: 195
gaatctcaaa gagaggattg aaag                                          24

<210> SEQ ID NO 196
<211> LENGTH: 30
<212> TYPE: DNA
<213> ORGANISM: Haloarcula hispanica

<400> SEQUENCE: 196
gtttcagacg aaccctcgtg gggttgaagc                                    30

<210> SEQ ID NO 197
<211> LENGTH: 32
<212> TYPE: DNA
<213> ORGANISM: Desulfovibrio vulgaris

<400> SEQUENCE: 197 gtcgccccccc acgcggggc gtggattgaa ac                                 32

<210> SEQ ID NO 198
<211> LENGTH: 24
<212> TYPE: DNA
<213> ORGANISM: Thermofilum pendens

<400> SEQUENCE: 198
ctcttagtct tgctgatttt gaac                                          24

<210> SEQ ID NO 199
<211> LENGTH: 29
<212> TYPE: DNA
<213> ORGANISM: Escherichia coli

<400> SEQUENCE: 199
gtgttccccg cgccagcggg gataaaccg                                     29

<210> SEQ ID NO 200
<211> LENGTH: 29
<212> TYPE: DNA
<213> ORGANISM: Escherichia coli

<400> SEQUENCE: 200
gagttccccg cgccagcggg gataaaccg                                     29
```

```
<210> SEQ ID NO 201
<211> LENGTH: 28
<212> TYPE: DNA
<213> ORGANISM: Pseudomonas aeruginosa

<400> SEQUENCE: 201
gttcactgcc gtataggcag ctaagaaa                                       28

<210> SEQ ID NO 202
<211> LENGTH: 28
<212> TYPE: DNA
<213> ORGANISM: Pseudomonas aeruginosa

<400> SEQUENCE: 202
gttcactgcc gtataggcag ctaagaaa                                       28

<210> SEQ ID NO 203
<211> LENGTH: 28
<212> TYPE: DNA
<213> ORGANISM: Pseudomonas aeruginosa

<400> SEQUENCE: 203
tttcttagct gcctacacgg cagtgaac                                       28

<210> SEQ ID NO 204
<211> LENGTH: 36
<212> TYPE: DNA
<213> ORGANISM: Campylobacter jejuni

<400> SEQUENCE: 204
gttttagtcc cttttttaaat ttctttatgg taaaat                             36

<210> SEQ ID NO 205
<211> LENGTH: 36
<212> TYPE: DNA
<213> ORGANISM: Streptococcus pyogenes

<400> SEQUENCE: 205
gttttagagc tatgctgttt tgaatggtcc caaaac                              36

<210> SEQ ID NO 206
<211> LENGTH: 37
<212> TYPE: DNA
<213> ORGANISM: Francisella novicida

<400> SEQUENCE: 206
gtttcagtag ctagattatt tgatatactg ctgttag                             37

<210> SEQ ID NO 207
<211> LENGTH: 36
<212> TYPE: DNA
<213> ORGANISM: Neisseria meningitides

<400> SEQUENCE: 207
attgtagcac tgcgaaatga gaaagggagc tacaac                              36

<210> SEQ ID NO 208
<211> LENGTH: 37
<212> TYPE: DNA
<213> ORGANISM: Staphylococcus epidermidis

<400> SEQUENCE: 208
gttctcgtcc cctttttcttc ggggtgggta tcgatcc                            37
```

```
<210> SEQ ID NO 209
<211> LENGTH: 24
<212> TYPE: DNA
<213> ORGANISM: Sulfolobus islandicus

<400> SEQUENCE: 209
ctttcaattc tatagtagat tatc                                              24

<210> SEQ ID NO 210
<211> LENGTH: 11
<212> TYPE: PRT
<213> ORGANISM: Artificial Sequence
<220> FEATURE:
<223> OTHER INFORMATION: Synthetic sequence

<400> SEQUENCE: 210

Tyr Gly Arg Lys Lys Arg Arg Gln Arg Arg Arg
1               5                   10

<210> SEQ ID NO 211
<211> LENGTH: 12
<212> TYPE: PRT
<213> ORGANISM: Artificial Sequence
<220> FEATURE:
<223> OTHER INFORMATION: Synthetic sequence

<400> SEQUENCE: 211

Arg Arg Gln Arg Arg Thr Ser Lys Leu Met Lys Arg
1               5                   10

<210> SEQ ID NO 212
<211> LENGTH: 27
<212> TYPE: PRT
<213> ORGANISM: Artificial Sequence
<220> FEATURE:
<223> OTHER INFORMATION: Synthetic sequence

<400> SEQUENCE: 212

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 213
<211> LENGTH: 33
<212> TYPE: PRT
<213> ORGANISM: Artificial Sequence
<220> FEATURE:
<223> OTHER INFORMATION: Synthetic sequence

<400> SEQUENCE: 213

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 214
<211> LENGTH: 16
<212> TYPE: PRT
<213> ORGANISM: Artificial Sequence
<220> FEATURE:
<223> OTHER INFORMATION: Synthetic sequence
```

```
<400> SEQUENCE: 214

Arg Gln Ile Lys Ile Trp Phe Gln Asn Arg Arg Met Lys Trp Lys Lys
1               5                   10                  15

<210> SEQ ID NO 215
<211> LENGTH: 9
<212> TYPE: PRT
<213> ORGANISM: Artificial Sequence
<220> FEATURE:
<223> OTHER INFORMATION: Synthetic sequence

<400> SEQUENCE: 215

Arg Lys Lys Arg Arg Gln Arg Arg Arg
1               5

<210> SEQ ID NO 216
<211> LENGTH: 8
<212> TYPE: PRT
<213> ORGANISM: Artificial Sequence
<220> FEATURE:
<223> OTHER INFORMATION: Synthetic sequence

<400> SEQUENCE: 216

Arg Lys Lys Arg Arg Gln Arg Arg
1               5

<210> SEQ ID NO 217
<211> LENGTH: 11
<212> TYPE: PRT
<213> ORGANISM: Artificial Sequence
<220> FEATURE:
<223> OTHER INFORMATION: Synthetic sequence

<400> SEQUENCE: 217

Tyr Ala Arg Ala Ala Ala Arg Gln Ala Arg Ala
1               5                   10

<210> SEQ ID NO 218
<211> LENGTH: 11
<212> TYPE: PRT
<213> ORGANISM: Artificial Sequence
<220> FEATURE:
<223> OTHER INFORMATION: Synthetic sequence

<400> SEQUENCE: 218

Thr His Arg Leu Pro Arg Arg Arg Arg Arg Arg
1               5                   10

<210> SEQ ID NO 219
<211> LENGTH: 11
<212> TYPE: PRT
<213> ORGANISM: Artificial Sequence
<220> FEATURE:
<223> OTHER INFORMATION: Synthetic sequence

<400> SEQUENCE: 219

Gly Gly Arg Arg Ala Arg Arg Arg Arg Arg Arg
1               5                   10

<210> SEQ ID NO 220
<211> LENGTH: 33
<212> TYPE: DNA
<213> ORGANISM: Artificial Sequence
<220> FEATURE:
<223> OTHER INFORMATION: Synthetic sequence
```

```
<400> SEQUENCE: 220
gcccaattta ctactcgttc tggtgtttct cgt                                33

<210> SEQ ID NO 221
<211> LENGTH: 33
<212> TYPE: DNA
<213> ORGANISM: Artificial Sequence
<220> FEATURE:
<223> OTHER INFORMATION: Synthetic sequence

<400> SEQUENCE: 221
acgagaaaca ccagaacgag tagtaaattg ggc                                33

<210> SEQ ID NO 222
<211> LENGTH: 20
<212> TYPE: DNA
<213> ORGANISM: Artificial Sequence
<220> FEATURE:
<223> OTHER INFORMATION: Synthetic sequence

<400> SEQUENCE: 222
ggccccagtg ctgcaatgat                                               20

<210> SEQ ID NO 223
<211> LENGTH: 40
<212> TYPE: DNA
<213> ORGANISM: Artificial Sequence
<220> FEATURE:
<223> OTHER INFORMATION: Synthetic sequence

<400> SEQUENCE: 223
gtgagcgtgg gtctcgcggt atcattgcag cactggggcc                         40

<210> SEQ ID NO 224
<211> LENGTH: 53
<212> TYPE: DNA
<213> ORGANISM: Artificial Sequence
<220> FEATURE:
<223> OTHER INFORMATION: Synthetic sequence

<400> SEQUENCE: 224
gcccaattta ctactcgttc tggtgtttct cgtaccgcga gacccacgct cac          53

<210> SEQ ID NO 225
<211> LENGTH: 33
<212> TYPE: DNA
<213> ORGANISM: Artificial Sequence
<220> FEATURE:
<223> OTHER INFORMATION: Synthetic sequence

<400> SEQUENCE: 225
acgagaaaca ccagaacgag tagtaaattg ggc                                33

<210> SEQ ID NO 226
<211> LENGTH: 58
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (57)..(58)
<223> OTHER INFORMATION: The bond between these two positions is a
      phosphorothioate bond
```

<400> SEQUENCE: 226
aatgatacgg cgaccaccga gatctacact ctttccctac acgacgctct tccgatct         58

<210> SEQ ID NO 227
<211> LENGTH: 57
<212> TYPE: DNA
<213> ORGANISM: Artificial Sequence
<220> FEATURE:
<223> OTHER INFORMATION: Synthetic sequence

<400> SEQUENCE: 227
gatcggaaga gcacacgtct gaactccagt cacatctcgt atgccgtctt ctgcttg          57

<210> SEQ ID NO 228
<211> LENGTH: 44
<212> TYPE: DNA
<213> ORGANISM: Artificial Sequence
<220> FEATURE:
<223> OTHER INFORMATION: Synthetic sequence

<400> SEQUENCE: 228
aatgatacgg cgaccaccga gatctacact ctttccctac acga                        44

<210> SEQ ID NO 229
<211> LENGTH: 24
<212> TYPE: DNA
<213> ORGANISM: Artificial Sequence
<220> FEATURE:
<223> OTHER INFORMATION: Synthetic sequence

<400> SEQUENCE: 229
caagcagaag acggcatacg agat                                              24

<210> SEQ ID NO 230
<211> LENGTH: 33
<212> TYPE: DNA
<213> ORGANISM: Artificial Sequence
<220> FEATURE:
<223> OTHER INFORMATION: Synthetic sequence

<400> SEQUENCE: 230
acgagaaaca ccagaacgag tagtaaattg ggc                                    33

<210> SEQ ID NO 231
<211> LENGTH: 33
<212> TYPE: DNA
<213> ORGANISM: Artificial Sequence
<220> FEATURE:
<223> OTHER INFORMATION: Synthetic sequence

<400> SEQUENCE: 231
gcccaattta ctactcgttc tggtgtttct cgt                                    33

<210> SEQ ID NO 232
<211> LENGTH: 32
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (30)..(32)
<223> OTHER INFORMATION: n is a, c, g, or t

<400> SEQUENCE: 232
gtgttccccg cgccagcggg gataaaccgn nn                                     32

```
<210> SEQ ID NO 233
<211> LENGTH: 31
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (29)..(31)
<223> OTHER INFORMATION: n is a, c, g, or t

<400> SEQUENCE: 233 ccaaatagggg gcgaccgcgc cccttgtgnn n                               31

<210> SEQ ID NO 234
<211> LENGTH: 32
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(3)
<223> OTHER INFORMATION: n is a, c, g, or t

<400> SEQUENCE: 234
nnncggttta tccccgctgg cgcggggaac ac                              32

<210> SEQ ID NO 235
<211> LENGTH: 31
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(3)
<223> OTHER INFORMATION: n is a, c, g, or t

<400> SEQUENCE: 235
nnncacaagg ggcgcggtcg ccccctatttg g                              31

<210> SEQ ID NO 236
<211> LENGTH: 20
<212> TYPE: DNA
<213> ORGANISM: Artificial Sequence
<220> FEATURE:
<223> OTHER INFORMATION: Synthetic sequence

<400> SEQUENCE: 236
ggccccagtg ctgcaatgat                                            20

<210> SEQ ID NO 237
<211> LENGTH: 40
<212> TYPE: DNA
<213> ORGANISM: Artificial Sequence
<220> FEATURE:
<223> OTHER INFORMATION: Synthetic sequence

<400> SEQUENCE: 237
gtgagcgtgg gtctcgcggt atcattgcag cactggggcc                      40

<210> SEQ ID NO 238
<211> LENGTH: 54
<212> TYPE: DNA
<213> ORGANISM: Artificial Sequence
<220> FEATURE:
<223> OTHER INFORMATION: Synthetic sequence
```

<400> SEQUENCE: 238
gccccaattt actactcgtt ctggtgtttc tcgtaccgcg agacccacgc tcac        54

<210> SEQ ID NO 239
<211> LENGTH: 34
<212> TYPE: DNA
<213> ORGANISM: Artificial Sequence
<220> FEATURE:
<223> OTHER INFORMATION: Synthetic sequence

<400> SEQUENCE: 239
gccccaattt actactcgtt ctggtgtttc tcgt        34

<210> SEQ ID NO 240
<211> LENGTH: 20
<212> TYPE: DNA
<213> ORGANISM: Artificial Sequence
<220> FEATURE:
<223> OTHER INFORMATION: Synthetic sequence

<400> SEQUENCE: 240
accgcgagac ccacgctcac        20

<210> SEQ ID NO 241
<211> LENGTH: 33
<212> TYPE: DNA
<213> ORGANISM: Artificial Sequence
<220> FEATURE:
<223> OTHER INFORMATION: Synthetic sequence

<400> SEQUENCE: 241
acgagaaaca ccagaacgag tagtaaattg ggc        33

<210> SEQ ID NO 242
<211> LENGTH: 108
<212> TYPE: PRT
<213> ORGANISM: Artificial Sequence
<220> FEATURE:
<223> OTHER INFORMATION: Synthetic sequence

<400> SEQUENCE: 242

Glu Pro Ala Pro Ala Arg Arg Ser Val Glu Gln Leu Arg Gly Ile Glu
1               5                   10                  15

Gly Ser Arg Val Arg Ala Thr Tyr Ala Leu Leu Ala Lys Gln Tyr Gly
            20                  25                  30

Val Thr Trp Asn Gly Arg Arg Tyr Asp Asp Thr Ile Asn Gln Cys Ile
        35                  40                  45

Ser Ala Ala Thr Ser Cys Leu Tyr Gly Val Thr Glu Ala Ala Ile Leu
    50                  55                  60

Ala Ala Gly Tyr Ala Pro Ala Ile Gly Phe Val His Thr Gly Lys Pro
65                  70                  75                  80

Leu Ser Phe Val Tyr Asp Ile Ala Asp Ile Ile Lys Phe Asp Thr Val
                85                  90                  95

Val Pro Lys Ala Phe Glu Ile Ala Arg Arg Asn Pro
            100                 105

<210> SEQ ID NO 243
<211> LENGTH: 133
<212> TYPE: PRT
<213> ORGANISM: Artificial Sequence
<220> FEATURE:
<223> OTHER INFORMATION: Synthetic sequence

<400> SEQUENCE: 243

Arg Lys Val Arg Ala Asp Ser Leu Thr Arg Tyr Lys Lys Ala Glu
1               5                   10                  15

Glu Ala Ser Asn Val Ser Glu Leu Met Gly Ile Glu Gly Asn Ala Arg
            20                  25                  30

Glu Glu Tyr Tyr Ser Met Ile Asp Ser Leu Val Ser Asp Glu Arg Arg
        35                  40                  45

Pro Pro Lys Asn Phe Ala Asn Thr Leu Ile Ser Phe Gly Asn Ser Leu
    50                  55                  60

Leu Tyr Thr Thr Val Leu Ser Leu Ile Tyr Gln Thr His Leu Asp Pro
65                  70                  75                  80

Arg Ile Gly Tyr Leu His Glu Thr Asn Phe Arg Arg Phe Ser Leu Asn
                85                  90                  95

Leu Asp Ile Ala Glu Leu Phe Lys Pro Ala Val Val Asp Arg Leu Phe
            100                 105                 110

Leu Asn Leu Val Asn Thr Arg Gln Ile Asn Glu Lys His Phe Asp Glu
        115                 120                 125

Ile Ser Glu Gly Leu
    130

<210> SEQ ID NO 244
<211> LENGTH: 126
<212> TYPE: PRT
<213> ORGANISM: Artificial Sequence
<220> FEATURE:
<223> OTHER INFORMATION: Synthetic sequence

<400> SEQUENCE: 244

Trp Gly Ile Lys Ala Lys Leu Ser Asp Tyr Leu Asp Glu Leu Asn Asp
1               5                   10                  15

Ala Arg Lys Ile Thr Glu Ile Met Asn Val Glu Ala Arg Ile Arg Gln
            20                  25                  30

Glu Tyr Tyr Ala Lys Trp Asp Glu Asn Leu Pro Lys Asn Glu Met Asn
        35                  40                  45

Ala Leu Ile Ser Phe Leu Asn Ser Arg Leu Tyr Ala Thr Ile Ile Thr
    50                  55                  60

Glu Ile Tyr Asn Thr Gln Leu Ala Pro Thr Ile Ser Tyr Leu His Glu
65                  70                  75                  80

Pro Ser Glu Arg Arg Phe Ser Leu Ser Leu Asp Leu Ser Glu Ile Phe
                85                  90                  95

Lys Pro Ile Ile Ala Asp Arg Val Ala Asn Arg Leu Val Lys Lys Gly
            100                 105                 110

Ser Leu Lys Lys Glu His Phe Arg Glu Asp Leu Asn Gly Val
        115                 120                 125

<210> SEQ ID NO 245
<211> LENGTH: 125
<212> TYPE: PRT
<213> ORGANISM: Artificial Sequence
<220> FEATURE:
<223> OTHER INFORMATION: Synthetic sequence

<400> SEQUENCE: 245

Ser Ala Asp Thr Tyr Leu Asn Lys Val Lys Glu Thr Asn Ser Ile Pro
1               5                   10                  15

Glu Leu Met Ser Val Glu Ala Glu Phe Arg Lys Leu Cys Tyr Lys Lys
            20                  25                  30

Leu Glu Glu Val Thr Gly Trp Glu Leu Pro Pro Gln Asn Pro Leu
         35                  40                  45

Asn Ala Leu Ile Ser Phe Gly Asn Ser Leu Thr Tyr Ala Lys Val Leu
 50                  55                  60

Gly Glu Ile Tyr Lys Thr Gln Leu Asn Pro Thr Val Ser Tyr Leu His
65                  70                  75                  80

Glu Pro Ser Arg Phe Ser Leu Ser Leu Asp Val Ala Glu Val Phe Lys
             85                  90                  95

Pro Ile Phe Val Asp Asn Leu Ile Ile Arg Leu Ile Gln Glu Asn Lys
            100                 105                 110

Ile Asp Lys Thr His Phe Ser Thr Glu Leu Asn Met Thr
            115                 120                 125

<210> SEQ ID NO 246
<211> LENGTH: 136
<212> TYPE: PRT
<213> ORGANISM: Artificial Sequence
<220> FEATURE:
<223> OTHER INFORMATION: Synthetic sequence

<400> SEQUENCE: 246

Arg Val Leu Arg Asp Ala Gly Phe Ala Val Asp Ala Thr Ala Leu Ala
1               5                   10                  15

Val Ala Val Glu Asp Ser Ala Arg Ala Leu Glu Gln Ala Pro Asn His
            20                  25                  30

Glu His Leu Leu Thr Glu Glu Ala Arg Leu Ser Lys Arg Leu Phe Lys
         35                  40                  45

Leu Ala Ala Gln Ala Thr Arg Tyr Gly Glu Phe Val Arg Ala Lys Arg
 50                  55                  60

Gly Ser Gly Gly Asp Pro Ala Asn Arg Phe Leu Asp His Gly Asn Tyr
65                  70                  75                  80

Leu Ala Tyr Gly Leu Ala Ala Thr Ala Thr Trp Val Leu Gly Ile Pro
             85                  90                  95

His Gly Leu Ala Val Leu His Gly Lys Thr Arg Arg Gly Gly Leu Val
            100                 105                 110

Phe Asp Val Ala Asp Leu Ile Lys Asp Ser Leu Ile Leu Pro Gln Ala
            115                 120                 125

Phe Leu Ser Ala Met Arg Gly Asp
            130                 135

<210> SEQ ID NO 247
<211> LENGTH: 100
<212> TYPE: DNA
<213> ORGANISM: Artificial Sequence
<220> FEATURE:
<223> OTHER INFORMATION: Synthetic sequence

<400> SEQUENCE: 247
tttagagtgt tccccgcgcc agcggggata aaccgagcac aaatatcatc gctcaaacca      60
cttacgggtg ttccccgcgc cagcggggat aaaccgcctc                           100

<210> SEQ ID NO 248
<211> LENGTH: 100
<212> TYPE: DNA
<213> ORGANISM: Artificial Sequence
<220> FEATURE:
<223> OTHER INFORMATION: Synthetic sequence

<400> SEQUENCE: 248
gaggcggttt atccccgctg gcgcggggaa cacccgtaag tggtttgagc gatgatattt    60
gtgctcggtt tatccccgct ggcgcgggga acactctaaa                        100

<210> SEQ ID NO 249
<211> LENGTH: 33
<212> TYPE: DNA
<213> ORGANISM: Artificial Sequence
<220> FEATURE:
<223> OTHER INFORMATION: Synthetic sequence

<400> SEQUENCE: 249
acgagaaaca ccagaacgag tagtaaattg ggc                               33

<210> SEQ ID NO 250
<211> LENGTH: 33
<212> TYPE: DNA
<213> ORGANISM: Artificial Sequence
<220> FEATURE:
<223> OTHER INFORMATION: Synthetic sequence

<400> SEQUENCE: 250
gcccaattta ctactcgttc tggtgtttct cgt                               33

<210> SEQ ID NO 251
<211> LENGTH: 33
<212> TYPE: DNA
<213> ORGANISM: Artificial Sequence
<220> FEATURE:
<223> OTHER INFORMATION: Synthetic sequence

<400> SEQUENCE: 251
acgagaaaca ccagaacgag tagtaaattg gga                               33

<210> SEQ ID NO 252
<211> LENGTH: 33
<212> TYPE: DNA
<213> ORGANISM: Artificial Sequence
<220> FEATURE:
<223> OTHER INFORMATION: Synthetic sequence

<400> SEQUENCE: 252
tcccaattta ctactcgttc tggtgtttct cgt                               33

<210> SEQ ID NO 253
<211> LENGTH: 33
<212> TYPE: DNA
<213> ORGANISM: Artificial Sequence
<220> FEATURE:
<223> OTHER INFORMATION: Synthetic sequence

<400> SEQUENCE: 253
gcgagaaaca ccagaacgag tagtaaattg ggc                               33

<210> SEQ ID NO 254
<211> LENGTH: 33
<212> TYPE: DNA
<213> ORGANISM: Artificial Sequence
<220> FEATURE:
<223> OTHER INFORMATION: Synthetic sequence

<400> SEQUENCE: 254
gcccaattta ctactcgttc tggtgtttct cgc                               33

```
<210> SEQ ID NO 255
<211> LENGTH: 99
<212> TYPE: PRT
<213> ORGANISM: Escherichia coli

<400> SEQUENCE: 255

Met Ala Leu Thr Lys Ala Glu Met Ser Glu Tyr Leu Phe Asp Lys Leu
1               5                   10                  15

Gly Leu Ser Lys Arg Asp Ala Lys Glu Leu Val Glu Leu Phe Phe Glu
            20                  25                  30

Glu Ile Arg Arg Ala Leu Glu Asn Gly Glu Gln Val Lys Leu Ser Gly
        35                  40                  45

Phe Gly Asn Phe Asp Leu Arg Asp Lys Asn Gln Arg Pro Gly Arg Asn
    50                  55                  60

Pro Lys Thr Gly Glu Asp Ile Pro Ile Thr Ala Arg Arg Val Val Thr
65                  70                  75                  80

Phe Arg Pro Gly Gln Lys Leu Lys Ser Arg Val Glu Asn Ala Ser Pro
                85                  90                  95

Lys Asp Glu

<210> SEQ ID NO 256
<211> LENGTH: 94
<212> TYPE: PRT
<213> ORGANISM: Escherichia coli

<400> SEQUENCE: 256

Met Thr Lys Ser Glu Leu Ile Glu Arg Leu Ala Thr Gln Gln Ser His
1               5                   10                  15

Ile Pro Ala Lys Thr Val Glu Asp Ala Val Lys Glu Met Leu Glu His
            20                  25                  30

Met Ala Ser Thr Leu Ala Gln Gly Glu Arg Ile Glu Ile Arg Gly Phe
        35                  40                  45

Gly Ser Phe Ser Leu His Tyr Arg Ala Pro Arg Thr Gly Arg Asn Pro
    50                  55                  60

Lys Thr Gly Asp Lys Val Glu Leu Glu Gly Lys Tyr Val Pro His Phe
65                  70                  75                  80

Lys Pro Gly Lys Glu Leu Arg Asp Arg Ala Asn Ile Tyr Gly
                85                  90
```